US012584177B2

(12) United States Patent
Taylor et al.

(10) Patent No.: US 12,584,177 B2
(45) Date of Patent: Mar. 24, 2026

(54) DETECTING ENDOMETRIAL CANCER

(71) Applicants: Mayo Foundation for Medical Education and Research, Rochester, MN (US); Exact Sciences Corporation, Madison, WI (US)

(72) Inventors: William R. Taylor, Lake City, MN (US); John B. Kisiel, Rochester, MN (US); Douglas W. Mahoney, Elgin, MN (US); David A. Ahlquist, Rochester, MN (US); Hatim T. Allawi, Middleton, WI (US); Maria Giakoumopoulos, Middleton, WI (US)

(73) Assignees: Mayo Foundation for Medical Education and Research, Rochester, MN (US); Exact Sciences Corporation, Madison, WI (US)

( * ) Notice: Subject to any disclaimer, the term of this patent is extended or adjusted under 35 U.S.C. 154(b) by 998 days.

(21) Appl. No.: 17/424,422

(22) PCT Filed: Jan. 24, 2020

(86) PCT No.: PCT/US2020/015059
§ 371 (c)(1),
(2) Date: Jul. 20, 2021

(87) PCT Pub. No.: WO2020/154665
PCT Pub. Date: Jul. 30, 2020

(65) Prior Publication Data
US 2022/0106644 A1 Apr. 7, 2022

Related U.S. Application Data

(60) Provisional application No. 62/796,384, filed on Jan. 24, 2019.

(51) Int. Cl.
*C12Q 1/6886* (2018.01)
*G16B 30/10* (2019.01)
*G16B 35/20* (2019.01)

(52) U.S. Cl.
CPC ........... *C12Q 1/6886* (2013.01); *G16B 30/10* (2019.02); *G16B 35/20* (2019.02)

(58) Field of Classification Search
CPC ............ C12Q 1/6886; C12Q 2600/154; C12Q 2537/143; G16B 30/10; G16B 35/20
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |

(Continued)

FOREIGN PATENT DOCUMENTS

| | | |
|---|---|---|
| EP | 2899275 | 7/2015 |
| IT | TO20070201 A1 | 10/2007 |

(Continued)

OTHER PUBLICATIONS

Murali et al., "Classification of endometrial carcinoma: more than two types," Lancet Oncol., vol. 15, pp. e268-78. (Year: 2014).*

(Continued)

*Primary Examiner* — Angela M. Bertagna
*Assistant Examiner* — Francesca Filippa Giammona
(74) *Attorney, Agent, or Firm* — Casimir Jones, S.C.; Peter J. Schlueter

(57) ABSTRACT

Provided herein is technology for endometrial cancer (EC) screening and particularly, but not exclusively, to methods, compositions, and related uses for detecting the presence of endometrial cancer and various subtypes of endometrial cancer.

29 Claims, 14 Drawing Sheets

Specification includes a Sequence Listing.

(56) References Cited

U.S. PATENT DOCUMENTS

| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,403,711 | A | 4/1995 | Walder et al. |
| 5,409,818 | A | 4/1995 | Davey et al. |
| 5,494,810 | A | 2/1996 | Barany et al. |
| 5,508,169 | A | 4/1996 | Deugau et al. |
| 5,624,802 | A | 4/1997 | Urdea et al. |
| 5,639,611 | A | 6/1997 | Wallace et al. |
| 5,660,988 | A | 8/1997 | Duck et al. |
| 5,710,264 | A | 1/1998 | Urdea et al. |
| 5,773,258 | A | 6/1998 | Birch et al. |
| 5,786,146 | A | 7/1998 | Herman et al. |
| 5,792,614 | A | 8/1998 | Western et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,914,230 | A | 6/1999 | Liu et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,013,170 | A | 1/2000 | Meade |
| 6,063,573 | A | 5/2000 | Kayyem |
| 6,090,543 | A | 7/2000 | Prudent et al. |
| 6,110,677 | A | 8/2000 | Western et al. |
| 6,110,684 | A | 8/2000 | Kemper et al. |
| 6,121,001 | A | 9/2000 | Western et al. |
| 6,150,097 | A | 11/2000 | Tyagi et al. |
| 6,183,960 | B1 | 2/2001 | Lizardi |
| 6,210,884 | B1 | 4/2001 | Lizardi |
| 6,221,583 | B1 | 4/2001 | Kayyem et al. |
| 6,235,502 | B1 | 5/2001 | Weissman et al. |
| 6,248,229 | B1 | 6/2001 | Meade |
| 6,251,594 | B1 | 6/2001 | Gonzalgo et al. |
| 6,265,171 | B1 | 7/2001 | Herman et al. |
| 6,872,816 | B1 | 3/2005 | Hall et al. |
| 7,037,650 | B2 | 5/2006 | Gonzalgo et al. |
| 7,662,594 | B2 | 2/2010 | Kong et al. |
| 8,361,720 | B2 | 1/2013 | Oldham-Haltom et al. |
| 8,715,937 | B2 | 5/2014 | Zou et al. |
| 8,741,567 | B2 | 6/2014 | He et al. |
| 8,808,990 | B2 | 8/2014 | Lidgard et al. |
| 8,916,344 | B2 | 12/2014 | Zou et al. |
| 9,000,146 | B2 | 4/2015 | Bruinsma et al. |
| 9,096,893 | B2 | 8/2015 | Allawi et al. |
| 9,169,511 | B2 | 10/2015 | Bruinsma et al. |
| 9,212,392 | B2 | 12/2015 | Allawi et al. |
| 9,670,552 | B2 | 6/2017 | An et al. |
| 10,030,272 | B2 | 7/2018 | Ahlquist et al. |
| 10,370,726 | B2 | 8/2019 | Ahlquist et al. |
| 10,927,415 | B2 | 2/2021 | Feinberg |
| 11,702,704 | B2 | 7/2023 | Taylor et al. |
| 2005/0176002 | A1 * | 8/2005 | Diamandis ........... C12Q 1/6886 424/1.49 |
| 2007/0202525 | A1 | 8/2007 | Quake et al. |
| 2009/0170087 | A1 | 7/2009 | Budiman et al. |
| 2012/0122088 | A1 | 5/2012 | Zou et al. |
| 2012/0122106 | A1 | 5/2012 | Zou et al. |
| 2012/0208180 | A1 * | 8/2012 | Durst ................... C12Q 1/6886 435/5 |
| 2012/0288868 | A1 | 11/2012 | Bruinsma et al. |
| 2013/0337439 | A1 | 12/2013 | Nobre et al. |
| 2014/0199696 | A1 | 7/2014 | Mansour et al. |
| 2015/0119350 | A1 | 4/2015 | Kebebew et al. |
| 2015/0275314 | A1 | 10/2015 | Ahlquist et al. |
| 2016/0010081 | A1 | 1/2016 | Allawi et al. |
| 2016/0017430 | A1 | 1/2016 | Badosa |
| 2016/0040246 | A1 | 2/2016 | Ahlquist et al. |
| 2016/0090634 | A1 | 3/2016 | Kisiel et al. |
| 2016/0194721 | A1 | 7/2016 | Allawi et al. |
| 2017/0121704 | A1 | 5/2017 | Allawi et al. |
| 2017/0314071 | A1 | 11/2017 | Ehrich et al. |
| 2017/0321286 | A1 | 11/2017 | Allawi et al. |
| 2018/0016643 | A1 | 1/2018 | An et al. |
| 2018/0030547 | A1 | 2/2018 | Hofmann et al. |
| 2019/0161806 | A1 | 5/2019 | Ahlquist et al. |
| 2019/0177769 | A1 | 6/2019 | Allawi et al. |
| 2020/0024643 | A1 | 1/2020 | Arensdorf et al. |
| 2020/0377954 | A1 | 12/2020 | Bitenc et al. |
| 2020/0377956 | A1 | 12/2020 | Vogelstein et al. |
| 2021/0130907 | A1 | 5/2021 | Taylor et al. |
| 2022/0071605 | A1 | 3/2022 | Eisele et al. |
| 2022/0349009 | A1 | 11/2022 | Taylor et al. |

FOREIGN PATENT DOCUMENTS

| JP | 2017514499 A | 6/2017 | |
| TW | 201632629 A | 9/2016 | |
| WO | WO 95/00669 | 1/1995 | |
| WO | WO 95/15373 | 6/1995 | |
| WO | WO 97/46705 | 12/1997 | |
| WO | WO 99/28498 | 6/1999 | |
| WO | WO 00/26401 | 5/2000 | |
| WO | WO 2005/023091 | 3/2005 | |
| WO | WO 2005/038051 | 4/2005 | |
| WO | WO 2007/067695 | 6/2007 | |
| WO | WO 2008/084219 | 7/2008 | |
| WO | WO 2009/102788 | 8/2009 | |
| WO | WO 2009/153667 | 12/2009 | |
| WO | WO 2010/089538 | 8/2010 | |
| WO | WO 2011/119934 | 9/2011 | |
| WO | WO 2012/104642 | 8/2012 | |
| WO | WO 2012/106525 | 8/2012 | |
| WO | WO 2012/150276 | 11/2012 | |
| WO | WO 2012/155072 | 11/2012 | |
| WO | WO 2013/070950 | 5/2013 | |
| WO | WO 2013/096661 | 6/2013 | |
| WO | WO 2013/103889 | 7/2013 | |
| WO | WO 2013/116375 | 8/2013 | |
| WO | WO 2013/142545 | 9/2013 | |
| WO | WO 2014/046200 | 3/2014 | |
| WO | WO 2014/159650 | 10/2014 | |
| WO | WO 2014/159652 | 10/2014 | |
| WO | WO 2015/066695 | 5/2015 | |
| WO | WO 2015/095689 | 6/2015 | |
| WO | WO 2015/116837 | 8/2015 | |
| WO | WO 2015/153283 | 10/2015 | |
| WO | WO 2015/153284 | 10/2015 | |
| WO | WO-2015169947 A1 | 11/2015 | |
| WO | WO 2016/094813 | 6/2016 | |
| WO | WO 2016/094839 | 6/2016 | |
| WO | WO 2016/160454 | 10/2016 | |
| WO | WO 2017/040627 | 3/2017 | |
| WO | WO-2017067477 A1 * | 4/2017 | |
| WO | WO 2017/075061 | 5/2017 | |
| WO | WO 2017/176630 | 10/2017 | |
| WO | WO 2017/180886 | 10/2017 | |
| WO | WO 2017/192221 | 11/2017 | |
| WO | WO-2017192221 A1 * | 11/2017 | ........... C12Q 1/6806 |
| WO | WO 2017/210372 | 12/2017 | |
| WO | WO 2018/017740 | 1/2018 | |
| WO | WO 2018/045322 | 3/2018 | |
| WO | WO 2018/140781 | 8/2018 | |
| WO | WO 2018/160576 | 9/2018 | |
| WO | WO 2019/108626 | 6/2019 | |
| WO | WO-2019199696 A1 | 10/2019 | |
| WO | WO 2020/089691 | 5/2020 | |
| WO | WO 2020/112869 | 6/2020 | |
| WO | WO 2020/115728 | 6/2020 | |
| WO | WO 2020/118274 | 6/2020 | |
| WO | WO 2020/154665 | 7/2020 | |
| WO | WO 2020/206256 | 10/2020 | |
| WO | WO 2020/227100 | 11/2020 | |
| WO | WO 2020/236939 | 11/2020 | |
| WO | WO 2020/264220 | 12/2020 | |
| WO | WO 2021041726 | 3/2021 | |
| WO | WO 2021/076969 | 4/2021 | |
| WO | WO 2021/087275 | 5/2021 | |
| WO | WO 2021/212031 | 10/2021 | |

(56)             References Cited

FOREIGN PATENT DOCUMENTS

| WO | WO 2021/226071 | 11/2021 |
| WO | WO 2021/226074 | 11/2021 |
| WO | WO 2022/039904 | 2/2022 |
| WO | WO 2022/040306 | 2/2022 |
| WO | WO-2022157369 A1 | 7/2022 |
| WO | WO 2022/165247 | 8/2022 |
| WO | WO 2022/187227 | 9/2022 |
| WO | WO 2022/187695 | 9/2022 |
| WO | WO 2023/081796 | 5/2023 |

OTHER PUBLICATIONS

Houshdaran et al., "Aberrant Endometrial DNA Methylome and Associated Gene Expression in Women with Endometriosis," Biology of Reproduction, vol. 95, No. 5, Article 93, pp. 1-16. (Year: 2016).*

Indermaur et al., "Genomic-directed targeted therapy increases endometrial cancer cell sensitivity to doxorubicin," American Journal of Obstetrics and Gynecology, vol. 203, No. 158, pp. e1-40. (Year: 2010).*

Liu et al., "Identification of key genes in endometrioid endometrial adenocarcinoma via TCGA database," Cancer Biomarkers, vol. 21, pp. 11-21. (Year: 2018).*

Yu et al., "Increased Association Between Endometriosis and Endometrial Cancer," International Journal of Gynecological Cancer, vol. 25, No. 3, pp. 447-452. (Year: 2015).*

Ahn et al., Identification of novel DNA hypermethylation of the adenylate kinase promoter in colorectal adenocarcinoma. Sci Rep. Jun. 16, 2021;11(1):12626.

Bakkum-Gamez et al. Methylated DNA markers for plasma detection of ovarian cancer: Discovery, validation, and clinical feasibility. Journal of Clinical Oncology. 2020. 38(15 suppl): 6072-6072.

Bakkum-Gamez et al., Detection of endometrial cancer using tampon-based collection and methylated DNA markers. Gynecol Oncol. Jul. 2023:174:11-20.

Bramblet et al., Methylated DNA Markers for Sporadic Colorectal and Endometrial Cancer Are Strongly Associated with Lynch Syndrome Cancers. Cancer Prev Res (Phila). Nov. 1, 2023;16(11):611-620.

Calin et al. Chronic lymphocytic leukemia: interplay between noncoding RNAs and protein-coding genes. Blood. Nov. 26, 2009;114(23):4761-70.

Chen et al., Methods for identifying differentially methylated regions for sequence- and array-based data. Brief Funct Genomics. Nov. 2016;15(6):485-490.

Earp et al. DNA methylation changes in epithelial ovarian cancer histotypes. Genomics. Dec. 2015;106(6):311-21.

He et al. Genome-wide profiles of methylation, microRNAs, and gene expression in chemoresistant breast cancer. Sci Rep. Apr. 20, 2016:6:24706.

Ito et al., Tet proteins can convert 5-methylcytosine to 5-formylcytosine and 5-carboxylcytosine. Science. Sep. 2, 2011;333(6047):1300-3.

Li et al. Cisplatin-induced pyroptosis is mediated via the CAPN1/CAPN2-BAK/BAX-caspase-9-caspase-3-GSDME axis in esophageal cancer. Chem Biol Interact. Jul. 1, 2022:361:109967.

Li et al., MethPrimer: designing primers for methylation PCRs. Bioinformatics. Nov. 2002;18(11):1427-31.

Liu et al., Bisulfite-free direct detection of 5-methylcytosine and 5-hydroxymethylcytosine at base resolution. Nat Biotechnol. Apr. 2019;37(4):424-429.

Marinelli et al. Methylated DNA markers for plasma detection of ovarian cancer: Discovery, validation, and clinical feasibility. Gynecol Oncol. Jun. 2022;165(3):568-576.

Matsushita et al, DNA-friendly Cu(ii)/TEMPO-catalyzed 5-hydroxymethylcytosine-specific oxidation. hem Commun (Camb). May 23, 2017;53(42):5756-5759.

Okamoto et al., 5-Hydroxymethylcytosine-selective oxidation with peroxotungstate. Chem Commun (Camb). Oct. 28, 2011;47(40):11231-3.

Robertson et al., The presence of 5-hydroxymethylcytosine at the gene promoter and not in the gene body negatively regulates gene expression. Biochem Biophys Res Commun. Jul. 22, 2011;411(1):40-3.

Shi et al., Endogenous PAD4 in Breast Cancer Cells Mediates Cancer Extracellular Chromatin Network Formation and Promotes Lung Metastasis. Mol Cancer Res. May 2020;18(5):735-747.

Sundararajan et al. SNAI1 recruits HDAC1 to suppress SNAI2 transcription during epithelial to mesenchymal transition. Sci Rep. Jun. 5, 2019;9(1):8295.

Talukdar et al. Genome-Wide DNA Methylation Profiling of Esophageal Squamous Cell Carcinoma from Global High-Incidence Regions Identifies Crucial Genes and Potential Cancer Markers. Cancer Res. May 15, 2021;81(10):2612-2624.

Zou et al., Sensitive quantification of methylated markers with a novel methylation specific technology. Clin Chem 2010. 56: A199 abstract D-144.

Supplementary Partial European Search Report for EP 20856304 Oct. 26, 2023. 13 pages.

International Search Report and Written Opinion for PCT/US2020/058235. Mailed Mar. 22, 2021. 32 pages.

International Search Report and Written Opinion for PCT/US2022/019010. Mailed Jul. 22, 2022. 28 pages.

Wu et al., Analysis of methylation profiling data of hyperplasia and primary and metastatic endometrial cancers. Eur J Obstet Gynecol Reprod Biol. Oct. 2017:217:161-166.

International Search Report and Written Opinion for PCT/US2023/031831, mailed Jan. 30, 2024, 16 pages.

International Search Report and Written Opinion for PCT/US20/15059. Mailed Jun. 22, 2020. 20 pages.

Ahlquist et al., Next-generation stool DNA test accurately detects colorectal cancer and large adenomas. Gastroenterology. Feb. 2012;142(2):248-56; quiz e25-6.

Antequera et al., High levels of de novo methylation and altered chromatin structure at CpG islands in cell lines. Cell. Aug. 10, 1990;62(3):503-14.

Arafa et al., High frequency of RASSF1A and RARb2 gene promoter methylation in morphologically normal endometrium adjacent to endometrioid adenocarcinoma. Histopathology. Nov. 2008;53(5):525-32.

Bakkum-Gamez et al., Detection of endometrial cancer via molecular analysis of DNA collected with vaginal tampons. Gynecol Oncol. Apr. 2015;137(1):14-21.

Ballabio et al., Screening for steroid sulfatase (STS) gene deletions by multiplex DNA amplification. Hum Genet. May 1990; 84(6):571-3.

Banno et al., Relationship of the aberrant DNA hypermethylation of cancer-related genes with carcinogenesis of endometrial cancer. Oncol Rep. Dec. 2006;16(6):1189-96.

Baranay. Genetic disease detection and DNA amplification using cloned thermostable ligase. Proc. Natl. Acad. Sci USA 1991. vol. 88, 189-93.

Bustin. Absolute quantification of mRNA using real-time reverse transcription polymerase chain reaction assays. J Mol Endocrinol. Oct. 2000;25(2):169-93.

Cancer Genome Atlas Research Network et al., Integrated genomic characterization of endometrial carcinoma. Nature. May 2, 2013;497(7447):67-73.

Chamberlain et al., Deletion screening of the Duchenne muscular dystrophy locus via multiplex DNA amplification. Nucleic Acids Res. Dec. 9, 1988;16(23):11141-56.

Chamberlin et al., New RNA polymerase from *Escherichia coli* infected with bacteriophage T7. Nature. Oct. 17, 1970;228(5268):227-31.

Chang et al., Increased epithelial stem cell traits in advanced endometrial endometrioid carcinoma. BMC Genomics. Dec. 16, 2009;10:613.

Chin et al., The significance of atypical glandular cells on routine cervical cytologic testing in a community-based population. Am J Obstet Gynecol. Jun. 2000;182(6):1278-82.

Don et al., 'Touchdown' PCR to circumvent spurious priming during gene amplification. Nucleic Acids Res. Jul. 25, 1991;19(14):4008.

(56)                     References Cited

OTHER PUBLICATIONS

Dowdy and Wearden, Statistics for Research, John Wiley & Sons, New York, 1983. TOC only. 6 pages.

Duffy et al., Methylated genes as new cancer biomarkers. Eur J Cancer. Feb. 2009;45(3):335-46.

Eads et al., CpG island hypermethylation in human colorectal tumors is not associated with DNA methyltransferase overexpression. Cancer Res. May 15, 1999;59(10):2302-6.

Egan. Signal Detection Theory and ROC Analysis, Academic Press, New York. 1975. TOC only. 9 pages.

Erlich (ed.), PCR Technology, Stockton Press. 1989. TOC only. 5 pages.

Feil et al., Methylation analysis on individual chromosomes: improved protocol for bisulphite genomic sequencing. Nucleic Acids Res. Feb. 25, 1994;22(4):695-6.

Felix et al., Factors associated with Type I and Type II endometrial cancer. Cancer Causes Control. Nov. 2010;21(11):1851-6.

Fiegl et al., Methylated DNA collected by tampons—a new tool to detect endometrial cancer. Cancer Epidemiol Biomarkers Prev. May 2004;13(5):882-8.

Fridley et al., Self-contained gene-set analysis of expression data: an evaluation of existing and novel methods. PLoS One. Sep. 17, 2010;5(9):e12693. 9 pages.

Frommer et al., A genomic sequencing protocol that yields a positive display of 5-methylcytosine residues in individual DNA strands. Proc Natl Acad Sci U S A. Mar. 1, 1992;89(5):1827-31.

Gardiner-Garden et al., CpG islands in vertebrate genomes.J Mol Biol. Jul. 20, 1987;196(2):261-82.

GenBank Accession No. NC_000002.11, Aug. 13, 2013, 2 pages.

Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.

Gonzalgo et al., Identification and characterization of differentially methylated regions of genomic DNA by methylation-sensitive arbitrarily primed PCR. Cancer Res. Feb. 15, 1997;57(4):594-9.

Grafstrom et al., The characteristics of DNA methylation in an in vitro DNA synthesizing system from mouse fibroblasts. Nucleic Acids Res. Apr. 25, 1985;13(8):2827-42.

Grigg et al., Sequencing 5-methylcytosine residues in genomic DNA. Bioessays. Jun. 1994;16(6):431-6.

Grigg. Sequencing 5-methylcytosine residues by the bisulphite method. DNA Seq. 1996;6(4):189-98.

Gu et al., Genome-scale DNA methylation mapping of clinical samples at single-nucleotide resolution. Nat Methods. Feb. 2010;7(2):133-6.

Gu et al., Preparation of reduced representation bisulfite sequencing libraries for genome-scale DNA methylation profiling. Nat Protoc. Apr. 2011;6(4):468-81.

Guida et al., Aberrant DNA hypermethylation of hMLH-1 and CDKN2A/p16 genes in benign, premalignant and malignant endometrial lesions. Eur J Gynaecol Oncol. 2009;30(3):267-70.

Guilfoyle et al., Ligation-mediated PCR amplification of specific fragments from a class-II restriction endonuclease total digest. Nucleic Acids Res. May 1, 1997;25(9):1854-8.

Hall et al., Sensitive detection of DNA polymorphisms by the serial invasive signal amplification reaction. Proc Natl Acad Sci U S A. Jul. 18, 2000;97(15):8272-7.

Hayden et al., Multiplex-ready PCR: a new method for multiplexed SSR and SNP genotyping. BMC Genomics. Feb. 18, 2008;9:80.

Hecker et al., High and low annealing temperatures increase both specificity and yield in touchdown and stepdown PCR. Biotechniques. Mar. 1996;20(3):478-85.

Herman et al., Methylation-specific PCR: a novel PCR assay for methylation status of CpG islands. Proc Natl Acad Sci U S A. Sep. 3, 1996;93(18):9821-6.

Higuchi et al., A general method of in vitro preparation and specific mutagenesis of DNA fragments: study of protein and DNA interactions. Nucleic Acids Res. Aug. 11, 1988;16(15):7351-67.

Higuchi et al., Kinetic PCR analysis: real-time monitoring of DNA amplification reactions. Biotechnology (N Y). Sep. 1993;11(9):1026-30.

Higuchi et al., Simultaneous amplification and detection of specific DNA sequences. Biotechnology (N Y). Apr. 1992;10(4):413-7.

Horowitz et al., Microsatellite instability, MLH1 promoter methylation, and loss of mismatch repair in endometrial cancer and concomitant atypical hyperplasia. Gynecol Oncol. Jul. 2002;86(1):62-8.

Huang et al., Promoter hypermethylation of CIDEA, HAAO and RXFP3 associated with microsatellite instability in endometrial carcinomas. Gynecol Oncol. May 2010;117(2):239-47.

Hussein et al., The Genomic Heterogeneity of FIGO Grade 3 Endometrioid Carcinoma Impacts Diagnostic Accuracy and Reproducibility. Int J Gynecol Pathol. Jan. 2016;35(1):16-24.

In re Herz, 537 F.2d 549, 551-52, 190 USPQ 461, 463 (CCPA 1976) 4 pages.

Kacian et al., A replicating RNA molecule suitable for a detailed analysis of extracellular evolution and replication. Proc Natl Acad Sci U S A. Oct. 1972;69(10):3038-42.

Kalinina et al., Nanoliter scale PCR with TaqMan detection. Nucleic Acids Res. May 15, 1997;25(10):1999-2004.

Kawai et al., Comparison of DNA methylation patterns among mouse cell lines by restriction landmark genomic scanning. Mol Cell Biol. Nov. 1994;14(11):7421-7.

Kinde et al., Evaluation of DNA from the Papanicolaou test to detect ovarian and endometrial cancers. Sci Transl Med. Jan. 9, 2013;5(167):167ra4. 21 pages.

Kisiel et al., New DNA Methylation Markers for Pancreatic Cancer: Discovery, Tissue Validation, and Pilot Testing in Pancreatic Juice. Clin Cancer Res. Oct. 1, 2015;21(19):4473-81.

Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.

Laird. Principles and challenges of genomewide DNA methylation analysis. Nat Rev Genet. Mar. 2010;11(3):191-203.

Lyamichev et al., Polymorphism identification and quantitative detection of genomic DNA by invasive cleavage of oligonucleotide probes. Nat Biotechnol. Mar. 1999;17(3):292-6.

Mariani et al., Prospective assessment of lymphatic dissemination in endometrial cancer: a paradigm shift in surgical staging. Gynecol Oncol. Apr. 2008;109(1):11-8.

Martin et al., Genomic sequencing indicates a correlation between DNA hypomethylation in the 5' region of the pS2 gene and its expression in human breast cancer cell lines. Gene. May 19, 1995;157(1-2):261-4.

Meissner et al., Genome-scale DNA methylation maps of pluripotent and differentiated cells. Nature. Aug. 7, 2008;454(7205):766-70.

Meissner et al., Reduced representation bisulfite sequencing for comparative high-resolution DNA methylation analysis. Nucleic Acids Res. Oct. 13, 2005;33(18):5868-77.

Moore et al., Uterine papillary serous carcinoma. Clin Obstet Gynecol. Jun. 2011;54(2):278-91.

Nelson et al., Key epigenetic changes associated with lung cancer development: results from dense methylation array profiling. Epigenetics. Jun. 1, 2012;7(6):559-66.

Nyce et al., Variable effects of DNA-synthesis inhibitors upon DNA methylation in mammalian cells. Nucleic Acids Res. May 27, 1986;14(10):4353-67.

Olek et al., A modified and improved method for bisulphite based cytosine methylation analysis. Nucleic Acids Res. Dec. 15, 1996;24(24):5064-6.

Olek et al., The pre-implantation ontogeny of the H19 methylation imprint. Nat Genet. Nov. 1997;17(3):275-6.

Parkin et al., Global cancer statistics, 2002. CA Cancer J Clin. Mar.-Apr. 2005;55(2):74-108.

Pijnenborg et al., RASSF1A methylation and K-ras and B-raf mutations and recurrent endometrial cancer. Ann Oncol. Mar. 2007;18(3):491-7.

Ramsahoye et al., Non-CpG methylation is prevalent in embryonic stem cells and may be mediated by DNA methyltransferase 3a. Proc Natl Acad Sci U S A. May 9, 2000;97(10):5237-42.

(56)　　　　References Cited

OTHER PUBLICATIONS

Rein et al., Identifying 5-methylcytosine and related modifications in DNA genomes. Nucleic Acids Res. May 15, 1998;26(10):2255-64.

Roux. Using mismatched primer-template pairs in touchdown PCR. Biotechniques. May 1994;16(5):812-4.

Sadri et al., Rapid analysis of DNA methylation using new restriction enzyme sites created by bisulfite modification. Nucleic Acids Res. Dec. 15, 1996;24(24):5058-9.

Salomon et al., Methylation of mouse DNA in vivo: di- and tripyrimidine sequences containing 5-methylcytosine. Biochim Biophys Acta. Apr. 15, 1970;204(2):340-51.

Sasaki et al., Hypermethylation can selectively silence multiple promoters of steroid receptors in cancers. Mol Cell Endocrinol. Apr. 28, 2003;202(1-2):201-7.

Sasaki et al., Progesterone receptor B gene inactivation and CpG hypermethylation in human uterine endometrial cancer. Cancer Res. Jan. 1, 2001;61(1):97-102.

Schouten et al., Relative quantification of 40 nucleic acid sequences by multiplex ligation-dependent probe amplification. Nucleic Acids Res. Jun. 15, 2002;30(12):e57. 13 pages.

Siegel et al., Cancer statistics, 2016. CA Cancer J Clin. Jan.-Feb. 2016;66(1):7-30.

Singer-Sam et al., A quantitative Hpall-PCR assay to measure methylation of DNA from a small number of cells. Nucleic Acids Res. Feb. 11, 1990;18(3):687.

Singer-Sam et al., A sensitive, quantitative assay for measurement of allele-specific transcripts differing by a single nucleotide. PCR Methods Appl. Feb. 1992;1(3):160-3.

Suehiro et al., Aneuploidy predicts outcome in patients with endometrial carcinoma and is related to lack of CDH13 hypermethylation. Clin Cancer Res. Jun. 1, 2008;14(11):3354-61.

Szabo et al., Allele-specific expression and total expression levels of imprinted genes during early mouse development: implications for imprinting mechanisms. Genes Dev. Dec. 15, 1995;9(24):3097-108.

Tao et al., DNA methylation in endometrial cancer. Epigenetics. Aug. 16, 2010;5(6):491-8.

Toyota et al., Identification of differentially methylated sequences in colorectal cancer by methylated CpG island amplification. Cancer Res. May 15, 1999;59(10):2307-12.

Triglia et al., A procedure for in vitro amplification of DNA segments that lie outside the boundaries of known sequences. Nucleic Acids Res. Aug. 25, 1988;16(16):8186.

Vogelstein et al., Digital PCR. Proc Natl Acad Sci U S A. Aug. 3, 1999;96(16):9236-41.

Wentzensen et al., Discovery and validation of methylation markers for endometrial cancer. Int J Cancer. Oct. 15, 2014;135(8):1860-8.

Woodcock et al., The majority of methylated deoxycytidines in human DNA are not in the CpG dinucleotide. Biochem Biophys Res Commun. Jun. 15, 1987;145(2):888-94.

Wu et al., The ligation amplification reaction (LAR)—amplification of specific DNA sequences using sequential rounds of template-dependent ligation. Genomics. May 1989;4(4):560-9.

Xiong et al., hMLH1 promoter methylation and silencing in primary endometrial cancers are associated with specific alterations in MBDs occupancy and histone modifications. Gynecol Oncol. Oct. 2006;103(1):321-8.

Xiong et al., COBRA: a sensitive and quantitative DNA methylation assay. Nucleic Acids Res. Jun. 15, 1997;25(12):2532-4.

Xiong et al., Epigenetic-mediated upregulation of progesterone receptor B gene in endometrial cancer cell lines. Gynecol Oncol. Oct. 2005;99(1):135-41.

Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.

Zhang et al., Comparative DNA methylome analysis of endometrial carcinoma reveals complex and distinct deregulation of cancer promoters and enhancers. BMC Genomics. Oct. 6, 2014;15(1):868.

Zhang et al., DNA methylation analysis of chromosome 21 gene promoters at single base pair and single allele resolution. PLoS Genet. Mar. 2009;5(3):e1000438. 15 pages.

Zighelboim et al., Differential methylation hybridization array of endometrial cancers reveals two novel cancer-specific methylation markers. Clin Cancer Res. May 15, 2007;13(10):2882-9.

Zou et al., Highly methylated genes in colorectal neoplasia: implications for screening. Cancer Epidemiol Biomarkers Prev. Dec. 2007;16(12):2686-96.

Zou et al., Quantification of methylated markers with a multiplex methylation-specific technology. Clin Chem. Feb. 2012;58(2):375-83.

Supplementary Partial European Search Report for EP 20744597. Dec. 23, 2022. 5 pages.

Chen et al., Quantitative DNA methylation analysis of selected genes in endometrial carcinogenesis. Taiwan J Obstet Gynecol. Oct. 2015;54(5):572-9.

Huang et al., Integrated Epigenomics Analysis Reveals a DNA Methylation Panel for Endometrial Cancer Detection Using Cervical Scrapings. Clin Cancer Res. Jan. 1, 2017;23(1):263-272.

Campan M., et al., "Genome-Scale Screen for DNA Methylation-Based Detection Markers for Ovarian Cancer," PLoS One, Supporting Information, Dec. 2011, vol. 6, No. 12, e28141, 23 Pages.

Extended European Search Report for European Application No. 20744597.4, mailed Apr. 17, 2023, 09 Pages.

Extended European Search Report for European Application No. 20881481.4, mailed Nov. 3, 2023, 12 Pages.

Farkas S.A., et al., "Genome-wide DNA Methylation Assay Reveals Novel Candidate Biomarker Genes in Cervical Cancer", Epigenetics, vol. 8, No. 11, Nov. 1, 2013, pp. 1213-1225.

Gasperov N.M., et al., "Methylated Host Cell Gene Promoters and Human Papillomavirus Type 16 and 18 Predicting Cervical Lesions and Cancer", PLoS One, vol. 10, No. 6, Jun. 9, 2015, e0129452, pp. 1-14.

Lai H-C., et al., "Identification of Novel DNA Methylation Markers in Cervical Cancer", International Journal of Cancer, John Wiley & Sons, Inc, US, vol. 123, No. 1, Apr. 8, 2008, pp. 161-167.

Ozols R F., et al., "Epithelial Ovarian Cancer," Principles and Practice of Gynecologic Oncology, Lippincott Williams & Wilkins; Philadelphia, PA, USA, 2000, pp. 981-1057 (80 Pages).

Supplementary Partial European Search Report in European Patent Application No. 22764185.9, dated Dec. 23, 2024, 15 Pages.

Vasiljevic N., et al., "Credentialing of DNA Methylation Assays for Human Genes as Diagnostic Biomarkers of Cervical Intraepithelial Neoplasia in High-risk HPV Positive Women", Gynecologic Oncology, vol. 132, No. 3, Feb. 6, 2014, pp. 709-714.

Wang R., et al., "Genome-wide Methylome Analysis Using MethylCap-seq Uncovers 4 Hypermethylated Markers with High Sensitivity for Both Adeno- and Squamous-cell Cervical Carcinoma", Oncotarget, vol. 7, No. 49, Dec. 6, 2016, pp. 80735-80750.

Yang H-J., et al., "Differential DNA Methylation Profiles in Gynecological Cancers and Correlation with Clinico-pathological Data", BMC Cancer, Biomed Central, London, GB, vol. 6, No. 1, Aug. 23, 2006, 212, pp. 1-10.

Brait M., et al., "Cysteine Dioxygenase 1 Is a Tumor Suppressor Gene Silenced by Promoter Methylation in Multiple Human Cancers", PLoS ONE, 2012, vol. 7, No. 9, e44951, pp. 1-19.

Supplementary European Search Report for European Application No. 22764185.9, dated Apr. 23, 2025, 18 Pages.

Patch A-M., et al., "Whole-Genome Characterization of Chemoresistant Ovarian Cancer", Macmillan Publishers Limited, Nature, vol. 521, May 28, 2015, 20 pages.

* cited by examiner

Endometrial Cancer vs. Benign Endometrium

| | AUC |
|---|---|
| SFMBT2 | 0.84 |
| NBPF8 | 0.88 |
| EMX2OS | 0.91 |
| BestFit | 0.98 |

Sensitivity

1-Specificity

FIG. 2

```
 1.  AGRN
 2.  AIM1
 3.  AKR7A3
 4.  C17orf107
 5.  DIDO1
 6.  EMX2OS
 7.  FKBP11
 8.  GDF7
 9.  JSRP1
10.  LHFPL2
11.  LOC100129726
12.  LRRC41
13.  LRRC8D
14.  MAX.chr10.2262
15.  MAX.chr14.1030
16.  MAX.chr7.10462
17.  MAX.chr7.10462B
18.  MDFI
19.  OBSCN
20.  RHBDL1
21.  SEPT9
22.  SFMBT2
23.  SPDYA
24.  ST3GAL2
25.  VILL
26.  ZNF323
27.  SLC13A5
28.  ZMIZ1
29.  MAX.chr8.1451
30.  C8orf73
31.  KBTBD11
32.  LOC100192379
33.  TRIM71
34.  LOC440925
35.  ARL5C
36.  STX16
37.  ITPKA
38.  IRF4
39.  CNTN4
40.  GRIN2A
41.  NOTCH3
42.  PAX1
43.  ZNF521
44.  VSX1
45.  CRHR2
46.  FAM19A5
47.  ASCL1
48.  GLT1D1
49.  T
50.  CAPN2
51.  RYR2_F
52.  SIM2
53.  TRH
54.  JAM3
55.  BARX1
56.  ZNF671
57.  TSPYL5
58.  MPZ_5554
59.  CXCL12
60.  PTGDR
```

```
AGRN
>hg19_dna range=chr1:975957-976046 5'pad=0 3'pad=0 strand=+
GGGCTGCGAGCACGGCAAGGTCTCTCAGGCTTGTGGACGTGGGTACGGGCGTCTCGGCACCCTGAGCTTTCTCCCCTACCCGCCCCAGCG
(SEQ ID NO:289)
BST:
GGGTTGCGAGTACGGTAAGGTTTTTTAGGTTTGTGGACGTGGGTACGGGCGTTTCGGTATTTTGAGTTTTTTTTTTTATTCGTTTTAGCG
(SEQ ID NO:290)
AGRN_FP       GGTTGCGAGTACGGTAAGGTTT (SEQ ID NO:291)
AGRN_RP       AAAACTCAAAATACCGAAACGCC (SEQ ID NO:292)
AGRN_Pb_A1    CGCGCCGAGG CCGTACCCACGTCCA/3C6/ (SEQ ID NO:293)
```

FIG. 2 (cont'd)

```
AIM1
>hg19_dna range=chr6:106960288-106960380 5'pad=0 3'pad=0 strand=+
CGCGGACGCCGAGCTCCCTGAGAGCGCTGCCAGGGACGACGCGGTGTTCGACGACGAGGTGGCGCCAAACGCGGCCAGCGATAACGCCTCGGC
(SEQ ID NO:294)

BST:
CGCGGACGTCGAGTTTTTTGAGAGCGTTGTTAGGGACGACGCGGTGTTCGACGACGAGGTGGCGTTAAACGCGGTTAGCGATAACGTTTCGGT
(SEQ ID NO:295)
AIM1_FP         TTGAGAGCGTTGTTAGGGACGAC (SEQ ID NO:296)
AIM1_RP         CGCGTTTAACGCCACCTC (SEQ ID NO:297)
AIM1_Pb_A5      AGGCCACGGACG CGTCGTCGAACACCG/3C6/(SEQ ID NO:298)
```

```
AKR7A3
>hg19_dna range=chr1:19615293-19615389 5'pad=0 3'pad=0 strand=+
GAGACGGGCTCGGGCCCCGCCCACCGGCGGGTGCAGCTGAGGGCGCGGCCGAAGGTGCCCGACGCCGCCCACGAGCTCGACTCCACGCTCGGCT
ACT (SEQ ID NO:299)

BST:
GAGACGGGTTCGGGTTTCGTTTATCGGCGGGTGTAGTTGAGGGCGCGGTCGAAGGTGTTCGACGTCGTTTACGAGTTCGATTTTACGTTCGGTT

ATT (SEQ ID NO:300)

AKR7A3_FP       CGGGTTTCGTTTATCGGCGG (SEQ ID NO:301)

AKR7A3_RP       AACGTAAAATCGAACTCGTAAACGAC (SEQ ID NO:302)

AKR7A3_Pb_A1    CGCGCCGAGG CGTCGAACACCTTCGAC/3C6/ (SEQ ID NO:303)
```

```
C17orf107
>hg19_dna range=chr17:4802690-4802828 5'pad=0 3'pad=0 strand=+
GGCGGGGCTTAGGGGACGAGGTTAGTACGAAGCCCCACCCCGACCCGGGCTGCACCGCCCCCTCCGCGCTTACGTGGCGCAGCCGCGGGGACAT
GGCGTGGGTGGTGGGCGTCCGCTGGGACACGTTGAGCACGATGAC (SEQ ID NO:304)

BST:
GGCGGGGTTTAGGGGACGAGGTTAGTACGAAGTTTTATTTCGATTCGGGTTGTATCGTTTTTTTCGCGTTTACGTGGCGTAGTCGCGGGGATAT
GGCGTGGGTGGTGGGCGTTCGTTGGGATACGTTGAGTACGATGAT (SEQ ID NO:305)

C17orf107_FP        CGAAGTTTTATTTCGATTCGGGTTGTATCG (SEQ ID NO:306)
C17orf107_RP        CCACGCCATATCCCCGC (SEQ ID NO:307)
C17orf107_Pb_A5     AGGCCACGGACG CGACTACGCCACGTAAA/3C6/ (SEQ ID NO:308)
```

```
DIDO1
>hg19_dna range=chr20:61560628-61560728 5'pad=0 3'pad=0 strand=+
GCCCAGGCCACCGGGCAGCGTCCAGGTCTCGGCCTTTGGGAGGGGAGCAGCGGGGGAGGGGCACGGGGAGGGGCGAGGGCGGGGCGCGCCTGGG
CCTCGGC (SEQ ID NO:309)

BST:
GCCGAGGTTATCGGGTAGCGTTTAGGTTTCGGTTTTTGGGAGGGGAGTAGCGGGGGAGGGGTACGGGGAGGGGCGAGGGCGGGGCGCGTTTGGG
TTTCGGT (SEQ ID NO:310)

DIDO1_FP        AGGTTATCGGGTAGCGTTTAGG (SEQ ID NO:311)
DIDO1_RP        CGTACCCCTCCCCCGCTAC (SEQ ID NO:312)
DIDO1_Pb_A1     CGCGCCGAGG GTTTCGGTTTTTGGGAGG/3C6/ (SEQ ID NO:313)
```

```
EMX2OS
>hg19_dna range=chr10:119294950-119295039 5'pad=0 3'pad=0 strand=+
CGCTGTGAGTCGCCCACGCGAGCGACGTGGGGATACGGGGCGCACGGAGTCTCAGCTGCCGCCACGCAGCGCTTGCCCTGCCCGAGCTTC
(SEQ ID NO:314)

BST:
CGTTGTGAGTCGTTTACGCGAGCGACGTGGGGATACGGGGCGTACGGAGTTTTAGTTGTCGTTACGTAGCGTTTGTTTTGTTCGAGTTTT
(SEQ ID NO:315)

EMX2OS_FP       GTCGTTTACGCGAGCGACG (SEQ ID NO:316)
EMX2OS_RP       CTCGAACAAAACAAACGCTACGTAAC (SEQ ID NO:317)
EMX2OS_Pb_A5    AGGCCACGGACG CGACAACTAAAACTCCGTACG/3C6/ (SEQ ID NO:318)
```

FIG. 2 (cont'd)

```
FKBP11
>hg19_dna range=chr12:49319059-49319168 5'pad=0 3'pad=0 strand=+
TGAGGGTCGGGACTATCTCCTCACCAGGGTCTCCACTTGGAGGGTCCGGACGGGACTTTCGGTTTCGAGCCCAGCCTCAGCCCGGCACACCGCC
GCACTGAGCAGCAGCA (SEQ ID NO:319)

BST:
TGAGGGTCGGGATTATTTTTTTATTAGGGTTTTTATTTGGAGGGTTCGGACGGGATTTTCGGTTTCGAGTTTAGTTTTAGTTCGGTATATCGTC
GTATTGAGTAGTAGTA (SEQ ID NO:320)

FKBP11_FP       GGTTTTTATTTGGAGGGTTCGGAC (SEQ ID NO:321)
FKBP11_RP       ACTACTCAATACGACGATATACCGAAC (SEQ ID NO:322)
FKBP11_Pb_A1    CGCGCCGAGG CGGGATTTTCGGTTTCGA/3C6/ (SEQ ID NO:323)
```

```
GDF7
>hg19_dna range=chr2:20866007-20866135 5'pad=0 3'pad=0 strand=+
GCCATCCCGGGGCTCTGCGCCGTCCGCTCTCCCGGCTCCTGGCCGCTCACGCACACAGCCGGTAGCTGGTTTTCGTTAGCCGCTGCCCTCGCCC
AGAAGGCGGGTGGAAGGTCGCCAGTTGGACGCACA (SEQ ID NO:324)

BST:
GTTATTTCGGGGTTTTGCGTCGTTCGTTTTTTCGGTTTTTGGTCGTTTACGTATATAGTCGGTAGTTGGTTTTCGTTAGTCGTTGTTTTCGTTT
AGAAGGCGGGTGGAAGGTCGTTAGTTGGACGTATA (SEQ ID NO:325)

GDF7_FP         TCGTTCGTTTTTTCGGTTTTTGGTC (SEQ ID NO:326)
GDF7_RP         CCTTCTAAACGAAAACAACGACTAACGAAA (SEQ ID NO:327)
GDF7_Pb_A5      AGGCCACGGACG CGTTTACGTATATAGTCGGTAGT/3C6/ (SEQ ID NO:328)
```

```
JSRP1
>hg19_dna range=chr19:2253227-2253345 5'pad=0 3'pad=0 strand=-
GTAGCGTTCTGCCGCCTTTCCCCTGCGCCCTCTCTGGGGACCGCTCAGCTCGTGAGCGCCCCCCGGGGGCACTCCTGCGACCCCTCCCTTGCTA
GGGGCCTCCTACAGCCCGTGGTCGG (SEQ ID NO:329)

GTAGCGTTTTGTCGTTTTTTTTTTGCGTTTTTTTTGGGGATCGTTTAGTTCGTGAGCGTTTTTCGGGGGTATTTTTGCGATTTTTTTTTTGTTA
GGGGTTTTTTATAGTTCGTGGTCGG (SEQ ID NO:330)

JSRP1_FP        TAGCGTTTTGTCGTTTTTTTTTTGCGT (SEQ ID NO:331)
JSRP1_RP        CGCAAAAATACCCCCGAAAAAC (SEQ ID NO:332)
JSRP1_Pb_A1     CGCGCCGAGG CGCTCACGAACTAAACGATCC/3C6/ (SEQ ID NO:333)
```

```
LHFPL2
>hg19_dna range=chr5:77806193-77806301 5'pad=0 3'pad=0 strand=+
CGGACCCAGAGCACCGCCTGCGGCCTCACCTAGGGGAGAGGGAGGGCGGTTAGCAGCGCCGCCAGGCCCCGCCCCGCCTTCCCGCCGCGCAGCG
ACACCGTCCAAGTCC (SEQ ID NO:334)

BST:
CGGATTTAGAGTATCGTTTGCGGTTTTATTTAGGGGAGAGGGAGGGCGGTTAGTAGCGTCGTTAGGTTTCGTTTCGTTTTTTCGTCGCGTAGCG
ATATCGTTTAAGTTT (SEQ ID NO:335)

LHFPL2_FP       GGAGGGCGGTTAGTAGCGT (SEQ ID NO:336)
LHFPL2_RP       ACGATATCGCTACGCGACGAAA (SEQ ID NO:337)
LHFPL2_Pb_A5    AGGCCACGGACG TCGTTAGGTTTCGTTTCGT/3C6/ (SEQ ID NO:338)
```

```
LOC100129726
>hg19_dna range=chr2:43452148-43452235 5'pad=0 3'pad=0 strand=+
CGACGGGAAGCCCGAGAAGCTGAGGCTGTGGTGCAACTTGGGCCGCGGCTCCCGCGGGAAGCCCAGGTGCAACGCATCGCGCGTGCCA
(SEQ ID NO:339)
BST:
CGACGGGAAGTTCGAGAAGTTGAGGTTGTGGTGTAATTTGGGTCGCGGTTTTCGCGGGAAGTTTAGGTGTAACGTATCGCGCGTGTTA
(SEQ ID NO:340)

LOC100129726_FP       GTTGTGGTGTAATTTGGGTCGC(SEQ ID NO:341)
LOC100129726_RP       ACACGCGCGATACGTTACAC (SEQ ID NO:342)
LOC100129726_Pb_A1    CGCGCCGAGG CGGTTTTCGCGGGA/3C6/(SEQ ID NO:343)
```

```
LRRC41
>hg19_dna range=chr1:46768830-46768913 5'pad=0 3'pad=0 strand=+
GCTCACCGCCCGCCCCGCACAGCTCGAACAGGGCGGGGGGAGCGTTGGGGCCCGAGGCCGAGCTCTTCGCTGGCGCCGCCTCCCG
(SEQ ID NO:344)
BST:
GTTTATCGTTCGTTCGTATAGTTCGAATAGGGCGGGGGGGAGCGTTGGGGTTCGAGGTCGAGTTTTTCGTTGGCGTCGTTTTTCG
(SEQ ID NO:345)
```

FIG. 2 (cont'd)

```
LRRC41_FP        CGTTCGTATAGTTCGAATAGGGCG (SEQ ID NO:346)
LRRC41_RP        CGACGCCAACGAAAAACTC (SEQ ID NO:347)
LRRC41_Pb_A5     AGGCCACGGACG CGACCTCGAACCCCAA/3C6/ (SEQ ID NO:348)
```

```
LRRC8D
>hg19_dna range=chr1:90308856-90308965 5'pad=0 3'pad=0 strand=+ repeatMasking=none
CGGCGGAGGAAGCGTGGAGTCCATTGATCTAGGTACTTGTGGGGAGGGGAGAACCCGAGCAGCAGCTGCAAACGGAAGGGCTGTGAGCGAGCGG
GCGGGCGGGTGGCTGG (SEQ ID NO:349)

BST:
CGGCGGAGGAAGCGTGGAGTTTATTGATTTAGGTATTTGTGGGGAGGGGAGAATTCGAGTAGTAGTTGTAAACGGAAGGGTTGTGAGCGAGCGG
GCGGGCGGGTGGTTGG (SEQ ID NO:350)

LRRC8D_FP        GGAGAATTCGAGTAGTAGTTGTAAACGGA (SEQ ID NO:351)
LRRC8D_RP        CAACCACCCGCCCGCC (SEQ ID NO:352)
LRRC8D_Pb_A1     CGCGCCGAGG CCGCTCGCTCACAA/3C6/ (SEQ ID NO:353)
```

```
MAX.chr10.2262
>hg19_dna range=chr10:22624470-22624553 5'pad=0 3'pad=0 strand=+
CTTGTCTACGTGGCATCGTCATTTCTTAACCGCGGTTTTACGAAATGCAAATTTCCCCCTGGCCTTCCTCCTCCGCGGCCGTCGACC
(SEQ ID NO:354)
BST:
TTTGTTTACGTGGTATCGTTATTTTTTAATCGCGGTTTTACGAAATGTAAATTTTTTTTTGGTTTTTTTTTTTCGCGGTCGTCGATT
(SEQ ID NO:355)
MAX.chr10.2262_FP     TGTTTACGTGGTATCGTTATTTTTTAATCGC(SEQ ID NO:356)
MAX.chr10.2262_RP     CGACGACCGCGAAAAAAAAAAACC(SEQ ID NO:357)
MAX.chr10.2262_Pb_A5  AGGCCACGGACG CGGTTTTACGAAATGTAAATTT/3C6/ (SEQ ID NO:358)
```

```
MAX.chr14.1030
>hg19_dna range=chr14:103021654-103021725 5'pad=0 3'pad=0 strand=+
CCGCCCCGTGGGGAACAGCAGGACGGCGCCGAGGCCGTTTCGCTTTCCTCCGCGCCCATTTGCCGGGAGGGG (SEQ ID NO:359)

BST:
TCGTTTCGTGGGGAATAGTAGGACGGCGTCGAGGTCGTTTCGTTTTTTTTCGCGTTTATTTGTCGGGAGGGG (SEQ ID NO:360)

MAX.chr14.1030_FP     TCGTGGGGAATAGTAGGACGGC (SEQ ID NO:361)
MAX.chr14.1030_RP     CCTCCCGACAAATAAACGCGA (SEQ ID NO:362)
MAX.chr14.1030_Pb_A1  CGCGCCGAGG CGTCGAGGTCGTTTCG/3C6/ (SEQ ID NO:363)
```

```
MAX.chr7.1046
>hg19_dna range=chr7:104624356-104624513 5'pad=0 3'pad=0 strand=+
CGGCCTAGGACGCGCCCTGCGTGGAGGCAGGCCCGCGCGGCGGAAGTGCGTTTCTGGGGCTCCTCCTGAAGAATGCGGAGGAGGAACTGAGCTG
GCGCGCGGGCCAGCTGTCCTCTCTTCTGATCCCGAAG (SEQ ID NO:364)

BST:
CGGTTTAGGACGCGTTTTGCGTGGAGGTAGGTTCGCGCGGCGGAAGTGCGTTTTTGGGGTTTTTTTTGAAGAATGCGGAGGAGGAATTGAGTTG
GCGCGCGGGTTAGTTGTTTTTTTTTTTTGATTTCGAAG (SEQ ID NO:365)

MAX.chr7.1046_FP     GGAGGTAGGTTCGCGCGG (SEQ ID NO:366)
MAX.chr7.1046_RP     CCAACTCAATTCCTCCTCCGC (SEQ ID NO:367)
MAX.chr7.1046_Pb_A5  AGGCCACGGACG GCGGAAGTGCGTT/3C6/ (SEQ ID NO:368)
```

```
MAX.chr7.1046B
>hg19_dna range=chr7:104624386-104624529 5'pad=0 3'pad=0 strand=+
GCCCGCGCGGCGGAAGTGCGTTTCTGGGGCTCCTCCTGAAGAATGCGGAGGAGGAACTGAGCTGGCGCGCGGGCCAGCTGTCCTCTCTTCTGAT
CCCGAAGACAGGATCGGATTATGGGTTGTTACCGGCTTGTGCGGCCCTGG (SEQ ID NO:369)

BST:
GTTCGCGCGGCGGAAGTGCGTTTTTGGGGTTTTTTTTGAAGAATGCGGAGGAGGAATTGAGTTGGCGCGCGGGTTAGTTGTTTTTTTTTTTTGAT
TTCGAAGATAGGATCGGATTATGGGTTGTTATCGGTTTGTGCGGTTTTGG (SEQ ID NO:370)

MAX.chr7.1046B_FP     GAGGAGGAATTGAGTTGGCGC (SEQ ID NO:371)
MAX.chr7.1046B_RP     CAACCCATAATCCGATCCTATCTTCGA (SEQ ID NO:372)
MAX.chr7.1046B_Pb_A1  CGCGCCGAGG CGCGGGTTAGTTGTT/3C6/ (SEQ ID NO:373)
```

FIG. 2 (cont'd)

```
MDFI
>hg19_dna range=chr6:41606379-41606439 5'pad=0 3'pad=0 strand=+
CGGCTCGCACGAGTGAGTGGACGTGGGAGGCGCGCATCTGCGGGGGAATCGCCCCTTGCCC (SEQ ID NO:374)

BST:
CGGTTCGTACGAGTGAGTGGACGTGGGAGGCGCGTATTTGCGGGGGAATCGTTTTTTGTTT (SEQ ID NO:375)

MDFI_FP          TTCGTACGAGTGAGTGGACG (SEQ ID NO:376)
MDFI_RP          CAAAAAACGATTCCCCCGCAAA (SEQ ID NO:377)
MDFI_Pb_A5       AGGCCACGGACG ATACGCGCCTCCCA/3C6/ (SEQ ID NO:378)
```

```
OBSCN
>hg19_dna range=chr1:228463593-228463689 5'pad=0 3'pad=0 strand=+
CGGGAAAGAACGTGGAGATCCACGCCGAGGGCGCCCGCCACCGCCTGGTTCTGCACAACGTAGGTTTTGCCGACCGTGGCTTCTTTGGCTGCGA
GAC (SEQ ID NO:379)

BST:
CGGGAAAGAACGTGGAGATTTACGTCGAGGGCGTTCGTTATCGTTTGGTTTTGTATAACGTAGGTTTTGTCGATCGTGGTTTTTTTGGTTGCGA
GAT (SEQ ID NO:380)

OBSCN_FP         TGGAGATTTACGTCGAGGGC (SEQ ID NO:381)
OBSCN_RP         CCACGATCGACAAAACCTACGT(SEQ ID NO:382)
OBSCN_Pb_A1      CGCGCCGAGG CGTTCGTTATCGTTTGGTTT/3C6/ (SEQ ID NO:383)
```

```
RHBDL1
>hg19_dna range=chr16:725588-725658 5'pad=0 3'pad=0 strand=+
GCGTGCAGGGTGCGCGCGTGTCTTGGCCGCGCGTGGCGGCGTGTGCGGCAGGGGCGGGCAGGCGGGCGACTCG (SEQ ID NO:384)

BST:

GCGTGTAGGGTGCGCGCGTGTGTTTTGGTCGCGCGTGGCGGCGTGTGCGGTAGGGGCGGGTAGGCGGGCGATTCG (SEQ ID NO:385)

RHBDL1_FP_V2    GCGCGTGTTTTGGTCGC (SEQ ID NO:386)
RHBDL1_RP_V2    TCGTCCGCCTACCCGCCC (SEQ ID NO:387)

RHBDL1_Pb_A5_V2 AGGCCACGGACG CCTACCGCACACGC/3C6/ (SEQ ID NO:388)
```

```
SEPT9
>hg19_dna range=chr17:75447656-75447829 5'pad=0 3'pad=0 strand=+
GGGGGCTCTCAGGTGGCGCGGCCGCCGAGGCGGACCCTGATGGCCATGGTGGCCGTGCCGGGAGCCACGCTGTCCCTGGGCCCCGGCCCGAGGCC
GGCAGGACCGAGCGGGGTCCCCAGGAGAGGGGTGGCGGGGAGCTCGATCTCCACGCGGGGACCAGATTTTCGGCCTCAAA (SEQ ID
NO:389)

BST:
GGGGGTTTTTAGGTGGCGCGGTCGCGAGGCGGATTTTGATGGTTATGGTGGCCGTGTCGGGAGTTACGTTGTTTTTGGGTTTCGGTTCGAGGTC
GGTAGGATCGAGCGGGGTTTTTAGGAGAGGGGTGGCGGGGAGTTCGATTTTTACGCGGGGATTAGATTTTCGGTTTTAAA (SEQ ID
NO:390)

SEPT9_FP         GGAGTTACGTTGTTTTTGGGTTTCG (SEQ ID NO:391)
SEPT9_RP         CTCTCCTAAAAACCCCGCTC (SEQ ID NO:392)
SEPT9_Pb_A1      CGCGCCGAGG CGATCCTACCGACCTCGA/3C6/ (SEQ ID NO:393)
```

```
SFMBT2_745
>hg19_dna range=chr10:7451008-7451110 5'pad=0 3'pad=0 strand=-
GAGGTGGGGGACCGGGACCGAAGCTTGGAGAAGACCAAAGTGGTGGTGGTGGTGGTGGGGTGGGGCAGAAGGGCGGGAGCGCGCGGCTCTGGGA
GACAAGCAC (SEQ ID NO:394)

BST:
GAGGTGGGGGATCGGGATCGAAGTTTGGAGAAGATTAAAGTGGTGGTGGTGGTGGTGGGGTGGGGTAGAAGGGCGGGAGCGCGCGGTTTTGGGA
GATAAGTAT (SEQ ID NO:395)

SFMBT2_745_FP       GGATCGGGATCGAAGTTTGGAGAA(SEQ ID NO:396)
SFMBT2_745_RP       CTTATCTCCCAAAACCGCGC(SEQ ID NO:397)
SFMBT2_745_Pb_A5    AGGCCACGGACG CGCTCCCGCCCTTCT/3C6/(SEQ ID NO:398)
```

FIG. 2 (cont'd)

SPDYA
>hg19_dna range=chr2:29033347-29033484 5'pad=0 3'pad=0 strand=+
AACCACGCTGTGCCCGCGTGTGCCGGGCGGGGAGGGGAGCCGCAGCCCCAGCCCCGGGGGCCTGGTTGTCTAATCGAAGGGAAGTAAACGGCC
CCAACGCAAGCCTGACTGCGAGACGTGCCCAAGGGAGGTAGGTC (SEQ ID NO:399)

BST:
AATTACGTTGTGTTCGCGTGTGTCGGGCGGGGAGGGGAGGTCGTAGTTTTAGTTTCGGGGGTTTGGTTGTTTAATCGAAGGGAAGTAAACGGTT
TTAACGTAAGTTTGATTGCGAGACGTGTTTAAGGGAGGTAGGTT (SEQ ID NO:400)

SPDYA_FP        TTGGTTGTTTAATCGAAGGGAAGTAAAC (SEQ ID NO:401)
SPDYA_RP        CTACCTCCCTTAAACACGTCTCG (SEQ ID NO:402)
SPDYA_Pb_A1     CGCGCCGAGG CGGTTTTAACGTAAGTTTGATTG/3C6/ (SEQ ID NO:403)

---

ST3GAL2
>hg19_dna range=chr16:70415003-70415106 5'pad=0 3'pad=0 strand=+
CGCAGGAAGCCCTGGGGGCGCAGCCATCCCACAGCGCGGCCGAGGTGGGACTGGGGGTCCCGCAGCGACCGCTTTTCTTTGGTGGGTCTGCACG
CACCTATCCG (SEQ ID NO:404)

BST:
CGTAGGAAGTTTTGGGGGCGTAGTTATTTTATAGCGCGGTCGAGGTGGGATTGGGGGTTTCGTAGCGATCGTTTTTTTTTGGTGGGTTTGTACG
TATTTATTCG (SEQ ID NO:405)

ST3GAL2_FP      GGGCGTAGTTATTTTATAGCGC (SEQ ID NO:406)
ST3GAL2_RP      CACCAAAAAAAAACGATCGCTACGAAA (SEQ ID NO:407)
ST3GAL2_Pb_A5   AGGCCACGGACG CGGTCGAGGTGGGA/3C6/ (SEQ ID NO:408)

---

VILL
>hg19_dna range=chr3:38035645-38035743 5'pad=0 3'pad=0 strand=- repeatMasking=none
CGGGTGTTTGTGTATATGTGTTGCGGGGAAGACGGAGGTGCGGGTGGAGAAGGGGAGGATGTACCAAGGGCCATGGGGAGACGCTAGGCAGGGG
CTTCC (SEQ ID NO:409)

CGGGTGTTTGTGTATATGTGTTGCGGGGAAGACGGAGGTGCGGGTGGAGAAGGGGAGGATGTATTAAGGGTTATGGGGAGACGTTAGGTAGGGG
TTTTT (SEQ ID NO:410)

VILL_FP         CGGGGAAGACGGAGGTG (SEQ ID NO:411)
VILL_RP         AAACCCCTACCTAACGTCTCCC (SEQ ID NO:412)
VILL_Pb_A1      CGCGCCGAGG GCGGGTGGAGAAGG/3C6/ (SEQ ID NO:413)
VILL_Pb_A5      AGGCCACGGACG GCGGGTGGAGAAGG/3C6/ (SEQ ID NO:414)

---

ZNF323
>hg19_dna range=chr6:28303870-28303974 5'pad=0 3'pad=0 strand=+
CGGCAAGCTACGGAACAGGTGGCGGGGCTGCAGCACCCCAATGACCGATCAACCGCAAAGGCCGGAAATGCGTCAGCCGTTCTGAGCCCACTGG
CTGAAGCCAGG (SEQ ID NO:415)

BST:
CGGTAAGTTACGGAATAGGTGGCGGGGTTGTAGTATTTTAATGATCGATTAATCGTAAAGGTCGGAAATGCGTTAGTCGTTTTGAGTTTATTGG
TTGAAGTTAGG (SEQ ID NO:416)

ZNF323_FP       CGGGGTTGTAGTATTTTAATGATCGA (SEQ ID NO:417)
ZNF323_RP       CTTCAACCAATAAACTCAAAACGACTAACG (SEQ ID NO:418)
ZNF323_Pb_A5    AGGCCACGGACG GCATTTCCGACCTTTACGA/3C6/ (SEQ ID NO:419)

---

SLC13A5
>hg19_dna range=chr17:6616765-6616852 5'pad=0 3'pad=0 strand=+
CCCCGCACGGGGGCGCCTCCCCGCGGCCCTGGGGCGGGGCCACCCCTCGGGGTCTGTGGGACGCGCCTGCCCCCAATTCTGCCACCCG (SEQ
ID NO:420)

BST:
TTTCGTACGGGGGCGTTTTTTCGCGGTTTTGGGGCGGGGTTATTTTTCGGGGTTTGTGGGACGCGTTTGTTTTTAATTTTGTTATTCG (SEQ
ID NO:421)

SLC13A5_FP      GGCGTTTTTTCGCGGTTTTG (SEQ ID NO:422)
SLC13A5_RP      GCGTCCCACAAACCCCG (SEQ ID NO:423)
SLC13A5_Pb_A1   CGCGCCGAGG GAAAAATAACCCCGCCC/3C6/ (SEQ ID NO:424)

FIG. 2 (cont'd)

```
ZMIZ1
>hg19_dna range=chr10:81002927-81003006 5'pad=0 3'pad=0 strand=+
GCGGGCACACGCAGGGTGGGTGGTCACGCCCGCAGGGTCCGCGAGCGCGGCGCAGAGCGCGGGCCGTGGGAAGTTTCTCC (SEQ ID
NO:425)

BST:
GCGGGTATACGTAGGGTGGGTGGTTACGTTCGTAGGGTTCGCGAGCGCGGCGTAGAGCGCGGGTCGTGGGAAGTTTTTTT (SEQ ID
NO:426)

ZMIZ1_FP        CGTAGGGTGGGTGGTTACGTTC (SEQ ID NO:427)
ZMIZ1_RP        AACTTCCCACGACCCG (SEQ ID NO:428)
ZMIZ1_Pb_A5     AGGCCACGGACG CGTAGGGTTCGCGAG/3C6/ (SEQ ID NO:429)
```

```
MAX.chr8.1451
>hg19_dna range=chr8:145103900-145103993 5'pad=0 3'pad=0 strand=+
GTGCCACGCGGCCTTCACCCCTGTGACTCCCCGCAGCTCGCGCGGATGCACCGACGAGTCAGCTTGTCCTCTGGAAGCCAATGAGTCTCCCCGG
(SEQ ID NO:430)

BST:
GTGTTACGCGGTTTTTATTTTTGTGATTTTTCGTAGTTCGCGCGGATGTATCGACGAGTTAGTTTGTTTTTTGGAAGTTAATGAGTTTTTTCGG
(SEQ ID NO:431)

MAX.chr8.1451_FP        GTTACGCGGTTTTTATTTTTGTGATTTTTCG (SEQ ID NO:432)
MAX.chr8.1451_RP        CTCATTAACTTCCAAAAAACAAACTAACTCGTC (SEQ ID NO:433)
MAX.chr8.1451_Pb_A1     CGCGCCGAGG CGATACATCCGCGCG/3C6/ (SEQ ID NO:434)
```

```
C8orf73
>hg19_dna range=chr8:144650834-144650919 5'pad=0 3'pad=0 strand=+
CGGCGCACCAGAGTCCCAAGGAGCCCGACGGCCGAGGCGCGGATTGAGTCCCGTGTCTGCGTGGGAGGGCGCAGTCAGGGCAGGCG
(SEQ ID NO:435)
BST:
CGGCGTATTAGAGTTTTAAGGAGTTCGACGGTCGAGGCGCGGATTGAGTTTCGTGTTTGCGTGGGAGGGCGTAGTTAGGGTAGGCG
(SEQ ID NO:436)
C8orf73_FP      GAGTTCGACGGTCGAGGCG (SEQ ID NO:437)
C8orf73_RP      ACTACGCCCTCCCACGC (SEQ ID NO:438)
C8orf73_Pb_A5   AGGCCACGGACG GCGGATTGAGTTTCGTG/3C6/ (SEQ ID NO:439)
```

```
KBTBD11
>hg19_dna range=chr8:1949507-1949586 5'pad=0 3'pad=0 strand=+
CGCCGCAGTCCCTCGCCTCAGCGGCGGAAGGCGCGGCCACCTCCCCGCCCTCCAGCGGTGGCCCGCGGGTGGTGGAGCGG
(SEQ ID NO:440)
BST:
CGTCGTAGTTTTTCGTTTTAGCGGCGGAAGGCGCGGTTATTTTTTCGTTTTTTTAGCGGTGGTTCGCGGGTGGTGGAGCGG
(SEQ ID NO:441)
KBTBD11_FP      TCGTTTTAGCGGCGGAAGG (SEQ ID NO:442)
KBTBD11_RP      CCCGCGAACCACCGC (SEQ ID NO:443)
KBTBD11_Pb_A5   AGGCCACGGACG GCGCGGTTATTTTTTCGT/3C6/ (SEQ ID NO:444)
```

```
LOC100192379
>hg19_dna range=chr4:122686300-122686377 5'pad=0 3'pad=0 strand=+
GCGGGCTGCAGCTGGAGGGCGAGCGCGCCGCCCGCACACCCACCTCCCGCACTCCCGCCCCTCGCGAGGGCGTCCCGC
(SEQ ID NO:445)
BST
GCGGGTTGTAGTTGGAGGGCGAGCGCGTCGTTCGTATATTTATTTTTCGTATTTTTCGTTTTTCGCGAGGGCGTTTCGT
(SEQ ID NO:446)
LOC100192379_FP         GGTTGTAGTTGGAGGGCGAG (SEQ ID NO:447)
LOC100192379_RP_v2      CGAAACGCCCTCGCGA (SEQ ID NO:448)
LOC100192379_Pb_A1      CGCGCCGAGG GCGCGTCGTTCGTATATTT/3C6/ (SEQ ID NO:449)
```

```
TRIM71
>hg19_dna range=chr3:32859592-32859712 5'pad=0 3'pad=0 strand=+
CCGATTTCCAGATCTGCTTGCTGTGCAAGGAGATGTGCGGCTCGCCGGCGCCGCTCTCCTCCAACTCGTCCGCGTCGTCGTCCTCCTCGCAGAC
GTCCACGTCGTCGGGGGGCGGCGGCGG (SEQ ID NO:450)

BST:
TCGATTTTTAGATTTGTTTGTTGTGTAAGGAGATGTGCGGTTCGTCGGCGTCGTTTTTTTTTTAATTCGTTCGCGTCGTCGTTTTTTTCGTAGAC
GTTTACGTCGTCGGGGGGCGGCGGCGG (SEQ ID NO:451)

TRIM71_FP       GTTGTGTAAGGAGATGTGCGGTTC (SEQ ID NO:452)
TRIM71_RP_v3    AAACGACGACGCGAACGAA (SEQ ID NO:453)
TRIM71_Pb_A5    AGGCCACGGACG CGTCGGCGTCGTTTT/3C6/ (SEQ ID NO:454)
```

FIG. 2 (cont'd)

```
LOC440925
>hg19_dna range=chr2:171570323-171570444 5'pad=0 3'pad=0 strand=+
GGCCGAGCTCCGGCGGCCACTCCGCAGTGCGCTCTCGCGAGCCGGGGCCGCGAGGCCTCCAACGCGGTTCCGCACCCCTAATGCCCCAGGGCGG
TGAGCACCCCGCGGTTCCCCGCCCGCCT (SEQ ID NO:455)

BST:
GGTCGAGTTTCGGCGGTTATTTCGTAGTGCGTTTTCGCGAGTCGGGGTCGCGAGGTTTTTAACGCGGTTTCGTATTTTTAATGTTTTAGGGCGG
TGAGTATTTCGCGGTTTTTCGTTCGTTT (SEQ ID NO:456)

LOC440925_FP         CGTAGTGCGTTTTCGCGAGTC (SEQ ID NO:457)
LOC440925_RP         CGCCCTAAAACATTAAAAATACGAAACCG (SEQ ID NO:458)
LOC440925_Pb_A1      CGCGCCGAGG GCGTTAAAAACCTCGCG/3C6/ (SEQ ID NO:459)
```

---

```
ARL5C
>hg19_dna range=chr17:37321564-37321723 5'pad=0 3'pad=0 strand=+
CGGTGGAAAAGACAGCTGAGCCCCCACCTCCCTTCACATTCCAGAAAAGTGTCTGAAAGGCCCGGGGCGCTTCGGGGCTTGCCAAGAGACGGTG
TTTAGAGAAAGAGCATAACGCGAAGTCACAATCGCAGGAAACTCGCAGCAGCCCCCCATCCCCGCC (SEQ ID NO:460)

BST:
CGGTGGAAAAGATAGTTGAGTTTTTATTTTTTTTTATATTTTAGAAAAGTGTTTGAAAGGTTCGGGGCGTTTCGGGGTTTGTTAAGAGACGGTG
TTTAGAGAAAGAGTATAACGCGAAGTTATAATCGTAGGAAATTCGTAGTAGTTTTTTATTTTCGTT (SEQ ID NO:461)

ARL5C_FP         GTTTCGGGGTTTGTTAAGAGACG (SEQ ID NO:462)
ARL5C_RP         ACTACTACGAATTTCCTACGATTATAACTTCG (SEQ ID NO:463)
ARL5C_Pb_A1      CGCGCCGAGG GCGTTATACTCTTTCTCTAAACAC/3C6/ (SEQ ID NO:464)
```

---

```
STX16_57224
>hg19_dna range=chr20:57224681-57224845 5'pad=0 3'pad=0 strand=+
CTGCAGCCTCCAGCCCGGCCCGCGCGGCGACCCAGTCCCCTGTCGCCCGAATCTTCCACCGCTGCGAAGCGTCCCCGGGCGAGCGCCCTGCTCT
CCGCGCTGCGCGGAAGCCAGAGCCGGTCCTCACAGTGAACTCGCCCAGCCCTGCTCGCGGCTCTCTCGATT (SEQ ID NO:465)

BST:
TTGTAGTTTTTAGTTCGGTTCGCGCGGCGATTTAGTTTTTTGTCGTTCGAATTTTTATCGTTGCGAAGCGTTTTCGGGCGAGCGTTTTGTTTT
TCGCGTTGCGCGGAAGTTAGAGTCGGTTTTTATAGTGAATTCGTTTAGTTTTGTTCGCGGTTTTTTCGATT (SEQ ID NO:466)

STX16_57224_FP       AGTTTTTAGTTCGGTTCGCGC (SEQ ID NO:467)
STX16_57224_RP       CCCGAAAACGCTTCGCAACG (SEQ ID NO:468)
STX16_57224_Pb_A5    AGGCCACGGACG CGGCCGATTTAGTTTTTTGTCG/3C6/ (SEQ ID NO:469)
```

---

```
ITPKA
>hg19_dna range=chr15:41787637-41787780 5'pad=0 3'pad=0 strand=+
CGCACAATCGGCTGGGACAAGGCAGGGAAGCTGTGGCGACCTGCAGGGGTTCACAAGCCCGGAGGCCGATGGGGTTTGTCAGTGACACCAGAGG
GGAAAAGCCTCACAGAGCAGGAACACCCCCCGCCGCCAGGTGCTGGGTGC (SEQ ID NO:470)

BST:
CGTATAATCGGTTGGGATAAGGTAGGGAAGTTGTGGCGATTTGTAGGGGTTTATAAGTTCGGAGGTCGATGGGGTTTGTTAGTGATATTAGAGG
GGAAAAGTTTTATAGAGTAGGAATATTTTTCGTCGTTAGGTGTTGGGTGT (SEQ ID NO:471)

ITPKA_FP         GATAAGGTAGGGAAGTTGTGGCG (SEQ ID NO:472)
ITPKA_RP         CCTCTAATATCACTAACAAACCCCATCG (SEQ ID NO:473)
ITPKA_Pb_A1      CGCGCCGAGG GACCTCCGAACTTATAAACCC/3C6/ (SEQ ID NO:474)
```

---

```
IRF4
>hg19_dna range=chr6:393188-393284 strand=+
CGGCATGAGCGCGGTGAGCTGCGGCAACGGGAAGCTCCGCCAGTGGCTGATCGACCAGATCGACAGCGGCAAGTACCCCGGGCTGGTGTGGGAG
AAC (SEQ ID NO:475)

BST:
CGGTATGAGCGCGGTGAGTTGCGGTAACGGGAAGTTTCGTTAGTGGTTGATCGATTAGATCGATAGCGGTAAGTATTTCGGGTTGGTGTGGGAG
AAT (SEQ ID NO:476)

IRF4_FP CGCGGTGAGTTGCGGTAAC (SEQ ID NO:477)
IRF4_RP CGAAATACTTACCGCTATCGATCTAATCGA (SEQ ID NO:478)
IRF4_Pb_A5 AGGCCACGGACG CGGGAAGTTTCGTTAGTGG/3C6/ (SEQ ID NO:479)
```

FIG. 2 (cont'd)

```
CNTN4
>hg19_dna range=chr3:2140464-2140527 strand=+
GGCAGCCCGAACTCCGGCGCGCCAGGTTTTTCCAGCCGCCGCGAGCGCCGGGAGGGAGGGCAGC (SEQ ID NO:480)

BST:
GGTAGTTCGAATTTCGGCGCGTTAGGTTTTTTTAGTCGTCGCGAGCGTCGGGAGGGAGGGTAGT (SEQ ID NO:481)

CNTN4_FP GGTAGTTCGAATTTCGGCGC (SEQ ID NO:482)
CNTN4_RP CTCCCTCCCGACGCTCG (SEQ ID NO:483)
CNTN4_Pb_A1 CGCGCCGAGG CGTTAGGTTTTTTTAGTCGTCG/3C6/ (SEQ ID NO:484)
```

```
GRIN2A
>hg19_dna range=chr16:10277158-10277320 strand=+
CGCAGTCCCTCGGCGGCGACGCGGAGCGCGGCCACCCGTTCCGAGAGCGCACGGCGGCAAATAAGGCCAGGATAGGTGGCTGGCTGGCGACGGG
GGCGCCTGCGGCGGCGCGCGCTGCTGTCCGTGGTGTTGGAACCACGCTCTCCGCCCGCTCCCGGGCGTC (SEQ ID NO:485)

BST:
CGTAGTTTTTCGGCGGCGACGCGGAGCGCGGTTATTCGTTTCGAGAGCGTACGGCGGTAAATAAGGTTAGGATAGGTGGTTGGTTGGCGACGGG
GGCGTTTGCGGCGGCGCGCGTTGTTGTTCGTGGTGTTGGAATTACGTTTTTCGTTCGTTTTCGGGCGTT (SEQ ID NO:486)

GRIN2A_FP GTAGTTTTTCGGCGGCGACG (SEQ ID NO:487)
GRIN2A_RP CCTTATTTACCGCCGTACGCT (SEQ ID NO:488)
GRIN2A_Pb_A5 AGGCCACGGACG TCTCGAAACGAATAACCGC/3C6/ (SEQ ID NO:489)
```

```
NOTCH3
>hg19_dna range=chr19:15306498-15306625 strand=-
CGCCCGGGGCGTCGGGAGGGGGCCCGCGCGGGTCGCGCCCTGCCTGGCGGTGGGACCAGCTATCCTCGGCGCCCAGCGCAGCGCGCCCCCTCCC
GACGCGCGGTCGGGGCCGCAGTGGTCGCCCTGCG (SEQ ID NO:490)

BST:
CGTTCGGGGCGTCGGGAGGGGGGTTCGCGCGGGTCGCGTTTTGTTTGGCGGTGGGATTAGTTATTTTCGGCGTTTAGCGTAGCGCGTTTTTTTTC
GACGCGCGGTCGGGGTCGTAGTGGTCGTTTTGCG (SEQ ID NO:491)

NOTCH3_FP GGTCGCGTTTTGTTTGGCG (SEQ ID NO:492)
NOTCH3_RP CGCGCGTCGAAAAAAAAACGCG (SEQ ID NO:493)
NOTCH3_Pb_A1 CGCGCCGAGG GCTACGCTAAACGCCG/3C6/ (SEQ ID NO:494)
```

```
PAX1
>hg19_dna range=chr20:21683741-21683893 strand=+
AGCTCGGGAACCCGCGATACCCGGCCGGGGGACGACAGGGGGCGACAAACTGTAAGGTTTTCCCTATGCCCGACCGTGCAGAAGGCTGCAGCGA
GGGCTGTGTGCTCCCGATCGCGCACAGCTGGCTGCGGGAAAGGGGCCAGGATTGAGACG (SEQ ID NO:495)

BST:
AGTTCGGGAATTCGCGATATTCGGTCGGGGGACGATAGGGGGCGATAAATTGTAAGGTTTTTTTTATGTTCGATCGTGTAGAAGGTTGTAGCGA
GGGTTGTGTGTTTCGATCGCGTATAGTTGGTTGCGGGAAAGGGGTTAGGATTGAGACG (SEQ ID NO:496)

PAX1_FP CGATCGTGTAGAAGGTTGTAGCG (SEQ ID NO:497)
PAX1_RP TTTCCCGCAACCAACTATACGCG (SEQ ID NO:498)
PAX1_Pb_A5 AGGCCACGGACG GATCGAAAACACACAACCC/3C6/ (SEQ ID NO:499)
```

```
ZNF521
>hg19_dna range=chr18:22929721-22929795 strand=+
GGGCCGCGCGGACCTCGGCGGGACCCAGCGGGCCCGGGCGGGCGCACCAGCCGCCCTTTGTCCTCCGCCTCCGGG (SEQ ID NO:500)
BST:
GGGTCGCGCGGATTTCGGCGGGATTTAGCGGGTTCGGGCGGGCGTATTAGTCGTTTTTTGTTTTTCGTTTTCGGG (SEQ ID NO:501)

ZNF521_FP CGGGATTTAGCGGGTTCGG (SEQ ID NO:502)
ZNF521_RP CCCGAAAACGAAAAACAAAAAACGAC (SEQ ID NO:503)
ZNF521_Pb_A1 CGCGCCGAGG GGCGGGCGTATTAGT/3C6/ (SEQ ID NO:504)
```

```
VSX1
>hg19_dna range=chr20:25065266-25065458 strand=+
GTCTGCAAGAGATAAAAAGCTAGCCCACGATCCACCCACAATCCTCGTGTCCCCGGGGTGCCCTCGCAGTTGCCAAACCTACGGGCCGCGTTTA
GGGGAAGCCTCCGCGTCCTGGCGGCCAAAAGAATGGGCTCCTTCCAGCTTCCCCCTACCGGATACCACCTGCAAATCTATTGCCAGAGGCGCAG
CTCCC (SEQ ID NO:505)
```

FIG. 2 (cont'd)

```
BST:
GTTTGTAAGAGATAAAAAGTTAGTTTACGATTTATTTATAATTTTCGTGTTTTCGGGGTGTTTTCGTAGTTGTTAAATTTACGGGTCGCGTTTA
GGGGAAGTTTTCGCGTTTTGGCGGTTAAAAGAATGGGTTTTTTTTAGTTTTTTTTTATCGGATATTATTTGTAAATTTATTGTTAGAGGCGTAG
(SEQ ID NO:506)
TTTTT

VSX1_FP TCGGGGTGTTTTCGTAGTTGTTAAATTTAC (SEQ ID NO:507)
VSX1_RP CATTCTTTTAACCGCCAAAACGCG (SEQ ID NO:508)
VSX1_Pb_A5 AGGCCACGGACG CGGGTCGCGTTTAGG/3C6/ (SEQ ID NO:509)
```

_____

```
CRHR2
>hg19_dna range=chr7:30721989-30722099 strand=+
GCGGGGTCCTGGCCCCCGCCAGCCCAGCCCCGATCTCCCGGGCAGCCTTTGGGCGCCACCTCCGGTCGCCCAGAGCTGTCAAGTGGGGACCTTC
CCGGAGAGGAGCCGCCG (SEQ ID NO:510)

BST:
GCGGGGTTTTGGTTTTCGTTAGTTTAGTTTCGATTTTTCGGGTAGTTTTTGGGCGTTATTTTCGGTCGTTTAGAGTTGTTAAGTGGGGATTTTT
TCGGAGAGGAGTCGTCG (SEQ ID NO:511)

CRHR2_FP GGGTTTTGGTTTTCGTTAGTTTAGTTTC (SEQ ID NO:512)
CRHR2_RP ACAACTCTAAACGACCGAAAATAACG (SEQ ID NO:513)
CRHR2_Pb_A5 AGGCCACGGACG CGATTTTTCGGGTAGTTTTTGG/3C6/ (SEQ ID NO:514)
```

_____

```
FAM19A5
>hg19_dna range=chr22:48885810-48885908 strand=+
CGGCGGTCGGAGCCCAGCCAGCGGCTTCCCGGCCGAGATGCGCGCTCAGGAGGCAGCCGCAGGTCGCGGAGGGCGGGCGGCGCTGCCGGGGTGT
CTGCG (SEQ ID NO:515)

BST:
CGGCGGTCGGAGTTTAGTTAGCGGTTTTTCGGTCGAGATGCGCGTTTAGGAGGTAGTCGTAGGTCGCGGAGGGCGGGCGGCGTTGTCGGGGTGT
TTGCG (SEQ ID NO:516)

FAM19A5_FP GCGGTCGGAGTTTAGTTAGCG (SEQ ID NO:517)
FAM19A5_RP ACCTACGACTACCTCCTAAACGCG (SEQ ID NO:518)
FAM19A5_Pb_A1 CGCGCCGAGG GGTTTTTCGGTCGAGATG/3C6/ (SEQ ID NO:519)
```

_____

```
ASCL1
>hg19_dna range=chr12:103352059-103352157 strand=+
GGCCAGCAGCCCCAGCCGCAGCCCCAGCAGCCCTTCCTGCCGCCCGCAGCCTGTTTCTTTGCCACGGCCGCAGCCGCGGCGGCCGCAGCCGCCG
CAGCG  (SEQ ID NO:520)

BST:
GGTTAGTAGTTTTAGTCGTAGTTTTAGTAGTTTTTTTTGTCGTTCGTAGTTTGTTTTTTTTGTTACGGTCGTAGTCGCGGCGGTCGTAGTCGTCG
TAGCG (SEQ ID NO:521)

ASCL1_FP GTCGTAGTTTTAGTAGTTTTTTTTGTCGTTCG (SEQ ID NO:522)
ASCL1_RP CGACCGCCGCGACTAC (SEQ ID NO:523)
ASCL1_Pb_A5 AGGCCACGGACG CGACCGTAACAAAAAAACAAAC/3C6/ (SEQ ID NO:524)
```

_____

```
GLT1D1
>hg19_dna range=chr12:129338254-129338322 strand=+
GGGACCCGGGGACGCGGGGCGCTCAGCCAGGCCCCCTCCAGCCGCGCCGGGGCCGTCCCGAGCCGCGCG (SEQ ID NO:525)

BST:
GGGATTCGGGGACGCGGGGCGTTTAGTTAGGTTTTTTTTAGTCGCGTCGGGGTCGTTTCGAGTCGCGCG (SEQ ID NO:526)

GLT1D1_FP GACGCGGGGCGTTTAGT (SEQ ID NO:527)
GLT1D1_RP CGACTCGAAACGACCCCGA (SEQ ID NO:528)
GLT1D1_Pb_A1 CGCGCCGAGG ACGCGACTAAAAAAAACCTAAC/3C6/ (SEQ ID NO:529)
```

_____

```
T
>hg19_dna range=chr6:166581961-166582112 strand=+
GGTGCACCTGTCCCCACACGTCCCTCGCCCACGGAGCCCCAGGCGGCGTTACGCACACCCAGGATCGTGGATCAGCCTGCCCCGGCGTCGGGTG
TCCCCGCGGCTCTCACCATCTGGAAAAGGAAGGTCCGCGCGCAGAGAGGGAAATGGAC (SEQ ID NO:530)

BST:
GGTGTATTTGTTTTTATACGTTTTTCGTTTACGGAGTTTTAGGCGGCGTTACGTATATTTAGGATCGTGGATTAGTTTGTTTCGGCGTCGGGTG
TTTTCGCGGTTTTTATTATTTGGAAAAGGAAGGTTCGCGCGTAGAGAGGGAAATGGAT (SEQ ID NO:531)
```

FIG. 2 (cont'd)

```
T_FP GGAGTTTTAGGCGGCGTTACG(SEQ ID NO:532)
T_RP ACCGCGAAAACACCCGAC (SEQ ID NO:533)
T_Pb_A5 AGGCCACGGACG CGCCGAAACAAACTAATCC/3C6/ (SEQ ID NO:534)
```

```
CAPN2
>hg19_dna range=chr1:223936903-223937040 strand=+
GGGCCCGCGCGGCCCCACGGTGGTCCAGTTTACACTCGGGCCCCGCACTCCTGAAGTTCCGCGCGGGAGGAGAAGGGCGTCCCTTTCGCAGCTC
GGGCGCCGGGTGCGCCGCGCTGCCACCTGGTGGCCGCAGTGGCC (SEQ ID NO:535)

BST:
GGGTTCGCGCGGTTTTACGGTGGTTTAGTTTATATTCGGGTTTCGTATTTTTGAAGTTTCGCGCGGGAGGAGAAGGGCGTTTTTTTCGTAGTTC
GGGCGTCGGGTGCGTCGCGTTGTTATTTGGTGGTCGTAGTGGTT (SEQ ID NO:536)

CAPN2_FP GTTCGCGCGGTTTTACGGT(SEQ ID NO:537)
CAPN2_RP CGCCCTTCTCCTCCCGC(SEQ ID NO:538)
CAPN2_Pb_A1 CGCGCCGAGG CGCGAAACTTCAAAAATACGA/3C6/ (SEQ ID NO:539)
```

_____

```
RYR2_F:
chr1:237205546-237205717 strand=+
TGCGGGGCTGCTTCCCCGCGTCCTCCGGGCCCGGGCCGCCCTCCTCCCGCACAGTGCGGAGCAGGGAGGCCCCGCGCCTCGACCACCCGCGCCC
GAGCGTCCGCGCCTCCTCCTCCGCTCTGCAGGCGGGGACCGCCCGGCGCTCGGCACCCGGCAGCGCGGCCCCCTCCAG (SEQ ID NO:540)

BST:
TGCGGGGTTGTTTTTTCGCGTTTTTCGGGTTCGGGTCGTTTTTTTTTTCGTATAGTGCGGAGTAGGGAGGTTTCGCGTTTCGATTATTCGCGTTC
GAGCGTTCGCGTTTTTTTTTTCGTTTTGTAGGCGGGGATCGTTCGGCGTTCGGTATTCGGTAGCGCGGTTTTTTTTTAG (SEQ ID NO:541)

RYR2_F_FP_v2   GGAGGTTTCGCGTTTCGATTA (SEQ ID NO:542)
RYR2_F_RP_v2   CGAACGATCCCCGCCTAC (SEQ ID NO:543)
RYR2_F_LQ_Pb_A5 AGGCCACGGACG ATTCGCGTTCGAGCG/3C6/ (SEQ ID NO:544)
```

_____

```
SIM2
>hg19_dna range=chr21:38119993-38120059 5'pad=0 3'pad=0 strand=-
GGGCCCAGCGCGGGCTCCTCGCGGTAGTGGCCGCAGCTCGGGAAGCTCGGGGGCGCGGTGTCCTCGC (SEQ ID NO:545)

BST:
GGGTTTAGCGCGGGTTTTTCGCGGTAGTGGTCGTAGTTCGGGAAGTTCGGGGGCGCGGTGTTTTCGT (SEQ ID NO:546)

SIM2_FP_v2 GGTTTAGCGCGGGTTTTTCG (SEQ ID NO:547)
SIM2_RP_v2 CCCCGAACTTCCCGAACT (SEQ ID NO:548)
SIM2_Pb_LQ_A5 AGGCCACGGACG GCGGTAGTGGTCGTAG/3C6/ (SEQ ID NO:549)
```

_____
___

```
TRH
>hg19_dna range=chr3:129693484-129693575 5'pad=0 3'pad=0 strand=+
GGCCGCGACCCCTCCCCGCTGACCTCACTCGAGCCGCCGCCTGGCGCAGATATAAGCGGCGGCCCATCTGAAGAGGGCTCGGCAGGCGCCCG
(SEQ ID NO:550)

BST:
GGTCGCGATTTTTTTTCGTTGATTTTATTCGAGTCGTCGTTTGGCGTAGATATAAGCGGCGGTTTATTTGAAGAGGGTTCGGTAGGCGTTCG
(SEQ ID NO:551)

TRH_FP TTTTCGTTGATTTTATTCGAGTCGTC (SEQ ID NO:552)
TRH_RP GAACCCTCTTCAAATAAACCGC (SEQ ID NO:553)
TRH_Pb_A5_63 AGGCCACGGACG CGTTTGGCGTAGATATAAGC/3C6/ (SEQ ID NO:554)
```

_____

```
JAM3
>hg19_dna range=chr11:133938908-133939011 strand=-
GAGCCGGAGTCGCGGTGGCCGCCTCAGCGCCATGTCGAGGGTTGCTGAGGGGCCAGCGGCAGCGCGGCGCGGCTTGTAGTCCCCGCGCGCATGC
GCCCAGCCTG (SEQ ID NO:555)

BST:
GAGTCGGAGTCGCGGTGGTCGTTTTAGCGTTATGTCGAGGGTTGTTGAGGGGTTAGCGGTAGCGCGGCGCGGTTTGTAGTTTTCGCGCGTATGC
GTTTAGTTTG (SEQ ID NO:556)

JAM3_FP TGGTCGTTTTAGCGTTATGTCG (SEQ ID NO:557)
JAM3_RP CGAAAACTACAAACCGCGC (SEQ ID NO:558)
JAM3_Pb_A5_LQ  AGGCCACGGACG CCGCGCTACCGCTA/3C6/ (SEQ ID NO:559)
```

FIG. 2 (cont'd)

```
JAM3_Pb_A1_LQ  CGCGCCGAGG CCGCGCTACCGCTA/3C6/  (SEQ ID NO:560)

_____
BARX1
>hg19_dna range=chr9:96721498-96721597 strand=-
GGCCCGGGGCCGCCTGGGCCCCTAGGGGCTGGACGTCAACCTGTTAGATAGAGGGCGTGGGACCCCCCGCAGGCGGCTGCTCGGACGACCGCAT
CCGGAG (SEQ ID NO:561)

BST:

GGTTCGGGGTCGTTTGGGTTTTTAGGGGTTGGACGTTAATTTGTTAGATAGAGGGCGTGGGATTTTTCGTAGGCGGTTGTTCGGACGATCGTAT

TCGGAG (SEQ ID NO:562)

BARX1_FP CGTTAATTTGTTAGATAGAGGGCG (SEQ ID NO:563)
BARX1_RP_universal TCCGAACAACCGCCTAC (SEQ ID NO:564)
BARX1_Pb_A5_63_v6 AGGCCACGGACG CGAAAAATCCCACGC/3C6/ (SEQ ID NO:565)

_____
ZNF671
>hg19_dna range=chr19:58238790-58238906 strand=+
CCGTGGGCGCGGACAGCTGCCGGGAGCGGCAGCCGTCTCGATCGGGGACGCAGGCACTTCCGTCCCTGCAGAGCATCAGACGCGTCTCGGGACA
CTGGGGACAACATCTCCTCCGCG (SEQ ID NO:566)

BST:
TCGTGGGCGCGGATAGTTGTCGGGAGCGGTAGGCGTTTCGATCGGGGACGTAGGTATTTTCGTTTTTGTAGAGTATTAGACGCGTTTCGGGATA
TTGGGGATAATATTTTTTTCGCG (SEQ ID NO:567)

ZNF671 FP  GTTGTCGGGAGCGGTAGG (SEQ ID NO:568)
ZNF671 RP  CCAATATCCCGAAACGCGTCT (SEQ ID NO:569)
ZNF671_Pb_A1_LQ CGCGCCGAGG GCGTTTCGATCGGGG/3C6/ (SEQ ID NO:570)
_____

MPZ_5554
>hg19_dna range=chr1:161275554-161276006 5'pad=0 3'pad=0 strand=- repeatMasking=none
TTAGCGGGCCGGGCGGGGGATCGGGGGTTAGGGGTGGAGTCCGCCAAAGGCCCAAAGGTGATGGTCATCGAGATGGAGCTACGAAAGGATGAGC
AGAGCCCGGAGCTCC (SEQ ID NO:571)

BST:
TTAGCGGGTCGGGCGGGGGATCGGGGGTTAGGGGTGGAGTTCGTTAAAGGTTTAAAGGTGATGGTTATCGAGATGGAGTTACGAAAGGATGAGT
AGAGTTCGGAGTTTT (SEQ ID NO:572)

MPZ_5554_FP        GGTTAGGGGTGGAGTTCGTTA (SEQ ID NO:573)
MPZ_5554_RP        ACTCCGAACTCTACTCATCCTTTC (SEQ ID NO:574)
MPZ_5554_Pb_A1_63  CGCGCCGAGG CGTAACTCCATCTCGATAACC/3C6/ (SEQ ID NO:575)
_____

CXCL12
>hg19_dna range=chr10:44881200-44881315 5'pad=0 3'pad=0 strand=+
AAGGCGCCGGCGGCTCTCAGTAAAAGCGAATGTAGCCTTTGTACTTCCGACCTCTCAATGGTGAAATGAGCTAATCACAGGCCCACCCCGCGGA
GTGGGACGGGAGATTCAATGAG (SEQ ID NO:576)

BST:
AAGGCGTCGGCGGTTTTTAGTAAAAGCGAATGTAGTTTTTGTATTTTCGATTTTTTAATGGTGAAATGAGTTAATTATAGGTTTATTTCGCGGA
GTGGGACGGGAGATTTAATGAG (SEQ ID NO:577)

CXCL12_FP TCGGCGGTTTTTAGTAAAAGCG (SEQ ID NO:578)
CXCL12_RP AAATCTCCCGTCCCACTCC (SEQ ID NO:579)
CXCL12_Pb_A1 CGCGCCGAGG CGCGAAATAAACCTATAATTAACTCA/3C6/ (SEQ ID NO:580)
_____

TSPYL5
>hg19_dna range=chr8:98290016-98290134 strand=+
GCCTTTGCCCCGGTTTTTGGCGCGGGAGGACTTTCGACCCCGACTTCGGCCGCTCATGGTGGCGGCGGAGGCAGCTTCAAAGACACGCTGTGAC
CCTGCGGCTCCTGACGCCAGCTCTC (SEQ ID NO:581)

BST:
GTTTTTGTTTCGGTTTTTGGCGCGGGAGGATTTTCGATTTCGATTTCGGTCGTTTATGGTGGCGGCGGAGGTAGTTTTAAAGATACGTTGTGAT
TTTGCGGTTTTTGACGTTAGTTTTT (SEQ ID NO:582)

TSPYL5_FP_V2 TTTGTTTCGGTTTTTGGCG  (SEQ ID NO:583)
TSPYL5_RP_v4 CGCCACCATAAACGACC  (SEQ ID NO:584)
TSPYL5_Pb_A5_63_v4 AGGCCACGGACG GCGGGAGGATTTTCGATTTC/3C6 (SEQ ID NO:585)
```

PTGDR
>hg19_dna range=chr14:52735270-52735400 5'pad=0 3'pad=0 strand=- repeatMasking=none
GCCTCGGGGCCCGGGGACTCACAATTACGGGCAGAGAACACATAGTGAAGAGCACGGTCATCAGCGCCAGCAGCAGGAGGTGATCCAGCTCCTC
CAGGGGCTGAGGG (SEQ ID NO:586)

BST:
GTTTCGGGGTTCGGGGATTTATAATTACGGGTAGAGAATATATAGTGAAGAGTACGGTTATTAGCGTTAGTAGTAGGAGGTGATTTAGTTTTTT
TAGGGGTTGAGGG (SEQ ID NO:587)

PTGDR_FP        GGGTTCGGGGATTTATAATTACGG (SEQ ID NO:588)
PTGDR_RP        CTAAATCACCTCCTACTACTAACGCTAATAAC (SEQ ID NO:589)
PTGDR_Pb_LQ_A1 CGCGCCGAGG CCGTACTCTTCACTATATATTCTCT/3C6/ (SEQ ID NO:590)

SEQUENCE LISTING

```
<160> NUMBER OF SEQ ID NOS: 589

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
gcgcgcggtt ttgggagata agtac                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
aaaaaaaaca acccctcgcc tcgac                                          25

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
aggtttttag gatatttagt tgagtggcgg                                     30

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
acctcgatcc cgaattcgaa ttcgac                                         26

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
gttttcggtt attcggtgac gg                                             22
```

-continued

```
<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
aaaaaactaa aaaacgaatc gcgct                                           25

<210> SEQ ID NO 7
<211> LENGTH: 29
<212> TYPE: DNA
<213> ORGANISM: Artificial Sequence
<220> FEATURE:
<223> OTHER INFORMATION: Synthetic

<400> SEQUENCE: 7
tttaatgatc gattaatcgt aaaggtcgg                                       29

<210> SEQ ID NO 8
<211> LENGTH: 28
<212> TYPE: DNA
<213> ORGANISM: Artificial Sequence
<220> FEATURE:
<223> OTHER INFORMATION: Synthetic

<400> SEQUENCE: 8
aaccaataaa ctcaaaacga ctaacgca                                        28

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
ttaggttttt agggggtttc ggcgt                                           25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
atcgtcttca ctactctata ccgtc                                           25

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
aattgggtaa ggagaagtcg gtcgt                                           25

<210> SEQ ID NO 12
<211> LENGTH: 25
<212> TYPE: DNA
<213> ORGANISM: Artificial Sequence
<220> FEATURE:
<223> OTHER INFORMATION: Synthetic
```

-continued

<400> SEQUENCE: 12
ataacgaaac ttaaacctcc ccgca                                        25

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
agttaagttt taacgggtgt ggcgg                                        25

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
aaacgtcgat aaaacgaacg tcgta                                        25

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
tatcgttgtt tcgagtcggg gacga                                        25

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
aaccgaaatt ccgacgacta cacgt                                        25

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
ggttcggagc ggtttaaata agcga                                        25

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18 cttaacccctt cccgcctatc cgtc                                        24

<210> SEQ ID NO 19

```
<211> LENGTH: 25
<212> TYPE: DNA
<213> ORGANISM: Artificial Sequence
<220> FEATURE:
<223> OTHER INFORMATION: Synthetic

<400> SEQUENCE: 19
ttgggggttg tcggtttttg gagac                                          25

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
ccgatctaaa taccccaaac gaaatcgaa                                      29

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
cgtttttaga tttagtggtg ggaatcgg                                       28

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
tcgaacgaaa aaaatcgaac tcgta                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
tttttcgcgg gtcgtttatt ttcgt                                          25

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
aaacgaataa actcgaacta tatcgaa                                        27

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
```

-continued

```
ttacgatcgg attataggg ttacgg                                    26

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
taccgaatct aaaaacgaaa acgaa                                    25

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
ggggagttat aggggtgaag gtcgc                                    25

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
gcctccgcca aactcgctac gtc                                      23

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
tatttggcgc gtggggagag gtc                                      23

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
tcccttccga aaattctacg acgaa                                    25

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
ttttagggta aatagcgggt ttcgt                                    25

<210> SEQ ID NO 32
<211> LENGTH: 26
<212> TYPE: DNA
```

-continued

<213> ORGANISM: Artificial Sequence
<220> FEATURE:
<223> OTHER INFORMATION: Synthetic

<400> SEQUENCE: 32
cgaccgccct acatacaatt catccg                                             26

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
gtgtgataga cgttagagcg gcgg                                               24

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
cgttttaatc aaaaaaatct cccgta                                             26

<210> SEQ ID NO 35
<211> LENGTH: 29
<212> TYPE: DNA
<213> ORGANISM: Artificial Sequence
<220> FEATURE:
<223> OTHER INFORMATION: Synthetic

<400> SEQUENCE: 35
gggagaattc gagtagtagt tgtaaacgg                                          29

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
aataacctcg ctaccaacca cccgc                                              25

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
gggcgttgtt tcgttttttt tatcgt                                            26

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
gaaacgcgct tacccgtcga a                                                 21

-continued

```
<210> SEQ ID NO 39
<211> LENGTH: 29
<212> TYPE: DNA
<213> ORGANISM: Artificial Sequence
<220> FEATURE:
<223> OTHER INFORMATION: Synthetic

<400> SEQUENCE: 39
gttcgttatc gtttggtttt gtataacgt                                        29

<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40
tatatcttat catccgacgt ctcgca                                           26

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
tatttgggat ttagagaggt agcgg                                            25

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
ccaaaaaccg aaacctaaac gct                                              23

<210> SEQ ID NO 43
<211> LENGTH: 25
<212> TYPE: DNA
<213> ORGANISM: Artificial Sequence
<220> FEATURE:
<223> OTHER INFORMATION: Synthetic

<400> SEQUENCE: 43
ttttatttcg tagacgattt ttcgt                                            25

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
gaaaaaaccg caactccgcg c                                                21

<210> SEQ ID NO 45
<211> LENGTH: 25
<212> TYPE: DNA
<213> ORGANISM: Artificial Sequence
<220> FEATURE:
```

-continued

<223> OTHER INFORMATION: Synthetic

<400> SEQUENCE: 45
aataatagga attagaggtt gtcgg                                                              25

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
aaataacaaa ctccgcgcgc gaa                                                                23

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
tacggttcgt acgagtgagt ggacgt                                                             26

<210> SEQ ID NO 48
<211> LENGTH: 25
<212> TYPE: DNA
<213> ORGANISM: Artificial Sequence
<220> FEATURE:
<223> OTHER INFORMATION: Synthetic

<400> SEQUENCE: 48
acgccgaaaa cgaacaaaaa acgat                                                              25

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
ggttttgggg gatttagggt tcgg                                                               24

<210> SEQ ID NO 50
<211> LENGTH: 25
<212> TYPE: DNA
<213> ORGANISM: Artificial Sequence
<220> FEATURE:
<223> OTHER INFORMATION: Synthetic

<400> SEQUENCE: 50
tccgcgaaaa cccctaccta acgtc                                                              25

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
tttttcgtag cgatcgtagc ggcgt                                                              25

-continued

```
<210> SEQ ID NO 52
<211> LENGTH: 25
<212> TYPE: DNA
<213> ORGANISM: Artificial Sequence
<220> FEATURE:
<223> OTHER INFORMATION: Synthetic

<400> SEQUENCE: 52
acctactaaa caaaccaaaa acgaa                                        25

<210> SEQ ID NO 53
<211> LENGTH: 26
<212> TYPE: DNA
<213> ORGANISM: Artificial Sequence
<220> FEATURE:
<223> OTHER INFORMATION: Synthetic

<400> SEQUENCE: 53
ttcgtttaga aggcgggtgg aaggtc                                       26

<210> SEQ ID NO 54
<211> LENGTH: 25
<212> TYPE: DNA
<213> ORGANISM: Artificial Sequence
<220> FEATURE:
<223> OTHER INFORMATION: Synthetic

<400> SEQUENCE: 54
aaaaaatctc gcgcgaaaat acgct                                        25

<210> SEQ ID NO 55
<211> LENGTH: 29
<212> TYPE: DNA
<213> ORGANISM: Artificial Sequence
<220> FEATURE:
<223> OTHER INFORMATION: Synthetic

<400> SEQUENCE: 55
ggaaggttag ggggaaattt gtatttcgt                                    29

<210> SEQ ID NO 56
<211> LENGTH: 28
<212> TYPE: DNA
<213> ORGANISM: Artificial Sequence
<220> FEATURE:
<223> OTHER INFORMATION: Synthetic

<400> SEQUENCE: 56
cgtaacatcg tcatttctta accgcgat                                     28

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
tttcgtatta aaattttatg ggcgt                                        25

<210> SEQ ID NO 58
<211> LENGTH: 22
<212> TYPE: DNA
<213> ORGANISM: Artificial Sequence
<220> FEATURE:
<223> OTHER INFORMATION: Synthetic
```

-continued

<400> SEQUENCE: 58
tctaatcccg cgaacgcaac cg                                              22

<210> SEQ ID NO 59
<211> LENGTH: 34
<212> TYPE: DNA
<213> ORGANISM: Artificial Sequence
<220> FEATURE:
<223> OTHER INFORMATION: Synthetic

<400> SEQUENCE: 59
tagttttgtt taggggtagg aggaatagaa agcg                                 34

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
acaccaacgc ttaccccgcg aa                                              22

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61
ttttcgatcg tggatgttcg gagtc                                           25

<210> SEQ ID NO 62
<211> LENGTH: 24
<212> TYPE: DNA
<213> ORGANISM: Artificial Sequence
<220> FEATURE:
<223> OTHER INFORMATION: Synthetic

<400> SEQUENCE: 62
gaaaaccgcg cgactcttac cgaa                                            24

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
gggaggggtc gtaggagtgt tttcg                                           25

<210> SEQ ID NO 64
<211> LENGTH: 28
<212> TYPE: DNA
<213> ORGANISM: Artificial Sequence
<220> FEATURE:
<223> OTHER INFORMATION: Synthetic

<400> SEQUENCE: 64
ataacgttct accgcctttc ccctacgc                                        28

<210> SEQ ID NO 65
<211> LENGTH: 23

-continued

```
<212> TYPE: DNA
<213> ORGANISM: Artificial Sequence
<220> FEATURE:
<223> OTHER INFORMATION: Synthetic

<400> SEQUENCE: 65
gaaagcgaaa cggtttcggc gtc                                              23

<210> SEQ ID NO 66
<211> LENGTH: 24
<212> TYPE: DNA
<213> ORGANISM: Artificial Sequence
<220> FEATURE:
<223> OTHER INFORMATION: Synthetic

<400> SEQUENCE: 66
caaacttccg aatcctaccc ccgc                                             24

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
tcgagagagg tcggtttttt ttatcgt                                          27

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
aaacttccga tcacgacccc acgtc                                            25

<210> SEQ ID NO 69
<211> LENGTH: 22
<212> TYPE: DNA
<213> ORGANISM: Artificial Sequence
<220> FEATURE:
<223> OTHER INFORMATION: Synthetic

<400> SEQUENCE: 69
tcgttggtaa atggagttac gg                                               22

<210> SEQ ID NO 70
<211> LENGTH: 26
<212> TYPE: DNA
<213> ORGANISM: Artificial Sequence
<220> FEATURE:
<223> OTHER INFORMATION: Synthetic

<400> SEQUENCE: 70
gaaaaaacta taaaaaaacg aacgat                                           26

<210> SEQ ID NO 71
<211> LENGTH: 25
<212> TYPE: DNA
<213> ORGANISM: Artificial Sequence
<220> FEATURE:
<223> OTHER INFORMATION: Synthetic

<400> SEQUENCE: 71
```
gtatttatcg cgttttcgag ttcga                                                    25

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
tataacgcga ccccaacgct                                                          20

<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
gtagtcggag ggagatttcg tcgg                                                     24

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74
ataaacttaa ccgaccacgc tcgaa                                                    25

<210> SEQ ID NO 75
<211> LENGTH: 23
<212> TYPE: DNA
<213> ORGANISM: Artificial Sequence
<220> FEATURE:
<223> OTHER INFORMATION: Synthetic

<400> SEQUENCE: 75
cgggttgtaa ttcgagtcgt cga                                                      23

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
caaaacctcc gaaaaaaatc cgaa                                                     24

<210> SEQ ID NO 77
<211> LENGTH: 25
<212> TYPE: DNA
<213> ORGANISM: Artificial Sequence
<220> FEATURE:
<223> OTHER INFORMATION: Synthetic

<400> SEQUENCE: 77
gtatagggcg tcgtttttag ttcga                                                    25

<210> SEQ ID NO 78
<211> LENGTH: 25
<212> TYPE: DNA
<213> ORGANISM: Artificial Sequence -continued
<220> FEATURE:
<223> OTHER INFORMATION: Synthetic

<400> SEQUENCE: 78
aaaaaatcta ccgaaaaatt ccgaa                                                      25

<210> SEQ ID NO 79
<211> LENGTH: 26
<212> TYPE: DNA
<213> ORGANISM: Artificial Sequence
<220> FEATURE:
<223> OTHER INFORMATION: Synthetic

<400> SEQUENCE: 79
ttggtttaat tcgttattcg tttcgt                                                     26

<210> SEQ ID NO 80
<211> LENGTH: 25
<212> TYPE: DNA
<213> ORGANISM: Artificial Sequence
<220> FEATURE:
<223> OTHER INFORMATION: Synthetic

<400> SEQUENCE: 80
aacaaacctt ttccgcttcg acgta                                                      25

<210> SEQ ID NO 81
<211> LENGTH: 26
<212> TYPE: DNA
<213> ORGANISM: Artificial Sequence
<220> FEATURE:
<223> OTHER INFORMATION: Synthetic

<400> SEQUENCE: 81
cgaagttcgg gtagggtaag cgttgc                                                     26

<210> SEQ ID NO 82
<211> LENGTH: 26
<212> TYPE: DNA
<213> ORGANISM: Artificial Sequence
<220> FEATURE:
<223> OTHER INFORMATION: Synthetic

<400> SEQUENCE: 82
cgacgtaaaa atacgaaacg cacgaa                                                     26

<210> SEQ ID NO 83
<211> LENGTH: 25
<212> TYPE: DNA
<213> ORGANISM: Artificial Sequence
<220> FEATURE:
<223> OTHER INFORMATION: Synthetic

<400> SEQUENCE: 83
gtgaggcggt tatacgagtt tcggc                                                      25

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
caaaaaacct ccacaaaata aacgat                                                     26

-continued

<210> SEQ ID NO 85
<211> LENGTH: 25
<212> TYPE: DNA
<213> ORGANISM: Artificial Sequence
<220> FEATURE:
<223> OTHER INFORMATION: Synthetic

<400> SEQUENCE: 85
tttttcgagt cgttttatttt cgcgg                                          25

<210> SEQ ID NO 86
<211> LENGTH: 25
<212> TYPE: DNA
<213> ORGANISM: Artificial Sequence
<220> FEATURE:
<223> OTHER INFORMATION: Synthetic

<400> SEQUENCE: 86
gaactccgaa cgccgcttaa acgta                                           25

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
cgcgtaggtg tttaacgtga ttagcgc                                         27

<210> SEQ ID NO 88
<211> LENGTH: 25
<212> TYPE: DNA
<213> ORGANISM: Artificial Sequence
<220> FEATURE:
<223> OTHER INFORMATION: Synthetic

<400> SEQUENCE: 88
cttacatcct caaaacccgc ccgac                                           25

<210> SEQ ID NO 89
<211> LENGTH: 25
<212> TYPE: DNA
<213> ORGANISM: Artificial Sequence
<220> FEATURE:
<223> OTHER INFORMATION: Synthetic

<400> SEQUENCE: 89
ttatggtggc ggtgtcggga gttac                                           25

<210> SEQ ID NO 90
<211> LENGTH: 25
<212> TYPE: DNA
<213> ORGANISM: Artificial Sequence
<220> FEATURE:
<223> OTHER INFORMATION: Synthetic

<400> SEQUENCE: 90
ccctctccta aaaacccgc tcgat                                            25

<210> SEQ ID NO 91
<211> LENGTH: 25
<212> TYPE: DNA
<213> ORGANISM: Artificial Sequence
<220> FEATURE:
<223> OTHER INFORMATION: Synthetic -continued

<400> SEQUENCE: 91
agttcgcgtt cggtttttt gttcg                                               25

<210> SEQ ID NO 92
<211> LENGTH: 22
<212> TYPE: DNA
<213> ORGANISM: Artificial Sequence
<220> FEATURE:
<223> OTHER INFORMATION: Synthetic

<400> SEQUENCE: 92
gtccgtcccg atcgcaatac ga                                                 22

<210> SEQ ID NO 93
<211> LENGTH: 23
<212> TYPE: DNA
<213> ORGANISM: Artificial Sequence
<220> FEATURE:
<223> OTHER INFORMATION: Synthetic

<400> SEQUENCE: 93
cgcgttgcgc ggaagttaga gtc                                                23

<210> SEQ ID NO 94
<211> LENGTH: 26
<212> TYPE: DNA
<213> ORGANISM: Artificial Sequence
<220> FEATURE:
<223> OTHER INFORMATION: Synthetic

<400> SEQUENCE: 94
ccacataaaa tcgaaaaaac cgcgaa                                             26

<210> SEQ ID NO 95
<211> LENGTH: 23
<212> TYPE: DNA
<213> ORGANISM: Artificial Sequence
<220> FEATURE:
<223> OTHER INFORMATION: Synthetic

<400> SEQUENCE: 95
gggtttataa gttcggaggt cga                                                23

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
cacccaacac ctaacgacga                                                    20

<210> SEQ ID NO 97
<211> LENGTH: 25
<212> TYPE: DNA
<213> ORGANISM: Artificial Sequence
<220> FEATURE:
<223> OTHER INFORMATION: Synthetic

<400> SEQUENCE: 97 agcgtttta gggagttcgg cgttc                                               25

<210> SEQ ID NO 98

```
<211> LENGTH: 25
<212> TYPE: DNA
<213> ORGANISM: Artificial Sequence
<220> FEATURE:
<223> OTHER INFORMATION: Synthetic

<400> SEQUENCE: 98
aatcgaaaaa acgaaaaaaa tcgca                                                 25

<210> SEQ ID NO 99
<211> LENGTH: 27
<212> TYPE: DNA
<213> ORGANISM: Artificial Sequence
<220> FEATURE:
<223> OTHER INFORMATION: Synthetic

<400> SEQUENCE: 99
ggggcgtata tattagttat cgagcga                                               27

<210> SEQ ID NO 100
<211> LENGTH: 25
<212> TYPE: DNA
<213> ORGANISM: Artificial Sequence
<220> FEATURE:
<223> OTHER INFORMATION: Synthetic

<400> SEQUENCE: 100
aaaaaaaacc ctaaaaaccg ccgaa                                                 25

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
taggtcgttt cgtcgtgcgc                                                       20

<210> SEQ ID NO 102
<211> LENGTH: 23
<212> TYPE: DNA
<213> ORGANISM: Artificial Sequence
<220> FEATURE:
<223> OTHER INFORMATION: Synthetic

<400> SEQUENCE: 102
ataaccttac cgacgccgcc gct                                                   23

<210> SEQ ID NO 103
<211> LENGTH: 25
<212> TYPE: DNA
<213> ORGANISM: Artificial Sequence
<220> FEATURE:
<223> OTHER INFORMATION: Synthetic

<400> SEQUENCE: 103
tttttgaaga gatcgttttc gacgg                                                 25

<210> SEQ ID NO 104
<211> LENGTH: 22
<212> TYPE: DNA
<213> ORGANISM: Artificial Sequence
<220> FEATURE:
<223> OTHER INFORMATION: Synthetic

<400> SEQUENCE: 104
```

-continued

```
cccccttaaa ccttaacccg aa                                          22

<210> SEQ ID NO 105
<211> LENGTH: 23
<212> TYPE: DNA
<213> ORGANISM: Artificial Sequence
<220> FEATURE:
<223> OTHER INFORMATION: Synthetic

<400> SEQUENCE: 105
ggcgtttcga tttttttcgtt cgg                                        23

<210> SEQ ID NO 106
<211> LENGTH: 29
<212> TYPE: DNA
<213> ORGANISM: Artificial Sequence
<220> FEATURE:
<223> OTHER INFORMATION: Synthetic

<400> SEQUENCE: 106
ccgaaactcc aacatctacc taacacgcc                                   29

<210> SEQ ID NO 107
<211> LENGTH: 26
<212> TYPE: DNA
<213> ORGANISM: Artificial Sequence
<220> FEATURE:
<223> OTHER INFORMATION: Synthetic

<400> SEQUENCE: 107
cgtaattttt ggcgagcgac gtttgc                                      26

<210> SEQ ID NO 108
<211> LENGTH: 25
<212> TYPE: DNA
<213> ORGANISM: Artificial Sequence
<220> FEATURE:
<223> OTHER INFORMATION: Synthetic

<400> SEQUENCE: 108
caaccttcga atcccccat ccgct                                        25

<210> SEQ ID NO 109
<211> LENGTH: 22
<212> TYPE: DNA
<213> ORGANISM: Artificial Sequence
<220> FEATURE:
<223> OTHER INFORMATION: Synthetic

<400> SEQUENCE: 109
ggttgcgagt acggtaaggt tt                                          22

<210> SEQ ID NO 110
<211> LENGTH: 23
<212> TYPE: DNA
<213> ORGANISM: Artificial Sequence
<220> FEATURE:
<223> OTHER INFORMATION: Synthetic

<400> SEQUENCE: 110
aaaactcaaa ataccgaaac gcc                                         23

<210> SEQ ID NO 111
<211> LENGTH: 23
<212> TYPE: DNA
```

-continued

```
<213> ORGANISM: Artificial Sequence
<220> FEATURE:
<223> OTHER INFORMATION: Synthetic

<400> SEQUENCE: 111
ttgagagcgt tgttagggac gac                                                23

<210> SEQ ID NO 112

<400> SEQUENCE: 112

000

<210> SEQ ID NO 113
<211> LENGTH: 18
<212> TYPE: DNA
<213> ORGANISM: Artificial Sequence
<220> FEATURE:
<223> OTHER INFORMATION: Synthetic

<400> SEQUENCE: 113
cgcgtttaac gccacctc                                                      18

<210> SEQ ID NO 114
<211> LENGTH: 26
<212> TYPE: DNA
<213> ORGANISM: Artificial Sequence
<220> FEATURE:
<223> OTHER INFORMATION: Synthetic

<400> SEQUENCE: 114
aacgtaaaat cgaactcgta aacgac                                             26

<210> SEQ ID NO 115
<211> LENGTH: 30
<212> TYPE: DNA
<213> ORGANISM: Artificial Sequence
<220> FEATURE:
<223> OTHER INFORMATION: Synthetic

<400> SEQUENCE: 115
cgaagtttta tttcgattcg ggttgtatcg                                         30

<210> SEQ ID NO 116
<211> LENGTH: 17
<212> TYPE: DNA
<213> ORGANISM: Artificial Sequence
<220> FEATURE:
<223> OTHER INFORMATION: Synthetic

<400> SEQUENCE: 116
ccacgccata tccccgc                                                       17

<210> SEQ ID NO 117
<211> LENGTH: 22
<212> TYPE: DNA
<213> ORGANISM: Artificial Sequence
<220> FEATURE:
<223> OTHER INFORMATION: Synthetic

<400> SEQUENCE: 117
aggttatcgg gtagcgttta gg                                                 22

<210> SEQ ID NO 118
<211> LENGTH: 19
<212> TYPE: DNA
```

<213> ORGANISM: Artificial Sequence
<220> FEATURE:
<223> OTHER INFORMATION: Synthetic

<400> SEQUENCE: 118
cgtacccctc ccccgctac                                                              19

<210> SEQ ID NO 119
<211> LENGTH: 19
<212> TYPE: DNA
<213> ORGANISM: Artificial Sequence
<220> FEATURE:
<223> OTHER INFORMATION: Synthetic

<400> SEQUENCE: 119
gtcgtttacg cgagcgacg                                                              19

<210> SEQ ID NO 120
<211> LENGTH: 26
<212> TYPE: DNA
<213> ORGANISM: Artificial Sequence
<220> FEATURE:
<223> OTHER INFORMATION: Synthetic

<400> SEQUENCE: 120
ctcgaacaaa acaaacgcta cgtaac                                                      26

<210> SEQ ID NO 121
<211> LENGTH: 24
<212> TYPE: DNA
<213> ORGANISM: Artificial Sequence
<220> FEATURE:
<223> OTHER INFORMATION: Synthetic

<400> SEQUENCE: 121
ggtttttatt tggagggttc ggac                                                        24

<210> SEQ ID NO 122
<211> LENGTH: 27
<212> TYPE: DNA
<213> ORGANISM: Artificial Sequence
<220> FEATURE:
<223> OTHER INFORMATION: Synthetic

<400> SEQUENCE: 122
actactcaat acgacgatat accgaac                                                     27

<210> SEQ ID NO 123
<211> LENGTH: 25
<212> TYPE: DNA
<213> ORGANISM: Artificial Sequence
<220> FEATURE:
<223> OTHER INFORMATION: Synthetic

<400> SEQUENCE: 123
tcgttcgttt tttcggtttt tggtc                                                       25

<210> SEQ ID NO 124
<211> LENGTH: 30
<212> TYPE: DNA
<213> ORGANISM: Artificial Sequence
<220> FEATURE:
<223> OTHER INFORMATION: Synthetic

<400> SEQUENCE: 124
ccttctaaac gaaaacaacg actaacgaaa                                                  30

<210> SEQ ID NO 125
<211> LENGTH: 27
<212> TYPE: DNA
<213> ORGANISM: Artificial Sequence
<220> FEATURE:
<223> OTHER INFORMATION: Synthetic

<400> SEQUENCE: 125
tagcgttttg tcgttttttt tttgcgt                                                  27

<210> SEQ ID NO 126
<211> LENGTH: 22
<212> TYPE: DNA
<213> ORGANISM: Artificial Sequence
<220> FEATURE:
<223> OTHER INFORMATION: Synthetic

<400> SEQUENCE: 126
cgcaaaaata cccccgaaaa ac                                                        22

<210> SEQ ID NO 127
<211> LENGTH: 19
<212> TYPE: DNA
<213> ORGANISM: Artificial Sequence
<220> FEATURE:
<223> OTHER INFORMATION: Synthetic

<400> SEQUENCE: 127
ggagggcggt tagtagcgt                                                           19

<210> SEQ ID NO 128
<211> LENGTH: 22
<212> TYPE: DNA
<213> ORGANISM: Artificial Sequence
<220> FEATURE:
<223> OTHER INFORMATION: Synthetic

<400> SEQUENCE: 128
acgatatcgc tacgcgacga aa                                                        22

<210> SEQ ID NO 129
<211> LENGTH: 22
<212> TYPE: DNA
<213> ORGANISM: Artificial Sequence
<220> FEATURE:
<223> OTHER INFORMATION: Synthetic

<400> SEQUENCE: 129
gttgtggtgt aatttgggtc gc                                                        22

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
acacgcgcga tacgttacac                                                          20

<210> SEQ ID NO 131
<211> LENGTH: 24
<212> TYPE: DNA
<213> ORGANISM: Artificial Sequence
<220> FEATURE:

-continued

```
<223> OTHER INFORMATION: Synthetic

<400> SEQUENCE: 131
cgttcgtata gttcgaatag ggcg                                      24

<210> SEQ ID NO 132
<211> LENGTH: 19
<212> TYPE: DNA
<213> ORGANISM: Artificial Sequence
<220> FEATURE:
<223> OTHER INFORMATION: Synthetic

<400> SEQUENCE: 132
cgacgccaac gaaaaactc                                            19

<210> SEQ ID NO 133
<211> LENGTH: 29
<212> TYPE: DNA
<213> ORGANISM: Artificial Sequence
<220> FEATURE:
<223> OTHER INFORMATION: Synthetic

<400> SEQUENCE: 133
ggagaattcg agtagtagtt gtaaacgga                                 29

<210> SEQ ID NO 134
<211> LENGTH: 16
<212> TYPE: DNA
<213> ORGANISM: Artificial Sequence
<220> FEATURE:
<223> OTHER INFORMATION: Synthetic

<400> SEQUENCE: 134
caaccacccg cccgcc                                               16

<210> SEQ ID NO 135
<211> LENGTH: 31
<212> TYPE: DNA
<213> ORGANISM: Artificial Sequence
<220> FEATURE:
<223> OTHER INFORMATION: Synthetic

<400> SEQUENCE: 135
tgtttacgtg gtatcgttat tttttaatcg c                              31

<210> SEQ ID NO 136
<211> LENGTH: 24
<212> TYPE: DNA
<213> ORGANISM: Artificial Sequence
<220> FEATURE:
<223> OTHER INFORMATION: Synthetic

<400> SEQUENCE: 136
cgacgaccgc gaaaaaaaa aacc                                       24

<210> SEQ ID NO 137
<211> LENGTH: 22
<212> TYPE: DNA
<213> ORGANISM: Artificial Sequence
<220> FEATURE:
<223> OTHER INFORMATION: Synthetic

<400> SEQUENCE: 137
tcgtggggaa tagtaggacg gc                                        22
```

-continued

```
<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
cctcccgaca aataaacgcg a                                            21

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
ggaggtaggt tcgcgcgg                                                18

<210> SEQ ID NO 140
<211> LENGTH: 21
<212> TYPE: DNA
<213> ORGANISM: Artificial Sequence
<220> FEATURE:
<223> OTHER INFORMATION: Synthetic

<400> SEQUENCE: 140
ccaactcaat tcctcctccg c                                            21

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141
gaggaggaat tgagttggcg c                                            21

<210> SEQ ID NO 142
<211> LENGTH: 27
<212> TYPE: DNA
<213> ORGANISM: Artificial Sequence
<220> FEATURE:
<223> OTHER INFORMATION: Synthetic

<400> SEQUENCE: 142
caacccataa tccgatccta tcttcga                                      27

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ttcgtacgag tgagtggacg                                              20

<210> SEQ ID NO 144
<211> LENGTH: 22
<212> TYPE: DNA
<213> ORGANISM: Artificial Sequence
<220> FEATURE:
<223> OTHER INFORMATION: Synthetic
```

<400> SEQUENCE: 144
caaaaaacga ttcccccgca aa                                                        22

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
tggagattta cgtcgagggc                                                           20

<210> SEQ ID NO 146
<211> LENGTH: 22
<212> TYPE: DNA
<213> ORGANISM: Artificial Sequence
<220> FEATURE:
<223> OTHER INFORMATION: Synthetic

<400> SEQUENCE: 146
ccacgatcga caaaacctac gt                                                        22

<210> SEQ ID NO 147
<211> LENGTH: 17
<212> TYPE: DNA
<213> ORGANISM: Artificial Sequence
<220> FEATURE:
<223> OTHER INFORMATION: Synthetic

<400> SEQUENCE: 147
gcgcgtgttt tggtcgc                                                              17

<210> SEQ ID NO 148
<211> LENGTH: 18
<212> TYPE: DNA
<213> ORGANISM: Artificial Sequence
<220> FEATURE:
<223> OTHER INFORMATION: Synthetic

<400> SEQUENCE: 148
tcgtccgcct acccgccc                                                             18

<210> SEQ ID NO 149
<211> LENGTH: 25
<212> TYPE: DNA
<213> ORGANISM: Artificial Sequence
<220> FEATURE:
<223> OTHER INFORMATION: Synthetic

<400> SEQUENCE: 149
ggagttacgt tgtttttggg tttcg                                                     25

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
ctctcctaaa aaccccgctc                                                           20

<210> SEQ ID NO 151
<211> LENGTH: 24

-continued

```
<212> TYPE: DNA
<213> ORGANISM: Artificial Sequence
<220> FEATURE:
<223> OTHER INFORMATION: Synthetic

<400> SEQUENCE: 151
ggatcgggat cgaagtttgg agaa                                          24

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
cttatctccc aaaaccgcgc                                               20

<210> SEQ ID NO 153
<211> LENGTH: 28
<212> TYPE: DNA
<213> ORGANISM: Artificial Sequence
<220> FEATURE:
<223> OTHER INFORMATION: Synthetic

<400> SEQUENCE: 153
ttggttgttt aatcgaaggg aagtaaac                                      28

<210> SEQ ID NO 154
<211> LENGTH: 23
<212> TYPE: DNA
<213> ORGANISM: Artificial Sequence
<220> FEATURE:
<223> OTHER INFORMATION: Synthetic

<400> SEQUENCE: 154
ctacctccct aaacacgtc tcg                                            23

<210> SEQ ID NO 155
<211> LENGTH: 22
<212> TYPE: DNA
<213> ORGANISM: Artificial Sequence
<220> FEATURE:
<223> OTHER INFORMATION: Synthetic

<400> SEQUENCE: 155
gggcgtagtt attttatagc gc                                            22

<210> SEQ ID NO 156
<211> LENGTH: 27
<212> TYPE: DNA
<213> ORGANISM: Artificial Sequence
<220> FEATURE:
<223> OTHER INFORMATION: Synthetic

<400> SEQUENCE: 156
caccaaaaaa aaacgatcgc tacgaaa                                       27

<210> SEQ ID NO 157
<211> LENGTH: 17
<212> TYPE: DNA
<213> ORGANISM: Artificial Sequence
<220> FEATURE:
<223> OTHER INFORMATION: Synthetic

<400> SEQUENCE: 157
```

-continued

```
cggggaagac ggaggtg                                                 17

<210> SEQ ID NO 158
<211> LENGTH: 22
<212> TYPE: DNA
<213> ORGANISM: Artificial Sequence
<220> FEATURE:
<223> OTHER INFORMATION: Synthetic

<400> SEQUENCE: 158
aaacccctac ctaacgtctc cc                                           22

<210> SEQ ID NO 159
<211> LENGTH: 26
<212> TYPE: DNA
<213> ORGANISM: Artificial Sequence
<220> FEATURE:
<223> OTHER INFORMATION: Synthetic

<400> SEQUENCE: 159
cggggttgta gtattttaat gatcga                                       26

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
cttcaaccaa taaactcaaa acgactaacg                                   30

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
ggcgtttttt cgcggttttg                                              20

<210> SEQ ID NO 162
<211> LENGTH: 17
<212> TYPE: DNA
<213> ORGANISM: Artificial Sequence
<220> FEATURE:
<223> OTHER INFORMATION: Synthetic

<400> SEQUENCE: 162
gcgtcccaca aaccccg                                                 17

<210> SEQ ID NO 163
<211> LENGTH: 22
<212> TYPE: DNA
<213> ORGANISM: Artificial Sequence
<220> FEATURE:
<223> OTHER INFORMATION: Synthetic

<400> SEQUENCE: 163
cgtagggtgg gtggttacgt tc                                           22

<210> SEQ ID NO 164
<211> LENGTH: 16
<212> TYPE: DNA
<213> ORGANISM: Artificial Sequence
```

-continued

```
<220> FEATURE:
<223> OTHER INFORMATION: Synthetic

<400> SEQUENCE: 164
aacttcccac gacccg                                                        16

<210> SEQ ID NO 165
<211> LENGTH: 31
<212> TYPE: DNA
<213> ORGANISM: Artificial Sequence
<220> FEATURE:
<223> OTHER INFORMATION: Synthetic

<400> SEQUENCE: 165
gttacgcggt ttttattttt gtgatttttc g                                       31

<210> SEQ ID NO 166
<211> LENGTH: 33
<212> TYPE: DNA
<213> ORGANISM: Artificial Sequence
<220> FEATURE:
<223> OTHER INFORMATION: Synthetic

<400> SEQUENCE: 166
ctcattaact tccaaaaaac aaactaactc gtc                                     33

<210> SEQ ID NO 167
<211> LENGTH: 19
<212> TYPE: DNA
<213> ORGANISM: Artificial Sequence
<220> FEATURE:
<223> OTHER INFORMATION: Synthetic

<400> SEQUENCE: 167
gagttcgacg gtcgaggcg                                                     19

<210> SEQ ID NO 168
<211> LENGTH: 17
<212> TYPE: DNA
<213> ORGANISM: Artificial Sequence
<220> FEATURE:
<223> OTHER INFORMATION: Synthetic

<400> SEQUENCE: 168
actacgccct cccacgc                                                       17

<210> SEQ ID NO 169
<211> LENGTH: 19
<212> TYPE: DNA
<213> ORGANISM: Artificial Sequence
<220> FEATURE:
<223> OTHER INFORMATION: Synthetic

<400> SEQUENCE: 169
tcgttttagc ggcggaagg                                                     19

<210> SEQ ID NO 170
<211> LENGTH: 14
<212> TYPE: DNA
<213> ORGANISM: Artificial Sequence
<220> FEATURE:
<223> OTHER INFORMATION: Synthetic

<400> SEQUENCE: 170
ccgcgaacca ccgc                                                          14
```

```
<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
ggttgtagtt ggagggcgag                                                20

<210> SEQ ID NO 172
<211> LENGTH: 16
<212> TYPE: DNA
<213> ORGANISM: Artificial Sequence
<220> FEATURE:
<223> OTHER INFORMATION: Synthetic

<400> SEQUENCE: 172
cgaaacgccc tcgcga                                                    16

<210> SEQ ID NO 173
<211> LENGTH: 24
<212> TYPE: DNA
<213> ORGANISM: Artificial Sequence
<220> FEATURE:
<223> OTHER INFORMATION: Synthetic

<400> SEQUENCE: 173
gttgtgtaag gagatgtgcg gttc                                           24

<210> SEQ ID NO 174
<211> LENGTH: 19
<212> TYPE: DNA
<213> ORGANISM: Artificial Sequence
<220> FEATURE:
<223> OTHER INFORMATION: Synthetic

<400> SEQUENCE: 174
aaacgacgac gcgaacgaa                                                 19

<210> SEQ ID NO 175
<211> LENGTH: 21
<212> TYPE: DNA
<213> ORGANISM: Artificial Sequence
<220> FEATURE:
<223> OTHER INFORMATION: Synthetic

<400> SEQUENCE: 175
cgtagtgcgt tttcgcgagt c                                              21

<210> SEQ ID NO 176
<211> LENGTH: 29
<212> TYPE: DNA
<213> ORGANISM: Artificial Sequence
<220> FEATURE:
<223> OTHER INFORMATION: Synthetic

<400> SEQUENCE: 176
cgccctaaaa cattaaaaat acgaaaccg                                      29

<210> SEQ ID NO 177
<211> LENGTH: 23
<212> TYPE: DNA
<213> ORGANISM: Artificial Sequence
<220> FEATURE:
<223> OTHER INFORMATION: Synthetic
```

-continued

<400> SEQUENCE: 177
gtttcggggt ttgttaagag acg                                        23

<210> SEQ ID NO 178
<211> LENGTH: 32
<212> TYPE: DNA
<213> ORGANISM: Artificial Sequence
<220> FEATURE:
<223> OTHER INFORMATION: Synthetic

<400> SEQUENCE: 178
actactacga atttcctacg attataactt cg                              32

<210> SEQ ID NO 179
<211> LENGTH: 21
<212> TYPE: DNA
<213> ORGANISM: Artificial Sequence
<220> FEATURE:
<223> OTHER INFORMATION: Synthetic

<400> SEQUENCE: 179
agtttttagt tcggttcgcg c                                          21

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
cccgaaaacg cttcgcaacg                                            20

<210> SEQ ID NO 181
<211> LENGTH: 23
<212> TYPE: DNA
<213> ORGANISM: Artificial Sequence
<220> FEATURE:
<223> OTHER INFORMATION: Synthetic

<400> SEQUENCE: 181
gataaggtag ggaagttgtg gcg                                        23

<210> SEQ ID NO 182
<211> LENGTH: 28
<212> TYPE: DNA
<213> ORGANISM: Artificial Sequence
<220> FEATURE:
<223> OTHER INFORMATION: Synthetic

<400> SEQUENCE: 182
cctctaatat cactaacaaa ccccatcg                                   28

<210> SEQ ID NO 183
<211> LENGTH: 19
<212> TYPE: DNA
<213> ORGANISM: Artificial Sequence
<220> FEATURE:
<223> OTHER INFORMATION: Synthetic

<400> SEQUENCE: 183
cgcggtgagt tgcggtaac                                             19

<210> SEQ ID NO 184

```
<211> LENGTH: 30
<212> TYPE: DNA
<213> ORGANISM: Artificial Sequence
<220> FEATURE:
<223> OTHER INFORMATION: Synthetic

<400> SEQUENCE: 184
cgaaatactt accgctatcg atctaatcga                                        30

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ggtagttcga atttcggcgc                                                   20

<210> SEQ ID NO 186
<211> LENGTH: 17
<212> TYPE: DNA
<213> ORGANISM: Artificial Sequence
<220> FEATURE:
<223> OTHER INFORMATION: Synthetic

<400> SEQUENCE: 186
ctccctcccg acgctcg                                                      17

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
gtagtttttc ggcggcgacg                                                   20

<210> SEQ ID NO 188
<211> LENGTH: 21
<212> TYPE: DNA
<213> ORGANISM: Artificial Sequence
<220> FEATURE:
<223> OTHER INFORMATION: Synthetic

<400> SEQUENCE: 188
ccttatttac cgccgtacgc t                                                 21

<210> SEQ ID NO 189
<211> LENGTH: 19
<212> TYPE: DNA
<213> ORGANISM: Artificial Sequence
<220> FEATURE:
<223> OTHER INFORMATION: Synthetic

<400> SEQUENCE: 189
ggtcgcgttt tgtttggcg                                                    19

<210> SEQ ID NO 190
<211> LENGTH: 21
<212> TYPE: DNA
<213> ORGANISM: Artificial Sequence
<220> FEATURE:
<223> OTHER INFORMATION: Synthetic

<400> SEQUENCE: 190
```

-continued

```
cgcgcgtcga aaaaaacgc g                                          21

<210> SEQ ID NO 191
<211> LENGTH: 23
<212> TYPE: DNA
<213> ORGANISM: Artificial Sequence
<220> FEATURE:
<223> OTHER INFORMATION: Synthetic

<400> SEQUENCE: 191
cgatcgtgta gaaggttgta gcg                                       23

<210> SEQ ID NO 192
<211> LENGTH: 23
<212> TYPE: DNA
<213> ORGANISM: Artificial Sequence
<220> FEATURE:
<223> OTHER INFORMATION: Synthetic

<400> SEQUENCE: 192
tttcccgcaa ccaactatac gcg                                       23

<210> SEQ ID NO 193
<211> LENGTH: 19
<212> TYPE: DNA
<213> ORGANISM: Artificial Sequence
<220> FEATURE:
<223> OTHER INFORMATION: Synthetic

<400> SEQUENCE: 193
cgggatttag cgggttcgg                                            19

<210> SEQ ID NO 194
<211> LENGTH: 26
<212> TYPE: DNA
<213> ORGANISM: Artificial Sequence
<220> FEATURE:
<223> OTHER INFORMATION: Synthetic

<400> SEQUENCE: 194
cccgaaaacg aaaaacaaaa aacgac                                    26

<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195
tcggggtgtt ttcgtagttg ttaaatttac                                30

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
cattctttta accgccaaaa cgcg                                      24

<210> SEQ ID NO 197
<211> LENGTH: 28
<212> TYPE: DNA
```

-continued

<213> ORGANISM: Artificial Sequence
<220> FEATURE:
<223> OTHER INFORMATION: Synthetic

<400> SEQUENCE: 197
gggttttggt tttcgttagt ttagtttc                                            28

<210> SEQ ID NO 198
<211> LENGTH: 26
<212> TYPE: DNA
<213> ORGANISM: Artificial Sequence
<220> FEATURE:
<223> OTHER INFORMATION: Synthetic

<400> SEQUENCE: 198
acaactctaa acgaccgaaa ataacg                                              26

<210> SEQ ID NO 199
<211> LENGTH: 21
<212> TYPE: DNA
<213> ORGANISM: Artificial Sequence
<220> FEATURE:
<223> OTHER INFORMATION: Synthetic

<400> SEQUENCE: 199
gcggtcggag tttagttagc g                                                   21

<210> SEQ ID NO 200
<211> LENGTH: 24
<212> TYPE: DNA
<213> ORGANISM: Artificial Sequence
<220> FEATURE:
<223> OTHER INFORMATION: Synthetic

<400> SEQUENCE: 200
acctacgact acctcctaaa cgcg                                                24

<210> SEQ ID NO 201
<211> LENGTH: 32
<212> TYPE: DNA
<213> ORGANISM: Artificial Sequence
<220> FEATURE:
<223> OTHER INFORMATION: Synthetic

<400> SEQUENCE: 201
gtcgtagttt tagtagtttt ttttgtcgtt cg                                       32

<210> SEQ ID NO 202
<211> LENGTH: 16
<212> TYPE: DNA
<213> ORGANISM: Artificial Sequence
<220> FEATURE:
<223> OTHER INFORMATION: Synthetic

<400> SEQUENCE: 202
cgaccgccgc gactac                                                         16

<210> SEQ ID NO 203
<211> LENGTH: 17
<212> TYPE: DNA
<213> ORGANISM: Artificial Sequence
<220> FEATURE:
<223> OTHER INFORMATION: Synthetic

<400> SEQUENCE: 203
gacgcggggc gtttagt                                                        17

-continued

```
<210> SEQ ID NO 204
<211> LENGTH: 19
<212> TYPE: DNA
<213> ORGANISM: Artificial Sequence
<220> FEATURE:
<223> OTHER INFORMATION: Synthetic

<400> SEQUENCE: 204
cgactcgaaa cgaccccga                                                   19

<210> SEQ ID NO 205
<211> LENGTH: 21
<212> TYPE: DNA
<213> ORGANISM: Artificial Sequence
<220> FEATURE:
<223> OTHER INFORMATION: Synthetic

<400> SEQUENCE: 205
ggagttttag gcggcgttac g                                                21

<210> SEQ ID NO 206
<211> LENGTH: 18
<212> TYPE: DNA
<213> ORGANISM: Artificial Sequence
<220> FEATURE:
<223> OTHER INFORMATION: Synthetic

<400> SEQUENCE: 206
accgcgaaaa cacccgac                                                    18

<210> SEQ ID NO 207
<211> LENGTH: 19
<212> TYPE: DNA
<213> ORGANISM: Artificial Sequence
<220> FEATURE:
<223> OTHER INFORMATION: Synthetic

<400> SEQUENCE: 207
gttcgcgcgg ttttacggt                                                   19

<210> SEQ ID NO 208
<211> LENGTH: 17
<212> TYPE: DNA
<213> ORGANISM: Artificial Sequence
<220> FEATURE:
<223> OTHER INFORMATION: Synthetic

<400> SEQUENCE: 208
cgcccttctc ctcccgc                                                     17

<210> SEQ ID NO 209
<211> LENGTH: 21
<212> TYPE: DNA
<213> ORGANISM: Artificial Sequence
<220> FEATURE:
<223> OTHER INFORMATION: Synthetic

<400> SEQUENCE: 209
ggaggtttcg cgtttcgatt a                                                21

<210> SEQ ID NO 210
<211> LENGTH: 18
<212> TYPE: DNA
<213> ORGANISM: Artificial Sequence
<220> FEATURE:
```

-continued

<223> OTHER INFORMATION: Synthetic

<400> SEQUENCE: 210
cgaacgatcc ccgcctac                                                      18

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
ggtttagcgc gggtttttcg                                                    20

<210> SEQ ID NO 212
<211> LENGTH: 18
<212> TYPE: DNA
<213> ORGANISM: Artificial Sequence
<220> FEATURE:
<223> OTHER INFORMATION: Synthetic

<400> SEQUENCE: 212
ccccgaactt cccgaact                                                      18

<210> SEQ ID NO 213
<211> LENGTH: 26
<212> TYPE: DNA
<213> ORGANISM: Artificial Sequence
<220> FEATURE:
<223> OTHER INFORMATION: Synthetic

<400> SEQUENCE: 213
ttttcgttga ttttattcga gtcgtc                                             26

<210> SEQ ID NO 214
<211> LENGTH: 22
<212> TYPE: DNA
<213> ORGANISM: Artificial Sequence
<220> FEATURE:
<223> OTHER INFORMATION: Synthetic

<400> SEQUENCE: 214
gaaccctctt caaataaacc gc                                                 22

<210> SEQ ID NO 215
<211> LENGTH: 22
<212> TYPE: DNA
<213> ORGANISM: Artificial Sequence
<220> FEATURE:
<223> OTHER INFORMATION: Synthetic

<400> SEQUENCE: 215
tggtcgtttt agcgttatgt cg                                                 22

<210> SEQ ID NO 216
<211> LENGTH: 19
<212> TYPE: DNA
<213> ORGANISM: Artificial Sequence
<220> FEATURE:
<223> OTHER INFORMATION: Synthetic

<400> SEQUENCE: 216
cgaaaactac aaaccgcgc                                                     19

-continued

```
<210> SEQ ID NO 217
<211> LENGTH: 24
<212> TYPE: DNA
<213> ORGANISM: Artificial Sequence
<220> FEATURE:
<223> OTHER INFORMATION: Synthetic

<400> SEQUENCE: 217
cgttaatttg ttagatagag ggcg                                        24

<210> SEQ ID NO 218
<211> LENGTH: 17
<212> TYPE: DNA
<213> ORGANISM: Artificial Sequence
<220> FEATURE:
<223> OTHER INFORMATION: Synthetic

<400> SEQUENCE: 218
tccgaacaac cgcctac                                                17

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
gttgtcggga gcggtagg                                               18

<210> SEQ ID NO 220
<211> LENGTH: 21
<212> TYPE: DNA
<213> ORGANISM: Artificial Sequence
<220> FEATURE:
<223> OTHER INFORMATION: Synthetic

<400> SEQUENCE: 220
ccaatatccc gaaacgcgtc t                                           21

<210> SEQ ID NO 221
<211> LENGTH: 19
<212> TYPE: DNA
<213> ORGANISM: Artificial Sequence
<220> FEATURE:
<223> OTHER INFORMATION: Synthetic

<400> SEQUENCE: 221
tttgtttcgg tttttggcg                                              19

<210> SEQ ID NO 222
<211> LENGTH: 17
<212> TYPE: DNA
<213> ORGANISM: Artificial Sequence
<220> FEATURE:
<223> OTHER INFORMATION: Synthetic

<400> SEQUENCE: 222
cgccaccata aacgacc                                                17

<210> SEQ ID NO 223
<211> LENGTH: 21
<212> TYPE: DNA
<213> ORGANISM: Artificial Sequence
<220> FEATURE:
<223> OTHER INFORMATION: Synthetic
```

-continued

<400> SEQUENCE: 223
ggttaggggt ggagttcgtt a                                                    21

<210> SEQ ID NO 224
<211> LENGTH: 24
<212> TYPE: DNA
<213> ORGANISM: Artificial Sequence
<220> FEATURE:
<223> OTHER INFORMATION: Synthetic

<400> SEQUENCE: 224
actccgaact ctactcatcc tttc                                                 24

<210> SEQ ID NO 225
<211> LENGTH: 22
<212> TYPE: DNA
<213> ORGANISM: Artificial Sequence
<220> FEATURE:
<223> OTHER INFORMATION: Synthetic

<400> SEQUENCE: 225
tcggcggttt ttagtaaaag cg                                                   22

<210> SEQ ID NO 226
<211> LENGTH: 19
<212> TYPE: DNA
<213> ORGANISM: Artificial Sequence
<220> FEATURE:
<223> OTHER INFORMATION: Synthetic

<400> SEQUENCE: 226
aaatctcccg tcccactcc                                                       19

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
gggttcgggg atttataatt acgg                                                 24

<210> SEQ ID NO 228
<211> LENGTH: 32
<212> TYPE: DNA
<213> ORGANISM: Artificial Sequence
<220> FEATURE:
<223> OTHER INFORMATION: Synthetic

<400> SEQUENCE: 228
ctaaatcacc tcctactact aacgctaata ac                                        32

<210> SEQ ID NO 229
<211> LENGTH: 25
<212> TYPE: DNA
<213> ORGANISM: Artificial Sequence
<220> FEATURE:
<223> OTHER INFORMATION: Synthetic

<400> SEQUENCE: 229
cgcgccgagg ccgtacccac gtcca                                                25

<210> SEQ ID NO 230
<211> LENGTH: 27

```
<212> TYPE: DNA
<213> ORGANISM: Artificial Sequence
<220> FEATURE:
<223> OTHER INFORMATION: Synthetic

<400> SEQUENCE: 230
aggccacgga cgcgtcgtcg aacaccg                                          27

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
cgcgccgagg cgtcgaacac cttcgac                                          27

<210> SEQ ID NO 232
<211> LENGTH: 29
<212> TYPE: DNA
<213> ORGANISM: Artificial Sequence
<220> FEATURE:
<223> OTHER INFORMATION: Synthetic

<400> SEQUENCE: 232
aggccacgga cgcgactacg ccacgtaaa                                        29

<210> SEQ ID NO 233
<211> LENGTH: 28
<212> TYPE: DNA
<213> ORGANISM: Artificial Sequence
<220> FEATURE:
<223> OTHER INFORMATION: Synthetic

<400> SEQUENCE: 233
cgcgccgagg gtttcggttt ttgggagg                                         28

<210> SEQ ID NO 234
<211> LENGTH: 33
<212> TYPE: DNA
<213> ORGANISM: Artificial Sequence
<220> FEATURE:
<223> OTHER INFORMATION: Synthetic

<400> SEQUENCE: 234
aggccacgga cgcgacaact aaaactccgt acg                                   33

<210> SEQ ID NO 235
<211> LENGTH: 28
<212> TYPE: DNA
<213> ORGANISM: Artificial Sequence
<220> FEATURE:
<223> OTHER INFORMATION: Synthetic

<400> SEQUENCE: 235
cgcgccgagg cgggattttc ggtttcga                                         28

<210> SEQ ID NO 236
<211> LENGTH: 35
<212> TYPE: DNA
<213> ORGANISM: Artificial Sequence
<220> FEATURE:
<223> OTHER INFORMATION: Synthetic

<400> SEQUENCE: 236
```

-continued aggccacgga cgcgtttacg tatatagtcg gtagt                                          35

<210> SEQ ID NO 237
<211> LENGTH: 31
<212> TYPE: DNA
<213> ORGANISM: Artificial Sequence
<220> FEATURE:
<223> OTHER INFORMATION: Synthetic

<400> SEQUENCE: 237
cgcgccgagg cgctcacgaa ctaaacgatc c                                              31

<210> SEQ ID NO 238
<211> LENGTH: 31
<212> TYPE: DNA
<213> ORGANISM: Artificial Sequence
<220> FEATURE:
<223> OTHER INFORMATION: Synthetic

<400> SEQUENCE: 238
aggccacgga cgtcgttagg tttcgtttcg t                                              31

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239
cgcgccgagg cggttttcgc ggga                                                      24

<210> SEQ ID NO 240
<211> LENGTH: 28
<212> TYPE: DNA
<213> ORGANISM: Artificial Sequence
<220> FEATURE:
<223> OTHER INFORMATION: Synthetic

<400> SEQUENCE: 240
aggccacgga cgcgacctcg aaccccaa                                                  28

<210> SEQ ID NO 241
<211> LENGTH: 24
<212> TYPE: DNA
<213> ORGANISM: Artificial Sequence
<220> FEATURE:
<223> OTHER INFORMATION: Synthetic

<400> SEQUENCE: 241
cgcgccgagg ccgctcgctc acaa                                                      24

<210> SEQ ID NO 242
<211> LENGTH: 34
<212> TYPE: DNA
<213> ORGANISM: Artificial Sequence
<220> FEATURE:
<223> OTHER INFORMATION: Synthetic

<400> SEQUENCE: 242
aggccacgga cgcggtttta cgaaatgtaa attt                                           34

<210> SEQ ID NO 243
<211> LENGTH: 26
<212> TYPE: DNA
<213> ORGANISM: Artificial Sequence -continued

```
<220> FEATURE:
<223> OTHER INFORMATION: Synthetic

<400> SEQUENCE: 243
cgcgccgagg cgtcgaggtc gtttcg                                          26

<210> SEQ ID NO 244
<211> LENGTH: 25
<212> TYPE: DNA
<213> ORGANISM: Artificial Sequence
<220> FEATURE:
<223> OTHER INFORMATION: Synthetic

<400> SEQUENCE: 244
aggccacgga cggcggaagt gcgtt                                           25

<210> SEQ ID NO 245
<211> LENGTH: 25
<212> TYPE: DNA
<213> ORGANISM: Artificial Sequence
<220> FEATURE:
<223> OTHER INFORMATION: Synthetic

<400> SEQUENCE: 245
cgcgccgagg cgcgggttag ttgtt                                           25

<210> SEQ ID NO 246
<211> LENGTH: 26
<212> TYPE: DNA
<213> ORGANISM: Artificial Sequence
<220> FEATURE:
<223> OTHER INFORMATION: Synthetic

<400> SEQUENCE: 246
aggccacgga cgatacgcgc ctccca                                          26

<210> SEQ ID NO 247
<211> LENGTH: 30
<212> TYPE: DNA
<213> ORGANISM: Artificial Sequence
<220> FEATURE:
<223> OTHER INFORMATION: Synthetic

<400> SEQUENCE: 247
cgcgccgagg cgttcgttat cgtttggttt                                      30

<210> SEQ ID NO 248
<211> LENGTH: 26
<212> TYPE: DNA
<213> ORGANISM: Artificial Sequence
<220> FEATURE:
<223> OTHER INFORMATION: Synthetic

<400> SEQUENCE: 248
aggccacgga cgcctaccgc acacgc                                          26

<210> SEQ ID NO 249
<211> LENGTH: 28
<212> TYPE: DNA
<213> ORGANISM: Artificial Sequence
<220> FEATURE:
<223> OTHER INFORMATION: Synthetic

<400> SEQUENCE: 249
cgcgccgagg cgatcctacc gacctcga                                        28
```

-continued

<210> SEQ ID NO 250
<211> LENGTH: 27
<212> TYPE: DNA
<213> ORGANISM: Artificial Sequence
<220> FEATURE:
<223> OTHER INFORMATION: Synthetic

<400> SEQUENCE: 250
aggccacgga cgcgctcccg cccttct                                                              27

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cgcgccgagg cggttttaac gtaagtttga ttg                                                       33

<210> SEQ ID NO 252
<211> LENGTH: 26
<212> TYPE: DNA
<213> ORGANISM: Artificial Sequence
<220> FEATURE:
<223> OTHER INFORMATION: Synthetic

<400> SEQUENCE: 252
aggccacgga cgcggtcgag gtggga                                                               26

<210> SEQ ID NO 253
<211> LENGTH: 24
<212> TYPE: DNA
<213> ORGANISM: Artificial Sequence
<220> FEATURE:
<223> OTHER INFORMATION: Synthetic

<400> SEQUENCE: 253
cgcgccgagg gcgggtggag aagg                                                                 24

<210> SEQ ID NO 254
<211> LENGTH: 26
<212> TYPE: DNA
<213> ORGANISM: Artificial Sequence
<220> FEATURE:
<223> OTHER INFORMATION: Synthetic

<400> SEQUENCE: 254
aggccacgga cggcgggtgg agaagg                                                               26

<210> SEQ ID NO 255
<211> LENGTH: 31
<212> TYPE: DNA
<213> ORGANISM: Artificial Sequence
<220> FEATURE:
<223> OTHER INFORMATION: Synthetic

<400> SEQUENCE: 255
aggccacgga cggcatttcc gacctttacg a                                                         31

<210> SEQ ID NO 256
<211> LENGTH: 27
<212> TYPE: DNA
<213> ORGANISM: Artificial Sequence
<220> FEATURE:
<223> OTHER INFORMATION: Synthetic -continued

<400> SEQUENCE: 256
cgcgccgagg gaaaaataac cccgccc                                27

<210> SEQ ID NO 257
<211> LENGTH: 27
<212> TYPE: DNA
<213> ORGANISM: Artificial Sequence
<220> FEATURE:
<223> OTHER INFORMATION: Synthetic

<400> SEQUENCE: 257
aggccacgga cgcgtagggt tcgcgag                                27

<210> SEQ ID NO 258
<211> LENGTH: 25
<212> TYPE: DNA
<213> ORGANISM: Artificial Sequence
<220> FEATURE:
<223> OTHER INFORMATION: Synthetic

<400> SEQUENCE: 258
cgcgccgagg cgatacatcc gcgcg                                 25

<210> SEQ ID NO 259
<211> LENGTH: 29
<212> TYPE: DNA
<213> ORGANISM: Artificial Sequence
<220> FEATURE:
<223> OTHER INFORMATION: Synthetic

<400> SEQUENCE: 259
aggccacgga cggcggattg agtttcgtg                             29

<210> SEQ ID NO 260
<211> LENGTH: 30
<212> TYPE: DNA
<213> ORGANISM: Artificial Sequence
<220> FEATURE:
<223> OTHER INFORMATION: Synthetic

<400> SEQUENCE: 260
aggccacgga cggcgcggtt attttttcgt                            30

<210> SEQ ID NO 261
<211> LENGTH: 29
<212> TYPE: DNA
<213> ORGANISM: Artificial Sequence
<220> FEATURE:
<223> OTHER INFORMATION: Synthetic

<400> SEQUENCE: 261
cgcgccgagg gcgcgtcgtt cgtatattt                             29

<210> SEQ ID NO 262
<211> LENGTH: 27
<212> TYPE: DNA
<213> ORGANISM: Artificial Sequence
<220> FEATURE:
<223> OTHER INFORMATION: Synthetic

<400> SEQUENCE: 262
aggccacgga cgcgtcggcg tcgtttt                               27

<210> SEQ ID NO 263

```
<211> LENGTH: 27
<212> TYPE: DNA
<213> ORGANISM: Artificial Sequence
<220> FEATURE:
<223> OTHER INFORMATION: Synthetic

<400> SEQUENCE: 263
cgcgccgagg gcgttaaaaa cctcgcg                                                27

<210> SEQ ID NO 264
<211> LENGTH: 34
<212> TYPE: DNA
<213> ORGANISM: Artificial Sequence
<220> FEATURE:
<223> OTHER INFORMATION: Synthetic

<400> SEQUENCE: 264
cgcgccgagg gcgttatact ctttctctaa acac                                        34

<210> SEQ ID NO 265
<211> LENGTH: 33
<212> TYPE: DNA
<213> ORGANISM: Artificial Sequence
<220> FEATURE:
<223> OTHER INFORMATION: Synthetic

<400> SEQUENCE: 265
aggccacgga cgcggcgatt tagttttttg tcg                                         33

<210> SEQ ID NO 266
<211> LENGTH: 31
<212> TYPE: DNA
<213> ORGANISM: Artificial Sequence
<220> FEATURE:
<223> OTHER INFORMATION: Synthetic

<400> SEQUENCE: 266
cgcgccgagg gacctccgaa cttataaacc c                                           31

<210> SEQ ID NO 267
<211> LENGTH: 31
<212> TYPE: DNA
<213> ORGANISM: Artificial Sequence
<220> FEATURE:
<223> OTHER INFORMATION: Synthetic

<400> SEQUENCE: 267
aggccacgga cgcgggaagt ttcgttagtg g                                           31

<210> SEQ ID NO 268
<211> LENGTH: 32
<212> TYPE: DNA
<213> ORGANISM: Artificial Sequence
<220> FEATURE:
<223> OTHER INFORMATION: Synthetic

<400> SEQUENCE: 268
cgcgccgagg cgttaggttt ttttagtcgt cg                                          32

<210> SEQ ID NO 269
<211> LENGTH: 31
<212> TYPE: DNA
<213> ORGANISM: Artificial Sequence
<220> FEATURE:
<223> OTHER INFORMATION: Synthetic

<400> SEQUENCE: 269
```

-continued

```
aggccacgga cgtctcgaaa cgaataaccg c                              31

<210> SEQ ID NO 270
<211> LENGTH: 26
<212> TYPE: DNA
<213> ORGANISM: Artificial Sequence
<220> FEATURE:
<223> OTHER INFORMATION: Synthetic

<400> SEQUENCE: 270
cgcgccgagg gctacgctaa acgccg                                   26

<210> SEQ ID NO 271
<211> LENGTH: 31
<212> TYPE: DNA
<213> ORGANISM: Artificial Sequence
<220> FEATURE:
<223> OTHER INFORMATION: Synthetic

<400> SEQUENCE: 271
aggccacgga cggatcgaaa acacacaacc c                              31

<210> SEQ ID NO 272
<211> LENGTH: 25
<212> TYPE: DNA
<213> ORGANISM: Artificial Sequence
<220> FEATURE:
<223> OTHER INFORMATION: Synthetic

<400> SEQUENCE: 272
cgcgccgagg ggcgggcgta ttagt                                    25

<210> SEQ ID NO 273
<211> LENGTH: 27
<212> TYPE: DNA
<213> ORGANISM: Artificial Sequence
<220> FEATURE:
<223> OTHER INFORMATION: Synthetic

<400> SEQUENCE: 273
aggccacgga cgcgggtcgc gtttagg                                  27

<210> SEQ ID NO 274
<211> LENGTH: 34
<212> TYPE: DNA
<213> ORGANISM: Artificial Sequence
<220> FEATURE:
<223> OTHER INFORMATION: Synthetic

<400> SEQUENCE: 274
aggccacgga cgcgattttt cgggtagttt ttgg                          34

<210> SEQ ID NO 275
<211> LENGTH: 28
<212> TYPE: DNA
<213> ORGANISM: Artificial Sequence
<220> FEATURE:
<223> OTHER INFORMATION: Synthetic

<400> SEQUENCE: 275
cgcgccgagg ggttttttcgg tcgagatg                                28

<210> SEQ ID NO 276
<211> LENGTH: 34
<212> TYPE: DNA
```

-continued

<213> ORGANISM: Artificial Sequence
<220> FEATURE:
<223> OTHER INFORMATION: Synthetic

<400> SEQUENCE: 276
aggccacgga cgcgaccgta acaaaaaaac aaac                               34

<210> SEQ ID NO 277
<211> LENGTH: 32
<212> TYPE: DNA
<213> ORGANISM: Artificial Sequence
<220> FEATURE:
<223> OTHER INFORMATION: Synthetic

<400> SEQUENCE: 277
cgcgccgagg acgcgactaa aaaaaaccta ac                                 32

<210> SEQ ID NO 278
<211> LENGTH: 31
<212> TYPE: DNA
<213> ORGANISM: Artificial Sequence
<220> FEATURE:
<223> OTHER INFORMATION: Synthetic

<400> SEQUENCE: 278
aggccacgga cgcgccgaaa caaactaatc c                                  31

<210> SEQ ID NO 279
<211> LENGTH: 31
<212> TYPE: DNA
<213> ORGANISM: Artificial Sequence
<220> FEATURE:
<223> OTHER INFORMATION: Synthetic

<400> SEQUENCE: 279
cgcgccgagg cgcgaaactt caaaaatacg a                                  31

<210> SEQ ID NO 280
<211> LENGTH: 27
<212> TYPE: DNA
<213> ORGANISM: Artificial Sequence
<220> FEATURE:
<223> OTHER INFORMATION: Synthetic

<400> SEQUENCE: 280
aggccacgga cgattcgcgt tcgagcg                                       27

<210> SEQ ID NO 281
<211> LENGTH: 28
<212> TYPE: DNA
<213> ORGANISM: Artificial Sequence
<220> FEATURE:
<223> OTHER INFORMATION: Synthetic

<400> SEQUENCE: 281
aggccacgga cggcggtagt ggtcgtag                                      28

<210> SEQ ID NO 282
<211> LENGTH: 32
<212> TYPE: DNA
<213> ORGANISM: Artificial Sequence
<220> FEATURE:
<223> OTHER INFORMATION: Synthetic

<400> SEQUENCE: 282
aggccacgga cgcgtttggc gtagatataa gc                                 32

<210> SEQ ID NO 283
<211> LENGTH: 26
<212> TYPE: DNA
<213> ORGANISM: Artificial Sequence
<220> FEATURE:
<223> OTHER INFORMATION: Synthetic

<400> SEQUENCE: 283
aggccacgga cgccgcgcta ccgcta                                    26

<210> SEQ ID NO 284
<211> LENGTH: 24
<212> TYPE: DNA
<213> ORGANISM: Artificial Sequence
<220> FEATURE:
<223> OTHER INFORMATION: Synthetic

<400> SEQUENCE: 284
cgcgccgagg ccgcgctacc gcta                                      24

<210> SEQ ID NO 285
<211> LENGTH: 27
<212> TYPE: DNA
<213> ORGANISM: Artificial Sequence
<220> FEATURE:
<223> OTHER INFORMATION: Synthetic

<400> SEQUENCE: 285
aggccacgga cgcgaaaaat cccacgc                                   27

<210> SEQ ID NO 286
<211> LENGTH: 25
<212> TYPE: DNA
<213> ORGANISM: Artificial Sequence
<220> FEATURE:
<223> OTHER INFORMATION: Synthetic

<400> SEQUENCE: 286
cgcgccgagg gcgtttcgat cgggg                                     25

<210> SEQ ID NO 287
<211> LENGTH: 32
<212> TYPE: DNA
<213> ORGANISM: Artificial Sequence
<220> FEATURE:
<223> OTHER INFORMATION: Synthetic

<400> SEQUENCE: 287
aggccacgga cggcgggagg attttcgatt tc                             32

<210> SEQ ID NO 288
<211> LENGTH: 31
<212> TYPE: DNA
<213> ORGANISM: Artificial Sequence
<220> FEATURE:
<223> OTHER INFORMATION: Synthetic

<400> SEQUENCE: 288
cgcgccgagg cgtaactcca tctcgataac c                              31

<210> SEQ ID NO 289
<211> LENGTH: 90
<212> TYPE: DNA
<213> ORGANISM: Homo sapiens

```
<400> SEQUENCE: 289
gggctgcgag cacggcaagg tctctcaggc ttgtggacgt gggtacgggc gtctcggcac        60
cctgagcttt ctcccctacc cgccccagcg                                        90

<210> SEQ ID NO 290
<211> LENGTH: 90
<212> TYPE: DNA
<213> ORGANISM: Artificial Sequence
<220> FEATURE:
<223> OTHER INFORMATION: Synthetic

<400> SEQUENCE: 290
gggttgcgag tacggtaagg tttttttaggt ttgtggacgt gggtacgggc gtttcggtat      60
tttgagtttt tttttttatt cgttttagcg                                        90

<210> SEQ ID NO 291
<211> LENGTH: 22
<212> TYPE: DNA
<213> ORGANISM: Artificial Sequence
<220> FEATURE:
<223> OTHER INFORMATION: Synthetic

<400> SEQUENCE: 291
ggttgcgagt acggtaaggt tt                                                 22

<210> SEQ ID NO 292
<211> LENGTH: 23
<212> TYPE: DNA
<213> ORGANISM: Artificial Sequence
<220> FEATURE:
<223> OTHER INFORMATION: Synthetic

<400> SEQUENCE: 292
aaaactcaaa ataccgaaac gcc                                                23

<210> SEQ ID NO 293
<211> LENGTH: 25
<212> TYPE: DNA
<213> ORGANISM: Artificial Sequence
<220> FEATURE:
<223> OTHER INFORMATION: Synthetic

<400> SEQUENCE: 293
cgcgccgagg ccgtacccac gtcca                                              25

<210> SEQ ID NO 294
<211> LENGTH: 93
<212> TYPE: DNA
<213> ORGANISM: Homo sapiens

<400> SEQUENCE: 294
cgcggacgcc gagctccctg agagcgctgc cagggacgac gcggtgttcg acgacgaggt       60
ggcgccaaac gcggccagcg ataacgcctc ggc                                     93

<210> SEQ ID NO 295
<211> LENGTH: 93
<212> TYPE: DNA
<213> ORGANISM: Artificial Sequence
<220> FEATURE:
<223> OTHER INFORMATION: Synthetic

<400> SEQUENCE: 295
cgcggacgtc gagtttttttg agagcgttgt tagggacgac gcggtgttcg acgacgaggt      60
```

```
ggcgttaaac gcggttagcg ataacgtttc ggt                              93

<210> SEQ ID NO 296
<211> LENGTH: 23
<212> TYPE: DNA
<213> ORGANISM: Artificial Sequence
<220> FEATURE:
<223> OTHER INFORMATION: Synthetic

<400> SEQUENCE: 296
ttgagagcgt tgttagggac gac                                         23

<210> SEQ ID NO 297
<211> LENGTH: 18
<212> TYPE: DNA
<213> ORGANISM: Artificial Sequence
<220> FEATURE:
<223> OTHER INFORMATION: Synthetic

<400> SEQUENCE: 297
cgcgtttaac gccacctc                                               18

<210> SEQ ID NO 298
<211> LENGTH: 27
<212> TYPE: DNA
<213> ORGANISM: Artificial Sequence
<220> FEATURE:
<223> OTHER INFORMATION: Synthetic

<400> SEQUENCE: 298
aggccacgga cgcgtcgtcg aacaccg                                     27

<210> SEQ ID NO 299
<211> LENGTH: 97
<212> TYPE: DNA
<213> ORGANISM: Homo sapiens

<400> SEQUENCE: 299
gagacgggct cgggccccgc ccaccggcgg gtgcagctga gggcgcggcc gaaggtgccc   60
gacgccgccc acgagctcga ctccacgctc ggctact                          97

<210> SEQ ID NO 300
<211> LENGTH: 97
<212> TYPE: DNA
<213> ORGANISM: Artificial Sequence
<220> FEATURE:
<223> OTHER INFORMATION: Synthetic

<400> SEQUENCE: 300
gagacgggtt cgggtttcgt ttatcggcgg gtgtagttga gggcgcggtc gaaggtgttc   60
gacgtcgttt acgagttcga ttttacgttc ggttatt                          97

<210> SEQ ID NO 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
cgggtttcgt ttatcggcgg                                             20

<210> SEQ ID NO 302
```

<211> LENGTH: 26
<212> TYPE: DNA
<213> ORGANISM: Artificial Sequence
<220> FEATURE:
<223> OTHER INFORMATION: Synthetic

<400> SEQUENCE: 302
aacgtaaaat cgaactcgta aacgac                                            26

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
cgcgccgagg cgtcgaacac cttcgac                                           27

<210> SEQ ID NO 304
<211> LENGTH: 139
<212> TYPE: DNA
<213> ORGANISM: Homo sapiens

<400> SEQUENCE: 304
ggcggggctt aggggacgag gttagtacga agccccaccc cgacccgggc tgcaccgccc       60
cctccgcgct tacgtggcgc agccgcgggg acatggcgtg ggtggtgggc gtccgctggg      120
acacgttgag cacgatgac                                                   139

<210> SEQ ID NO 305
<211> LENGTH: 139
<212> TYPE: DNA
<213> ORGANISM: Artificial Sequence
<220> FEATURE:
<223> OTHER INFORMATION: Synthetic

<400> SEQUENCE: 305
ggcggggttt aggggacgag gttagtacga agttttattt cgattcgggt tgtatcgttt       60
ttttcgcgtt tacgtggcgt agtcgcgggg atatggcgtg ggtggtgggc gttcgttggg      120
atacgttgag tacgatgat                                                   139

<210> SEQ ID NO 306
<211> LENGTH: 30
<212> TYPE: DNA
<213> ORGANISM: Artificial Sequence
<220> FEATURE:
<223> OTHER INFORMATION: Synthetic

<400> SEQUENCE: 306
cgaagtttta tttcgattcg ggttgtatcg                                        30

<210> SEQ ID NO 307
<211> LENGTH: 17
<212> TYPE: DNA
<213> ORGANISM: Artificial Sequence
<220> FEATURE:
<223> OTHER INFORMATION: Synthetic

<400> SEQUENCE: 307
ccacgccata tccccgc                                                      17

<210> SEQ ID NO 308
<211> LENGTH: 29

```
<212> TYPE: DNA
<213> ORGANISM: Artificial Sequence
<220> FEATURE:
<223> OTHER INFORMATION: Synthetic

<400> SEQUENCE: 308
aggccacgga cgcgactacg ccacgtaaa                                          29

<210> SEQ ID NO 309
<211> LENGTH: 101
<212> TYPE: DNA
<213> ORGANISM: Homo sapiens

<400> SEQUENCE: 309
gccgaggcca ccgggcagcg tccaggtctc ggcctttggg aggggagcag cggggggaggg      60 gcacggggag gggcgagggc ggggcgcgcc tgggcctcgg c                           101

<210> SEQ ID NO 310
<211> LENGTH: 101
<212> TYPE: DNA
<213> ORGANISM: Artificial Sequence
<220> FEATURE:
<223> OTHER INFORMATION: Synthetic

<400> SEQUENCE: 310
gccgaggtta tcgggtagcg tttaggtttc ggtttttggg aggggagtag cggggggaggg      60 gtacggggag gggcgagggc ggggcgcgtt tgggtttcgg t                           101

<210> SEQ ID NO 311
<211> LENGTH: 22
<212> TYPE: DNA
<213> ORGANISM: Artificial Sequence
<220> FEATURE:
<223> OTHER INFORMATION: Synthetic

<400> SEQUENCE: 311
aggttatcgg gtagcgttta gg                                                22

<210> SEQ ID NO 312
<211> LENGTH: 19
<212> TYPE: DNA
<213> ORGANISM: Artificial Sequence
<220> FEATURE:
<223> OTHER INFORMATION: Synthetic

<400> SEQUENCE: 312
cgtacccctc ccccgctac                                                    19

<210> SEQ ID NO 313
<211> LENGTH: 28
<212> TYPE: DNA
<213> ORGANISM: Artificial Sequence
<220> FEATURE:
<223> OTHER INFORMATION: Synthetic

<400> SEQUENCE: 313
cgcgccgagg gtttcggttt ttgggagg                                          28

<210> SEQ ID NO 314
<211> LENGTH: 90
<212> TYPE: DNA
<213> ORGANISM: Homo sapiens

<400> SEQUENCE: 314
```

-continued

```
cgctgtgagt cgcccacgcg agcgacgtgg ggatacgggg cgcacggagt ctcagctgcc        60
gccacgcagc gcttgccctg cccgagcttc                                         90

<210> SEQ ID NO 315
<211> LENGTH: 90
<212> TYPE: DNA
<213> ORGANISM: Artificial Sequence
<220> FEATURE:
<223> OTHER INFORMATION: Synthetic

<400> SEQUENCE: 315
cgttgtgagt cgtttacgcg agcgacgtgg ggatacgggg cgtacggagt tttagttgtc        60
gttacgtagc gtttgttttg ttcgagtttt                                         90

<210> SEQ ID NO 316
<211> LENGTH: 19
<212> TYPE: DNA
<213> ORGANISM: Artificial Sequence
<220> FEATURE:
<223> OTHER INFORMATION: Synthetic

<400> SEQUENCE: 316
gtcgtttacg cgagcgacg                                                     19

<210> SEQ ID NO 317
<211> LENGTH: 26
<212> TYPE: DNA
<213> ORGANISM: Artificial Sequence
<220> FEATURE:
<223> OTHER INFORMATION: Synthetic

<400> SEQUENCE: 317
ctcgaacaaa acaaacgcta cgtaac                                             26

<210> SEQ ID NO 318
<211> LENGTH: 33
<212> TYPE: DNA
<213> ORGANISM: Artificial Sequence
<220> FEATURE:
<223> OTHER INFORMATION: Synthetic

<400> SEQUENCE: 318
aggccacgga cgcgacaact aaaactccgt acg                                     33

<210> SEQ ID NO 319
<211> LENGTH: 110
<212> TYPE: DNA
<213> ORGANISM: Homo sapiens

<400> SEQUENCE: 319
tgagggtcgg gactatctcc tcaccagggt ctccacttgg agggtccgga cgggactttc        60
ggtttcgagc ccagcctcag cccggcacac cgccgcactg agcagcagca                   110

<210> SEQ ID NO 320
<211> LENGTH: 110
<212> TYPE: DNA
<213> ORGANISM: Artificial Sequence
<220> FEATURE:
<223> OTHER INFORMATION: Synthetic

<400> SEQUENCE: 320
tgagggtcgg gattattttt ttattagggt ttttatttgg agggttcgga cgggattttc        60
ggtttcgagt ttagtttttag ttcggtatat cgtcgtattg agtagtagta                  110
```

231                                                                                          232

-continued

<210> SEQ ID NO 321
<211> LENGTH: 24
<212> TYPE: DNA
<213> ORGANISM: Artificial Sequence
<220> FEATURE:
<223> OTHER INFORMATION: Synthetic

<400> SEQUENCE: 321
ggtttttatt tggagggttc ggac                                                    24

<210> SEQ ID NO 322
<211> LENGTH: 27
<212> TYPE: DNA
<213> ORGANISM: Artificial Sequence
<220> FEATURE:
<223> OTHER INFORMATION: Synthetic

<400> SEQUENCE: 322
actactcaat acgacgatat accgaac                                                 27

<210> SEQ ID NO 323
<211> LENGTH: 28
<212> TYPE: DNA
<213> ORGANISM: Artificial Sequence
<220> FEATURE:
<223> OTHER INFORMATION: Synthetic

<400> SEQUENCE: 323
cgcgccgagg cgggattttc ggtttcga                                                28

<210> SEQ ID NO 324
<211> LENGTH: 129
<212> TYPE: DNA
<213> ORGANISM: Homo sapiens

<400> SEQUENCE: 324
gccatcccgg ggctctgcgc cgtccgctct cccggctcct ggccgctcac gcacacagcc     60
ggtagctggt tttcgttagc cgctgccctc gcccagaagg cgggtggaag gtcgccagtt     120
ggacgcaca                                                                    129

<210> SEQ ID NO 325
<211> LENGTH: 129
<212> TYPE: DNA
<213> ORGANISM: Artificial Sequence
<220> FEATURE:
<223> OTHER INFORMATION: Synthetic

<400> SEQUENCE: 325
gttatttcgg ggttttgcgt cgttcgtttt ttcggttttt ggtcgtttac gtatatagtc     60
ggtagttggt tttcgttagt cgttgttttc gtttagaagg cgggtggaag gtcgttagtt     120
ggacgtata                                                                    129

<210> SEQ ID NO 326
<211> LENGTH: 25
<212> TYPE: DNA
<213> ORGANISM: Artificial Sequence
<220> FEATURE:
<223> OTHER INFORMATION: Synthetic

<400> SEQUENCE: 326
tcgttcgttt tttcggtttt tggtc                                                   25

```
<210> SEQ ID NO 327
<211> LENGTH: 30
<212> TYPE: DNA
<213> ORGANISM: Artificial Sequence
<220> FEATURE:
<223> OTHER INFORMATION: Synthetic

<400> SEQUENCE: 327
ccttctaaac gaaaacaacg actaacgaaa                                        30

<210> SEQ ID NO 328
<211> LENGTH: 35
<212> TYPE: DNA
<213> ORGANISM: Artificial Sequence
<220> FEATURE:
<223> OTHER INFORMATION: Synthetic

<400> SEQUENCE: 328
aggccacgga cgcgtttacg tatatagtcg gtagt                                  35

<210> SEQ ID NO 329
<211> LENGTH: 119
<212> TYPE: DNA
<213> ORGANISM: Homo sapiens

<400> SEQUENCE: 329
gtagcgttct gccgcctttc ccctgcgccc tctctgggga ccgctcagct cgtgagcgcc       60
ccccgggggc actcctgcga cccctccctt gctaggggcc tcctacagcc cgtggtcgg       119

<210> SEQ ID NO 330
<211> LENGTH: 119
<212> TYPE: DNA
<213> ORGANISM: Artificial Sequence
<220> FEATURE:
<223> OTHER INFORMATION: Synthetic

<400> SEQUENCE: 330
gtagcgtttt gtcgtttttt ttttgcgttt tttttgggga tcgtttagtt cgtgagcgtt       60
tttcgggggt attttttgcga ttttttttttt gttaggggtt ttttatagtt cgtggtcgg     119

<210> SEQ ID NO 331
<211> LENGTH: 27
<212> TYPE: DNA
<213> ORGANISM: Artificial Sequence
<220> FEATURE:
<223> OTHER INFORMATION: Synthetic

<400> SEQUENCE: 331
tagcgttttg tcgttttttt tttgcgt                                           27

<210> SEQ ID NO 332
<211> LENGTH: 22
<212> TYPE: DNA
<213> ORGANISM: Artificial Sequence
<220> FEATURE:
<223> OTHER INFORMATION: Synthetic

<400> SEQUENCE: 332
cgcaaaaata cccccgaaaa ac                                                22

<210> SEQ ID NO 333
<211> LENGTH: 31
<212> TYPE: DNA
<213> ORGANISM: Artificial Sequence
```

```
<220> FEATURE:
<223> OTHER INFORMATION: Synthetic

<400> SEQUENCE: 333
cgcgccgagg cgctcacgaa ctaaacgatc c                                    31

<210> SEQ ID NO 334
<211> LENGTH: 109
<212> TYPE: DNA
<213> ORGANISM: Homo sapiens

<400> SEQUENCE: 334
cggacccaga gcaccgcctg cggcctcacc taggggagag ggagggcggt tagcagcgcc     60
gccaggcccc gccccgcctt cccgccgcgc agcgacaccg tccaagtcc                109

<210> SEQ ID NO 335
<211> LENGTH: 109
<212> TYPE: DNA
<213> ORGANISM: Artificial Sequence
<220> FEATURE:
<223> OTHER INFORMATION: Synthetic

<400> SEQUENCE: 335
cggatttaga gtatcgtttg cggtttatt tagggagag ggaggcggt tagtagcgtc        60 gttaggtttc gtttcgtttt ttcgtcgcgt agcgatatcg tttaagttt               109

<210> SEQ ID NO 336
<211> LENGTH: 19
<212> TYPE: DNA
<213> ORGANISM: Artificial Sequence
<220> FEATURE:
<223> OTHER INFORMATION: Synthetic

<400> SEQUENCE: 336
ggagggcggt tagtagcgt                                                  19

<210> SEQ ID NO 337
<211> LENGTH: 22
<212> TYPE: DNA
<213> ORGANISM: Artificial Sequence
<220> FEATURE:
<223> OTHER INFORMATION: Synthetic

<400> SEQUENCE: 337
acgatatcgc tacgcgacga aa                                              22

<210> SEQ ID NO 338
<211> LENGTH: 31
<212> TYPE: DNA
<213> ORGANISM: Artificial Sequence
<220> FEATURE:
<223> OTHER INFORMATION: Synthetic

<400> SEQUENCE: 338
aggccacgga cgtcgttagg tttcgtttcg t                                    31

<210> SEQ ID NO 339
<211> LENGTH: 88
<212> TYPE: DNA
<213> ORGANISM: Homo sapiens

<400> SEQUENCE: 339
cgacgggaag cccgagaagc tgaggctgtg gtgcaacttg ggccgcggct cccgcgggaa     60
```

-continued gcccaggtgc aacgcatcgc gcgtgcca                                          88

<210> SEQ ID NO 340
<211> LENGTH: 88
<212> TYPE: DNA
<213> ORGANISM: Artificial Sequence
<220> FEATURE:
<223> OTHER INFORMATION: Synthetic

<400> SEQUENCE: 340
cgacgggaag ttcgagaagt tgaggttgtg gtgtaatttg ggtcgcggtt ttcgcgggaa      60
gtttaggtgt aacgtatcgc gcgtgtta                                         88

<210> SEQ ID NO 341
<211> LENGTH: 22
<212> TYPE: DNA
<213> ORGANISM: Artificial Sequence
<220> FEATURE:
<223> OTHER INFORMATION: Synthetic

<400> SEQUENCE: 341
gttgtggtgt aatttgggtc gc                                               22

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
acacgcgcga tacgttacac                                                  20

<210> SEQ ID NO 343
<211> LENGTH: 24
<212> TYPE: DNA
<213> ORGANISM: Artificial Sequence
<220> FEATURE:
<223> OTHER INFORMATION: Synthetic

<400> SEQUENCE: 343
cgcgccgagg cggttttcgc ggga                                             24

<210> SEQ ID NO 344
<211> LENGTH: 84
<212> TYPE: DNA
<213> ORGANISM: Homo sapiens

<400> SEQUENCE: 344
gctcaccgcc cgcccgcaca gctcgaacag ggcgggggga gcgttggggc ccgaggccga      60
gctcttcgct ggcgccgcct cccg                                             84

<210> SEQ ID NO 345
<211> LENGTH: 84
<212> TYPE: DNA
<213> ORGANISM: Artificial Sequence
<220> FEATURE:
<223> OTHER INFORMATION: Synthetic

<400> SEQUENCE: 345
gtttatcgtt cgttcgtata gttcgaatag ggcgggggga gcgttggggt tcgaggtcga      60
gtttttcgtt ggcgtcgttt ttcg                                             84

<210> SEQ ID NO 346
<211> LENGTH: 24
<212> TYPE: DNA
<213> ORGANISM: Artificial Sequence
<220> FEATURE:
<223> OTHER INFORMATION: Synthetic

<400> SEQUENCE: 346
cgttcgtata gttcgaatag ggcg                                               24

<210> SEQ ID NO 347
<211> LENGTH: 19
<212> TYPE: DNA
<213> ORGANISM: Artificial Sequence
<220> FEATURE:
<223> OTHER INFORMATION: Synthetic

<400> SEQUENCE: 347
cgacgccaac gaaaaactc                                                     19

<210> SEQ ID NO 348
<211> LENGTH: 28
<212> TYPE: DNA
<213> ORGANISM: Artificial Sequence
<220> FEATURE:
<223> OTHER INFORMATION: Synthetic

<400> SEQUENCE: 348
aggccacgga cgcgacctcg aaccccaa                                           28

<210> SEQ ID NO 349
<211> LENGTH: 110
<212> TYPE: DNA
<213> ORGANISM: Homo sapiens

<400> SEQUENCE: 349
cggcggagga agcgtggagt ccattgatct aggtacttgt ggggagggga gaacccgagc        60
agcagctgca aacggaaggg ctgtgagcga gcgggcgggc gggtggctgg                   110

<210> SEQ ID NO 350
<211> LENGTH: 110
<212> TYPE: DNA
<213> ORGANISM: Artificial Sequence
<220> FEATURE:
<223> OTHER INFORMATION: Synthetic

<400> SEQUENCE: 350
cggcggagga agcgtggagt ttattgattt aggtatttgt ggggagggga gaattcgagt        60
agtagttgta aacggaaggg ttgtgagcga gcgggcgggc gggtggttgg                   110

<210> SEQ ID NO 351
<211> LENGTH: 29
<212> TYPE: DNA
<213> ORGANISM: Artificial Sequence
<220> FEATURE:
<223> OTHER INFORMATION: Synthetic

<400> SEQUENCE: 351
ggagaattcg agtagtagtt gtaaacgga                                          29

<210> SEQ ID NO 352
<211> LENGTH: 16
<212> TYPE: DNA
<213> ORGANISM: Artificial Sequence
<220> FEATURE:

-continued

```
<223> OTHER INFORMATION: Synthetic

<400> SEQUENCE: 352
caaccacccg cccgcc                                                    16

<210> SEQ ID NO 353
<211> LENGTH: 24
<212> TYPE: DNA
<213> ORGANISM: Artificial Sequence
<220> FEATURE:
<223> OTHER INFORMATION: Synthetic

<400> SEQUENCE: 353
cgcgccgagg ccgctcgctc acaa                                           24

<210> SEQ ID NO 354
<211> LENGTH: 87
<212> TYPE: DNA
<213> ORGANISM: Homo sapiens

<400> SEQUENCE: 354
cttgtctacg tggcatcgtc atttcttaac cgcggtttta cgaaatgcaa atttcccct     60 ggccttcctc ctccgcggcc gtcgacc                                        87

<210> SEQ ID NO 355
<211> LENGTH: 87
<212> TYPE: DNA
<213> ORGANISM: Artificial Sequence
<220> FEATURE:
<223> OTHER INFORMATION: Synthetic

<400> SEQUENCE: 355
tttgtttacg tggtatcgtt attttttaat cgcggtttta cgaaatgtaa attttttttt     60
ggtttttttt tttcgcggtc gtcgatt                                        87

<210> SEQ ID NO 356
<211> LENGTH: 31
<212> TYPE: DNA
<213> ORGANISM: Artificial Sequence
<220> FEATURE:
<223> OTHER INFORMATION: Synthetic

<400> SEQUENCE: 356
tgtttacgtg gtatcgttat tttttaatcg c                                   31

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
cgacgaccgc gaaaaaaaaa aacc                                           24

<210> SEQ ID NO 358
<211> LENGTH: 34
<212> TYPE: DNA
<213> ORGANISM: Artificial Sequence
<220> FEATURE:
<223> OTHER INFORMATION: Synthetic

<400> SEQUENCE: 358
aggccacgga cgcggtttta cgaaatgtaa attt                                34
```

<210> SEQ ID NO 359
<211> LENGTH: 72
<212> TYPE: DNA
<213> ORGANISM: Homo sapiens

<400> SEQUENCE: 359
ccgccccgtg gggaacagca ggacggcgcc gaggccgttt cgctttcctc cgcgcccatt      60
tgccgggagg gg                                                           72

<210> SEQ ID NO 360
<211> LENGTH: 72
<212> TYPE: DNA
<213> ORGANISM: Artificial Sequence
<220> FEATURE:
<223> OTHER INFORMATION: Synthetic

<400> SEQUENCE: 360
tcgtttcgtg gggaatagta ggacggcgtc gaggtcgttt cgtttttttt cgcgtttatt      60
tgtcgggagg gg                                                           72

<210> SEQ ID NO 361
<211> LENGTH: 22
<212> TYPE: DNA
<213> ORGANISM: Artificial Sequence
<220> FEATURE:
<223> OTHER INFORMATION: Synthetic

<400> SEQUENCE: 361
tcgtggggaa tagtaggacg gc                                                22

<210> SEQ ID NO 362
<211> LENGTH: 21
<212> TYPE: DNA
<213> ORGANISM: Artificial Sequence
<220> FEATURE:
<223> OTHER INFORMATION: Synthetic

<400> SEQUENCE: 362
cctcccgaca aataaacgcg a                                                 21

<210> SEQ ID NO 363
<211> LENGTH: 26
<212> TYPE: DNA
<213> ORGANISM: Artificial Sequence
<220> FEATURE:
<223> OTHER INFORMATION: Synthetic

<400> SEQUENCE: 363
cgcgccgagg cgtcgaggtc gtttcg                                            26

<210> SEQ ID NO 364
<211> LENGTH: 131
<212> TYPE: DNA
<213> ORGANISM: Homo sapiens

<400> SEQUENCE: 364
cggcctagga cgcgccctgc gtggaggcag gcccgcgcgg cggaagtgcg tttctggggc      60
tcctcctgaa gaatgcggag gaggaactga gctggcgcgc gggccagctg tcctctcttc     120
tgatcccgaa g                                                          131

<210> SEQ ID NO 365

-continued

```
<211> LENGTH: 131
<212> TYPE: DNA
<213> ORGANISM: Artificial Sequence
<220> FEATURE:
<223> OTHER INFORMATION: Synthetic

<400> SEQUENCE: 365
cggtttagga cgcgttttgc gtggaggtag gttcgcgcgg cggaagtgcg tttttggggt     60 ttttttttgaa gaatgcggag gaggaattga gttggcgcgc gggttagttg tttttttttt    120
tgatttcgaa g                                                         131

<210> SEQ ID NO 366
<211> LENGTH: 18
<212> TYPE: DNA
<213> ORGANISM: Artificial Sequence
<220> FEATURE:
<223> OTHER INFORMATION: Synthetic

<400> SEQUENCE: 366
ggaggtaggt tcgcgcgg                                                   18

<210> SEQ ID NO 367
<211> LENGTH: 21
<212> TYPE: DNA
<213> ORGANISM: Artificial Sequence
<220> FEATURE:
<223> OTHER INFORMATION: Synthetic

<400> SEQUENCE: 367
ccaactcaat tcctcctccg c                                               21

<210> SEQ ID NO 368
<211> LENGTH: 25
<212> TYPE: DNA
<213> ORGANISM: Artificial Sequence
<220> FEATURE:
<223> OTHER INFORMATION: Synthetic

<400> SEQUENCE: 368
aggccacgga cggcggaagt gcgtt                                           25

<210> SEQ ID NO 369
<211> LENGTH: 144
<212> TYPE: DNA
<213> ORGANISM: Homo sapiens

<400> SEQUENCE: 369
gcccgcgcgg cggaagtgcg tttctggggc tcctcctgaa gaatgcggag gaggaactga     60
gctggcgcgc gggccagctg tcctctcttc tgatcccgaa gacaggatcg gattatgggt    120
tgttaccggc ttgtgcggcc ctgg                                           144

<210> SEQ ID NO 370
<211> LENGTH: 144
<212> TYPE: DNA
<213> ORGANISM: Artificial Sequence
<220> FEATURE:
<223> OTHER INFORMATION: Synthetic

<400> SEQUENCE: 370
gttcgcgcgg cggaagtgcg tttttggggt tttttttgaa gaatgcggag gaggaattga     60
gttggcgcgc gggttagttg tttttttttt tgatttcgaa gataggatcg gattatgggt    120
tgttatcggt ttgtgcggtt ttgg                                           144
```

<210> SEQ ID NO 371
<211> LENGTH: 21
<212> TYPE: DNA
<213> ORGANISM: Artificial Sequence
<220> FEATURE:
<223> OTHER INFORMATION: Synthetic

<400> SEQUENCE: 371
gaggaggaat tgagttggcg c                                          21

<210> SEQ ID NO 372
<211> LENGTH: 27
<212> TYPE: DNA
<213> ORGANISM: Artificial Sequence
<220> FEATURE:
<223> OTHER INFORMATION: Synthetic

<400> SEQUENCE: 372
caacccataa tccgatccta tcttcga                                    27

<210> SEQ ID NO 373
<211> LENGTH: 25
<212> TYPE: DNA
<213> ORGANISM: Artificial Sequence
<220> FEATURE:
<223> OTHER INFORMATION: Synthetic

<400> SEQUENCE: 373
cgcgccgagg cgcgggttag ttgtt                                      25

<210> SEQ ID NO 374
<211> LENGTH: 61
<212> TYPE: DNA
<213> ORGANISM: Homo sapiens

<400> SEQUENCE: 374
cggctcgcac gagtgagtgg acgtgggagg cgcgcatctg cggggggaatc gccccttgcc   60 c                                                                61

<210> SEQ ID NO 375
<211> LENGTH: 61
<212> TYPE: DNA
<213> ORGANISM: Artificial Sequence
<220> FEATURE:
<223> OTHER INFORMATION: Synthetic

<400> SEQUENCE: 375
cggttcgtac gagtgagtgg acgtgggagg cgcgtatttg cgggggaatc gttttttgtt    60
t                                                                61

<210> SEQ ID NO 376
<211> LENGTH: 20
<212> TYPE: DNA
<213> ORGANISM: Artificial Sequence
<220> FEATURE:
<223> OTHER INFORMATION: Synthetic

<400> SEQUENCE: 376
ttcgtacgag tgagtggacg                                            20

<210> SEQ ID NO 377
<211> LENGTH: 22
<212> TYPE: DNA

<213> ORGANISM: Artificial Sequence
<220> FEATURE:
<223> OTHER INFORMATION: Synthetic

<400> SEQUENCE: 377
caaaaaacga ttcccccgca aa                                                         22

<210> SEQ ID NO 378
<211> LENGTH: 26
<212> TYPE: DNA
<213> ORGANISM: Artificial Sequence
<220> FEATURE:
<223> OTHER INFORMATION: Synthetic

<400> SEQUENCE: 378
aggccacgga cgatacgcgc ctccca                                                     26

<210> SEQ ID NO 379
<211> LENGTH: 97
<212> TYPE: DNA
<213> ORGANISM: Homo sapiens

<400> SEQUENCE: 379
cgggaaagaa cgtggagatc cacgccgagg gcgcccgcca ccgcctggtt ctgcacaacg    60
taggttttgc cgaccgtggc ttctttggct gcgagac                                   97

<210> SEQ ID NO 380
<211> LENGTH: 97
<212> TYPE: DNA
<213> ORGANISM: Artificial Sequence
<220> FEATURE:
<223> OTHER INFORMATION: Synthetic

<400> SEQUENCE: 380
cgggaaagaa cgtggagatt tacgtcgagg gcgttcgtta tcgtttggtt ttgtataacg    60
taggttttgt cgatcgtggt ttttttggtt gcgagat                                   97

<210> SEQ ID NO 381
<211> LENGTH: 20
<212> TYPE: DNA
<213> ORGANISM: Artificial Sequence
<220> FEATURE:
<223> OTHER INFORMATION: Synthetic

<400> SEQUENCE: 381
tggagattta cgtcgagggc                                                            20

<210> SEQ ID NO 382
<211> LENGTH: 22
<212> TYPE: DNA
<213> ORGANISM: Artificial Sequence
<220> FEATURE:
<223> OTHER INFORMATION: Synthetic

<400> SEQUENCE: 382
ccacgatcga caaaacctac gt                                                         22

<210> SEQ ID NO 383
<211> LENGTH: 30
<212> TYPE: DNA
<213> ORGANISM: Artificial Sequence
<220> FEATURE:
<223> OTHER INFORMATION: Synthetic

<400> SEQUENCE: 383

-continued

```
cgcgccgagg cgttcgttat cgtttggttt                                      30

<210> SEQ ID NO 384
<211> LENGTH: 73
<212> TYPE: DNA
<213> ORGANISM: Homo sapiens

<400> SEQUENCE: 384
gcgtgcaggg tgcgcgcgtg tcttggccgc gcgtggcggc gtgtgcggca ggggcgggca    60
ggcgggcgac tcg                                                        73

<210> SEQ ID NO 385
<211> LENGTH: 73
<212> TYPE: DNA
<213> ORGANISM: Artificial Sequence
<220> FEATURE:
<223> OTHER INFORMATION: Synthetic

<400> SEQUENCE: 385
gcgtgtaggg tgcgcgcgtg ttttggtcgc gcgtggcggc gtgtgcggta ggggcgggta    60
ggcgggcgat tcg                                                        73

<210> SEQ ID NO 386
<211> LENGTH: 17
<212> TYPE: DNA
<213> ORGANISM: Artificial Sequence
<220> FEATURE:
<223> OTHER INFORMATION: Synthetic

<400> SEQUENCE: 386
gcgcgtgttt tggtcgc                                                    17

<210> SEQ ID NO 387
<211> LENGTH: 18
<212> TYPE: DNA
<213> ORGANISM: Artificial Sequence
<220> FEATURE:
<223> OTHER INFORMATION: Synthetic

<400> SEQUENCE: 387
tcgtccgcct acccgccc                                                   18

<210> SEQ ID NO 388
<211> LENGTH: 26
<212> TYPE: DNA
<213> ORGANISM: Artificial Sequence
<220> FEATURE:
<223> OTHER INFORMATION: Synthetic

<400> SEQUENCE: 388
aggccacgga cgcctaccgc acacgc                                          26

<210> SEQ ID NO 389
<211> LENGTH: 174
<212> TYPE: DNA
<213> ORGANISM: Homo sapiens

<400> SEQUENCE: 389
gggggctctc aggtggcgcg gccgcgaggc ggaccctgat ggccatggtg gcggtgccgg    60
gagccacgct gtccctgggc cccggcccga ggcggcagg accgagcggg gtccccagga    120
gaggggtggc ggggagctcg atctccacgc ggggaccaga ttttcggcct caaa          174
```

<210> SEQ ID NO 390
<211> LENGTH: 174
<212> TYPE: DNA
<213> ORGANISM: Artificial Sequence
<220> FEATURE:
<223> OTHER INFORMATION: Synthetic

<400> SEQUENCE: 390
gggggttttt aggtggcgcg gtcgcgaggc ggattttgat ggttatggtg gcggtgtcgg      60
gagttacgtt gtttttgggt ttcggttcga ggtcggtagg atcgagcggg gtttttagga     120
gaggggtggc ggggagttcg atttttacgc ggggattaga ttttcggttt taaa           174

<210> SEQ ID NO 391
<211> LENGTH: 25
<212> TYPE: DNA
<213> ORGANISM: Artificial Sequence
<220> FEATURE:
<223> OTHER INFORMATION: Synthetic

<400> SEQUENCE: 391
ggagttacgt tgtttttggg tttcg                                            25

<210> SEQ ID NO 392
<211> LENGTH: 20
<212> TYPE: DNA
<213> ORGANISM: Artificial Sequence
<220> FEATURE:
<223> OTHER INFORMATION: Synthetic

<400> SEQUENCE: 392
ctctcctaaa aaccccgctc                                                  20

<210> SEQ ID NO 393
<211> LENGTH: 28
<212> TYPE: DNA
<213> ORGANISM: Artificial Sequence
<220> FEATURE:
<223> OTHER INFORMATION: Synthetic

<400> SEQUENCE: 393
cgcgccgagg cgatcctacc gacctcga                                         28

<210> SEQ ID NO 394
<211> LENGTH: 103
<212> TYPE: DNA
<213> ORGANISM: Homo sapiens

<400> SEQUENCE: 394
gaggtggggg accgggaccg aagcttggag aagaccaaag tggtggtggt ggtggtgggg      60
tggggcagaa gggcgggagc gcgcggctct gggagacaag cac                       103

<210> SEQ ID NO 395
<211> LENGTH: 103
<212> TYPE: DNA
<213> ORGANISM: Artificial Sequence
<220> FEATURE:
<223> OTHER INFORMATION: Synthetic

<400> SEQUENCE: 395
gaggtggggg atcgggatcg aagtttggag aagattaaag tggtggtggt ggtggtgggg      60
tggggtagaa gggcgggagc gcgcggtttt gggagataag tat                       103

<210> SEQ ID NO 396
<211> LENGTH: 24
<212> TYPE: DNA
<213> ORGANISM: Artificial Sequence
<220> FEATURE:
<223> OTHER INFORMATION: Synthetic

<400> SEQUENCE: 396
ggatcgggat cgaagtttgg agaa                                          24

<210> SEQ ID NO 397
<211> LENGTH: 20
<212> TYPE: DNA
<213> ORGANISM: Artificial Sequence
<220> FEATURE:
<223> OTHER INFORMATION: Synthetic

<400> SEQUENCE: 397
cttatctccc aaaaccgcgc                                               20

<210> SEQ ID NO 398
<211> LENGTH: 27
<212> TYPE: DNA
<213> ORGANISM: Artificial Sequence
<220> FEATURE:
<223> OTHER INFORMATION: Synthetic

<400> SEQUENCE: 398
aggccacgga cgcgctcccg cccttct                                       27

<210> SEQ ID NO 399
<211> LENGTH: 138
<212> TYPE: DNA
<213> ORGANISM: Homo sapiens

<400> SEQUENCE: 399
aaccacgctg tgcccgcgtg tgccgggcgg ggaggggagg ccgcagcccc agccccgggg    60
gcctggttgt ctaatcgaag ggaagtaaac ggccccaacg caagcctgac tgcgagacgt   120
gcccaaggga ggtaggtc                                                138

<210> SEQ ID NO 400
<211> LENGTH: 138
<212> TYPE: DNA
<213> ORGANISM: Artificial Sequence
<220> FEATURE:
<223> OTHER INFORMATION: Synthetic

<400> SEQUENCE: 400
aattacgttg tgttcgcgtg tgtcgggcgg ggaggggagg tcgtagtttt agtttcgggg    60
gtttggttgt ttaatcgaag ggaagtaaac ggttttaacg taagtttgat tgcgagacgt   120
gtttaaggga ggtaggtt                                                138

<210> SEQ ID NO 401
<211> LENGTH: 28
<212> TYPE: DNA
<213> ORGANISM: Artificial Sequence
<220> FEATURE:
<223> OTHER INFORMATION: Synthetic

<400> SEQUENCE: 401
ttggttgttt aatcgaaggg aagtaaac                                      28

<210> SEQ ID NO 402

-continued

<211> LENGTH: 23
<212> TYPE: DNA
<213> ORGANISM: Artificial Sequence
<220> FEATURE:
<223> OTHER INFORMATION: Synthetic

<400> SEQUENCE: 402
ctacctccct taaacacgtc tcg                                                                    23

<210> SEQ ID NO 403
<211> LENGTH: 33
<212> TYPE: DNA
<213> ORGANISM: Artificial Sequence
<220> FEATURE:
<223> OTHER INFORMATION: Synthetic

<400> SEQUENCE: 403
cgcgccgagg cggttttaac gtaagtttga ttg                                                         33

<210> SEQ ID NO 404
<211> LENGTH: 104
<212> TYPE: DNA
<213> ORGANISM: Homo sapiens

<400> SEQUENCE: 404
cgcaggaagc cctgggggcg cagccatccc acagcgcggc cgaggtggga ctgggggtcc              60
cgcagcgacc gcttttcttt ggtgggtctg cacgcaccta tccg                              104

<210> SEQ ID NO 405
<211> LENGTH: 104
<212> TYPE: DNA
<213> ORGANISM: Artificial Sequence
<220> FEATURE:
<223> OTHER INFORMATION: Synthetic

<400> SEQUENCE: 405
cgtaggaagt tttgggggcg tagttatttt atagcgcggt cgaggtggga ttggggggttt            60 cgtagcgatc gttttttttt ggtgggtttg tacgtattta ttcg                             104

<210> SEQ ID NO 406
<211> LENGTH: 22
<212> TYPE: DNA
<213> ORGANISM: Artificial Sequence
<220> FEATURE:
<223> OTHER INFORMATION: Synthetic

<400> SEQUENCE: 406
gggcgtagtt attttatagc gc                                                                     22

<210> SEQ ID NO 407
<211> LENGTH: 27
<212> TYPE: DNA
<213> ORGANISM: Artificial Sequence
<220> FEATURE:
<223> OTHER INFORMATION: Synthetic

<400> SEQUENCE: 407
caccaaaaaa aaacgatcgc tacgaaa                                                                27

<210> SEQ ID NO 408
<211> LENGTH: 26
<212> TYPE: DNA
<213> ORGANISM: Artificial Sequence
<220> FEATURE:
<223> OTHER INFORMATION: Synthetic -continued

```
<400> SEQUENCE: 408
aggccacgga cgcggtcgag gtggga                                       26

<210> SEQ ID NO 409
<211> LENGTH: 99
<212> TYPE: DNA
<213> ORGANISM: Homo sapiens

<400> SEQUENCE: 409
cgggtgtttg tgtatatgtg ttgcggggaa gacggaggtg cgggtggaga aggggaggat    60
gtaccaaggg ccatggggag acgctaggca ggggcttcc                          99

<210> SEQ ID NO 410
<211> LENGTH: 99
<212> TYPE: DNA
<213> ORGANISM: Artificial Sequence
<220> FEATURE:
<223> OTHER INFORMATION: Synthetic

<400> SEQUENCE: 410
cgggtgtttg tgtatatgtg ttgcggggaa gacggaggtg cgggtggaga aggggaggat    60
gtattaaggg ttatggggag acgttaggta ggggttttt                          99

<210> SEQ ID NO 411
<211> LENGTH: 17
<212> TYPE: DNA
<213> ORGANISM: Artificial Sequence
<220> FEATURE:
<223> OTHER INFORMATION: Synthetic

<400> SEQUENCE: 411
cggggaagac ggaggtg                                                  17

<210> SEQ ID NO 412
<211> LENGTH: 22
<212> TYPE: DNA
<213> ORGANISM: Artificial Sequence
<220> FEATURE:
<223> OTHER INFORMATION: Synthetic

<400> SEQUENCE: 412
aaacccctac ctaacgtctc cc                                            22

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
cgcgccgagg gcgggtggag aagg                                          24

<210> SEQ ID NO 414
<211> LENGTH: 105
<212> TYPE: DNA
<213> ORGANISM: Homo sapiens

<400> SEQUENCE: 414
cggcaagcta cggaacaggt ggcggggctg cagcacccca atgaccgatc aaccgcaaag    60
gccggaaatg cgtcagccgt tctgagccca ctggctgaag ccagg                   105
```

-continued

```
<210> SEQ ID NO 415
<211> LENGTH: 105
<212> TYPE: DNA
<213> ORGANISM: Artificial Sequence
<220> FEATURE:
<223> OTHER INFORMATION: Synthetic

<400> SEQUENCE: 415
cggtaagtta cggaataggt ggcggggttg tagtatttta atgatcgatt aatcgtaaag      60
gtcggaaatg cgttagtcgt tttgagttta ttggttgaag ttagg                     105

<210> SEQ ID NO 416
<211> LENGTH: 26
<212> TYPE: DNA
<213> ORGANISM: Artificial Sequence
<220> FEATURE:
<223> OTHER INFORMATION: Synthetic

<400> SEQUENCE: 416
cggggttgta gtattttaat gatcga                                           26

<210> SEQ ID NO 417
<211> LENGTH: 30
<212> TYPE: DNA
<213> ORGANISM: Artificial Sequence
<220> FEATURE:
<223> OTHER INFORMATION: Synthetic

<400> SEQUENCE: 417
cttcaaccaa taaactcaaa acgactaacg                                       30

<210> SEQ ID NO 418
<211> LENGTH: 31
<212> TYPE: DNA
<213> ORGANISM: Artificial Sequence
<220> FEATURE:
<223> OTHER INFORMATION: Synthetic

<400> SEQUENCE: 418
aggccacgga cggcatttcc gacctttacg a                                     31

<210> SEQ ID NO 419
<211> LENGTH: 88
<212> TYPE: DNA
<213> ORGANISM: Homo sapiens

<400> SEQUENCE: 419
ccccgcacgg gggcgcctcc ccgcggccct ggggcggggc cacccctcgg ggtctgtggg      60
acgcgcctgc ccccaattct gccacccg                                         88

<210> SEQ ID NO 420
<211> LENGTH: 88
<212> TYPE: DNA
<213> ORGANISM: Artificial Sequence
<220> FEATURE:
<223> OTHER INFORMATION: Synthetic

<400> SEQUENCE: 420
tttcgtacgg gggcgttttt tcgcggtttt ggggcggggt tattttttcgg ggtttgtggg     60 acgcgtttgt ttttaatttt gttattcg                                         88

<210> SEQ ID NO 421
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 421
ggcgtttttt cgcggttttg                                                        20

<210> SEQ ID NO 422
<211> LENGTH: 17
<212> TYPE: DNA
<213> ORGANISM: Artificial Sequence
<220> FEATURE:
<223> OTHER INFORMATION: Synthetic

<400> SEQUENCE: 422
gcgtcccaca aaccccg                                                           17

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423
cgcgccgagg gaaaaataac cccgccc                                                27

<210> SEQ ID NO 424
<211> LENGTH: 80
<212> TYPE: DNA
<213> ORGANISM: Homo sapiens

<400> SEQUENCE: 424
gcgggcacac gcagggtggg tggtcacgcc cgcagggtcc gcgagcgcgg cgcagagcgc          60
gggccgtggg aagtttctcc                                                        80

<210> SEQ ID NO 425
<211> LENGTH: 80
<212> TYPE: DNA
<213> ORGANISM: Artificial Sequence
<220> FEATURE:
<223> OTHER INFORMATION: Synthetic

<400> SEQUENCE: 425
gcgggtatac gtagggtggg tggttacgtt cgtagggttc gcgagcgcgg cgtagagcgc          60
gggtcgtggg aagttttttt                                                        80

<210> SEQ ID NO 426
<211> LENGTH: 22
<212> TYPE: DNA
<213> ORGANISM: Artificial Sequence
<220> FEATURE:
<223> OTHER INFORMATION: Synthetic

<400> SEQUENCE: 426
cgtagggtgg gtggttacgt tc                                                     22

<210> SEQ ID NO 427
<211> LENGTH: 16
<212> TYPE: DNA
<213> ORGANISM: Artificial Sequence
<220> FEATURE:
<223> OTHER INFORMATION: Synthetic
```

-continued

```
<400> SEQUENCE: 427
aacttcccac gacccg                                                      16

<210> SEQ ID NO 428
<211> LENGTH: 27
<212> TYPE: DNA
<213> ORGANISM: Artificial Sequence
<220> FEATURE:
<223> OTHER INFORMATION: Synthetic

<400> SEQUENCE: 428
aggccacgga cgcgtagggt tcgcgag                                          27

<210> SEQ ID NO 429
<211> LENGTH: 94
<212> TYPE: DNA
<213> ORGANISM: Homo sapiens

<400> SEQUENCE: 429
gtgccacgcg gccttcaccc ctgtgactcc ccgcagctcg cgcggatgca ccgacgagtc    60
agcttgtcct ctggaagcca atgagtctcc ccgg                                 94

<210> SEQ ID NO 430
<211> LENGTH: 94
<212> TYPE: DNA
<213> ORGANISM: Artificial Sequence
<220> FEATURE:
<223> OTHER INFORMATION: Synthetic

<400> SEQUENCE: 430
gtgttacgcg gtttttattt ttgtgatttt tcgtagttcg cgcggatgta tcgacgagtt    60
agtttgtttt ttggaagtta atgagttttt tcgg                                 94

<210> SEQ ID NO 431
<211> LENGTH: 31
<212> TYPE: DNA
<213> ORGANISM: Artificial Sequence
<220> FEATURE:
<223> OTHER INFORMATION: Synthetic

<400> SEQUENCE: 431
gttacgcggt ttttattttt gtgatttttc g                                    31

<210> SEQ ID NO 432
<211> LENGTH: 33
<212> TYPE: DNA
<213> ORGANISM: Artificial Sequence
<220> FEATURE:
<223> OTHER INFORMATION: Synthetic

<400> SEQUENCE: 432
ctcattaact tccaaaaaac aaactaactc gtc                                   33

<210> SEQ ID NO 433
<211> LENGTH: 25
<212> TYPE: DNA
<213> ORGANISM: Artificial Sequence
<220> FEATURE:
<223> OTHER INFORMATION: Synthetic

<400> SEQUENCE: 433
cgcgccgagg cgatacatcc gcgcg                                           25
```

-continued

```
<210> SEQ ID NO 434
<211> LENGTH: 86
<212> TYPE: DNA
<213> ORGANISM: Homo sapiens

<400> SEQUENCE: 434
cggcgcacca gagtcccaag gagcccgacg gccgaggcgc ggattgagtc ccgtgtctgc      60
gtgggagggc gcagtcaggg caggcg                                          86

<210> SEQ ID NO 435
<211> LENGTH: 86
<212> TYPE: DNA
<213> ORGANISM: Artificial Sequence
<220> FEATURE:
<223> OTHER INFORMATION: Synthetic

<400> SEQUENCE: 435
cggcgtatta gagtttttaag gagttcgacg gtcgaggcgc ggattgagtt tcgtgtttgc     60
gtgggagggc gtagttaggg taggcg                                          86

<210> SEQ ID NO 436
<211> LENGTH: 19
<212> TYPE: DNA
<213> ORGANISM: Artificial Sequence
<220> FEATURE:
<223> OTHER INFORMATION: Synthetic

<400> SEQUENCE: 436
gagttcgacg gtcgaggcg                                                  19

<210> SEQ ID NO 437
<211> LENGTH: 17
<212> TYPE: DNA
<213> ORGANISM: Artificial Sequence
<220> FEATURE:
<223> OTHER INFORMATION: Synthetic

<400> SEQUENCE: 437
actacgccct cccacgc                                                    17

<210> SEQ ID NO 438
<211> LENGTH: 29
<212> TYPE: DNA
<213> ORGANISM: Artificial Sequence
<220> FEATURE:
<223> OTHER INFORMATION: Synthetic

<400> SEQUENCE: 438
aggccacgga cggcggattg agtttcgtg                                       29

<210> SEQ ID NO 439
<211> LENGTH: 80
<212> TYPE: DNA
<213> ORGANISM: Homo sapiens

<400> SEQUENCE: 439
cgccgcagtc cctcgcctca gcggcggaag gcgcggccac ctccccgccc tccagcggtg      60
gcccgcgggt ggtggagcgg                                                 80

<210> SEQ ID NO 440
<211> LENGTH: 80
<212> TYPE: DNA
<213> ORGANISM: Artificial Sequence
<220> FEATURE:
```

-continued

<223> OTHER INFORMATION: Synthetic

<400> SEQUENCE: 440
cgtcgtagtt tttcgtttta gcggcggaag gcgcggttat tttttcgttt tttagcggtg      60
gttcgcgggt ggtggagcgg                                                  80

<210> SEQ ID NO 441
<211> LENGTH: 19
<212> TYPE: DNA
<213> ORGANISM: Artificial Sequence
<220> FEATURE:
<223> OTHER INFORMATION: Synthetic

<400> SEQUENCE: 441
tcgttttagc ggcggaagg                                                   19

<210> SEQ ID NO 442
<211> LENGTH: 14
<212> TYPE: DNA
<213> ORGANISM: Artificial Sequence
<220> FEATURE:
<223> OTHER INFORMATION: Synthetic

<400> SEQUENCE: 442
ccgcgaacca ccgc                                                        14

<210> SEQ ID NO 443
<211> LENGTH: 30
<212> TYPE: DNA
<213> ORGANISM: Artificial Sequence
<220> FEATURE:
<223> OTHER INFORMATION: Synthetic

<400> SEQUENCE: 443
aggccacgga cggcgcggtt attttttcgt                                       30

<210> SEQ ID NO 444
<211> LENGTH: 78
<212> TYPE: DNA
<213> ORGANISM: Homo sapiens

<400> SEQUENCE: 444
gcgggctgca gctggagggc gagcgcgccg cccgcacacc cacctcccgc actcccgccc      60
ctcgcgaggg cgtcccgc                                                    78

<210> SEQ ID NO 445
<211> LENGTH: 78
<212> TYPE: DNA
<213> ORGANISM: Artificial Sequence
<220> FEATURE:
<223> OTHER INFORMATION: Synthetic

<400> SEQUENCE: 445
gcgggttgta gttggagggc gagcgcgtcg ttcgtatatt tatttttcgt attttcgttt      60
ttcgcgaggg cgtttcgt                                                    78

<210> SEQ ID NO 446
<211> LENGTH: 20
<212> TYPE: DNA
<213> ORGANISM: Artificial Sequence
<220> FEATURE:
<223> OTHER INFORMATION: Synthetic

<400> SEQUENCE: 446

-continued ggttgtagtt ggagggcgag                                                    20

<210> SEQ ID NO 447
<211> LENGTH: 16
<212> TYPE: DNA
<213> ORGANISM: Artificial Sequence
<220> FEATURE:
<223> OTHER INFORMATION: Synthetic

<400> SEQUENCE: 447
cgaaacgccc tcgcga                                                        16

<210> SEQ ID NO 448
<211> LENGTH: 29
<212> TYPE: DNA
<213> ORGANISM: Artificial Sequence
<220> FEATURE:
<223> OTHER INFORMATION: Synthetic

<400> SEQUENCE: 448
cgcgccgagg gcgcgtcgtt cgtatattt                                          29

<210> SEQ ID NO 449
<211> LENGTH: 121
<212> TYPE: DNA
<213> ORGANISM: Homo sapiens

<400> SEQUENCE: 449
ccgatttcca gatctgcttg ctgtgcaagg agatgtgcgg ctcgccggcg ccgctctcct        60
ccaactcgtc cgcgtcgtcg tcctcctcgc agacgtccac gtcgtcgggg ggcggcggcg       120
g                                                                       121

<210> SEQ ID NO 450
<211> LENGTH: 121
<212> TYPE: DNA
<213> ORGANISM: Artificial Sequence
<220> FEATURE:
<223> OTHER INFORMATION: Synthetic

<400> SEQUENCE: 450 tcgatttta gatttgtttg ttgtgtaagg agatgtgcgg ttcgtcggcg tcgttttttt        60
ttaattcgtt cgcgtcgtcg tttttttcgt agacgtttac gtcgtcgggg ggcggcggcg       120
g                                                                       121

<210> SEQ ID NO 451
<211> LENGTH: 24
<212> TYPE: DNA
<213> ORGANISM: Artificial Sequence
<220> FEATURE:
<223> OTHER INFORMATION: Synthetic

<400> SEQUENCE: 451
gttgtgtaag gagatgtgcg gttc                                               24

<210> SEQ ID NO 452
<211> LENGTH: 19
<212> TYPE: DNA
<213> ORGANISM: Artificial Sequence
<220> FEATURE:
<223> OTHER INFORMATION: Synthetic

<400> SEQUENCE: 452

```
aaacgacgac gcgaacgaa                                                    19

<210> SEQ ID NO 453
<211> LENGTH: 27
<212> TYPE: DNA
<213> ORGANISM: Artificial Sequence
<220> FEATURE:
<223> OTHER INFORMATION: Synthetic

<400> SEQUENCE: 453
aggccacgga cgcgtcggcg tcgtttt                                           27

<210> SEQ ID NO 454
<211> LENGTH: 122
<212> TYPE: DNA
<213> ORGANISM: Homo sapiens

<400> SEQUENCE: 454
ggccgagctc cggcggccac tccgcagtgc gctctcgcga gccggggccg cgaggcctcc      60
aacgcggttc cgcacccta atgccccagg gcggtgagca ccccgcggtt ccccgcccgc      120
ct                                                                     122

<210> SEQ ID NO 455
<211> LENGTH: 122
<212> TYPE: DNA
<213> ORGANISM: Artificial Sequence
<220> FEATURE:
<223> OTHER INFORMATION: Synthetic

<400> SEQUENCE: 455
ggtcgagttt cggcggttat ttcgtagtgc gttttcgcga gtcggggtcg cgaggttttt      60
aacgcggttt cgtattttta atgtttttagg gcggtgagta tttcgcggtt tttcgttcgt     120
tt                                                                     122

<210> SEQ ID NO 456
<211> LENGTH: 21
<212> TYPE: DNA
<213> ORGANISM: Artificial Sequence
<220> FEATURE:
<223> OTHER INFORMATION: Synthetic

<400> SEQUENCE: 456
cgtagtgcgt tttcgcgagt c                                                 21

<210> SEQ ID NO 457
<211> LENGTH: 29
<212> TYPE: DNA
<213> ORGANISM: Artificial Sequence
<220> FEATURE:
<223> OTHER INFORMATION: Synthetic

<400> SEQUENCE: 457
cgccctaaaa cattaaaaat acgaaaccg                                         29

<210> SEQ ID NO 458
<211> LENGTH: 27
<212> TYPE: DNA
<213> ORGANISM: Artificial Sequence
<220> FEATURE:
<223> OTHER INFORMATION: Synthetic

<400> SEQUENCE: 458
cgcgccgagg gcgttaaaaa cctcgcg                                          27
```

-continued

```
<210> SEQ ID NO 459
<211> LENGTH: 160
<212> TYPE: DNA
<213> ORGANISM: Homo sapiens

<400> SEQUENCE: 459
cggtggaaaa gacagctgag cccccacctc ccttcacatt ccagaaaagt gtctgaaagg      60 cccgggcgc ttcggggctt gccaagagac ggtgtttaga gaaagagcat aacgcgaagt     120
cacaatcgca ggaaactcgc agcagccccc catccccgcc                           160

<210> SEQ ID NO 460
<211> LENGTH: 160
<212> TYPE: DNA
<213> ORGANISM: Artificial Sequence
<220> FEATURE:
<223> OTHER INFORMATION: Synthetic

<400> SEQUENCE: 460
cggtggaaaa gatagttgag tttttatttt tttttatatt ttagaaaagt gtttgaaagg      60 ttcgggcgt ttcggggttt gttaagagac ggtgtttaga gaaagagtat aacgcgaagt     120
tataatcgta ggaaattcgt agtagttttt tattttcgtt                           160

<210> SEQ ID NO 461
<211> LENGTH: 23
<212> TYPE: DNA
<213> ORGANISM: Artificial Sequence
<220> FEATURE:
<223> OTHER INFORMATION: Synthetic

<400> SEQUENCE: 461
gtttcggggt ttgttaagag acg                                             23

<210> SEQ ID NO 462
<211> LENGTH: 32
<212> TYPE: DNA
<213> ORGANISM: Artificial Sequence
<220> FEATURE:
<223> OTHER INFORMATION: Synthetic

<400> SEQUENCE: 462
actactacga atttcctacg attataactt cg                                   32

<210> SEQ ID NO 463
<211> LENGTH: 34
<212> TYPE: DNA
<213> ORGANISM: Artificial Sequence
<220> FEATURE:
<223> OTHER INFORMATION: Synthetic

<400> SEQUENCE: 463
cgcgccgagg gcgttatact ctttctctaa acac                                 34

<210> SEQ ID NO 464
<211> LENGTH: 165
<212> TYPE: DNA
<213> ORGANISM: Homo sapiens

<400> SEQUENCE: 464
ctgcagcctc cagcccggcc cgcgcggcga cccagtcccc tgtcgcccga atcttccacc      60
gctgcgaagc gtccccgggc gagcgccctg ctctccgcgc tgcgcggaag ccagagccgg     120
```
tcctcacagt gaactcgccc agccctgctc gcggctctct cgatt                    165

<210> SEQ ID NO 465
<211> LENGTH: 165
<212> TYPE: DNA
<213> ORGANISM: Artificial Sequence
<220> FEATURE:
<223> OTHER INFORMATION: Synthetic

<400> SEQUENCE: 465
ttgtagtttt tagttcggtt cgcgcggcga tttagttttt tgtcgttcga attttttatc    60
gttgcgaagc gttttcgggc gagcgttttg ttttcgcgt tgcgcggaag ttagagtcgg      120
tttttatagt gaattcgttt agttttgttc gcggtttttt cgatt                   165

<210> SEQ ID NO 466
<211> LENGTH: 21
<212> TYPE: DNA
<213> ORGANISM: Artificial Sequence
<220> FEATURE:
<223> OTHER INFORMATION: Synthetic

<400> SEQUENCE: 466
agtttttagt tcggttcgcg c                                              21

<210> SEQ ID NO 467
<211> LENGTH: 20
<212> TYPE: DNA
<213> ORGANISM: Artificial Sequence
<220> FEATURE:
<223> OTHER INFORMATION: Synthetic

<400> SEQUENCE: 467
cccgaaaacg cttcgcaacg                                                20

<210> SEQ ID NO 468
<211> LENGTH: 33
<212> TYPE: DNA
<213> ORGANISM: Artificial Sequence
<220> FEATURE:
<223> OTHER INFORMATION: Synthetic

<400> SEQUENCE: 468
aggccacgga cgcggcgatt tagttttttg tcg                                 33

<210> SEQ ID NO 469
<211> LENGTH: 144
<212> TYPE: DNA
<213> ORGANISM: Homo sapiens

<400> SEQUENCE: 469
cgcacaatcg gctgggacaa ggcagggaag ctgtggcgac ctgcaggggt tcacaagccc    60
ggaggccgat ggggtttgtc agtgacacca gaggggaaaa gcctcacaga gcaggaacac    120
cccccgccgc caggtgctgg gtgc                                          144

<210> SEQ ID NO 470
<211> LENGTH: 144
<212> TYPE: DNA
<213> ORGANISM: Artificial Sequence
<220> FEATURE:
<223> OTHER INFORMATION: Synthetic

<400> SEQUENCE: 470
cgtataatcg gttgggataa ggtagggaag ttgtggcgat ttgtaggggt ttataagttc    60

-continued

```
ggaggtcgat ggggtttgtt agtgatatta gaggggaaaa gttttataga gtaggaatat      120
ttttcgtcgt taggtgttgg gtgt                                             144

<210> SEQ ID NO 471
<211> LENGTH: 23
<212> TYPE: DNA
<213> ORGANISM: Artificial Sequence
<220> FEATURE:
<223> OTHER INFORMATION: Synthetic

<400> SEQUENCE: 471
gataaggtag ggaagttgtg gcg                                              23

<210> SEQ ID NO 472
<211> LENGTH: 28
<212> TYPE: DNA
<213> ORGANISM: Artificial Sequence
<220> FEATURE:
<223> OTHER INFORMATION: Synthetic

<400> SEQUENCE: 472
cctctaatat cactaacaaa ccccatcg                                         28

<210> SEQ ID NO 473
<211> LENGTH: 31
<212> TYPE: DNA
<213> ORGANISM: Artificial Sequence
<220> FEATURE:
<223> OTHER INFORMATION: Synthetic

<400> SEQUENCE: 473
cgcgccgagg gacctccgaa cttataaacc c                                     31

<210> SEQ ID NO 474
<211> LENGTH: 97
<212> TYPE: DNA
<213> ORGANISM: Homo sapiens

<400> SEQUENCE: 474
cggcatgagc gcggtgagct gcggcaacgg gaagctccgc cagtggctga tcgaccagat      60
cgacagcggc aagtaccccg ggctggtgtg ggagaac                               97

<210> SEQ ID NO 475
<211> LENGTH: 97
<212> TYPE: DNA
<213> ORGANISM: Artificial Sequence
<220> FEATURE:
<223> OTHER INFORMATION: Synthetic

<400> SEQUENCE: 475
cggtatgagc gcggtgagtt gcggtaacgg gaagtttcgt tagtggttga tcgattagat      60
cgatagcggt aagtatttcg ggttggtgtg ggagaat                               97

<210> SEQ ID NO 476
<211> LENGTH: 19
<212> TYPE: DNA
<213> ORGANISM: Artificial Sequence
<220> FEATURE:
<223> OTHER INFORMATION: Synthetic

<400> SEQUENCE: 476
cgcggtgagt tgcggtaac                                                   19
```

```
<210> SEQ ID NO 477
<211> LENGTH: 30
<212> TYPE: DNA
<213> ORGANISM: Artificial Sequence
<220> FEATURE:
<223> OTHER INFORMATION: Synthetic

<400> SEQUENCE: 477
cgaaatactt accgctatcg atctaatcga                                              30

<210> SEQ ID NO 478
<211> LENGTH: 31
<212> TYPE: DNA
<213> ORGANISM: Artificial Sequence
<220> FEATURE:
<223> OTHER INFORMATION: Synthetic

<400> SEQUENCE: 478
aggccacgga cgcgggaagt ttcgttagtg g                                            31

<210> SEQ ID NO 479
<211> LENGTH: 64
<212> TYPE: DNA
<213> ORGANISM: Homo sapiens

<400> SEQUENCE: 479
ggcagcccga actccggcgc gccaggtttt tccagccgcc gcgagcgccg ggagggaggg           60
cagc                                                                          64

<210> SEQ ID NO 480
<211> LENGTH: 64
<212> TYPE: DNA
<213> ORGANISM: Artificial Sequence
<220> FEATURE:
<223> OTHER INFORMATION: Synthetic

<400> SEQUENCE: 480
ggtagttcga atttcggcgc gttaggtttt tttagtcgtc gcgagcgtcg ggagggaggg           60
tagt                                                                          64

<210> SEQ ID NO 481
<211> LENGTH: 20
<212> TYPE: DNA
<213> ORGANISM: Artificial Sequence
<220> FEATURE:
<223> OTHER INFORMATION: Synthetic

<400> SEQUENCE: 481
ggtagttcga atttcggcgc                                                         20

<210> SEQ ID NO 482
<211> LENGTH: 17
<212> TYPE: DNA
<213> ORGANISM: Artificial Sequence
<220> FEATURE:
<223> OTHER INFORMATION: Synthetic

<400> SEQUENCE: 482
ctccctcccg acgctcg                                                            17

<210> SEQ ID NO 483
<211> LENGTH: 32
<212> TYPE: DNA
<213> ORGANISM: Artificial Sequence
```

-continued

<220> FEATURE:
<223> OTHER INFORMATION: Synthetic

<400> SEQUENCE: 483
cgcgccgagg cgttaggttt ttttagtcgt cg                                             32

<210> SEQ ID NO 484
<211> LENGTH: 163
<212> TYPE: DNA
<213> ORGANISM: Homo sapiens

<400> SEQUENCE: 484
cgcagtccct cggcggcgac gcggagcgcg gccacccgtt ccgagagcgc acggcggcaa    60
ataaggccag gataggtggc tggctggcga cgggggcgcc tgcggcggcg cgcgctgctg    120
tccgtggtgt tggaaccacg ctctccgccc gctcccgggc gtc                       163

<210> SEQ ID NO 485
<211> LENGTH: 163
<212> TYPE: DNA
<213> ORGANISM: Artificial Sequence
<220> FEATURE:
<223> OTHER INFORMATION: Synthetic

<400> SEQUENCE: 485
cgtagttttt cggcggcgac gcggagcgcg gttattcgtt tcgagagcgt acggcggtaa    60
ataaggttag gataggtggt tggttggcga cgggggcgtt tgcggcggcg cgcgttgttg    120
ttcgtggtgt tggaattacg tttttcgttc gttttcgggc gtt                       163

<210> SEQ ID NO 486
<211> LENGTH: 20
<212> TYPE: DNA
<213> ORGANISM: Artificial Sequence
<220> FEATURE:
<223> OTHER INFORMATION: Synthetic

<400> SEQUENCE: 486
gtagtttttc ggcggcgacg                                                   20

<210> SEQ ID NO 487
<211> LENGTH: 21
<212> TYPE: DNA
<213> ORGANISM: Artificial Sequence
<220> FEATURE:
<223> OTHER INFORMATION: Synthetic

<400> SEQUENCE: 487
ccttatttac cgccgtacgc t                                                 21

<210> SEQ ID NO 488
<211> LENGTH: 31
<212> TYPE: DNA
<213> ORGANISM: Artificial Sequence
<220> FEATURE:
<223> OTHER INFORMATION: Synthetic

<400> SEQUENCE: 488
aggccacgga cgtctcgaaa cgaataaccg c                                      31

<210> SEQ ID NO 489
<211> LENGTH: 128
<212> TYPE: DNA
<213> ORGANISM: Homo sapiens -continued

```
<400> SEQUENCE: 489
cgcccggggc gtcgggaggg ggcccgcgcg ggtcgcgccc tgcctggcgg tgggaccagc      60
tatcctcggc gcccagcgca gcgcgccccc tcccgacgcg cggtcggggc cgcagtggtc     120
gccctgcg                                                              128

<210> SEQ ID NO 490
<211> LENGTH: 128
<212> TYPE: DNA
<213> ORGANISM: Artificial Sequence
<220> FEATURE:
<223> OTHER INFORMATION: Synthetic

<400> SEQUENCE: 490
cgttcggggc gtcgggaggg ggttcgcgcg ggtcgcgttt tgtttggcgg tgggattagt      60
tattttcggc gtttagcgta gcgcgttttt tttcgacgcg cggtcggggt cgtagtggtc     120
gttttgcg                                                              128

<210> SEQ ID NO 491
<211> LENGTH: 19
<212> TYPE: DNA
<213> ORGANISM: Artificial Sequence
<220> FEATURE:
<223> OTHER INFORMATION: Synthetic

<400> SEQUENCE: 491
ggtcgcgttt tgtttggcg                                                   19

<210> SEQ ID NO 492
<211> LENGTH: 21
<212> TYPE: DNA
<213> ORGANISM: Artificial Sequence
<220> FEATURE:
<223> OTHER INFORMATION: Synthetic

<400> SEQUENCE: 492
cgcgcgtcga aaaaaacgc g                                                 21

<210> SEQ ID NO 493
<211> LENGTH: 26
<212> TYPE: DNA
<213> ORGANISM: Artificial Sequence
<220> FEATURE:
<223> OTHER INFORMATION: Synthetic

<400> SEQUENCE: 493
cgcgccgagg gctacgctaa acgccg                                           26

<210> SEQ ID NO 494
<211> LENGTH: 153
<212> TYPE: DNA
<213> ORGANISM: Homo sapiens

<400> SEQUENCE: 494
agctcgggaa cccgcgatac ccggccgggg gacgacaggg ggcgacaaac tgtaaggttt      60
tccctatgcc cgaccgtgca gaaggctgca gcgagggctg tgtgctcccg atcgcgcaca     120
gctggctgcg ggaaagggc caggattgag acg                                   153

<210> SEQ ID NO 495
<211> LENGTH: 153
<212> TYPE: DNA
<213> ORGANISM: Artificial Sequence
```

-continued

```
<220> FEATURE:
<223> OTHER INFORMATION: Synthetic

<400> SEQUENCE: 495
agttcgggaa ttcgcgatat tcggtcgggg gacgataggg ggcgataaat tgtaaggttt      60
tttttatgtt cgatcgtgta gaaggttgta gcgaggggttg tgtgttttcg atcgcgtata     120
gttggttgcg ggaaaggggt taggattgag acg                                   153

<210> SEQ ID NO 496
<211> LENGTH: 23
<212> TYPE: DNA
<213> ORGANISM: Artificial Sequence
<220> FEATURE:
<223> OTHER INFORMATION: Synthetic

<400> SEQUENCE: 496
cgatcgtgta gaaggttgta gcg                                               23

<210> SEQ ID NO 497
<211> LENGTH: 23
<212> TYPE: DNA
<213> ORGANISM: Artificial Sequence
<220> FEATURE:
<223> OTHER INFORMATION: Synthetic

<400> SEQUENCE: 497
tttcccgcaa ccaactatac gcg                                               23

<210> SEQ ID NO 498
<211> LENGTH: 31
<212> TYPE: DNA
<213> ORGANISM: Artificial Sequence
<220> FEATURE:
<223> OTHER INFORMATION: Synthetic

<400> SEQUENCE: 498
aggccacgga cggatcgaaa acacacaacc c                                      31

<210> SEQ ID NO 499
<211> LENGTH: 75
<212> TYPE: DNA
<213> ORGANISM: Homo sapiens

<400> SEQUENCE: 499
gggccgcgcg gacctcggcg ggacccagcg ggcccgggcg ggcgcaccag ccgcccttttg      60 tcctccgcct ccggg                                                        75

<210> SEQ ID NO 500
<211> LENGTH: 75
<212> TYPE: DNA
<213> ORGANISM: Artificial Sequence
<220> FEATURE:
<223> OTHER INFORMATION: Synthetic

<400> SEQUENCE: 500
gggtcgcgcg gatttcggcg ggatttagcg ggttcgggcg ggcgtattag tcgttttttg       60
tttttcgttt tcggg                                                        75

<210> SEQ ID NO 501
<211> LENGTH: 19
<212> TYPE: DNA
<213> ORGANISM: Artificial Sequence
<220> FEATURE:
```

-continued

<223> OTHER INFORMATION: Synthetic

<400> SEQUENCE: 501
cgggatttag cgggttcgg                                                    19

<210> SEQ ID NO 502
<211> LENGTH: 26
<212> TYPE: DNA
<213> ORGANISM: Artificial Sequence
<220> FEATURE:
<223> OTHER INFORMATION: Synthetic

<400> SEQUENCE: 502
cccgaaaacg aaaaacaaaa aacgac                                            26

<210> SEQ ID NO 503
<211> LENGTH: 25
<212> TYPE: DNA
<213> ORGANISM: Artificial Sequence
<220> FEATURE:
<223> OTHER INFORMATION: Synthetic

<400> SEQUENCE: 503
cgcgccgagg ggcgggcgta ttagt                                             25

<210> SEQ ID NO 504
<211> LENGTH: 193
<212> TYPE: DNA
<213> ORGANISM: Homo sapiens

<400> SEQUENCE: 504
gtctgcaaga gataaaaagc tagcccacga tccacccaca atcctcgtgt ccccggggtg       60
ccctcgcagt tgccaaacct acgggccgcg tttaggggaa gcctccgcgt cctggcggcc      120
aaaagaatgg gctccttcca gcttccccct accggatacc acctgcaaat ctattgccag      180
aggcgcagct ccc                                                        193

<210> SEQ ID NO 505
<211> LENGTH: 188
<212> TYPE: DNA
<213> ORGANISM: Artificial Sequence
<220> FEATURE:
<223> OTHER INFORMATION: Synthetic

<400> SEQUENCE: 505
gtttgtaaga gataaaaagt tagtttacga tttatttata attttcgtgt tttcggggtg       60
ttttcgtagt tgttaaattt acgggtcgcg tttaggggaa gttttcgcgt tttggcggtt      120
aaaagaatgg gttttttttta gttttttttt atcggatatt atttgtaaat ttattgttag      180
aggcgtag                                                              188

<210> SEQ ID NO 506
<211> LENGTH: 30
<212> TYPE: DNA
<213> ORGANISM: Artificial Sequence
<220> FEATURE:
<223> OTHER INFORMATION: Synthetic

<400> SEQUENCE: 506
tcggggtgtt ttcgtagttg ttaaatttac                                        30

<210> SEQ ID NO 507
<211> LENGTH: 24

-continued

```
<212> TYPE: DNA
<213> ORGANISM: Artificial Sequence
<220> FEATURE:
<223> OTHER INFORMATION: Synthetic

<400> SEQUENCE: 507
cattctttta accgccaaaa cgcg                                           24

<210> SEQ ID NO 508
<211> LENGTH: 27
<212> TYPE: DNA
<213> ORGANISM: Artificial Sequence
<220> FEATURE:
<223> OTHER INFORMATION: Synthetic

<400> SEQUENCE: 508
aggccacgga cgcgggtcgc gtttagg                                        27

<210> SEQ ID NO 509
<211> LENGTH: 111
<212> TYPE: DNA
<213> ORGANISM: Homo sapiens

<400> SEQUENCE: 509
gcggggtcct ggcccccgcc agcccagccc cgatctcccg ggcagccttt gggcgccacc    60
tccggtcgcc cagagctgtc aagtggggac cttcccggag aggagccgcc g            111

<210> SEQ ID NO 510
<211> LENGTH: 111
<212> TYPE: DNA
<213> ORGANISM: Artificial Sequence
<220> FEATURE:
<223> OTHER INFORMATION: Synthetic

<400> SEQUENCE: 510
gcggggtttt ggttttcgtt agtttagttt cgatttttcg ggtagttttt gggcgttatt    60
ttcggtcgtt tagagttgtt aagtggggat tttttcggag aggagtcgtc g            111

<210> SEQ ID NO 511
<211> LENGTH: 28
<212> TYPE: DNA
<213> ORGANISM: Artificial Sequence
<220> FEATURE:
<223> OTHER INFORMATION: Synthetic

<400> SEQUENCE: 511
gggttttggt tttcgttagt ttagtttc                                      28

<210> SEQ ID NO 512
<211> LENGTH: 26
<212> TYPE: DNA
<213> ORGANISM: Artificial Sequence
<220> FEATURE:
<223> OTHER INFORMATION: Synthetic

<400> SEQUENCE: 512
acaactctaa acgaccgaaa ataacg                                        26

<210> SEQ ID NO 513
<211> LENGTH: 34
<212> TYPE: DNA
<213> ORGANISM: Artificial Sequence
<220> FEATURE:
<223> OTHER INFORMATION: Synthetic
```

-continued

```
<400> SEQUENCE: 513
aggccacgga cgcgattttt cgggtagttt ttgg                           34

<210> SEQ ID NO 514
<211> LENGTH: 99
<212> TYPE: DNA
<213> ORGANISM: Homo sapiens

<400> SEQUENCE: 514
cggcggtcgg agcccagcca gcggcttccc ggccgagatg cgcgctcagg aggcagccgc   60
aggtcgcgga gggcgggcgg cgctgccggg gtgtctgcg                       99

<210> SEQ ID NO 515
<211> LENGTH: 99
<212> TYPE: DNA
<213> ORGANISM: Artificial Sequence
<220> FEATURE:
<223> OTHER INFORMATION: Synthetic

<400> SEQUENCE: 515
cggcggtcgg agtttagtta gcggtttttc ggtcgagatg cgcgtttagg aggtagtcgt   60
aggtcgcgga gggcgggcgg cgttgtcggg gtgtttgcg                       99

<210> SEQ ID NO 516
<211> LENGTH: 21
<212> TYPE: DNA
<213> ORGANISM: Artificial Sequence
<220> FEATURE:
<223> OTHER INFORMATION: Synthetic

<400> SEQUENCE: 516
gcggtcggag tttagttagc g                                         21

<210> SEQ ID NO 517
<211> LENGTH: 24
<212> TYPE: DNA
<213> ORGANISM: Artificial Sequence
<220> FEATURE:
<223> OTHER INFORMATION: Synthetic

<400> SEQUENCE: 517
acctacgact acctcctaaa cgcg                                      24

<210> SEQ ID NO 518
<211> LENGTH: 28
<212> TYPE: DNA
<213> ORGANISM: Artificial Sequence
<220> FEATURE:
<223> OTHER INFORMATION: Synthetic

<400> SEQUENCE: 518
cgcgccgagg ggtttttcgg tcgagatg                                  28

<210> SEQ ID NO 519
<211> LENGTH: 99
<212> TYPE: DNA
<213> ORGANISM: Homo sapiens

<400> SEQUENCE: 519
ggccagcagc cccagccgca gccccagcag cccttcctgc cgcccgcagc ctgtttcttt   60
gccacggccg cagccgcggc ggccgcagcc gccgcagcg                       99
```

-continued

```
<210> SEQ ID NO 520
<211> LENGTH: 99
<212> TYPE: DNA
<213> ORGANISM: Artificial Sequence
<220> FEATURE:
<223> OTHER INFORMATION: Synthetic

<400> SEQUENCE: 520
ggttagtagt tttagtcgta gttttagtag ttttttttgt cgttcgtagt ttgttttttt      60
gttacggtcg tagtcgcggc ggtcgtagtc gtcgtagcg                             99

<210> SEQ ID NO 521
<211> LENGTH: 32
<212> TYPE: DNA
<213> ORGANISM: Artificial Sequence
<220> FEATURE:
<223> OTHER INFORMATION: Synthetic

<400> SEQUENCE: 521
gtcgtagttt tagtagtttt ttttgtcgtt cg                                    32

<210> SEQ ID NO 522
<211> LENGTH: 16
<212> TYPE: DNA
<213> ORGANISM: Artificial Sequence
<220> FEATURE:
<223> OTHER INFORMATION: Synthetic

<400> SEQUENCE: 522
cgaccgccgc gactac                                                      16

<210> SEQ ID NO 523
<211> LENGTH: 34
<212> TYPE: DNA
<213> ORGANISM: Artificial Sequence
<220> FEATURE:
<223> OTHER INFORMATION: Synthetic

<400> SEQUENCE: 523
aggccacgga cgcgaccgta acaaaaaaac aaac                                  34

<210> SEQ ID NO 524
<211> LENGTH: 69
<212> TYPE: DNA
<213> ORGANISM: Homo sapiens

<400> SEQUENCE: 524
gggacccggg gacgcggggc gctcagccag gcccctcca gccgcgccgg ggccgtcccg       60
agccgcgcg                                                              69

<210> SEQ ID NO 525
<211> LENGTH: 69
<212> TYPE: DNA
<213> ORGANISM: Artificial Sequence
<220> FEATURE:
<223> OTHER INFORMATION: Synthetic

<400> SEQUENCE: 525
gggattcggg gacgcggggc gtttagttag gtttttttta gtcgcgtcgg ggtcgtttcg      60
agtcgcgcg                                                              69

<210> SEQ ID NO 526
<211> LENGTH: 17
<212> TYPE: DNA
```

-continued

```
<213> ORGANISM: Artificial Sequence
<220> FEATURE:
<223> OTHER INFORMATION: Synthetic

<400> SEQUENCE: 526
gacgcggggc gtttagt                                                      17

<210> SEQ ID NO 527
<211> LENGTH: 19
<212> TYPE: DNA
<213> ORGANISM: Artificial Sequence
<220> FEATURE:
<223> OTHER INFORMATION: Synthetic

<400> SEQUENCE: 527
cgactcgaaa cgaccccga                                                    19

<210> SEQ ID NO 528
<211> LENGTH: 32
<212> TYPE: DNA
<213> ORGANISM: Artificial Sequence
<220> FEATURE:
<223> OTHER INFORMATION: Synthetic

<400> SEQUENCE: 528
cgcgccgagg acgcgactaa aaaaaaccta ac                                     32

<210> SEQ ID NO 529
<211> LENGTH: 152
<212> TYPE: DNA
<213> ORGANISM: Homo sapiens

<400> SEQUENCE: 529
ggtgcacctg tccccacacg tccctcgccc acggagcccc aggcggcgtt acgcacaccc       60
aggatcgtgg atcagcctgc cccggcgtcg ggtgtccccg cggctctcac catctggaaa      120
aggaaggtcc gcgcgcagag agggaaatgg ac                                    152

<210> SEQ ID NO 530
<211> LENGTH: 152
<212> TYPE: DNA
<213> ORGANISM: Artificial Sequence
<220> FEATURE:
<223> OTHER INFORMATION: Synthetic

<400> SEQUENCE: 530
ggtgtatttg tttttatacg tttttcgttt acggagtttt aggcggcgtt acgtatattt       60
aggatcgtgg attagtttgt ttcggcgtcg ggtgttttcg cggttttat tatttggaaa      120 aggaaggttc gcgcgtagag agggaaatgg at                                    152

<210> SEQ ID NO 531
<211> LENGTH: 21
<212> TYPE: DNA
<213> ORGANISM: Artificial Sequence
<220> FEATURE:
<223> OTHER INFORMATION: Synthetic

<400> SEQUENCE: 531 ggagtttttag gcggcgttac g                                                21

<210> SEQ ID NO 532
<211> LENGTH: 18
<212> TYPE: DNA
<213> ORGANISM: Artificial Sequence
```

```
<220> FEATURE:
<223> OTHER INFORMATION: Synthetic

<400> SEQUENCE: 532
accgcgaaaa cacccgac                                                   18

<210> SEQ ID NO 533
<211> LENGTH: 31
<212> TYPE: DNA
<213> ORGANISM: Artificial Sequence
<220> FEATURE:
<223> OTHER INFORMATION: Synthetic

<400> SEQUENCE: 533
aggccacgga cgcgccgaaa caaactaatc c                                    31

<210> SEQ ID NO 534
<211> LENGTH: 138
<212> TYPE: DNA
<213> ORGANISM: Homo sapiens

<400> SEQUENCE: 534
gggcccgcgc ggccccacgg tggtccagtt tacactcggg ccccgcactc ctgaagttcc      60
gcgcgggagg agaagggcgt ccctttcgca gctcgggcgc cgggtgcgcc gcgctgccac     120
ctggtggccg cagtggcc                                                  138

<210> SEQ ID NO 535
<211> LENGTH: 138
<212> TYPE: DNA
<213> ORGANISM: Artificial Sequence
<220> FEATURE:
<223> OTHER INFORMATION: Synthetic

<400> SEQUENCE: 535
gggttcgcgc ggttttacgg tggtttagtt tatattcggg tttcgtattt ttgaagtttc      60
gcgcgggagg agaagggcgt ttttttcgta gttcgggcgt cgggtgcgtc gcgttgttat     120
ttggtggtcg tagtggtt                                                  138

<210> SEQ ID NO 536
<211> LENGTH: 19
<212> TYPE: DNA
<213> ORGANISM: Artificial Sequence
<220> FEATURE:
<223> OTHER INFORMATION: Synthetic

<400> SEQUENCE: 536
gttcgcgcgg ttttacggt                                                  19

<210> SEQ ID NO 537
<211> LENGTH: 17
<212> TYPE: DNA
<213> ORGANISM: Artificial Sequence
<220> FEATURE:
<223> OTHER INFORMATION: Synthetic

<400> SEQUENCE: 537
cgcccttctc ctcccgc                                                    17

<210> SEQ ID NO 538
<211> LENGTH: 31
<212> TYPE: DNA
<213> ORGANISM: Artificial Sequence
<220> FEATURE:
```

-continued

<223> OTHER INFORMATION: Synthetic

<400> SEQUENCE: 538
cgcgccgagg cgcgaaactt caaaaatacg a                                    31

<210> SEQ ID NO 539
<211> LENGTH: 172
<212> TYPE: DNA
<213> ORGANISM: Homo sapiens

<400> SEQUENCE: 539
tgcggggctg cttccccgcg tcctccgggc ccgggccgcc ctcctccgc acagtgcgga       60 gcagggaggc cccgcgcctc gaccacccgc gcccgagcgt ccgcgcctcc tcctccgctc      120
tgcaggcggg gaccgcccgg cgctcggcac ccggcagcgc ggccccctcc ag             172

<210> SEQ ID NO 540
<211> LENGTH: 172
<212> TYPE: DNA
<213> ORGANISM: Artificial Sequence
<220> FEATURE:
<223> OTHER INFORMATION: Synthetic

<400> SEQUENCE: 540
tgcggggttg ttttttcgcg tttttcgggt tcgggtcgtt ttttttttcgt atagtgcgga     60 gtagggaggt ttcgcgtttc gattattcgc gttcgagcgt tcgcgttttt tttttcgttt     120
tgtaggcggg gatcgttcgg cgttcggtat tcggtagcgc ggtttttttt ag             172

<210> SEQ ID NO 541
<211> LENGTH: 21
<212> TYPE: DNA
<213> ORGANISM: Artificial Sequence
<220> FEATURE:
<223> OTHER INFORMATION: Synthetic

<400> SEQUENCE: 541
ggaggtttcg cgtttcgatt a                                              21

<210> SEQ ID NO 542
<211> LENGTH: 18
<212> TYPE: DNA
<213> ORGANISM: Artificial Sequence
<220> FEATURE:
<223> OTHER INFORMATION: Synthetic

<400> SEQUENCE: 542
cgaacgatcc ccgcctac                                                  18

<210> SEQ ID NO 543
<211> LENGTH: 27
<212> TYPE: DNA
<213> ORGANISM: Artificial Sequence
<220> FEATURE:
<223> OTHER INFORMATION: Synthetic

<400> SEQUENCE: 543
aggccacgga cgattcgcgt tcgagcg                                        27

<210> SEQ ID NO 544
<211> LENGTH: 67
<212> TYPE: DNA
<213> ORGANISM: Homo sapiens

<400> SEQUENCE: 544

-continued

```
gggcccagcg cgggctcctc gcggtagtgg ccgcagctcg ggaagctcgg gggcgcggtg      60
tcctcgc                                                               67

<210> SEQ ID NO 545
<211> LENGTH: 67
<212> TYPE: DNA
<213> ORGANISM: Artificial Sequence
<220> FEATURE:
<223> OTHER INFORMATION: Synthetic

<400> SEQUENCE: 545
gggtttagcg cgggtttttc gcggtagtgg tcgtagttcg ggaagttcgg gggcgcggtg      60
ttttcgt                                                               67

<210> SEQ ID NO 546
<211> LENGTH: 20
<212> TYPE: DNA
<213> ORGANISM: Artificial Sequence
<220> FEATURE:
<223> OTHER INFORMATION: Synthetic

<400> SEQUENCE: 546
ggtttagcgc gggtttttcg                                                 20

<210> SEQ ID NO 547
<211> LENGTH: 18
<212> TYPE: DNA
<213> ORGANISM: Artificial Sequence
<220> FEATURE:
<223> OTHER INFORMATION: Synthetic

<400> SEQUENCE: 547
ccccgaactt cccgaact                                                   18

<210> SEQ ID NO 548
<211> LENGTH: 28
<212> TYPE: DNA
<213> ORGANISM: Artificial Sequence
<220> FEATURE:
<223> OTHER INFORMATION: Synthetic

<400> SEQUENCE: 548
aggccacgga cggcggtagt ggtcgtag                                        28

<210> SEQ ID NO 549
<211> LENGTH: 92
<212> TYPE: DNA
<213> ORGANISM: Homo sapiens

<400> SEQUENCE: 549
ggccgcgacc cctccccgct gacctcactc gagccgccgc ctggcgcaga tataagcggc      60
ggcccatctg aagagggctc ggcaggcgcc cg                                   92

<210> SEQ ID NO 550
<211> LENGTH: 92
<212> TYPE: DNA
<213> ORGANISM: Artificial Sequence
<220> FEATURE:
<223> OTHER INFORMATION: Synthetic

<400> SEQUENCE: 550
ggtcgcgatt ttttttcgtt gattttattc gagtcgtcgt ttggcgtaga tataagcggc      60
```

-continued

```
ggtttatttg aagagggttc ggtaggcgtt cg                                 92

<210> SEQ ID NO 551
<211> LENGTH: 26
<212> TYPE: DNA
<213> ORGANISM: Artificial Sequence
<220> FEATURE:
<223> OTHER INFORMATION: Synthetic

<400> SEQUENCE: 551
ttttcgttga ttttattcga gtcgtc                                        26

<210> SEQ ID NO 552
<211> LENGTH: 22
<212> TYPE: DNA
<213> ORGANISM: Artificial Sequence
<220> FEATURE:
<223> OTHER INFORMATION: Synthetic

<400> SEQUENCE: 552
gaaccctctt caaataaacc gc                                            22

<210> SEQ ID NO 553
<211> LENGTH: 32
<212> TYPE: DNA
<213> ORGANISM: Artificial Sequence
<220> FEATURE:
<223> OTHER INFORMATION: Synthetic

<400> SEQUENCE: 553
aggccacgga cgcgtttggc gtagatataa gc                                 32

<210> SEQ ID NO 554
<211> LENGTH: 104
<212> TYPE: DNA
<213> ORGANISM: Homo sapiens

<400> SEQUENCE: 554
gagccggagt cgcggtggcc gcctcagcgc catgtcgagg gttgctgagg ggccagcggc   60
agcgcggcgc ggcttgtagt ccccgcgcgc atgcgcccag cctg                    104

<210> SEQ ID NO 555
<211> LENGTH: 104
<212> TYPE: DNA
<213> ORGANISM: Artificial Sequence
<220> FEATURE:
<223> OTHER INFORMATION: Synthetic

<400> SEQUENCE: 555
gagtcggagt cgcggtggtc gttttagcgt tatgtcgagg gttgttgagg ggttagcggt   60
agcgcggcgc ggtttgtagt tttcgcgcgt atgcgtttag tttg                    104

<210> SEQ ID NO 556
<211> LENGTH: 22
<212> TYPE: DNA
<213> ORGANISM: Artificial Sequence
<220> FEATURE:
<223> OTHER INFORMATION: Synthetic

<400> SEQUENCE: 556
tggtcgtttt agcgttatgt cg                                            22

<210> SEQ ID NO 557
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 557
cgaaaactac aaaccgcgc                                                        19

<210> SEQ ID NO 558
<211> LENGTH: 26
<212> TYPE: DNA
<213> ORGANISM: Artificial Sequence
<220> FEATURE:
<223> OTHER INFORMATION: Synthetic

<400> SEQUENCE: 558
aggccacgga cgccgcgcta ccgcta                                                26

<210> SEQ ID NO 559
<211> LENGTH: 24
<212> TYPE: DNA
<213> ORGANISM: Artificial Sequence
<220> FEATURE:
<223> OTHER INFORMATION: Synthetic

<400> SEQUENCE: 559
cgcgccgagg ccgcgctacc gcta                                                  24

<210> SEQ ID NO 560
<211> LENGTH: 100
<212> TYPE: DNA
<213> ORGANISM: Homo sapiens

<400> SEQUENCE: 560
ggcccggggc cgcctgggcc cctaggggct ggacgtcaac ctgttagata gagggcgtgg          60
gaccccccgc aggcggctgc tcggacgacc gcatccggag                                100

<210> SEQ ID NO 561
<211> LENGTH: 100
<212> TYPE: DNA
<213> ORGANISM: Artificial Sequence
<220> FEATURE:
<223> OTHER INFORMATION: Synthetic

<400> SEQUENCE: 561
ggttcggggt cgtttgggtt tttaggggtt ggacgttaat ttgttagata gagggcgtgg          60
gatttttcgt aggcggttgt tcggacgatc gtattcggag                                100

<210> SEQ ID NO 562
<211> LENGTH: 24
<212> TYPE: DNA
<213> ORGANISM: Artificial Sequence
<220> FEATURE:
<223> OTHER INFORMATION: Synthetic

<400> SEQUENCE: 562
cgttaatttg ttagatagag ggcg                                                 24

<210> SEQ ID NO 563
<211> LENGTH: 17
<212> TYPE: DNA
<213> ORGANISM: Artificial Sequence
<220> FEATURE:
<223> OTHER INFORMATION: Synthetic
```

-continued

```
<400> SEQUENCE: 563
tccgaacaac cgcctac                                                    17

<210> SEQ ID NO 564
<211> LENGTH: 27
<212> TYPE: DNA
<213> ORGANISM: Artificial Sequence
<220> FEATURE:
<223> OTHER INFORMATION: Synthetic

<400> SEQUENCE: 564
aggccacgga cgcgaaaaat cccacgc                                         27

<210> SEQ ID NO 565
<211> LENGTH: 117
<212> TYPE: DNA
<213> ORGANISM: Homo sapiens

<400> SEQUENCE: 565
ccgtgggcgc ggacagctgc cgggagcggc aggcgtctcg atcggggacg caggcacttc     60
cgtccctgca gagcatcaga cgcgtctcgg gacactgggg acaacatctc ctccgcg        117

<210> SEQ ID NO 566
<211> LENGTH: 117
<212> TYPE: DNA
<213> ORGANISM: Artificial Sequence
<220> FEATURE:
<223> OTHER INFORMATION: Synthetic

<400> SEQUENCE: 566
tcgtgggcgc ggatagttgt cgggagcggt aggcgtttcg atcggggacg taggtatttt     60
cgtttttgta gagtattaga cgcgtttcgg gatattgggg ataatatttt tttcgcg        117

<210> SEQ ID NO 567
<211> LENGTH: 18
<212> TYPE: DNA
<213> ORGANISM: Artificial Sequence
<220> FEATURE:
<223> OTHER INFORMATION: Synthetic

<400> SEQUENCE: 567
gttgtcggga gcggtagg                                                   18

<210> SEQ ID NO 568
<211> LENGTH: 21
<212> TYPE: DNA
<213> ORGANISM: Artificial Sequence
<220> FEATURE:
<223> OTHER INFORMATION: Synthetic

<400> SEQUENCE: 568
ccaatatccc gaaacgcgtc t                                               21

<210> SEQ ID NO 569
<211> LENGTH: 25
<212> TYPE: DNA
<213> ORGANISM: Artificial Sequence
<220> FEATURE:
<223> OTHER INFORMATION: Synthetic

<400> SEQUENCE: 569
cgcgccgagg gcgtttcgat cgggg                                           25
```

-continued

```
<210> SEQ ID NO 570
<211> LENGTH: 109
<212> TYPE: DNA
<213> ORGANISM: Artificial Sequence
<220> FEATURE:
<223> OTHER INFORMATION: Synthetic

<400> SEQUENCE: 570
ttagcgggcc gggcgggggga tcgggggtta ggggtggagt ccgccaaagg cccaaaggtg      60
atggtcatcg agatggagct acgaaaggat gagcagagcc cggagctcc                  109

<210> SEQ ID NO 571
<211> LENGTH: 109
<212> TYPE: DNA
<213> ORGANISM: Artificial Sequence
<220> FEATURE:
<223> OTHER INFORMATION: Synthetic

<400> SEQUENCE: 571
ttagcgggtc gggcgggggga tcgggggtta ggggtggagt tcgttaaagg tttaaaggtg      60
atggttatcg agatggagtt acgaaaggat gagtagagtt cggagtttt                  109

<210> SEQ ID NO 572
<211> LENGTH: 21
<212> TYPE: DNA
<213> ORGANISM: Artificial Sequence
<220> FEATURE:
<223> OTHER INFORMATION: Synthetic

<400> SEQUENCE: 572
ggttaggggt ggagttcgtt a                                                21

<210> SEQ ID NO 573
<211> LENGTH: 24
<212> TYPE: DNA
<213> ORGANISM: Artificial Sequence
<220> FEATURE:
<223> OTHER INFORMATION: Synthetic

<400> SEQUENCE: 573
actccgaact ctactcatcc tttc                                             24

<210> SEQ ID NO 574
<211> LENGTH: 31
<212> TYPE: DNA
<213> ORGANISM: Artificial Sequence
<220> FEATURE:
<223> OTHER INFORMATION: Synthetic

<400> SEQUENCE: 574
cgcgccgagg cgtaactcca tctcgataac c                                     31

<210> SEQ ID NO 575
<211> LENGTH: 116
<212> TYPE: DNA
<213> ORGANISM: Homo sapiens

<400> SEQUENCE: 575
aaggcgccgg cggctctcag taaaagcgaa tgtagccttt gtacttccga cctctcaatg      60
gtgaaatgag ctaatcacag gcccaccccg cggagtggga cgggagattc aatgag         116

<210> SEQ ID NO 576
<211> LENGTH: 116
<212> TYPE: DNA
```

-continued

<213> ORGANISM: Artificial Sequence
<220> FEATURE:
<223> OTHER INFORMATION: Synthetic

<400> SEQUENCE: 576
aaggcgtcgg cggtttttag taaaagcgaa tgtagttttt gtattttcga tttttaatg      60 gtgaaatgag ttaattatag gtttatttcg cggagtggga cgggagattt aatgag        116

<210> SEQ ID NO 577
<211> LENGTH: 22
<212> TYPE: DNA
<213> ORGANISM: Artificial Sequence
<220> FEATURE:
<223> OTHER INFORMATION: Synthetic

<400> SEQUENCE: 577
tcggcggttt ttagtaaaag cg                                              22

<210> SEQ ID NO 578
<211> LENGTH: 19
<212> TYPE: DNA
<213> ORGANISM: Artificial Sequence
<220> FEATURE:
<223> OTHER INFORMATION: Synthetic

<400> SEQUENCE: 578
aaatctcccg tcccactcc                                                  19

<210> SEQ ID NO 579
<211> LENGTH: 36
<212> TYPE: DNA
<213> ORGANISM: Artificial Sequence
<220> FEATURE:
<223> OTHER INFORMATION: Synthetic

<400> SEQUENCE: 579
cgcgccgagg cgcgaaataa acctataatt aactca                               36

<210> SEQ ID NO 580
<211> LENGTH: 119
<212> TYPE: DNA
<213> ORGANISM: Homo sapiens

<400> SEQUENCE: 580
gcctttgccc cggtttttgg cgcgggagga ctttcgaccc cgacttcggc cgctcatggt      60
ggcggcggag gcagcttcaa agacacgctg tgaccctgcg gctcctgacg ccagctctc      119

<210> SEQ ID NO 581
<211> LENGTH: 119
<212> TYPE: DNA
<213> ORGANISM: Artificial Sequence
<220> FEATURE:
<223> OTHER INFORMATION: Synthetic

<400> SEQUENCE: 581
gtttttgttt cggtttttgg cgcgggagga ttttcgattt cgatttcggt cgtttatggt      60
ggcggcggag gtagttttaa agatacgttg tgattttgcg gtttttgacg ttagttttt      119

<210> SEQ ID NO 582
<211> LENGTH: 19
<212> TYPE: DNA
<213> ORGANISM: Artificial Sequence
<220> FEATURE:
<223> OTHER INFORMATION: Synthetic

<400> SEQUENCE: 582
tttgtttcgg tttttggcg                                                                                      19

<210> SEQ ID NO 583
<211> LENGTH: 17
<212> TYPE: DNA
<213> ORGANISM: Artificial Sequence
<220> FEATURE:
<223> OTHER INFORMATION: Synthetic

<400> SEQUENCE: 583
cgccaccata aacgacc                                                                                        17

<210> SEQ ID NO 584
<211> LENGTH: 12
<212> TYPE: DNA
<213> ORGANISM: Artificial Sequence
<220> FEATURE:
<223> OTHER INFORMATION: Synthetic

<400> SEQUENCE: 584
aggccacgga cg                                                                                             12

<210> SEQ ID NO 585
<211> LENGTH: 107
<212> TYPE: DNA
<213> ORGANISM: Homo sapiens

<400> SEQUENCE: 585
gcctcggggc ccggggactc acaattacgg gcagagaaca catagtgaag agcacggtca                                          60
tcagcgccag cagcaggagg tgatccagct cctccagggg ctgaggg                                                       107

<210> SEQ ID NO 586
<211> LENGTH: 107
<212> TYPE: DNA
<213> ORGANISM: Artificial Sequence
<220> FEATURE:
<223> OTHER INFORMATION: Synthetic

<400> SEQUENCE: 586
gtttcggggt tcggggattt ataattacgg gtagagaata tatagtgaag agtacggtta                                          60
ttagcgttag tagtaggagg tgatttagtt tttttagggg ttgaggg                                                       107

<210> SEQ ID NO 587
<211> LENGTH: 24
<212> TYPE: DNA
<213> ORGANISM: Artificial Sequence
<220> FEATURE:
<223> OTHER INFORMATION: Synthetic

<400> SEQUENCE: 587
gggttcgggg atttataatt acgg                                                                                24

<210> SEQ ID NO 588
<211> LENGTH: 32
<212> TYPE: DNA
<213> ORGANISM: Artificial Sequence
<220> FEATURE:
<223> OTHER INFORMATION: Synthetic

<400> SEQUENCE: 588
ctaaatcacc tcctactact aacgctaata ac                                                                       32

<210> SEQ ID NO 589
<211> LENGTH: 35
<212> TYPE: DNA
<213> ORGANISM: Artificial Sequence
<220> FEATURE:
<223> OTHER INFORMATION: Synthetic

<400> SEQUENCE: 589
cgcgccgagg ccgtactctt cactatatat tctct                                35

DETECTING ENDOMETRIAL CANCER

CROSS REFERENCE TO RELATED APPLICATIONS

The present application is a U.S. 371 national phase entry of International Patent Application No. PCT/US2020/015059, filed Dec. 30, 2019, which claims priority to U.S. Provisional Application No. 62/796,384, filed Jan. 24, 2019, which are hereby incorporated by reference in their entireties.

REFERENCE TO A SEQUENCE LISTING

The contents of the electronic sequence listing (File Name: 37456-252_ST25.txt; Size: 116,000,000 bytes; Date of Creation: Jul. 20, 2021), submitted on Jul. 20, 2021 is herein incorporated by reference in its entirety.

FIELD OF INVENTION

Provided herein is technology for endometrial cancer (EC) screening and particularly, but not exclusively, to methods, compositions, and related uses for detecting the presence of endometrial cancer and various subtypes of endometrial cancer.

BACKGROUND

Early detection approaches for endometrial cancer (EC) are lacking, despite the fact that EC is the most common gynecologic malignancy in the United States and in many other developed countries (see, Siegel, R. L., et al., Cancer statistics, 2016. CA Cancer J Clin, 2016. 66(1): p. 7-30; Parkin, D., et al., Global cancer statistics, 2002. CA Cancer J Clin., 2005. 55(2): p. 74-108). While low-risk, early stage EC has an excellent prognosis with 5-year overall survival (OS) >95%, 5-year OS when diagnosed at stage III or IV is sobering at 68% and 17%, respectively (see, Fridley, B. L., et al., PLoS ONE, 2010. 5(9): p. e12693). Most EC are low-grade endometrioid histology and preceded by hyperplasia precursors; however, the more aggressive grade 3 endometrioid, serous, clear cell, and carcinosarcoma histologies comprise 10-15% of newly diagnosed EC and can be highly lethal (see, Felix, A. S., et al., Cancer Causes Control, 2010. 21(11): p. 1851-6; Moore, K. N. and A. N. Fader, Clin Obstet Gynecol, 2011. 54(2): p. 278-91; Cancer Genome Atlas Research, N., et al., Nature, 2013. 497(7447): p. 67-73; Hussein, Y. R., et al., Int J Gynecol Pathol, 2016. 35(1): p. 16-24). Early detection increases the chance of cure (see, Mariani, A., et al., Gynecologic Oncology, 2008. 109(1): p. 11-18).

Improved methods for detecting EC and various subtypes of EC are needed.

The present invention addresses these needs.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Epigenetic methylation of DNA at cytosine-phosphate-guanine (CpG) island sites by DNA methyltransferases has been studied as a potential class of biomarkers in the tissues of most tumor types. In a biologically attractive mechanism, acquired methylation events in promotor regions of tumor suppressor genes are thought to silence expression, contributing to oncogenesis. DNA methylation may be a more chemically and biologically stable diagnostic tool than RNA or protein expression. Furthermore, in other cancers like sporadic colon cancer, aberrant methylation markers are more broadly informative and sensitive than are individual DNA mutations and offer excellent specificity.

Several methods are available to search for novel methylation markers. While microarray based interrogation of CpG methylation is a reasonable, high-throughput approach, this strategy is biased towards known regions of interest, mainly established tumor suppressor promotors. Alternative methods for genome-wide analysis of DNA methylation have been developed in the last decade. There are three basic approaches. The first employs digestion of DNA by restriction enzymes which recognize specific methylated sites, followed by several possible analytic techniques which provide methylation data limited to the enzyme recognition site or the primers used to amplify the DNA in quantification steps (such as methylation-specific PCR; MSP). A second approach enriches methylated fractions of genomic DNA using anti-bodies directed to methyl-cytosine or other methylation-specific binding domains followed by microarray analysis or sequencing to map the fragment to a reference genome. This approach does not provide single nucleotide resolution of all methylated sites within the fragment. A third approach begins with bisulfite treatment of the DNA to convert all unmethylated cytosines to uracil, followed by restriction enzyme digestion and complete sequencing of all fragments after coupling to an adapter ligand. The choice of restriction enzymes can enrich the fragments for CpG dense regions, reducing the number of redundant sequences which may map to multiple gene positions during analysis.

RRBS yields CpG methylation status data at single nucleotide resolution of 80-90% of all CpG islands and a majority of tumor suppressor promoters at medium to high read coverage. In cancer case—control studies, analysis of these reads results in the identification of differentially methylated regions (DMRs). In previous RRBS analysis of pancreatic cancer specimens, hundreds of DMRs were uncovered, many of which had never been associated with carcinogenesis and many of which were unannotated. Further validation studies on independent tissue samples sets confirmed marker CpGs which were 100% sensitive and specific in terms of performance.

EC spontaneously sheds tumor cells (see, Chin, A. B., et al., American Journal of Obstetrics and Gynecology, 2000. 182(6): p. 1278-1282) and detection of EC biomarkers via minimally invasive methods is a promising approach (see, Kinde, I., et al., Science Translational Medicine, 2013. 5(167): p. 167ra4; Bakkum-Gamez, J. N., et al., Gynecologic Oncology, 2015. 137(1): p. 14-22; Wentzensen, N., et al., International Journal of Cancer, 2014. 135(8): p. 1860-1868; Fiegl H, G. C., et al., Cancer Epidemiol Biomarkers Prev, 2004. 13(5): p. 882-8); however, optimization of markers, standardization of collection methods, and improvement in specificity are needed. DNA methylation is an early event in EC carcinogenesis (see, Tao, M. H. and J. L. Freudenheim, Epigenetics, 2010. 5(6): p. 491-8); RASSF1 is methylated in morphologically normal appearing endometrium adjacent to ECs (see, Fiegl H, G. C., et al., Cancer Epidemiol Biomarkers Prev, 2004. 13(5): p. 882-8; Pijnenborg, J., et al., Annals of Oncology, 2007. 18(3): p. 491-497; Suehiro, Y., et al., Clinical Cancer Research, 2008. 14(11): p. 3354-3361; Arafa, M., et al., Histopathology, 2008. 53(5): p. 525-532); MLH1 methylation occurs in atypical hyperplasia (see, Suehiro, Y., et al., Clinical Cancer Research, 2008. 14(11): p. 3354-3361; Horowitz, N., et al., Gynecologic Oncology, 2002. 86(1): p. 62-68; Xiong, Y., et al., Gynecologic Oncology, 2006. 103(1): p. 321-328; Banno K, Y. M., et al., Oncol Rep, 2006. 16(6): p. 1189-96; Zighelboim, I., et al., Clinical Cancer Research, 2007. 13(10): p. 2882-2889; Guida M, S. F., et al., Eur J Gynaecol Oncol., 2009. 30(3): p. 267-70). These and other genes are established as methylated in EC (see, Fiegl H, G. C., et al., Cancer Epidemiol Biomarkers Prev, 2004. 13(5): p. 882-8; Suehiro, Y., et al., Clinical Cancer Research, 2008. 14(11): p. 3354-3361; Zighelboim, I., et al., Clinical Cancer Research, 2007. 13(10): p. 2882-2889; Wentzensen, N., et al., International Journal of Cancer, 2014: p. [Epub ahead of print]; Tao M H, F. J., DNA methylation in EC. Epigenetics, 2010. 5(6): p. 491-8; Integrated genomic characterization of endometrial carcinoma. Nature, 2013. 497(7447): p. 67-73; Huang, Y.-W., et al., Gynecologic Oncology, 2010. 117(2): p. 239-247; Xiong, Y., et al., Gynecologic Oncology, 2005. 99(1): p. 135-141; Sasaki, M., et al., Cancer Research, 2001. 61(1): p. 97-102; Sasaki, M., et al., Molecular and Cellular Endocrinology, 2003. 202(1-2): p. 201-207) and cell-free methylated DNA released from necrotic tumor cells is an attractive target and has been detected in a variety of biological fluids, including sputum, plasma, peritoneal fluid, stool, nipple aspirates, urine, pancreatic juice, and vaginal fluid (see, Bakkum-Gamez, J. N., et al., Gynecologic Oncology, 2015. 137(1): p. 14-22; Fiegl H, G. C., et al., Cancer Epidemiol Biomarkers Prev, 2004. 13(5): p. 882-8; Duffy M J, N. R., et al., Eur J Cancer, 2009. 45(3): p. 335-46; Ahlquist, D. A., et al., Gastroenterology, 2012. 142(2): p. 248-256; Duffy, M. J., et al., Eur J Cancer, 2009. 45(3): p. 335-46; Kisiel, J. B., et al., Clinical Cancer Research, 2015. 21(19): p. 4473-4481).

Provided herein is technology for EC screening and particularly, but not exclusively, to methods, compositions, and related uses for detecting the presence of EC and various subtypes of EC (e.g., clear cell EC, carcinosarcoma EC, endometrioid EC, serous EC).

Indeed, as described in Examples I, II and III, experiments conducted during the course for identifying embodiments for the present invention identified a novel set of differentially methylated regions (DMRs) for discriminating cancer of the endometrium derived DNA from non-neoplastic control DNA.

Such experiments list and describe 499 novel DNA methylation markers distinguishing EC tissue (and various subtypes of EC tissue) from benign endometrial tissue (see, Tables 1, 8, and 21, Examples 1, 2 and 3).

From these 499 novel DNA methylation markers, further experiments identified the following markers and/or panels of markers capable of distinguishing EC tissue from benign endometrial tissue:

AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90 (see, Table 2, Example 1);

EMX2OS, CYTH2, C17orf107_A, DIDO1_A, GDF6, NBPF8, MAX.chr14.103021656-103021718, JSRP1_A, GATA2_B, and SFMBT2_B (see, Table 3, Example 1);

SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A (see, Table 15, Example 1); and EMX2OS, CYTH2, NBPF8, MAX.chr10.22624479-22624553 (see, Table 20, Example 1).

From these 499 novel DNA methylation markers, further experiments identified the following markers and/or panels of markers for detecting EC in blood samples (e.g., plasma samples, whole blood samples, leukocyte samples, serum samples):

ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A (see, Table 9, Example 1).

From these 499 novel DNA methylation markers, further experiments identified the following markers and/or panels of markers capable of distinguishing clear cell EC tissue from benign endometrial tissue:

DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422 (see, Table 4, Example 1);

ZNF323_A, MAX.chr7.104624356-104624730, NDRG2, DIDO1_A, MDFI_B, MAX.chr14.103021656-103021718, MMP23B, SEPT9_B, and STX16_A (see, Table 11, Example 1);

SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A (see, Table 16, Example 1); and MAX.chr7:104624386-104624529, EMX2OS, DIDO1_B, and OBSCN_B (see, Table 24, Example 3).

From these 499 novel DNA methylation markers, further experiments identified the following markers and/or panels of markers for detecting clear cell EC in blood samples (e.g., plasma samples, whole blood samples, leukocyte samples, serum samples):

SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC.

From these 499 novel DNA methylation markers, further experiments identified the following markers and/or panels of markers capable of distinguishing carcinosarcoma EC tissue from benign endometrial tissue:

EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B (see, Table 5, Example 1);

EMX2OS, and LRRC34 (see, Table 13, Example 1);

ZNF506, ZNF90, MAX.chr8.145103829-145103992, LRRC8D_A, OBSCN_A, MAX.chr10.22624479-22624553, JSRP1_A, EMX2OS, NBPF8, and VILL (see, Table 18, Example 1); and TRH, MAX.chr7:104624386-104624529, EMX2OS, DIDO1_B, and ST3GAL2_B (see, Table 24, Example 3).

From these 499 novel DNA methylation markers, further experiments identified the following markers and/or panels of markers for detecting carcinosarcoma EC in blood samples (e.g., plasma samples, whole blood samples, leukocyte samples, serum samples):

SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL (see, Table 13, Example 1).

From these 499 novel DNA methylation markers, further experiments identified the following markers and/or panels of markers capable of distinguishing serous EC tissue from benign endometrial tissue:

EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B (see, Table 7, Example 1);

MAX.chr7.104624356-104624730, EMX2OS, and LRRC41_C (see, Table 12, Example 1);

MAX.chr8.145103829-145103992, CYTH2, LRRC8D_A, OBSCN_A, DIDO1_A, EMX2OS, LRRC41_C, and VILL (see, Table 17, Example 1); and EMX2OS, and LRRC41_D (see, Table 24, Example 3).

From these 499 novel DNA methylation markers, further experiments identified the following markers and/or panels of markers for detecting serous EC in blood samples (e.g., plasma samples, whole blood samples, leukocyte samples, serum samples):

SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A (see, Table 12, Example 1).

From these 499 novel DNA methylation markers, further experiments identified the following markers and/or panels of markers capable of distinguishing endometrioid EC tissue from benign endometrial tissue:

MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B (see, Table 6, Example 1);

MAX.chr8.145103829-145103992, CYTH2, DIDO1_A, MAX.chr10.22624479-22624553, JSRP1_A, SBNO2, NBPF8, and VILL (see, Table 14, Example 1); and SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A (see, Table 19, Example 1).

From these 499 novel DNA methylation markers, further experiments identified the following markers and/or panels of markers for detecting endometrioid EC in blood samples (e.g., plasma samples, whole blood samples, leukocyte samples, serum samples):

SFMBT2_B, SMTN, SQSTM1, ZNF506, ZNF90, CLDN7, LRRC41_B, FKBP11_A, MAX.chr8.145103829-145103992, AHSA2, CYTH2,

7

GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A (see, Table 14, Example 1).

From these 499 novel DNA methylation markers, further experiments identified the following markers and/or panels of markers capable of distinguishing endometrioid EC Grade 1 tissue from benign endometrial tissue:

TSPYL5, TRH, JAM3, FAM19A5, PTGDR, SFMBT2_E, JSRP1_B, and ARL5C (see, Table 25, Example 3).

From these 499 novel DNA methylation markers, further experiments identified the following markers and/or panels of markers capable of distinguishing endometrioid EC Grade 2 tissue from benign endometrial tissue:

TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B (see, Table 25, Example 3).

From these 499 novel DNA methylation markers, further experiments identified the following markers and/or panels of markers capable of distinguishing endometrioid EC Grade 3 tissue from benign endometrial tissue:

TSPYL5, MPZ_B, TRH, and PTGDR (see, Table 25, Example 3).

As described herein, the technology provides a number of methylated DNA markers and subsets thereof (e.g., sets of 2, 3, 4, 5, 6, 7, or 8 markers) with high discrimination for EC overall and various types of EC (e.g., clear cell EC, carcinosarcoma EC, endometrioid EC, serous EC). Experiments applied a selection filter to candidate markers to identify markers that provide a high signal to noise ratio and a low background level to provide high specificity for purposes of EC screening or diagnosis.

In some embodiments, the technology is related to assessing the presence of and methylation state of one or more of the markers identified herein in a biological sample (e.g., endometrial tissue sample, blood sample). These markers comprise one or more differentially methylated regions (DMR) as discussed herein, e.g., as provided in Tables 1, 8 and 21. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes or methylation-dependent restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR

8

(MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits contain a reagent capable of modifying DNA in a methylation-specific manner (e.g., a methylation-sensitive restriction enzyme, a methylation-dependent restriction enzyme, and a bisulfite reagent). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-499 as provided in Tables 1, 8 and 21); comparing methylation states (e.g., of one or more DMR, e.g., DMR 1-499 as provided in Tables 1, 8 and 21); generating standard curves; determining a Ct value; calculating a fraction, frequency, or percentage of methylation (e.g., of one or more DMR, e.g., DMR 1-499 as provided in Tables 1, 8 and 21); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 2, 18 and 26). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 1, 8 and 21). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, California and Motorola Corporation of Schaumburg, Illinois Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for EC and/or various forms of EC (e.g., clear cell EC, carcinosarcoma EC, endometrioid EC, serous EC) in a sample obtained from a subject, the method comprising assaying a methylation state of a marker in a sample obtained from a subject (e.g., endometrial tissue) (e.g., a blood sample) and identifying the subject as having EC and/or a specific form of EC when the methylation state of the marker is different than a methylation state of the marker assayed in a subject that does not have EC, wherein the marker comprises a base in a differentially methylated region (DMR) selected from a group consisting of DMR 1-499 as provided in Tables 1, 8 and 21.

In some embodiments wherein the sample obtained from the subject is endometrial tissue and the methylation state of one or more of the following markers is different than a methylation state of the one or more markers assayed in a subject that does not have EC indicates the subject has EC: AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90 (see, Table 2, Example 1).

In some embodiments wherein the sample obtained from the subject is endometrial tissue and the methylation state of one or more of the following markers is different than a methylation state of the one or more markers assayed in a subject that does not have EC indicates the subject has EC: EMX2OS, CYTH2, C17orf107_A, DIDO1_A, GDF6, NBPF8, MAX.chr14.103021656-103021718, JSRP1_A, GATA2_B, and SFMBT2_B (see, Table 3, Example 1).

In some embodiments wherein the sample obtained from the subject is endometrial tissue and the methylation state of one or more of the following markers is different than a methylation state of the one or more markers assayed in a subject that does not have EC indicates the subject has EC: SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A (see, Table 15, Example 1).

In some embodiments wherein the sample obtained from the subject is endometrial tissue and the methylation state of one or more of the following markers is different than a methylation state of the one or more markers assayed in a subject that does not have EC indicates the subject has EC: EMX2OS, CYTH2, NBPF8, MAX.chr10.22624479-22624553 (see, Table 20, Example 1).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have EC indicates the subject has EC: ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A (see, Table 9, Example 1).

In some embodiments wherein the sample obtained from the subject is endometrial tissue and the methylation state of one or more of the following markers is different than a methylation state of the one or more markers assayed in a subject that does not have EC indicates the subject has clear cell EC: DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422 (see, Table 4, Example 1).

In some embodiments wherein the sample obtained from the subject is endometrial tissue and the methylation state of one or more of the following markers is different than a methylation state of the one or more markers assayed in a subject that does not have EC indicates the subject has clear cell EC: ZNF323_A, MAX.chr7.104624356-104624730, NDRG2, DIDO1_A, MDFI_B, MAX.chr14.103021656-103021718, MMP23B, SEPT9_B, and STX16_A (see, Table 11, Example 1).

In some embodiments wherein the sample obtained from the subject is endometrial tissue and the methylation state of one or more of the following markers is different than a methylation state of the one or more markers assayed in a subject that does not have EC indicates the subject has clear cell EC: SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A (see, Table 16, Example 1).

In some embodiments wherein the sample obtained from the subject is endometrial tissue and the methylation state of one or more of the following markers is different than a methylation state of the one or more markers assayed in a subject that does not have EC indicates the subject has clear cell EC: MAX.chr7:104624386-104624529, EMX2OS, DIDO1_B, and OBSCN_B (see, Table 24, Example 3).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have EC indicates the subject has clear cell EC: SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC.

In some embodiments wherein the sample obtained from the subject is endometrial tissue and the methylation state of one or more of the following markers is different than a methylation state of the one or more markers assayed in a subject that does not have EC indicates the subject has carcinosarcoma EC: EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B (see, Table 5, Example 1).

In some embodiments wherein the sample obtained from the subject is endometrial tissue and the methylation state of one or more of the following markers is different than a methylation state of the one or more markers assayed in a subject that does not have EC indicates the subject has carcinosarcoma EC: EMX2OS, and LRRC34 (see, Table 13, Example 1).

In some embodiments wherein the sample obtained from the subject is endometrial tissue and the methylation state of one or more of the following markers is different than a methylation state of the one or more markers assayed in a subject that does not have EC indicates the subject has carcinosarcoma EC: ZNF506, ZNF90, MAX.chr8.145103829-145103992, LRRC8D_A, OBSCN_A, MAX.chr10.22624479-22624553, JSRP1_A, EMX2OS, NBPF8, and VILL (see, Table 18, Example 1).

In some embodiments wherein the sample obtained from the subject is endometrial tissue and the methylation state of one or more of the following markers is different than a methylation state of the one or more markers assayed in a subject that does not have EC indicates the subject has carcinosarcoma EC: TRH, MAX.chr7:104624386-104624529, EMX2OS, DIDO1_B, and ST3GAL2_B (see, Table 24, Example 3).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have EC indicates the subject has carcinosarcoma EC: SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL (see, Table 13, Example 1).

In some embodiments wherein the sample obtained from the subject is endometrial tissue and the methylation state of one or more of the following markers is different than a methylation state of the one or more markers assayed in a subject that does not have EC indicates the subject has serous EC: EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B (see, Table 7, Example 1).

In some embodiments wherein the sample obtained from the subject is endometrial tissue and the methylation state of one or more of the following markers is different than a methylation state of the one or more markers assayed in a subject that does not have EC indicates the subject has serous EC: MAX.chr7.104624356-104624730, EMX2OS, and LRRC41_C (see, Table 12, Example 1).

In some embodiments wherein the sample obtained from the subject is endometrial tissue and the methylation state of one or more of the following markers is different than a methylation state of the one or more markers assayed in a subject that does not have EC indicates the subject has serous EC: MAX.chr8.145103829-145103992, CYTH2, LRRC8D_A, OBSCN_A, DIDO1_A, EMX2OS, LRRC41_C, and VILL (see, Table 17, Example 1).

In some embodiments wherein the sample obtained from the subject is endometrial tissue and the methylation state of one or more of the following markers is different than a methylation state of the one or more markers assayed in a subject that does not have EC indicates the subject has serous EC: EMX2OS, and LRRC41_D (see, Table 24, Example 3).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have EC indicates the subject has serous EC: SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A (see, Table 12, Example 1).

In some embodiments wherein the sample obtained from the subject is endometrial tissue and the methylation state of one or more of the following markers is different than a methylation state of the one or more markers assayed in a subject that does not have EC indicates the subject has endometrioid EC: MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B (see, Table 6, Example 1).

In some embodiments wherein the sample obtained from the subject is endometrial tissue and the methylation state of one or more of the following markers is different than a methylation state of the one or more markers assayed in a subject that does not have EC indicates the subject has endometrioid EC: MAX.chr8.145103829-145103992, CYTH2, DIDO1_A, MAX.chr10.22624479-22624553, JSRP1_A, SBNO2, NBPF8, and VILL (see, Table 14, Example 1).

In some embodiments wherein the sample obtained from the subject is endometrial tissue and the methylation state of one or more of the following markers is different than a methylation state of the one or more markers assayed in a subject that does not have EC indicates the subject has endometrioid EC: SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A (see, Table 19, Example 1).

In some embodiments wherein the sample obtained from the subject is a blood sample (e.g., plasma sample, whole blood sample, leukocyte sample, serum sample) and the methylation state of one or more of the following markers is different than a methylation state of the one or more markers assayed in a subject that does not have EC indicates the subject has endometrioid EC: SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A (see, Table 14, Example 1).

In some embodiments wherein the sample obtained from the subject is endometrial tissue and the methylation state of one or more of the following markers is different than a methylation state of the one or more markers assayed in a subject that does not have EC indicates the subject has endometrioid Grade 1 EC: TSPYL5, TRH, JAM3, FAM19A5, PTGDR, SFMBT2_E, JSRP1_B, and ARL5C (see, Table 25, Example 3).

In some embodiments wherein the sample obtained from the subject is endometrial tissue and the methylation state of one or more of the following markers is different than a methylation state of the one or more markers assayed in a subject that does not have EC indicates the subject has endometrioid Grade 2 EC: TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B (see, Table 25, Example 3).

In some embodiments wherein the sample obtained from the subject is endometrial tissue and the methylation state of one or more of the following markers is different than a methylation state of the one or more markers assayed in a subject that does not have EC indicates the subject has endometrioid Grade 3 EC: TSPYL5, MPZ_B, TRH, and PTGDR (see, Table 25, Example 3).

The technology is related to identifying and discriminating EC and/or various forms of EC (e.g., clear cell EC, carcinosarcoma EC, endometrioid EC, serous EC). Some embodiments provide methods comprising assaying a plurality of markers, e.g., comprising assaying 2 to 11 to 100 or 120 or 499 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., endometrial tissue sample), a blood sample (e.g., plasma, leukocyte, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-499 (see, Tables 1, 8 and 21). In some embodiments are provided an oligonucleotide comprising a sequence complementary to a chromosomal region having a base in a DMR, e.g., an oligonucleotide sensitive to methylation state of a DMR.

The technology provides various panels of markers use for identifying EC, e.g., in some embodiments the marker comprises a chromosomal region having an annotation that is AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90 (see, Table 2, Example 1).

The technology provides various panels of markers use for identifying EC, e.g., in some embodiments the marker comprises a chromosomal region having an annotation that is EMX2OS, CYTH2, C17orf107_A, DIDO1_A, GDF6, NBPF8, MAX.chr14.103021656-103021718, JSRP1_A, GATA2_B, and SFMBT2_B (see, Table 3, Example 1).

The technology provides various panels of markers use for identifying EC, e.g., in some embodiments the marker comprises a chromosomal region having an annotation that is SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A (see, Table 15, Example 1)

The technology provides various panels of markers use for identifying EC, e.g., in some embodiments the marker comprises a chromosomal region having an annotation that is EMX2OS, CYTH2, NBPF8, MAX.chr10.22624479-22624553 (see, Table 20, Example 1).

The technology provides various panels of markers use for identifying EC, e.g., in some embodiments the marker comprises a chromosomal region having an annotation that is ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239,
MAX.chr15.95128144-95128248, MAX.chr16.11327016-11327312, MAX.chr3.187676577-187676668,
MAX.chr4.174430676-174430847, MAX.chr8.145900783-145900914, MAX.chr8.80804237-80804301, N4BP3,
NCOR2, NFATC1_A, NFATC1_B, NKX2-6, NR2F6, OSM,
PALLD_C, PIK3CD, PRKAR1B, RAD52, STX16_A,
SUCLG2, TNFRSF1B, TNFRSF4, ZDHHC18, and
ZNF671_A (see, Table 9, Example 1).

The technology provides various panels of markers use
for identifying clear cell EC, e.g., in some embodiments the
marker comprises a chromosomal region having an annotation that is DIDO1_A, NDRG4, MAX.chr14.103021656-103021718, MMP23B, EMX2OS, SEPT9_B, NBPF8,
EEF1A2, AIM1_A, BMP4_B, MAX.chr8.145103829-145103992, OBSCN, PYCARD, GDF6, MDFI_B,
MIAT_A, SCL8A3, ZNF323_A, SQSTM1, AFF3, C1orf70,
GDF7_A, JSRP1_A, LRRC8D_A, FEV, and
MAX.chr8.145104263-145104422 (see, Table 4, Example
1).

The technology provides various panels of markers use
for identifying clear cell EC, e.g., in some embodiments the
marker comprises a chromosomal region having an annotation that is ZNF323_A, MAX.chr7.104624356-104624730,
NDRG2, DIDO1_A, MDFI_B, MAX.chr14.103021656-103021718, MMP23B, SEPT9_B, and STX16_A (see, Table
11, Example 1).

The technology provides various panels of markers use
for identifying clear cell EC, e.g., in some embodiments the
marker comprises a chromosomal region having an annotation that is SFMBT2_B, SQSTM1, ZNF323_A, ZNF90,
MAX.chr8.145103829-145103992, CYTH2, LRRC8D_A,
OBSCN_A, DIDO1_A, MDFI_B, GDF7_A,
MAX.chr10.22624479-22624553, JSRP1_A,
MAX.chr14.103021656-103021718, EMX2OS, LRRC34,
NBPF8, SEPT9_B, EEF1A2, LRRC41_C, VILL, and
MPZ_A (see, Table 16, Example 1).

The technology provides various panels of markers use
for identifying clear cell EC, e.g., in some embodiments the
marker comprises a chromosomal region having an annotation that is MAX.chr7:104624386-104624529, EMX2OS,
DIDO1_B, and OBSCN_B (see, Table 24, Example 3).

The technology provides various panels of markers use
for identifying clear cell EC, e.g., in some embodiments the
marker comprises a chromosomal region having an annotation that is SFMBT2_B, SQSTM1, ZNF323_A, ZNF506,
ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6,
MAX.chr10.130339363-130339534, MDFI_B, DLL4,
GDF7_A, MIAT_A, PYCARD, BMP4_B, JSRP1_A,
MAX.chr14.103021656-103021718, EMX2, MMP23B,
EMX2OS, MAX.chr17.73073716-73073814, NBPF8,
SEPT9_B, LOC440925_A, STX16_A, ITPKA, EEF1A2,
FEV, LRRC41_C, and NFIC (see, Table 11, Example 1).

The technology provides various panels of markers use
for identifying carcinosarcoma EC, e.g., in some embodiments the marker comprises a chromosomal region having
an annotation that is EMX2OS, DIDO1_A, SBNO2,
AMIGO3_A, PCOLCE, CLDN7, CYTH2, OBSCN_A,
AHSA2, DLL4, EMX2, MAX.chr14.74100620-74100870,
LRRC4, PPP2R5C_A, SQSTM1, MAX.chr17.73073716-73073814, CYP11A1, ACOXL_A, and AIM1_B (see, Table
5, Example 1).

The technology provides various panels of markers use
for identifying carcinosarcoma EC, e.g., in some embodiments the marker comprises a chromosomal region having
an annotation that is EMX2OS, and LRRC34 (see, Table 13,
Example 1).

The technology provides various panels of markers use
for identifying carcinosarcoma EC, e.g., in some embodiments the marker comprises a chromosomal region having
an annotation that is ZNF506, ZNF90,
MAX.chr8.145103829-145103992, LRRC8D_A,
OBSCN_A, MAX.chr10.22624479-22624553, JSRP1_A,
EMX2OS, NBPF8, and VILL (see, Table 18, Example 1).

The technology provides various panels of markers use
for identifying carcinosarcoma EC, e.g., in some embodiments the marker comprises a chromosomal region having
an annotation that is TRH, MAX.chr7:104624386-104624529, EMX2OS, DIDO1_B, and ST3GAL2_B (see,
Table 24, Example 3).

The technology provides various panels of markers use
for identifying carcinosarcoma EC, e.g., in some embodiments the marker comprises a chromosomal region having
an annotation that is SFMBT2_B, SMTN, ZNF506, ZNF90,
CLDN7, LRRC41_B, CYP11A1, MAX.chr8.145103829-145103992, AHSA2, CYTH2, GATA2_B, LRRC8D_A,
MAX.chr8.145104263-145104422, OBSCN_A, DIDO1_A,
GDF6, DLL4, MAX.chr10.22624479-22624553,
PYCARD, BMP4_B, JSRP1_A, MAX.chr14.103021656-103021718, MIAT_B, EMX2OS, LRRC34, NBPF8,
LOC440925_A, ITPKA, NFIC, and VILL (see, Table 13,
Example 1).

The technology provides various panels of markers use
for identifying serous EC, e.g., in some embodiments the
marker comprises a chromosomal region having an annotation that is EMX2OS, KANK1, C1orf70_B, AMIGO3_A,
DIDO1_A, LRRC41_C, NFIC, FKBP11_A, C17orf107_A,
SMTN, LRRC41_B, LRRC8D_A, OBSCN_A,
MAX.chr7.104624356-104624730, MIAT_B (see, Table 7,
Example 1).

The technology provides various panels of markers use
for identifying serous EC, e.g., in some embodiments the
marker comprises a chromosomal region having an annotation that is MAX.chr7.104624356-104624730, EMX2OS,
and LRRC41_C (see, Table 12, Example 1).

The technology provides various panels of markers use
for identifying serous EC, e.g., in some embodiments the
marker comprises a chromosomal region having an annotation that is MAX.chr8.145103829-145103992, CYTH2,
LRRC8D_A, OBSCN_A, DIDO1_A, EMX2OS,
LRRC41_C, and VILL (see, Table 17, Example 1).

The technology provides various panels of markers use
for identifying serous EC, e.g., in some embodiments the
marker comprises a chromosomal region having an annotation that is EMX2OS, and LRRC41_D (see, Table 24,
Example 3).

The technology provides various panels of markers use
for identifying serous EC, e.g., in some embodiments the
marker comprises a chromosomal region having an annotation that is SFMBT2_B, SMTN, SQSTM1, ZNF90,
CLDN7, LRRC41_B, MAX.chr7.104624356-104624730,
CYP11A1, FKBP11_A, MAX.chr8.145103829-145103992,
AHSA2, CYTH2, LRRC8D_A, MAX.chr8.145104263-145104422, OBSCN_A, GDGF6, DLL4, PYCARD,
BMP4_B, JSRP1_A, MIAT_B, KANK1, EMX2OS,
NBPF8, LOC440925_A, ITPKA, EEF1A2, FEV,
LRRC41_C, NFIC, VILL, MPZ_A (see, Table 12, Example
1).

The technology provides various panels of markers use
for identifying endometrioid EC, e.g., in some embodiments
the marker comprises a chromosomal region having an annotation that is MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B (see, Table 6, Example 1).

The technology provides various panels of markers use for identifying endometrioid EC, e.g., in some embodiments the marker comprises a chromosomal region having an annotation that is MAX.chr8.145103829-145103992, CYTH2, DIDO1_A, MAX.chr10.22624479-22624553, JSRP1_A, SBNO2, NBPF8, and VILL (see, Table 14, Example 1).

The technology provides various panels of markers use for identifying endometrioid EC, e.g., in some embodiments the marker comprises a chromosomal region having an annotation that is SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A (see, Table 19, Example 1).

The technology provides various panels of markers use for identifying endometrioid EC, e.g., in some embodiments the marker comprises a chromosomal region having an annotation that is SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A (see, Table 14, Example 1).

The technology provides various panels of markers use for identifying endometrioid Grade 1 EC, e.g., in some embodiments the marker comprises a chromosomal region having an annotation that is TSPYL5, TRH, JAM3, FAM19A5, PTGDR, SFMBT2_E, JSRP1_B, and ARL5C (see, Table 25, Example 3).

The technology provides various panels of markers use for identifying endometrioid Grade 2 EC, e.g., in some embodiments the marker comprises a chromosomal region having an annotation that is TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B (see, Table 25, Example 3).

The technology provides various panels of markers use for identifying endometrioid Grade 3 EC, e.g., in some embodiments the marker comprises a chromosomal region having an annotation that is TSPYL5, MPZ_B, TRH, and PTGDR (see, Table 25, Example 3).

Kit embodiments are provided, e.g., a kit comprising a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-499 (from Tables 1, 8 and 21) and having a methylation state associated with a subject who does not have EC. In some embodiments, kits comprise a bisulfite reagent and an oligonucleotide as described herein. In some embodiments, kits comprise a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of of DMR 1-499 (from Tables 1, 8 and 21) and having a methylation state associated with a subject who has EC. Some kit embodiments comprise a sample collector for obtaining a sample from a subject (e.g., a stool sample; endometrial tissue sample; blood sample); a reagent capable of modifying DNA in a methylation-specific manner (e.g., a methylation-sensitive restriction enzyme, a methylation-dependent restriction enzyme, and a bisulfite reagent); and an oligonucleotide as described herein.

The technology is related to embodiments of compositions (e.g., reaction mixtures). In some embodiments are provided a composition comprising a nucleic acid comprising a DMR and a reagent capable of modifying DNA in a methylation-specific manner (e.g., a methylation-sensitive restriction enzyme, a methylation-dependent restriction enzyme, and a bisulfite reagent). Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for EC and/or various forms of EC (e.g., clear cell EC, carcinosarcoma EC, endometrioid EC, serous EC) in a sample obtained from a subject (e.g., endometrial tissue sample; blood sample; stool sample), e.g., a method comprising determining a methylation state of a marker in the sample comprising a base in a DMR that is one or more of DMR 1-499 (from Tables 1, 8 and 21); comparing the methylation state of the marker from the subject sample to a methylation state of the marker from a normal control sample from a subject who does not have EC (e.g., EC, clear cell EC, carcinosarcoma EC, endometrioid EC, serous EC); and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a reagent capable of modifying nucleic acid in a methylation-specific manner (e.g., a methylation-sensitive restriction enzyme, a methylation-dependent restriction enzyme, and a bisulfite reagent) to produce, for example, nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have EC and/or a form of EC to identify differences in the two sequences; and identifying the subject as having EC (e.g., EC and/or a form of EC: clear cell EC, carcinosarcoma EC, endometrioid EC, serous EC) when a difference is present.

Systems for screening for EC in a sample obtained from a subject are provided by the technology. Exemplary embodiments of systems include, e.g., a system for screening for EC and/or types of EC (e.g., clear cell EC, carcinosarcoma EC, endometrioid EC, serous EC) in a sample obtained from a subject (e.g., endometrial tissue sample; plasma sample; stool sample), the system comprising an analysis component configured to determine the methylation state of a sample, a software component configured to compare the methylation state of the sample with a control sample or a reference sample methylation state recorded in a database, and an alert component configured to alert a user of a EC-associated methylation state. An alert is determined in some embodiments by a software component that receives the results from multiple assays (e.g., determining the methylation states of multiple markers, e.g., DMR, e.g., as provided in Tables 1, 8 and 21) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have EC and/or specific types of EC (e.g., clear cell EC, carcinosarcoma EC, endometrioid EC, serous EC). Also provided are nucleic acids, e.g., a set of nucleic acids, each nucleic acid having a sequence comprising a DMR. In some embodiments the set of nucleic acids wherein each nucleic acid has a sequence from a subject who does not have EC and/or specific types of EC. Related system embodiments comprise a set of nucleic acids as described and a database of nucleic acid sequences associated with the set of nucleic acids. Some embodiments further comprise a reagent capable of modifying DNA in a methylation-specific manner (e.g., a methylation-sensitive restriction enzyme, a methylation-dependent restriction enzyme, and a bisulfite reagent). And, some embodiments further comprise a nucleic acid sequencer.

In certain embodiments, methods for characterizing a sample (e.g., endometrial tissue sample; blood sample; stool sample) from a human patient are provided. For example, in some embodiments such embodiments comprise obtaining DNA from a sample of a human patient; assaying a methylation state of a DNA methylation marker comprising a base in a differentially methylated region (DMR) selected from a group consisting of DMR 1-499 from Tables 1, 8 and 21; and comparing the assayed methylation state of the one or more DNA methylation markers with methylation level references for the one or more DNA methylation markers for human patients not having EC and/or specific types of EC (e.g., clear cell EC, carcinosarcoma EC, endometrioid EC, serous EC).

Such methods are not limited to a particular type of sample from a human patient. In some embodiments, the sample is an endometrial tissue sample. In some embodiments, the sample is a plasma sample. In some embodiments, the sample is a stool sample, a tissue sample, an endometrial tissue sample, a blood sample (e.g., leukocyte sample, plasma sample, whole blood sample, serum sample), or a urine sample.

In some embodiments, such methods comprise assaying a plurality of DNA methylation markers. In some embodiments, such methods comprise assaying 2 to 11 DNA methylation markers. In some embodiments, such methods comprise assaying 12 to 120 DNA methylation markers. In some embodiments, such methods comprise assaying 2 to 499 DNA methylation markers. In some embodiments, such methods comprise assaying the methylation state of the one or more DNA methylation markers in the sample comprises determining the methylation state of one base. In some embodiments, such methods comprise assaying the methylation state of the one or more DNA methylation markers in the sample comprises determining the extent of methylation at a plurality of bases. In some embodiments, such methods comprise assaying a methylation state of a forward strand or assaying a methylation state of a reverse strand.

In some embodiments, the DNA methylation marker is a region of 100 or fewer bases. In some embodiments, the DNA methylation marker is a region of 500 or fewer bases. In some embodiments, the DNA methylation marker is a region of 1000 or fewer bases. In some embodiments, the DNA methylation marker is a region of 5000 or fewer bases. In some embodiments, the DNA methylation marker is one base. In some embodiments, the DNA methylation marker is in a high CpG density promoter.

In some embodiments, the assaying comprises using methylation specific polymerase chain reaction, nucleic acid sequencing, mass spectrometry, methylation specific nuclease, mass-based separation, or target capture.

In some embodiments, the assaying comprises use of a methylation specific oligonucleotide. In some embodiments, the methylation specific oligonucleotide is selected from the group consisting of SEQ ID NO: 1-499 (Tables 1, 8 and 21).

In some embodiments, a chromosomal region having an annotation selected from the group consisting of AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90 (see, Table 2, Example 1) comprises the DNA methylation marker.

In some embodiments, a chromosomal region having an annotation selected from the group consisting of EMX2OS, CYTH2, C17orf107_A, DIDO1_A, GDF6, NBPF8, MAX.chr14.103021656-103021718, JSRP1_A, GATA2_B, and SFMBT2_B (see, Table 3, Example 1) comprises the DNA methylation marker.

In some embodiments, a chromosomal region having an annotation selected from the group consisting of SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A (see, Table 15, Example 1) comprises the DNA methylation marker.

In some embodiments, a chromosomal region having an annotation selected from the group consisting of EMX2OS, CYTH2, NBPF8, MAX.chr10.22624479-22624553 (see, Table 20, Example 1) comprises the DNA methylation marker.

In some embodiments, a chromosomal region having an annotation selected from the group consisting of ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A (see, Table 9, Example 1) comprises the DNA methylation marker.

In some embodiments, a chromosomal region having an annotation selected from the group consisting of DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422 (see, Table 4, Example 1) comprises the DNA methylation marker.

In some embodiments, a chromosomal region having an annotation selected from the group consisting of ZNF323_A, MAX.chr7.104624356-104624730, NDRG2, DIDO1_A, MDFI_B, MAX.chr14.103021656-103021718, MMP23B, SEPT9_B, and STX16_A (see, Table 11, Example 1) comprises the DNA methylation marker.

In some embodiments, a chromosomal region having an annotation selected from the group consisting of SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A (see, Table 16, Example 1) comprises the DNA methylation marker.

In some embodiments, a chromosomal region having an annotation selected from the group consisting of MAX.chr7: 104624386-104624529, EMX2OS, DIDO1_B, and OBSCN_B (see, Table 24, Example 3) comprises the DNA methylation marker.

In some embodiments, a chromosomal region having an annotation selected from the group consisting of SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC (see, Table 11, Example 1) comprises the DNA methylation marker.

In some embodiments, a chromosomal region having an annotation selected from the group consisting of EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B (see, Table 5, Example 1) comprises the DNA methylation marker.

In some embodiments, a chromosomal region having an annotation selected from the group consisting of EMX2OS, and LRRC34 (see, Table 13, Example 1) comprises the DNA methylation marker.

In some embodiments, a chromosomal region having an annotation selected from the group consisting of ZNF506, ZNF90, MAX.chr8.145103829-145103992, LRRC8D_A, OBSCN_A, MAX.chr10.22624479-22624553, JSRP1_A, EMX2OS, NBPF8, and VILL (see, Table 18, Example 1) comprises the DNA methylation marker.

In some embodiments, a chromosomal region having an annotation selected from the group consisting of TRH, MAX.chr7:104624386-104624529, EMX2OS, DIDO1_B, and ST3GAL2_B (see, Table 24, Example 3) comprises the DNA methylation marker.

In some embodiments, a chromosomal region having an annotation selected from the group consisting of SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL (see, Table 13, Example 1) comprises the DNA methylation marker.

In some embodiments, a chromosomal region having an annotation selected from the group consisting EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B (see, Table 7, Example 1) comprises the DNA methylation marker.

In some embodiments, a chromosomal region having an annotation selected from the group consisting of MAX.chr7.104624356-104624730, EMX2OS, and LRRC41_C (see, Table 12, Example 1) comprises the DNA methylation marker.

In some embodiments, a chromosomal region having an annotation selected from the group consisting of MAX.chr8.145103829-145103992, CYTH2, LRRC8D_A, OBSCN_A, DIDO1_A, EMX2OS, LRRC41_C, and VILL (see, Table 17, Example 1) comprises the DNA methylation marker.

In some embodiments, a chromosomal region having an annotation selected from the group consisting of EMX2OS, and LRRC41_D (see, Table 24, Example 3) comprises the DNA methylation marker.

In some embodiments, a chromosomal region having an annotation selected from the group consisting of SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A (see, Table 12, Example 1) comprises the DNA methylation marker.

In some embodiments, a chromosomal region having an annotation selected from the group consisting of MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B (see, Table 6, Example 1) comprises the DNA methylation marker.

In some embodiments, a chromosomal region having an annotation selected from the group consisting of MAX.chr8.145103829-145103992, CYTH2, DIDO1_A, MAX.chr10.22624479-22624553, JSRP1_A, SBNO2, NBPF8, and VILL (see, Table 14, Example 1) comprises the DNA methylation marker.

In some embodiments, a chromosomal region having an annotation selected from the group consisting of SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A (see, Table 19, Example 1) comprises the DNA methylation marker.

In some embodiments, a chromosomal region having an annotation selected from the group consisting of SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A (see, Table 14, Example 1) comprises the DNA methylation marker.

In some embodiments, a chromosomal region having an annotation selected from the group consisting of TSPYL5, TRH, JAM3, FAM19A5, PTGDR, SFMBT2_E, JSRP1_B, and ARL5C (see, Table 25, Example 3) comprises the DNA methylation marker.

In some embodiments, a chromosomal region having an annotation selected from the group consisting of TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B (see, Table 25, Example 3) comprises the DNA methylation marker.

In some embodiments, a chromosomal region having an annotation selected from the group consisting of TSPYL5, MPZ_B, TRH, and PTGDR (see, Table 25, Example 3) comprises the DNA methylation marker.

In some embodiments, such methods comprise determining the methylation state of two DNA methylation markers. In some embodiments, such methods comprise determining the methylation state of a pair of DNA methylation markers provided in a row of Tables 1, 8 and/or 21.

In certain embodiments, the technology provides methods for characterizing a sample (e.g., endometrial tissue sample; leukocyte sample; plasma sample; whole blood sample; serum sample; stool sample) obtained from a human patient. In some embodiments, such methods comprise determining a methylation state of a DNA methylation marker in the sample comprising a base in a DMR selected from a group consisting of DMR 1-499 from Tables 1, 8 or 21; comparing the methylation state of the DNA methylation marker from the patient sample to a methylation state of the DNA methylation marker from a normal control sample from a human subject who does not have a EC and/or a specific form of EC (e.g., clear cell EC, carcinosarcoma EC, endometrioid EC, serous EC); and determining a confidence interval and/or a p value of the difference in the methylation state of the human patient and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001.

In certain embodiments, the technology provides methods for characterizing a sample obtained from a human subject (e.g., endometrial tissue sample; leukocyte sample; plasma sample; whole blood sample; serum sample; stool sample), the method comprising reacting a nucleic acid comprising a DMR with a reagent capable of modifying DNA in a methylation-specific manner (e.g., a methylation-sensitive restriction enzyme, a methylation-dependent restriction enzyme, and a bisulfite reagent) to produce nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have EC to identify differences in the two sequences.

In certain embodiments, the technology provides systems for characterizing a sample obtained from a human subject (e.g., endometrial tissue sample; plasma sample; stool sample), the system comprising an analysis component configured to determine the methylation state of a sample, a software component configured to compare the methylation state of the sample with a control sample or a reference sample methylation state recorded in a database, and an alert component configured to determine a single value based on a combination of methylation states and alert a user of a EC-associated methylation state. In some embodiments, the sample comprises a nucleic acid comprising a DMR.

In some embodiments, such systems further comprise a component for isolating a nucleic acid. In some embodiments, such systems further comprise a component for collecting a sample.

In some embodiments, the sample is a stool sample, a tissue sample, an endometrial tissue sample, a blood sample (e.g., plasma sample, leukocyte sample, whole blood sample, serum sample), or a urine sample.

In some embodiments, the database comprises nucleic acid sequences comprising a DMR. In some embodiments, the database comprises nucleic acid sequences from subjects who do not have EC.

Additional embodiments will be apparent to persons skilled in the relevant art based on the teachings contained herein.

BRIEF DESCRIPTION OF THE DRAWINGS

FIG. 2: Marker chromosomal regions used for the 61 methylation markers (e.g., methylated regions distinguishing EC tissue from normal endometrial tissue) and related primer and probe information.

DEFINITIONS

Figure 1:
FIG. 1: A cross-validated 3-MDM panel was derived from rPART modeling (EMX2OS, NBPF8, SFMBT2) which discriminated overall EC from BE with 97% specificity and 97% sensitivity with an AUC of 0.98. The data was plotted in a heat matrix format which allowed complementarity visualization.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in *In re Herz*, 537F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and poly adenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula R=(A×B)/(C×D), where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. Examples of such reagents include, but are not limited to, a methylation-sensitive restriction enzyme, a methylation-dependent restriction enzyme, and a bisulfite reagent.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "MethyLight™" refers to the art-recognized fluorescence-based real-time PCR technique described by Eads et al. (1999) Cancer Res. 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Nat. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The term "methylation-specific restriction enzyme" refers to a restriction enzyme that selectively digests a nucleic acid dependent on the methylation state of its recognition site. In the case of a restriction enzyme that specifically cuts if the recognition site is not methylated or is hemi-methylated (a methylation-sensitive enzyme), the cut will not take place (or will take place with a significantly reduced efficiency) if the recognition site is methylated on one or both strands. In the case of a restriction enzyme that specifically cuts only if the recognition site is methylated (a methylation-dependent enzyme), the cut will not take place (or will take place with a significantly reduced efficiency) if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Provided herein is technology for EC screening and particularly, but not exclusively, to methods, compositions, and related uses for detecting the presence of EC and/or specific forms of EC (e.g., clear cell EC, carcinosarcoma EC, endometrioid EC, serous EC). As the technology is described herein, the section headings used are for organizational purposes only and are not to be construed as limiting the subject matter in any way.

Indeed, as described in Examples 1, 2 and 3, experiments conducted during the course for identifying embodiments for the present invention identified a novel set of 499 differentially methylated regions (DMRs) for discriminating cancer of the endometrium derived DNA from non-neoplastic control DNA. From these 499 novel DNA methylation markers, further experiments identified markers capable of distinguishing different types of EC from normal endometrial tissue. For example, separate sets of DMRs were identified capable of distinguishing 1) EC from normal endometrial tissue; 2) clear cell EC from normal endometrial tissue; 3) serous EC from normal endometrial tissue; 4) carcinosarcoma EC from normal endometrial tissue; and 5) endometrioid EC from normal endometrial tissue.

Although the disclosure herein refers to certain illustrated embodiments, it is to be understood that these embodiments are presented by way of example and not by way of limitation.

In particular aspects, the present technology provides compositions and methods for identifying, determining, and/or classifying a cancer such as EC. The methods comprise determining the methylation status of at least one methylation marker in a biological sample isolated from a subject (e.g., stool sample, endometrial tissue sample, plasma sample), wherein a change in the methylation state of the marker is indicative of the presence, class, or site of EC. Particular embodiments relate to markers comprising a differentially methylated region (DMR, e.g., DMR 1-499, see Tables 1, 8 and 21) that are used for diagnosis (e.g., screening) of EC and various types of EC (e.g., clear cell EC, carcinosarcoma EC, endometrioid EC, serous EC).

In addition to embodiments wherein the methylation analysis of at least one marker, a region of a marker, or a base of a marker comprising a DMR (e.g., DMR, e.g., DMR 1-499) provided herein and listed in Tables 1, 8 and 21 is analyzed, the technology also provides panels of markers comprising at least one marker, region of a marker, or base of a marker comprising a DMR with utility for the detection of cancers, in particular EC.

Some embodiments of the technology are based upon the analysis of the CpG methylation status of at least one marker, region of a marker, or base of a marker comprising a DMR.

In some embodiments, the present technology provides for the use of a reagent that modifies DNA in a methylation-specific manner (e.g., a methylation-sensitive restriction enzyme, a methylation-dependent restriction enzyme, and a bisulfite reagent) in combination with one or more methylation assays to determine the methylation status of CpG dinucleotide sequences within at least one marker comprising a DMR (e.g., DMR 1-499, see Tables 1, 8 and 21). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as EC.

Combinations of Markers

In some embodiments, the technology relates to assessing the methylation state of combinations of markers comprising a DMR from Tables 1, 8 and 21 (e.g., DMR Nos. 1-499). In some embodiments, assessing the methylation state of more than one marker increases the specificity and/or sensitivity of a screen or diagnostic for identifying a neoplasm in a subject (e.g., EC).

Various cancers are predicted by various combinations of markers, e.g., as identified by statistical techniques related to specificity and sensitivity of prediction. The technology provides methods for identifying predictive combinations and validated predictive combinations for some cancers.

Methods for Assaying Methylation State

In certain embodiments, methods for analyzing a nucleic acid for the presence of 5-methylcytosine involves treatment of DNA with a reagent that modifies DNA in a methylation-specific manner. Examples of such reagents include, but are not limited to, a methylation-sensitive restriction enzyme, a methylation-dependent restriction enzyme, and a bisulfite reagent.

A frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; and in U.S. Pat. Nos. 8,361, 720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis"

*Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-specific restriction enzymes, e.g., methylation-sensitive or methylation-dependent enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components. Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199), and U.S. Pat. Nos. 8,361,720; 8,715,937; 8,916,344; and 9,212,392, each of which is incorporated herein by reference for all purposes.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxyben-zone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, fragments of the treated DNA are amplified using sets of primer oligonucleotides according to the present invention (e.g., see Tables 10, 19 and 20) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-499, Tables 1, 8 and 21) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer. Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, leukocytes, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events. The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

Methods

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90, and 2) detecting EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of EMX2OS, CYTH2, C17orf107_A, DIDO1_A, GDF6, NBPF8, MAX.chr14.103021656-103021718, JSRP1_A, GATA2_B, and SFMBT2_B, and 2) detecting EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A, and 2) detecting EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of EMX2OS, CYTH2, NBPF8, MAX.chr10.22624479-22624553, and 2) detecting EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from a blood sample (e.g., plasma sample, whole blood sample, leukocyte sample, serum sample) obtained from the subject with at least one reagent or series of reagents that distinguishes between methylated and non-methylated CpG dinucleotides within at least one marker selected from a chromosomal region having an annotation selected from the group consisting of ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A, and 2) detecting EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422, and 2) detecting clear cell EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting of ZNF323_A, MAX.chr7.104624356-104624730, NDRG2, DIDO1_A, MDFI_B, MAX.chr14.103021656-103021718, MMP23B, SEPT9_B, and STX16_A, and 2) detecting clear cell EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A, and 2) detecting clear cell EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting MAX.chr7: 104624386-104624529, EMX2OS, DIDO1_B, and OBSCN_B, and 2) detecting clear cell EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from a blood sample (e.g., plasma sample, whole blood sample, leukocyte sample, serum sample)) obtained from the subject with at least one reagent or series of reagents that distinguishes between methylated and non-methylated CpG dinucleotides within at least one marker selected from a chromosomal region having an annotation selected from the group consisting SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC, and 2) detecting clear cell EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B, and 2) detecting carcinosarcoma EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting EMX2OS, and LRRC34, and 2) detecting carcinosarcoma EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting ZNF506, ZNF90, MAX.chr8.145103829-145103992, LRRC8D_A, OBSCN_A, MAX.chr10.22624479-22624553, JSRP1_A, EMX2OS, NBPF8, and VILL, and 2) detecting carcinosarcoma EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting TRH, MAX.chr7:104624386-104624529, EMX2OS, DIDO1_B, and ST3GAL2_B, and 2) detecting carcinosarcoma EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from a blood sample (e.g., plasma sample, whole blood sample, leukocyte sample, serum sample)) obtained from the subject with at least one reagent or series of reagents that distinguishes between methylated and non-methylated CpG dinucleotides within at least one marker selected from a chromosomal region having an annotation selected from the group consisting SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL, and 2) detecting carcinosarcoma EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B, and 2) detecting serous EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting MAX.chr7.104624356-104624730, EMX2OS, and LRRC41_C, and 2) detecting serous EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting MAX.chr8.145103829-145103992, CYTH2, LRRC8D_A, OBSCN_A, DIDO1_A, EMX2OS, LRRC41_C, and VILL, and 2) detecting serous EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting EMX2OS, and LRRC41_D, and 2) detecting serous EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from a blood sample (e.g., plasma sample, whole blood sample, leukocyte sample, serum sample)) obtained from the subject with at least one reagent or series of reagents that distinguishes between methylated and non-methylated CpG dinucleotides within at least one marker selected from a chromosomal region having an annotation selected from the group consisting SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A, and 2) detecting serous EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B, and 2) detecting endometrioid EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting MAX.chr8.145103829-145103992, CYTH2, DIDO1_A, MAX.chr10.22624479-22624553, JSRP1_A, SBNO2, NBPF8, and VILL, and 2) detecting endometrioid EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A, and 2) detecting endometrioid EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from a blood sample (e.g., plasma sample, whole blood sample, leukocyte sample, serum sample)) obtained from the subject with at least one reagent or series of reagents that distinguishes between methylated and non-methylated CpG dinucleotides within at least one marker selected from a chromosomal region having an annotation selected from the group consisting SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A, and 2) detecting endometrioid EC (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting TSPYL5, TRH, JAM3, FAM19A5, PTGDR, SFMBT2_E, JSRP1_B, and ARL5C, and 2) detecting endometrioid EC Grade 1 (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B, and 2) detecting endometrioid EC Grade 2 (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from endometrial tissue) obtained from the subject with at least one reagent or series of reagents that distinguishes between methylated and non-methylated CpG dinucleotides within at least one marker selected from a chromosomal region having an annotation selected from the group consisting TSPYL5, MPZ_B, TRH, and PTGDR, and 2) detecting endometrioid EC Grade 3 (e.g., afforded with a sensitivity of greater than or equal to 80% and a specificity of greater than or equal to 80%).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

(i) AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90;

(ii) EMX2OS, CYTH2, C17orf107_A, DIDO1_A, GDF6, NBPF8, MAX.chr14.103021656-103021718, JSRP1_A, GATA2_B, and SFMBT2_B;

(iii) SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A;

(iv) EMX2OS, CYTH2, NBPF8, MAX.chr10.22624479-22624553; and (v) ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

(i) DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422;

(ii) ZNF323_A, MAX.chr7.104624356-104624730, NDRG2, DIDO1_A, MDFI_B, MAX.chr14.103021656-103021718, MMP23B, SEPT9_B, and STX16_A;

(iii) SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A;

(iv) MAX.chr7:104624386-104624529, EMX2OS, DIDO1_B, and OBSCN_B; and (v) SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

(i) EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B;

(ii) EMX2OS, and LRRC34;

(iii) ZNF506, ZNF90, MAX.chr8.145103829-145103992, LRRC8D_A, OBSCN_A, MAX.chr10.22624479-22624553, JSRP1_A, EMX2OS, NBPF8, and VILL;

(iv) TRH, MAX.chr7:104624386-104624529, EMX2OS, DIDO1_B, and ST3GAL2_B; and (v) SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

(i) EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B;

(ii) MAX.chr7.104624356-104624730, EMX2OS, and LRRC41_C;

(iii) MAX.chr8.145103829-145103992, CYTH2, LRRC8D_A, OBSCN_A, DIDO1_A, EMX2OS, LRRC41_C, and VILL;

(iv) EMX2OS, and LRRC41_D; and (v) SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF4, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfite reagent, a methylation-sensitive restriction enzyme, or a methylation-dependent restriction enzyme), wherein the one or more genes is selected from one of the following groups:

(i) MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B;

(ii) MAX.chr8.145103829-145103992, CYTH2, DIDO1_A, MAX.chr10.22624479-22624553, JSRP1_A, SBNO2, NBPF8, and VILL;

(iii) SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A;

(iv) SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A;

(v) TSPYL5, TRH, JAM3, FAM19A5, PTGDR, SFMBT2_E, JSRP1_B, and ARL5C;

(vi) TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B; and (vii) TSPYL5, MPZ_B, TRH, and PTGDR.

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

(i) AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90;

(ii) EMX2OS, CYTH2, C17orf107_A, DIDO1_A, GDF6, NBPF8, MAX.chr14.103021656-103021718, JSRP1_A, GATA2_B, and SFMBT2_B;

(iii) SFMBT2_B, ZNF90, MAX.chr8.145103829-145103992, CYTH2, LRRC8D_A, OBSCN_A,

DIDO1_A, MAX.chr10.22624479-22624553, JSRP1_A, EMX2OS, NBPF8, and MPZ_A;

(iv) EMX2OS, CYTH2, NBPF8, MAX.chr10.22624479-22624553; and (v) ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring an amount of at least one methylated marker gene in DNA from the sample, wherein the one or more genes is selected from one of the following groups:

(i) DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422;

(ii) ZNF323_A, MAX.chr7.104624356-104624730, NDRG2, DIDO1_A, MDFI_B, MAX.chr14.103021656-103021718, MMP23B, SEPT9_B, and STX16_A;

(iii) SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A;

(iv) MAX.chr7:104624386-104624529, EMX2OS, DIDO1_B, and OBSCN_B; and (v) SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring an amount of at least one methylated marker gene in DNA from the sample, wherein the one or more genes is selected from one of the following groups:

(i) EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B;

(ii) EMX2OS, and LRRC34;

(iii) ZNF506, ZNF90, MAX.chr8.145103829-145103992, LRRC8D_A, OBSCN_A, MAX.chr10.22624479-22624553, JSRP1_A, EMX2OS, NBPF8, and VILL;

(iv) TRH, MAX.chr7:104624386-104624529, EMX2OS, DIDO1_B, and ST3GAL2_B; and (v) SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring an amount of at least one methylated marker gene in DNA from the sample, wherein the one or more genes is selected from one of the following groups:

(i) EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B;

(ii) MAX.chr7.104624356-104624730, EMX2OS, and LRRC41_C;

(iii) MAX.chr8.145103829-145103992, CYTH2, LRRC8D_A, OBSCN_A, DIDO1_A, EMX2OS, LRRC41_C, and VILL;

(iv) EMX2OS, and LRRC41_D; and (v) SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring an amount of at least one methylated marker gene in DNA from the sample, wherein the one or more genes is selected from one of the following groups:

(i) MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B;

(ii) MAX.chr8.145103829-145103992, CYTH2, DIDO1_A, MAX.chr10.22624479-22624553, JSRP1_A, SBNO2, NBPF8, and VILL;

(iii) SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A;

(iv) SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A;

(v) TSPYL5, TRH, JAM3, FAM19A5, PTGDR, SFMBT2_E, JSRP1_B, and ARL5C;

(vi) TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B; and (vii) TSPYL5, MPZ_B, TRH, and PTGDR;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) AFF3, AIM1_A, AMIGO3_A, BMP4_B, C17orf107_A, C1orf70_B, C5orf52, CLDN7, DIDO1_A, EEF1A2, EMX2OS, FEV, FKBP11_A, GDF6, GDF7_A, JSRP1_A, KCTD15_A, KLHL21, LRRC8D_A, NBPF8, MAX.chr10.130339363-130339534, MAX.chr10.22624479-22624553, MAX.chr14.103021656-103021718, MAX.chr8.145103829-145103992, MAX.chr8.145104263-145104422, MDFI_B, MIAT_A, MMP23B, NDRG2, OBSCN_A, PCOLCE, PYCARD, SEPT9_B, SLC6A3_A, SLC8A3_B, SQSTM1, VILL, ZNF302, ZNF323_A, ZNF506, and ZNF90;

(ii) EMX2OS, CYTH2, C17orf107_A, DIDO1_A, GDF6, NBPF8, MAX.chr14.103021656-103021718, JSRP1_A, GATA2_B, and SFMBT2_B;

(iii) SFMBT2_B, ZNF90, MAX.chr8.145103829-145103992, CYTH2, LRRC8D_A, OBSCN_A, DIDO1_A, MAX.chr10.22624479-22624553, JSRP1_A, EMX2OS, NBPF8, and MPZ_A;

(iv) EMX2OS, CYTH2, NBPF8, MAX.chr10.22624479-22624553; and (v) ANKRD35, ARL5C, ARRB1, BCL2L11_A, BCL2L11_B, BCL2L11_C, BZRAP1, C16orf54, C17orf101, C6orf132, CACNA2D4, DEDD2, EPS15L1, FAIM2, FAM125B, FAM189B, FAM78A, FOXP4, GYPC_A, GYPC_B, IFFO1_A, IFFO1_B, ITPKA, KLF16, LIMD2, LOC389333, LOC440925_A, LOC646278, LYL1, LYPLAL1, MAX.chr11.32355226-32355251, MAX.chr14.102172621-102172686, MAX.chr14.105512122-105512239, MAX.chr15.95128144-95128248, MAX.chr16.11327016-11327312, MAX.chr3.187676577-187676668, MAX.chr4.174430676-174430847, MAX.chr8.145900783-145900914, MAX.chr8.80804237-80804301, N4BP3, NCOR2, NFATC1_A, NFATC1_B, NKX2-6, NR2F6, OSM, PALLD_C, PIK3CD, PRKAR1B, RAD52, STX16_A, SUCLG2, TNFRSF1B, TNFRSF4, ZDHHC18, and ZNF671_A.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) DIDO1_A, NDRG4, MAX.chr14.103021656-103021718, MMP23B, EMX2OS, SEPT9_B, NBPF8, EEF1A2, AIM1_A, BMP4_B, MAX.chr8.145103829-145103992, OBSCN, PYCARD, GDF6, MDFI_B, MIAT_A, SCL8A3, ZNF323_A, SQSTM1, AFF3, C1orf70, GDF7_A, JSRP1_A, LRRC8D_A, FEV, and MAX.chr8.145104263-145104422;

(ii) ZNF323_A, MAX.chr7.104624356-104624730, NDRG2, DIDO1_A, MDFI_B, MAX.chr14.103021656-103021718, MMP23B, SEPT9_B, and STX16_A;

(iii) SFMBT2_B, SQSTM1, ZNF323_A, ZNF90, MAX.chr8.145103829-145103992, CYTH2, LRRC8D_A, OBSCN_A, DIDO1_A, MDFI_B, GDF7_A, MAX.chr10.22624479-22624553, JSRP1_A, MAX.chr14.103021656-103021718, EMX2OS, LRRC34, NBPF8, SEPT9_B, EEF1A2, LRRC41_C, VILL, and MPZ_A;

(iv) MAX.chr7:104624386-104624529, EMX2OS, DIDO1_B, and OBSCN_B; and (v) SFMBT2_B, SQSTM1, ZNF323_A, ZNF506, ZNF90, CLDN7, LRRC41_B, MAX.chr7.104624356-104624730, NDRG2, CYP11A1, MAX.chr8.145103829-145103992, CYTH2, LRRC8D_A, MAX.chr8.145104263-145104422, OBSCN_A, DIDO1_A, GDF6, MAX.chr10.130339363-130339534, MDFI_B, DLL4, GDF7_A, MIAT_A, PYCARD, BMP4_B, JSRP1_A, MAX.chr14.103021656-103021718, EMX2, MMP23B, EMX2OS, MAX.chr17.73073716-73073814, NBPF8, SEPT9_B, LOC440925_A, STX16_A, ITPKA, EEF1A2, FEV, LRRC41_C, and NFIC.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) EMX2OS, DIDO1_A, SBNO2, AMIGO3_A, PCOLCE, CLDN7, CYTH2, OBSCN_A, AHSA2, DLL4, EMX2, MAX.chr14.74100620-74100870, LRRC4, PPP2R5C_A, SQSTM1, MAX.chr17.73073716-73073814, CYP11A1, ACOXL_A, and AIM1_B;

(ii) EMX2OS, and LRRC34;

(iii) ZNF506, ZNF90, MAX.chr8.145103829-145103992, LRRC8D_A, OBSCN_A, MAX.chr10.22624479-22624553, JSRP1_A, EMX2OS, NBPF8, and VILL;

(iv) TRH, MAX.chr7:104624386-104624529, EMX2OS, DIDO1_B, and ST3GAL2_B; and (v) SFMBT2_B, SMTN, ZNF506, ZNF90, CLDN7, LRRC41_B, CYP11A1, MAX.chr8.145103829-145103992, AHSA2, CYTH2, GATA2_B, LRRC8D_A, MAX.chr8.145104263-145104422, OBSCN_A, DIDO1_A, GDF6, DLL4, MAX.chr10.22624479-22624553, PYCARD, BMP4_B, JSRP1_A, MAX.chr14.103021656-103021718, MIAT_B, EMX2OS, LRRC34, NBPF8, LOC440925_A, ITPKA, NFIC, and VILL.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) EMX2OS, KANK1, C1orf70_B, AMIGO3_A, DIDO1_A, LRRC41_C, NFIC, FKBP11_A, C17orf107_A, SMTN, LRRC41_B, LRRC8D_A, OBSCN_A, MAX.chr7.104624356-104624730, MIAT_B;

(ii) MAX.chr7.104624356-104624730, EMX2OS, and LRRC41_C;

(iii) MAX.chr8.145103829-145103992, CYTH2, LRRC8D_A, OBSCN_A, DIDO1_A, EMX2OS, LRRC41_C, and VILL;

(iv) EMX2OS, and LRRC41_D; and (v) SFMBT2_B, SMTN, SQSTM1, ZNF90, CLDN7, LRRC41_B, MAX.chr7.104624356-104624730, CYP11A1, FKBP11_A, MAX.chr8.145103829-145103992, AHSA2, CYTH2, LRRC8D_A, MAX.chr8.145104263-145104422, OBSCN_A, GDGF6, DLL4, PYCARD, BMP4_B, JSRP1_A, MIAT_B, KANK1, EMX2OS, NBPF8, LOC440925_A, ITPKA, EEF1A2, FEV, LRRC41_C, NFIC, VILL, MPZ_A.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) MAX.chr10.130339363-130339534, SFMBT2_C, CYTH2, SLC6A3, VILL, EMX2OS, MAX.chr10.22624479-22624553, GDF6, ZNF90, ZNF506, JSRP1_A, c5orf52, SFMBT2_B, NBPF8, RHBDL1_A, DIDO1_A, KANK1, and GATA2_B;

(ii) MAX.chr8.145103829-145103992, CYTH2, DIDO1_A, MAX.chr10.22624479-22624553, JSRP1_A, SBNO2, NBPF8, and VILL;

(iii) SFMBT2_B, ZNF90, MAX.chr8.145103829-145103992, CYTH2, MAX.chr8.145104263-145104422, OBSCN_A, MAX.chr10.22624479-22624553, JSRP1_A, EMX2OS, NBPF8, and MPZ_A;

(iv) SFMBT2_B, SMTN, SQSTM1, ZNF506, ZNF90, CLDN7, LRRC41_B, FKBP11_A, MAX.chr8.145103829-145103992, AHSA2, CYTH2, GATA2_B, LRRC8D_A, MAX.chr8.145104263-145104422, DIDO1_A, GDF6, MAX.chr10.130339363-130339534, DLL4, MAX.chr10.22624479-22624553, MIAT_A, PYCARD, BMP4_B, JSRP1_A, MAX.chr14.103021656-103021718, MIAT_B, KANK1, SBNO2, c5orf52, EMX206, LRRC34, NBPF8, LOC440925_A, ITPKA, NFIC, VILL, and MPZ_A;

(v) TSPYL5, TRH, JAM3, FAM19A5, PTGDR, SFMBT2_E, JSRP1_B, and ARL5C;

(vi) TSPYL5, MPZ_B, TRH, CNTN4, FAM19A5, GLT1D1, RYR2_F, PTGDR, EMX2OS, MAX.chr10:22624470-22624553, SPDYA_B, SFMBT2_E, and JSRP1_B; and (vii) TSPYL5, MPZ_B, TRH, and PTGDR.

Preferably, the sensitivity for such methods is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, breast tissue, endometrial tissue, leukocytes, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-499 e.g., as provided by Tables 1, 8 and 21).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfite (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-499, e.g., as provided in Tables 1, 8 and 21). The method of analysis may be selected from those known in the art, including those listed herein, e.g., QuARTS and MSP as described herein.

Aberrant methylation, more specifically hypermethylation of a marker comprising a DMR (e.g., DMR 1-499, e.g., as provided by Tables 1, 8 and 21) is associated with EC and/or a type of EC (e.g., clear cell EC, carcinosarcoma EC, endometrioid EC, serous EC).

The technology relates to the analysis of any sample associated with an EC. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from a breast biopsy, and/or cells recovered from stool. In some embodiments, the sample comprises endometrial tissue. In some embodiments, the subject is human. The sample may include cells, secretions, or tissues from the endometrium, breast, liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample. In some embodiments, the sample is an endometrial tissue sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with EC, with early stage EC, or who may develop EC) (e.g., a patient with one or more clear cell EC, carcinosarcoma EC, endometrioid EC, serous EC), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing an EC in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of EC, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with EC risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from an EC) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or ap value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biamarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with an EC. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having an EC if, when compared to a control methylation state, there is a measurable difference in the methylation state of at least one biomarker in the sample. Conversely, when no change in methylation state is identified in the biological sample, the subject can be identified as not having EC, not being at risk for the cancer, or as having a low risk of the cancer. In this regard, subjects having the cancer or risk thereof can be differentiated from subjects having low to substantially no cancer or risk thereof. Those subjects having a risk of developing an EC can be placed on a more intensive and/or regular screening schedule, including endoscopic surveillance. On the other hand, those subjects having low to substantially no risk may avoid being subjected to additional testing for EC (e.g., invasive procedure), until such time as a future screening, for example, a screening conducted in accordance with the present technology, indicates that a risk of EC has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, an EC indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a system for diagnosing a EC and/or a specific form of EC (e.g., clear cell EC, carcinosarcoma EC, endometrioid EC, serous EC) in a subject. The system can be provided, for example, as a commercial kit that can be used to screen for a risk of an EC or diagnose an EC cancer in a subject from whom a biological sample has been collected. An exemplary system provided in accordance with the present technology includes assessing the methylation state of a DMR as provided in Tables 1, 8 and 21.

EXAMPLES

Example I

This example describes the discovery and validation of novel DNA methylation markers for the detection of endometrial cancer (EC) and histological subtypes of EC (e.g., serous EC, clear cell EC, carcinosarcoma EC, and endometrioid EC) through methylome-wide analysis selection.

A proprietary methodology of sample preparation, sequencing, analyses pipelines, and filters were utilized to identify and narrow differentially methylated regions (DMRs) to those which would pinpoint EC and various histological subtypes of EC (e.g., serous EC, clear cell EC, carcinosarcoma EC, and endometrioid EC) and excel in a clinical testing environment.

From the tissue to tissue analysis 318 hypermethylated EC DMRs were identified (Table 1). Table 2 shows the area-under-the-curve and fold-change in comparison to EC controls for the markers recited in Table 1.

TABLE 1

Identified methylated regions distinguishing endometrial cancer tissue from normal endometrial tissue.

| DMR No. | Gene Annotation | Chromosome No. | Region on Chromosome (starting base-ending base) |
|---|---|---|---|
| 1 | ACCN1 | 17 | 31619687-31619729 |
| 2 | ACOXL__A | 2 | 111875367-111875453 |
| 3 | ADAL__A | 15 | 43622287-43622368 |
| 4 | ADAL__B | 15 | 43622411-43622462 |
| 5 | ADAL__C | 15 | 43622604-43622732 |
| 6 | AES | 19 | 3061334-3061694 |
| 7 | AFF3 | 2 | 100721707-100721817 |
| 8 | AGBL2 | 11 | 47736766-47736965 |
| 9 | AGRN__A | 1 | 975957-976051 |
| 10 | AHSA2 | 2 | 61405232-61405286 |
| 11 | AIM1__A | 6 | 106960032-106960380 |
| 12 | AIM1__B | 6 | 106960531-106960593 |
| 13 | AMIGO3__A | 3 | 49756685-49756736 |
| 14 | AMIGO3__B | 3 | 49757071-49757168 |
| 15 | ANKAR | 2 | 190539103-190539193 |
| 16 | ANKRD33B | 5 | 10563557-10563627 |
| 17 | ANO8 | 19 | 17439445-17439539 |
| 18 | ARHGAP20__A | 11 | 110582609-110582670 |
| 19 | ARHGAP20__B | 11 | 110583216-110583345 |
| 20 | ARL10 | 5 | 175792690-175792780 |
| 21 | ARMC4 | 10 | 28287932-28287982 |
| 22 | ATP10A | 15 | 26108587-26108685 |
| 23 | BCAT1 | 12 | 25102116-25102197 |
| 24 | BCL6 | 3 | 187456434-187456528 |
| 25 | BMP4__A | 14 | 54421048-54421118 |
| 26 | BMP4__B | 14 | 54421619-54421918 |
| 27 | C14orf169 | 14 | 73957777-73957867 |
| 28 | C17orf107__A | 17 | 4802544-4802828 |
| 29 | C18orf18__A | 18 | 5237508-5237617 |
| 30 | C18orf18__B | 18 | 5237862-5237960 |
| 31 | C18orf18__C | 18 | 5238088-5238139 |
| 32 | C1orf103 | 1 | 111506798-111506903 |
| 33 | C1orf177 | 1 | 55266904-55266944 |

TABLE 1-continued

Identified methylated regions distinguishing endometrial cancer tissue from normal endometrial tissue.

| DMR No. | Gene Annotation | Chromosome No. | Region on Chromosome (starting base-ending base) |
|---|---|---|---|
| 34 | C1orf70__A | 1 | 1475622-1475650 |
| 35 | C1orf70__B | 1 | 1475957-1476127 |
| 36 | C1QL3 | 10 | 16563604-16563702 |
| 37 | C21orf58 | 21 | 47743021-47743081 |
| 38 | C2orf43 | 2 | 21022503-21022588 |
| 39 | C2orf62 | 2 | 219232460-219232543 |
| 40 | C5orf52 | 5 | 157098189-157098379 |
| 41 | C7orf51 | 7 | 100091227-100091353 |
| 42 | C8orf73__A | 8 | 144650834-144650918 |
| 43 | CABP7 | 22 | 30116807-30116866 |
| 44 | CACNA1A | 19 | 13318767-13318855 |
| 45 | CCDC102A | 16 | 57571055-57571105 |
| 46 | CCDC48 | 3 | 128720910-128720950 |
| 47 | CCDC85B | 11 | 65658914-65658969 |
| 48 | CCND2__A | 12 | 4380216-4380297 |
| 49 | CCND2__B | 12 | 4384302-4384354 |
| 50 | CCNI2 | 5 | 132082878-132082968 |
| 51 | CD14 | 5 | 140012292-140012386 |
| 52 | CELSR3 | 3 | 48693776-48694065 |
| 53 | CES4A | 16 | 67034701-67034744 |
| 54 | CHMP2A | 19 | 59066468-59066653 |
| 55 | CLDN7 | 17 | 7164898-7164949 |
| 56 | CLIP4 | 2 | 29338393-29338448 |
| 57 | CYP11A1 | 15 | 74658391-74658452 |
| 58 | CYP2R1 | 11 | 14912680-14912762 |
| 59 | CYTH2 | 19 | 48984043-48984140 |
| 60 | DAB2IP__A | 9 | 124461305-124461390 |
| 61 | DAB2IP__B | 9 | 124461600-124461696 |
| 62 | DEM1 | 1 | 40974518-40974785 |
| 63 | DIDO1__A | 20 | 61560557-61560728 |
| 64 | DLEC1__A | 3 | 38080673-38080754 |
| 65 | DLEC1__B | 3 | 38080864-38081010 |
| 66 | DLEC1__C | 3 | 38081058-38081100 |
| 67 | DLL4 | 15 | 41218290-41218501 |
| 68 | DNAJC6 | 1 | 65731433-65731660 |
| 69 | DPP7 | 9 | 140008731-140008820 |
| 70 | DSCAML1 | 11 | 117667818-117667979 |
| 71 | DSEL | 18 | 65184250-65184305 |
| 72 | DTX1 | 12 | 113494626-113494665 |
| 73 | DTX3L | 3 | 122283010-122283080 |
| 74 | EDARADD | 1 | 236558654-236558751 |
| 75 | EEF1A2 | 20 | 62119741-62119795 |
| 76 | EGR2 | 10 | 64574899-64574948 |
| 77 | EME2 | 16 | 1821271-1821566 |
| 78 | EMILIN2__A | 18 | 2906050-2906082 |
| 79 | EMILIN2__B | 18 | 2906258-2906313 |
| 80 | EMX2 | 10 | 119297161-119297228 |
| 81 | EMX2OS | 10 | 119294950-119295039 |
| 82 | EPN3 | 17 | 48619601-48619768 |
| 83 | FAM109B | 22 | 42470299-42470599 |
| 84 | FAM89A | 1 | 231175193-231175307 |
| 85 | FER1L4__A | 20 | 34189084-34189184 |
| 86 | FER1L4__B | 20 | 34189488-34189566 |
| 87 | FEV | 2 | 219849013-219849064 |
| 88 | FKBP11__A | 12 | 49318865-49319221 |
| 89 | FLJ22184 | 19 | 7933862-7934065 |
| 90 | FLJ22536 | 6 | 21666442-21666683 |
| 91 | FLJ42875 | 1 | 2985432-2985534 |
| 92 | FLJ43390 | 14 | 62584120-62584204 |
| 93 | FLOT1 | 6 | 30711556-30711726 |
| 94 | FUT11 | 10 | 75532571-75532762 |
| 95 | GABBR2__A | 9 | 101471226-101471281 |
| 96 | GABBR2__B | 9 | 101471435-101471481 |
| 97 | GABBR2__C | 9 | 101471498-101471518 |
| 98 | GALR3 | 22 | 38214828-38214926 |
| 99 | GATA2__A | 3 | 128211202-128211292 |
| 100 | GATA2__B | 3 | 128216370-128216468 |
| 101 | GBGT1 | 9 | 136039231-136039283 |
| 102 | GDF6 | 8 | 97157670-97157756 |
| 103 | GDF7__A | 2 | 20866007-20866400 |
| 104 | GHITM | 10 | 85899387-85899545 |
| 105 | GNB2 | 7 | 100273805-100273883 |
| 106 | GNE | 9 | 36258402-36258585 |

TABLE 1-continued

Identified methylated regions distinguishing endometrial
cancer tissue from normal endometrial tissue.

| DMR No. | Gene Annotation | Chromosome No. | Region on Chromosome (starting base-ending base) |
|---|---|---|---|
| 107 | GPR135 | 14 | 59931440-59931647 |
| 108 | GPX1_A | 3 | 49394997-49395054 |
| 109 | GPX1_B | 3 | 49395134-49395366 |
| 110 | GRASP | 12 | 52400510-52400570 |
| 111 | GSTM4 | 1 | 110198575-110198883 |
| 112 | HLA-A | 6 | 29910301-29910371 |
| 113 | HNRNPF | 10 | 43892386-43892538 |
| 114 | HOPX_A | 4 | 57521826-57521992 |
| 115 | HOXB2 | 17 | 46621333-46621372 |
| 116 | HOXC8 | 12 | 54403025-54403114 |
| 117 | HS3ST3B1_A | 17 | 14202739-14202781 |
| 118 | HS3ST3B1_B | 17 | 14203182-14203258 |
| 119 | IL12RB2 | 1 | 67773620-67773674 |
| 120 | IL13 | 5 | 131992171-131992245 |
| 121 | ITGA4_A | 2 | 182322199-182322409 |
| 122 | ITGB2 | 21 | 46352018-46352116 |
| 123 | ITPKB | 1 | 226925140-226925336 |
| 124 | JSRP1_A | 19 | 2253201-2253345 |
| 125 | JUN | 1 | 59247951-59248035 |
| 126 | KANK1 | 9 | 706956-707230 |
| 127 | KBTBD11_A | 8 | 1949493-1949584 |
| 128 | KCNA3 | 1 | 111217656-111217716 |
| 129 | KCNK17 | 6 | 39281347-39281518 |
| 130 | KCNK9 | 8 | 140716494-140716600 |
| 131 | KCNQ5 | 6 | 73331959-73332019 |
| 132 | KCTD15_A | 19 | 34288324-34288423 |
| 133 | KCTD15_B | 19 | 34288611-34288741 |
| 134 | KLHL21 | 1 | 6663497-6663683 |
| 135 | KREMEN1 | 22 | 29467629-29467716 |
| 136 | KRT86 | 12 | 52702379-52702559 |
| 137 | LHFPL2_A | 5 | 77806193-77806291 |
| 138 | LOC100192379_A | 4 | 122686333-122686376 |
| 139 | LOC100507463 | 6 | 32811543-32811624 |
| 140 | LOC157627_A | 8 | 9763927-9763997 |
| 141 | LOC157627_B | 8 | 9764220-9764309 |
| 142 | LOC338799 | 12 | 122243001-122243268 |
| 143 | LOC402778 | 11 | 1770349-1770441 |
| 144 | LOC729678 | 5 | 180258409-180258505 |
| 145 | LRRC32 | 11 | 76381971-76382070 |
| 146 | LRRC34 | 3 | 169530340-169530527 |
| 147 | LRRC41_A | 1 | 46767677-46767761 |
| 148 | LRRC41_B | 1 | 46767939-46768016 |
| 149 | LRRC41_C | 1 | 46768188-46768283 |
| 150 | LRRC41_D | 1 | 46768830-46768913 |
| 151 | LRRC41_E | 1 | 46769340-46769650 |
| 152 | LRRC8D_A | 1 | 90308856-90308955 |
| 153 | LRRK2 | 12 | 40618745-40618814 |
| 154 | LRRN1 | 3 | 3841364-3841692 |
| 155 | MACROD1 | 11 | 63767975-63768042 |
| 156 | MAST1 | 19 | 12978432-12978558 |
| 157 | MATK | 19 | 3786252-3786339 |
| 158 | MAX.chr1.110627072-110627257 | 1 | 110627072-110627257 |
| 159 | MAX.chr1.111098121-111098213 | 1 | 111098121-111098213 |
| 160 | MAX.chr1.116710856-116710945 | 1 | 116710856-116710945 |
| 161 | MAX.chr1.148000592-148000777 | 1 | 148000592-148000777 |
| 162 | NBPF8 | 1 | 148247951-148248032 |
| 163 | MAX.chr1.61519712-61519821 | 1 | 61519712-61519821 |
| 164 | MAX.chr10.102497246-102497372 | 10 | 102497246-102497372 |
| 165 | MAX.chr10.130339363-130339534 | 10 | 130339363-130339534 |
| 166 | MAX.chr10.22541502-22541587 | 10 | 22541502-22541587 |
| 167 | MAX.chr10.22624479-22624553 | 10 | 22624479-22624553 |
| 168 | MAX.chr11.123301058-123301153 | 11 | 123301058-123301153 |

TABLE 1-continued

Identified methylated regions distinguishing endometrial
cancer tissue from normal endometrial tissue.

| DMR No. | Gene Annotation | Chromosome No. | Region on Chromosome (starting base-ending base) |
|---|---|---|---|
| 169 | MAX.chr11.8040594-8040647 | 11 | 8040594-8040647 |
| 170 | MAX.chr12.125534393-125534458 | 12 | 125534393-125534458 |
| 171 | MAX.chr12.133485161-133485240 | 12 | 133485161-133485240 |
| 172 | MAX.chr12.133485417-133485505 | 12 | 133485417-133485505 |
| 173 | MAX.chr12.133485542-133485675 | 12 | 133485542-133485675 |
| 174 | MAX.chr14.103021656-103021718 | 14 | 103021656-103021718 |
| 175 | MAX.chr14.103557994-103558154 | 14 | 103557994-103558154 |
| 176 | MAX.chr14.103558061-103558154 | 14 | 103558061-103558154 |
| 177 | MAX.chr14.74100620-74100870 | 14 | 74100620-74100870 |
| 178 | MAX.chr17.29335358-29335628 | 17 | 29335358-29335628 |
| 179 | MAX.chr17.46089738-46089851 | 17 | 46089738-46089851 |
| 180 | MAX.chr17.73073716-73073814 | 17 | 73073716-73073814 |
| 181 | MAX.chr19.31210519-31210593 | 19 | 31210519-31210593 |
| 182 | MAX.chr19.37288607-37288752 | 19 | 37288607-37288752 |
| 183 | MAX.ch12.102867766-102867826 | 2 | 102867766-102867826 |
| 184 | MAX.ch12.127783244-127783311 | 2 | 127783244-127783311 |
| 185 | MAX.ch12.233283604-233283736 | 2 | 233283604-233283736 |
| 186 | MAX.ch12.43038072-43038159 | 2 | 43038072-43038159 |
| 187 | MAX.chr2.96192422-96192520 | 2 | 96192422-96192520 |
| 188 | MAX.chr2.96192422-96192610 | 2 | 96192422-96192610 |
| 189 | MAX.chr20.37302903-37302984 | 20 | 37302903-37302984 |
| 190 | MAX.chr21.30375011-30375136 | 21 | 30375011-30375136 |
| 191 | MAX.chr21.38936278-38936494 | 21 | 38936278-38936494 |
| 192 | MAX.chr22.42679801-42679979 | 22 | 42679801-42679979 |
| 193 | MAX.chr3.128336893-128336988 | 3 | 128336893-128336988 |
| 194 | MAX.chr3.18486889-18486958 | 3 | 18486889-18486958 |
| 195 | MAX.chr3.44038012-44038064 | 3 | 44038012-44038064 |
| 196 | MAX.chr4.186049532-186049660 | 4 | 186049532-186049660 |
| 197 | MAX.chr5.177371520-177371612 | 5 | 177371520-177371612 |
| 198 | MAX.chr5.42950901-42951088 | 5 | 42950901-42951088 |
| 199 | MAX.chr5.64398959-64399179 | 5 | 64398959-64399179 |
| 200 | MAX.chr6.130687108-130687268 | 6 | 130687108-130687268 |
| 201 | MAX.chr6.26171901-26172479 | 6 | 26171901-26172479 |
| 202 | MAX.chr6.26172225-26172432 | 6 | 26172225-26172432 |
| 203 | MAX.chr6.30923280-30923382 | 6 | 30923280-30923382 |
| 204 | MAX.chr7.104624356-104624730 | 7 | 104624356-104624730 |

TABLE 1-continued

Identified methylated regions distinguishing endometrial
cancer tissue from normal endometrial tissue.

| DMR No. | Gene Annotation | Chromosome No. | Region on Chromosome (starting base-ending base) |
|---|---|---|---|
| 205 | MAX.chr8.142216090-142216173 | 8 | 142216090-142216173 |
| 206 | MAX.chr8.143532758-143532822 | 8 | 143532758-143532822 |
| 207 | MAX.chr8.145103829-145103992 | 8 | 145103829-145103992 |
| 208 | MAX.chr8.145104263-145104422 | 8 | 145104263-145104422 |
| 209 | MAZ | 16 | 29818932-29819149 |
| 210 | MBLAC1 | 7 | 99725558-99725690 |
| 211 | MDFI_A | 6 | 41606074-41606165 |
| 212 | MDFI_B | 6 | 41606379-41606439 |
| 213 | MFSD2B | 2 | 24232924-24233011 |
| 214 | MIAT_A | 22 | 27053316-27053559 |
| 215 | MIAT_B | 22 | 27068733-27069240 |
| 216 | MIDN | 19 | 1252654-1252814 |
| 217 | MIR155HG | 21 | 26934273-26934466 |
| 218 | MMP23B | 1 | 1567450-1567633 |
| 219 | MRPS21 | 1 | 150266158-150266227 |
| 220 | MRPS33 | 7 | 140714767-140714925 |
| 221 | MYOZ3 | 5 | 150036505-150036584 |
| 222 | N4BP2L1_A | 13 | 33001508-33001672 |
| 223 | N4BP2L1_B | 13 | 33001696-33001851 |
| 224 | NCKIPSD | 3 | 48723553-48723614 |
| 225 | NCRNA00085 | 19 | 52207418-52207571 |
| 226 | NDRG2 | 14 | 21493523-21494033 |
| 227 | NEAT1_A | 11 | 65189991-65190140 |
| 228 | NEAT1_B | 11 | 65190826-65190987 |
| 229 | NEK9 | 14 | 75593252-75593340 |
| 230 | NFIC | 19 | 3361080-3361200 |
| 231 | NR1I2 | 3 | 119528931-119529062 |
| 232 | NTRK3_A | 15 | 88799070-88799125 |
| 233 | NTRK3_B | 15 | 88799973-88800085 |
| 234 | OBSCN_A | 1 | 228463593-228463692 |
| 235 | OLFM1 | 9 | 137979377-137979641 |
| 236 | PALLD_A | 4 | 169753101-169753185 |
| 237 | PALLD_B | 4 | 169753319-169753406 |
| 238 | PCOLCE | 7 | 100202395-100202728 |
| 239 | PDGFRA | 4 | 55092628-55092682 |
| 240 | PHLDB1_A | 11 | 118481753-118481830 |
| 241 | PISD | 22 | 32026307-32026516 |
| 242 | PODN | 1 | 53528224-53528302 |
| 243 | PPP2R5C_A | 14 | 102247689-102247929 |
| 244 | PPP2R5C_B | 14 | 102248127-102248216 |
| 245 | PTCH2 | 1 | 45285985-45286035 |
| 246 | PTPRN2 | 7 | 157361644-157361762 |
| 247 | PXMP4 | 20 | 32307913-32308002 |
| 248 | PYCARD | 16 | 31213623-31213709 |
| 249 | RAM | 17 | 17627101-17627256 |
| 250 | RBM20 | 10 | 112432331-112432394 |
| 251 | RFTN1 | 3 | 16554709-16554808 |
| 252 | RHBDL1_A | 16 | 725291-725617 |
| 253 | RIMS2 | 8 | 104512743-104512831 |
| 254 | RLTPR | 16 | 67678899-67678952 |
| 255 | RTN4RL2 | 11 | 57244132-57244225 |
| 256 | SBNO2 | 19 | 1131812-1132072 |
| 257 | SEPT11 | 4 | 77869938-77870029 |
| 258 | SEPT9_A | 17 | 75447455-75447554 |
| 259 | SEPT9_B | 17 | 75447656-75448049 |
| 260 | SERPINB9 | 6 | 2903415-2903513 |
| 261 | SFMBT2_A | 10 | 7450743-7450831 |
| 262 | SFMBT2_B | 10 | 7451000-7451098 |
| 263 | SFMBT2_C | 10 | 7451771-7451869 |
| 264 | SFMBT2_D | 10 | 7452346-7452367 |
| 265 | SIGIRR | 11 | 407086-407183 |
| 266 | SIX4 | 14 | 61188239-61188329 |
| 267 | SLC12A8 | 3 | 124860700-124860798 |
| 268 | SLC13A5_A | 17 | 6616764-6616852 |
| 269 | SLC43A3 | 11 | 57194548-57194650 |
| 270 | SLC6A3 | 5 | 1445562-1445659 |
| 271 | SLC8A3 | 14 | 70654774-70654899 |
| 272 | SLCO4C1 | 5 | 101632152-101632237 |
| 273 | SMTN | 22 | 31481122-31481208 |

TABLE 1-continued

Identified methylated regions distinguishing endometrial
cancer tissue from normal endometrial tissue.

| DMR No. | Gene Annotation | Chromosome No. | Region on Chromosome (starting base-ending base) |
|---|---|---|---|
| 274 | SNTG2 | 2 | 946417-946458 |
| 275 | SPOCK2_A | 10 | 73847389-73847446 |
| 276 | SPOCK2_B | 10 | 73847890-73848209 |
| 277 | SPON1 | 11 | 13985007-13985088 |
| 278 | SQSTM1 | 5 | 179243864-179243955 |
| 279 | ST3GAL2_A | 16 | 70415734-70415777 |
| 280 | SV2A | 1 | 149889374-149889466 |
| 281 | TBX1 | 22 | 19754292-19754349 |
| 282 | TCF3 | 19 | 1651268-1651408 |
| 283 | TECR | 19 | 14667597-14667690 |
| 284 | TEPP | 16 | 58018744-58018831 |
| 285 | TFR2 | 7 | 100230996-100231069 |
| 286 | THAP4 | 2 | 242549705-242549757 |
| 287 | TICAM2 | 5 | 114937802-114937980 |
| 288 | TMCO1_A | 1 | 165737880-165737973 |
| 289 | TMCO1_B | 1 | 165738121-165738246 |
| 290 | TMEM130 | 7 | 98467740-98467817 |
| 291 | TMEM163 | 2 | 135475828-135475890 |
| 292 | TMEM63B | 6 | 44119717-44119780 |
| 293 | TNFRSF10D | 8 | 23021299-23021396 |
| 294 | TRIM71_A | 3 | 32859463-32859793 |
| 295 | TSHZ3_A | 19 | 31839967-31840038 |
| 296 | TSHZ3_B | 19 | 31840244-31840330 |
| 297 | TSHZ3_C | 19 | 31841427-31841476 |
| 298 | TSPAN2 | 1 | 115632183-115632276 |
| 299 | TTBK1 | 6 | 43242971-43243178 |
| 300 | TTC14 | 3 | 180320089-180320177 |
| 301 | UST_A | 6 | 149068948-149069040 |
| 302 | VILL | 3 | 38035645-38035743 |
| 303 | WNT1 | 12 | 49373374-49373532 |
| 304 | WNT7B | 22 | 46366771-46366866 |
| 305 | ZMIZ1_A | 10 | 81002372-81002568 |
| 306 | ZMIZ1_B | 10 | 81002818-81003006 |
| 307 | ZMIZ1_C | 10 | 81002928-81002991 |
| 308 | ZNF167 | 3 | 44596832-44596885 |
| 309 | ZNF292 | 6 | 87861730-87861807 |
| 310 | ZNF302 | 19 | 35168826-35168915 |
| 311 | ZNF304 | 19 | 57862463-57862983 |
| 312 | ZNF323_A | 6 | 28303870-28304162 |
| 313 | ZNF354C | 5 | 178487210-178487466 |
| 314 | ZNF506 | 19 | 19932386-19932525 |
| 315 | ZNF568_A | 19 | 37407197-37407284 |
| 316 | ZNF586_B | 19 | 58281309-58281368 |
| 317 | ZNF880 | 19 | 52873064-52873107 |
| 318 | ZNF90 | 19 | 20189032-20189134 |

TABLE 2

Area-under-the-curve, fold-change, and p-value for EC tissue in
comparison to EC controls for the markers recited in Table 1.

| DMR No. | Gene Annotation | AUC EC vs. EC control | Fold Change EC vs. EC control | p value EC vs. EC control |
|---|---|---|---|---|
| 1 | ACCN1 | 0.6618 | 21.88 | 0.0005565 |
| 2 | ACOXL__A | 0.8597 | 50.89 | 0.007356 |
| 3 | ADAL__A | 0.6656 | 110 | 0.006193 |
| 4 | ADAL__B | 0.6627 | 21.39 | 0.0005691 |
| 5 | ADAL__C | 0.7773 | 47.72 | 0.0001428 |
| 6 | AES | 0.6948 | 83.12 | 4.00E−08 |
| 7 | AFF3 | 0.9188 | 31.72 | 2.95E−09 |
| 8 | AGBL2 | 0.6667 | 375.3 | 3.74E−05 |
| 9 | AGRN__A | 0.863 | 597.6 | 1.36E−05 |
| 10 | AHSA2 | 0.8978 | 59.27 | 0.001032 |
| 11 | AIM1__A | 0.9408 | 369.2 | 5.34E−06 |
| 12 | AIM1__B | 0.7828 | 21.43 | 0.0003948 |
| 13 | AMIGO3__A | 0.9306 | 40 | 0.00008386 |
| 14 | AMIGO3__B | 0.6818 | 101.4 | 0.003578 |
| 15 | ANKAR | 0.703 | 99.07 | 0.001126 |
| 16 | ANKRD33B | 0.6869 | 143 | 3.54E−05 |
| 17 | ANO8 | 0.765 | 5.712 | 0.001607 |
| 18 | ARHGAP20__A | 0.6516 | 33.86 | 0.000001454 |
| 19 | ARHGAP20__B | 0.7344 | 23.35 | 0.0004238 |
| 20 | ARL10 | 0.8325 | 255.7 | 1.05E−07 |
| 21 | ARMC4 | 0.7164 | 17.89 | 0.005436 |
| 22 | ATP10A | 0.7597 | 66.21 | 0.0002969 |
| 23 | BCAT1 | 0.8932 | 47.95 | 1.49E−07 |
| 24 | BCL6 | 0.7222 | 30.29 | 0.002576 |
| 25 | BMP4__A | 0.6585 | 21.31 | 0.0003743 |
| 26 | BMP4__B | 0.9408 | 33.04 | 1.179E−08 |
| 27 | C14orf169 | 0.6655 | 90.03 | 0.00124 |
| 28 | C17orf107__A | 0.907 | 93.14 | 6.96E−12 |
| 29 | C18orf18__A | 0.75 | 15.49 | 2.14E−05 |
| 30 | C18orf18__B | 0.7507 | 66.92 | 0.00001497 |
| 31 | C18orf18__C | 0.8582 | 107 | 0.00003015 |
| 32 | C1orf103 | 0.6555 | 15.58 | 4.442E−08 |
| 33 | C1orf177 | 0.6508 | 506.2 | 0.001782 |
| 34 | C1orf70__A | 0.7483 | 97.16 | 2.41E−07 |
| 35 | C1orf70__B | 0.9134 | 252.1 | 1.56E−07 |
| 36 | C1QL3 | 0.852 | 43.14 | 1.45E−07 |
| 37 | C21orf58 | 0.7227 | 23.94 | 9.62E−05 |
| 38 | C2orf43 | 0.677 | 7.064 | 0.0004705 |
| 39 | C2orf62 | 0.8221 | 41.27 | 2.974E−07 |
| 40 | C5orf52 | 0.9047 | 165.5 | 1.655E−07 |
| 41 | C7orf51 | 0.8093 | 29.63 | 0.0001685 |
| 42 | C8orf73__A | 0.8768 | 48.29 | 7.25E−07 |
| 43 | CABP7 | 0.821 | 490 | 0.003538 |
| 44 | CACNA1A | 0.745 | 32.19 | 5.80E−05 |
| 45 | CCDC102A | 0.7417 | 13.76 | 8.518E−10 |
| 46 | CCDC48 | 0.6835 | 20.97 | 0.003088 |
| 47 | CCDC85B | 0.6688 | 17.2 | 0.0002735 |
| 48 | CCND2__A | 0.7801 | 12.08 | 7.18E−06 |
| 49 | CCND2__B | 0.6608 | 9.469 | 8.33E−06 |
| 50 | CCNI2 | 0.6574 | 16.09 | 0.0006968 |
| 51 | CD14 | 0.6903 | 458.2 | 0.003672 |
| 52 | CELSR3 | 0.8034 | 33.68 | 0.00002479 |
| 53 | CES4A | 0.6623 | 22.78 | 0.0006918 |
| 54 | CHMP2A | 0.7432 | 123.8 | 0.001936 |
| 55 | CLDN7 | 0.913 | 61.86 | 0.005037 |
| 56 | CLIP4 | 0.6758 | 72.6 | 0.004004 |
| 57 | CYP11A1 | 0.8646 | 60.77 | 0.001696 |
| 58 | CYP2R1 | 0.6638 | 61.08 | 6.43E−05 |
| 59 | CYTH2 | 0.8351 | 10.35 | 0.00007307 |
| 60 | DAB2IP__A | 0.7647 | 287.3 | 0.0005537 |
| 61 | DAB2IP__B | 0.7273 | 48.72 | 3.44E−05 |
| 62 | DEM1 | 0.7546 | 307.8 | 0.003765 |
| 63 | DIDO1__A | 0.9809 | 238.3 | 5.6E−12 |
| 64 | DLEC1__A | 0.6568 | 34.04 | 7.97E−06 |
| 65 | DLEC1__B | 0.7992 | 99.03 | 3.00E−05 |
| 66 | DLEC1__C | 0.6941 | 551.8 | 2.79E−05 |
| 67 | DLL4 | 0.8963 | 16.68 | 0.0001774 |
| 68 | DNAJC6 | 0.8065 | 70.75 | 7.229E−07 |
| 69 | DPP7 | 0.8643 | 97.69 | 2.89E−05 |
| 70 | DSCAML1 | 0.6913 | 37.53 | 1.26E−06 |
| 71 | DSEL | 0.6707 | 45.39 | 0.001035 |
| 72 | DTX1 | 0.7321 | 865.9 | 0.001687 |
| 73 | DTX3L | 0.6583 | 152.6 | 4.39E−05 |

TABLE 2-continued

Area-under-the-curve, fold-change, and p-value for EC tissue in
comparison to EC controls for the markers recited in Table 1.

| DMR No. | Gene Annotation | AUC EC vs. EC control | Fold Change EC vs. EC control | p value EC vs. EC control |
|---|---|---|---|---|
| 74 | EDARADD | 0.7337 | 236.2 | 0.005977 |
| 75 | EEF1A2 | 0.9532 | 67.76 | 0.000003221 |
| 76 | EGR2 | 0.7083 | 25.5 | 0.000008596 |
| 77 | EME2 | 0.6861 | 139.5 | 0.00005428 |
| 78 | EMILIN2__A | 0.7266 | 265 | 8.81E−05 |
| 79 | EMILIN2__B | 0.6722 | 102.4 | 5.74E−07 |
| 80 | EMX2 | 0.6606 | 160.6 | 6.34E−05 |
| 81 | EMX2OS | 0.9709 | 235.4 | 1.486E−07 |
| 82 | EPN3 | 0.6991 | 47.75 | 0.0005864 |
| 83 | FAM109B | 0.8416 | 56.4 | 0.000003558 |
| 84 | FAM89A | 0.7633 | 119.1 | 0.005136 |
| 85 | FER1L4__A | 0.8381 | 115.3 | 1.34E−06 |
| 86 | FER1L4__B | 0.8457 | 418.6 | 0.0001132 |
| 87 | FEV | 0.9004 | 14.43 | 1.075E−09 |
| 88 | FKBP11__A | 0.9091 | 721.9 | 0.001236 |
| 89 | FLJ22184 | 0.7844 | 53.15 | 8.099E−08 |
| 90 | FLJ22536 | 0.7792 | 49.09 | 6.41E−05 |
| 91 | FLJ42875 | 0.6562 | 64.58 | 0.000001282 |
| 92 | FLJ43390 | 0.6647 | 13.09 | 0.001351 |
| 93 | FLOT1 | 0.7566 | 34.14 | 1.308E−08 |
| 94 | FUT11 | 0.6861 | 1144 | 0.004405 |
| 95 | GABBR2__A | 0.7711 | 58.41 | 0.00001818 |
| 96 | GABBR2__B | 0.7276 | 24.2 | 0.0001021 |
| 97 | GABBR2__C | 0.6635 | 30.79 | 0.0000827 |
| 98 | GALR3 | 0.8157 | 169.5 | 0.009018 |
| 99 | GATA2__A | 0.7206 | 6.751 | 0.0006726 |
| 100 | GATA2__B | 0.888 | 24.4 | 9.709E−09 |
| 101 | GBGT1 | 0.6765 | 32.52 | 0.001294 |
| 102 | GDF6 | 0.929 | 38.04 | 7.975E−07 |
| 103 | GDF7__A | 0.9133 | 53.71 | 2.737E−08 |
| 104 | GHITM | 0.6536 | 76.28 | 0.0037 |
| 105 | GNB2 | 0.7125 | 93.16 | 1.05E−05 |
| 106 | GNE | 0.7 | 360.7 | 0.001421 |
| 107 | GPR135 | 0.6529 | 106.8 | 8.52E−05 |
| 108 | GPX1__A | 0.7786 | 61.03 | 1.89E−06 |
| 109 | GPX1__B | 0.7716 | 42.37 | 0.0008024 |
| 110 | GRASP | 0.7014 | 53.88 | 0.004852 |
| 111 | GSTM4 | 0.6722 | 73.93 | 0.001751 |
| 112 | HLA-A | 0.6709 | 123 | 0.003296 |
| 113 | HNRNPF | 0.8736 | 533.7 | 0.007898 |
| 114 | HOPX | 0.6616 | 33.21 | 0.000002593 |
| 115 | HOXB2 | 0.7143 | 45.08 | 0.000256 |
| 116 | HOXC8 | 0.6599 | 21.32 | 0.000192 |
| 117 | HS3ST3B1__A | 0.7727 | 7.377 | 0.0005749 |
| 118 | HS3ST3B1__B | 0.8182 | 12.17 | 2.44E−06 |
| 119 | IL12RB2 | 0.701 | 445.5 | 0.005105 |
| 120 | IL13 | 0.8421 | 85.78 | 0.009485 |
| 121 | ITGA4 | 0.6935 | 53.03 | 0.00001091 |
| 122 | ITGB2 | 0.7078 | 9.851 | 0.000122 |
| 123 | ITPKB | 0.8362 | 105.4 | 1.38E−05 |
| 124 | JSRP1__A | 0.907 | 72.11 | 5.16E−10 |
| 125 | JUN | 0.6875 | 59.16 | 0.000889 |
| 126 | KANK1 | 0.8884 | 135.4 | 0.000001051 |
| 127 | KBTBD11__A | 0.8143 | 278.1 | 0.0001492 |
| 128 | KCNA3 | 0.7775 | 45.7 | 0.000001416 |
| 129 | KCNK17 | 0.7758 | 21.29 | 5.81E−06 |
| 130 | KCNK9 | 0.8312 | 54.29 | 0.00002916 |
| 131 | KCNQ5 | 0.7401 | 17.31 | 0.0006638 |
| 132 | KCTD15__A | 0.9266 | 27.56 | 0.002706 |
| 133 | KCTD15__B | 0.87 | 64.21 | 0.0003926 |
| 134 | KLHL21 | 0.9277 | 115.9 | 0.0003778 |
| 135 | KREMEN1 | 0.7411 | 49.03 | 0.0005224 |
| 136 | KRT86 | 0.6819 | 47.5 | 0.002128 |
| 137 | LHFPL2__A | 0.8115 | 928.7 | 0.001375 |
| 138 | LOC100192379__A | 0.6905 | 41.04 | 0.00005452 |
| 139 | LOC100507463 | 0.6883 | 24.82 | 6.97E−05 |
| 140 | LOC157627__A | 0.6999 | 22.5 | 0.00001095 |
| 141 | LOC157627__B | 0.7064 | 25.83 | 0.001724 |
| 142 | LOC338799 | 0.6984 | 108.8 | 0.001105 |
| 143 | LOC402778 | 0.7145 | 79.33 | 0.0002123 |
| 144 | LOC729678 | 0.7667 | 113.4 | 0.00001356 |
| 145 | LRRC32 | 0.7805 | 10.73 | 1.389E−07 |
| 146 | LRRC34 | 0.7909 | 155.5 | 0.00003603 |

TABLE 2-continued

Area-under-the-curve, fold-change, and p-value for EC tissue in
comparison to EC controls for the markers recited in Table 1.

| DMR No. | Gene Annotation | AUC EC vs. EC control | Fold Change EC vs. EC control | p value EC vs. EC control |
|---|---|---|---|---|
| 147 | LRRC41_A | 0.7716 | 29.68 | 3.37E−09 |
| 148 | LRRC41_B | 0.7955 | 237 | 6.97E−07 |
| 149 | LRRC41_C | 0.789 | 69.55 | 3.11E−08 |
| 150 | LRRC41_D | 0.7677 | 133.1 | 4.95E−06 |
| 151 | LRRC41_E | 0.7316 | 479.6 | 5.30E−05 |
| 152 | LRRC8D_A | 0.9026 | 27.37 | 9.12E−05 |
| 153 | LRRK2 | 0.7284 | 53.89 | 0.005952 |
| 154 | LRRN1 | 0.7202 | 14.85 | 0.00000822 |
| 155 | MACROD1 | 0.7012 | 200.4 | 0.0003994 |
| 156 | MAST1 | 0.7232 | 50.03 | 0.00318 |
| 157 | MATK | 0.6571 | 21.21 | 0.00007402 |
| 158 | MAX.chr1.110627072-110627257 | 0.8366 | 36.7 | 1.23E−07 |
| 159 | MAX.chr1.111098121-111098213 | 0.7737 | 166 | 0.004094 |
| 160 | MAX.chr1.116710856-116710945 | 0.8219 | 22.41 | 0.0000407 |
| 161 | MAX.chr1.148000592-148000777 | 0.7051 | 77.72 | 0.00004245 |
| 162 | NBPF8 | 0.9697 | 53.41 | 1.606E−08 |
| 163 | MAX.chr1.61519712-61519821 | 0.7167 | 43.36 | 2.02E−08 |
| 164 | MAX.chr10.102497246-102497372 | 0.7528 | 18.98 | 1.14E−05 |
| 165 | MAX.chr10.130339363-130339534 | 0.9709 | 29.28 | 0.000001534 |
| 166 | MAX.chr10.22541502-22541587 | 0.6588 | 11.22 | 0.001261 |
| 167 | MAX.chr10.22624479-22624553 | 0.9172 | 62.87 | 1.417E−10 |
| 168 | MAX.chr11.123301058-123301153 | 0.6975 | 28.22 | 4.74E−06 |
| 169 | MAX.chr11.8040594-8040647 | 0.8311 | 40.67 | 0.00003799 |
| 170 | MAX.chr12.125534393-125534458 | 0.8414 | 23.5 | 7.617E−07 |
| 171 | MAX.chr12.133485161-133485240 | 0.7591 | 40.03 | 0.0001313 |
| 172 | MAX.chr12.133485417-133485505 | 0.7125 | 57.66 | 0.0001017 |
| 173 | MAX.chr12.133485542-133485675 | 0.6853 | 40.55 | 0.00001341 |
| 174 | MAX.chr14.103021656-103021718 | 0.9766 | 127 | 5.89E−07 |
| 175 | MAX.chr14.103557994-103558154 | 0.7488 | 113.7 | 0.0001156 |
| 176 | MAX.chr14.103558061-103558154 | 0.6882 | 49.76 | 0.0003841 |
| 177 | MAX.chr14.74100620-74100870 | 0.8808 | 49.39 | 0.0005545 |
| 178 | MAX.chr17.29335358-29335628 | 0.8279 | 201.5 | 0.002438 |
| 179 | MAX.chr17.46089738-46089851 | 0.7339 | 287.6 | 0.0001518 |
| 180 | MAX.chr17.73073716-73073814 | 0.8737 | 394.1 | 1.38E−05 |
| 181 | MAX.chr19.31210519-31210593 | 0.6504 | 41.46 | 0.00398 |
| 182 | MAX.chr19.37288607-37288752 | 0.811 | 88.11 | 0.000003103 |
| 183 | MAX.chr2.102867766-102867826 | 0.6968 | 28.75 | 0.0002521 |
| 184 | MAX.chr2.127783244-127783311 | 0.7289 | 30.07 | 0.00003288 |
| 185 | MAX.chr2.233283604-233283736 | 0.875 | 45.08 | 0.0001526 |
| 186 | MAX.chr2.43038072-43038159 | 0.6579 | 40.43 | 0.005182 |
| 187 | MAX.chr2.96192422-96192520 | 0.667 | 9.372 | 0.003974 |
| 188 | MAX.chr2.96192422-96192610 | 0.827 | 37.66 | 1.602E−08 |
| 189 | MAX.chr20.37302903-37302984 | 0.7703 | 19.49 | 0.00000328 |
| 190 | MAX.chr21.30375011-30375136 | 0.6519 | 118.9 | 0.002865 |
| 191 | MAX.chr21.38936278-38936494 | 0.6512 | 34.05 | 0.0002117 |
| 192 | MAX.chr22.42679801-42679979 | 0.8457 | 46.57 | 5.42E−07 |
| 193 | MAX.chr3.128336893-128336988 | 0.8505 | 207.8 | 3.97E−05 |
| 194 | MAX.chr3.18486889-18486958 | 0.875 | 45.35 | 1.268E−07 |
| 195 | MAX.chr3.44038012-44038064 | 0.7214 | 26.7 | 0.00005333 |
| 196 | MAX.chr4.186049532-186049660 | 0.7656 | 31.4 | 0.000865 |
| 197 | MAX.chr5.177371520-177371612 | 0.8 | 33.61 | 0.002158 |
| 198 | MAX.chr5.42950901-42951088 | 0.8615 | 28.06 | 0.00005216 |
| 199 | MAX.chr5.64398959-64399179 | 0.6882 | 27.48 | 0.00001 |
| 200 | MAX.chr6.130687108-130687268 | 0.7631 | 53.84 | 0.0002403 |
| 201 | MAX.chr6.26171901-26172479 | 0.7333 | 14.26 | 0.0004651 |
| 202 | MAX.chr6.26172225-26172432 | 0.6614 | 82.29 | 0.004157 |
| 203 | MAX.chr6.30923280-30923382 | 0.8799 | 35.99 | 1.61E−05 |
| 204 | MAX.chr7.104624356-104624730 | 0.8723 | 1101 | 1.93E−05 |
| 205 | MAX.chr8.142216090-142216173 | 0.7464 | 100.8 | 0.0007861 |
| 206 | MAX.chr8.143532758-143532822 | 0.741 | 5.751 | 0.0001482 |
| 207 | MAX.chr8.145103829-145103992 | 0.9351 | 26.27 | 6.522E−08 |
| 208 | MAX.chr8.145104263-145104422 | 0.9004 | 51.51 | 0.0001458 |
| 209 | MAZ | 0.7927 | 125.9 | 0.0002086 |
| 210 | MBLAC1 | 0.7812 | 15.75 | 2.83E−08 |
| 211 | MDFI_A | 0.7424 | 13.66 | 0.0003535 |
| 212 | MDFI_B | 0.9286 | 80.17 | 3.453E−07 |
| 213 | MFSD2B | 0.8432 | 53.41 | 0.0003069 |
| 214 | MIAT_A | 0.9264 | 68.47 | 4.28E−07 |
| 215 | MIAT_B | 0.8605 | 47.34 | 0.0000377 |
| 216 | MIDN | 0.7849 | 21.42 | 0.000005938 |
| 217 | MIR155HG | 0.733 | 36.79 | 0.008797 |
| 218 | MMP23B | 0.974 | 87.98 | 4.161E−10 |
| 219 | MRPS21 | 0.6753 | 11.41 | 0.001936 |

TABLE 2-continued

Area-under-the-curve, fold-change, and p-value for EC tissue in
comparison to EC controls for the markers recited in Table 1.

| DMR No. | Gene Annotation | AUC EC vs. EC control | Fold Change EC vs. EC control | p value EC vs. EC control |
|---|---|---|---|---|
| 220 | MRPS33 | 0.7068 | 33.47 | 0.0004814 |
| 221 | MYOZ3 | 0.7949 | 74.89 | 0.0002419 |
| 222 | N4BP2L1__A | 0.7495 | 1311 | 0.0008957 |
| 223 | N4BP2L1__B | 0.704 | 1324 | 0.002896 |
| 224 | NCKIPSD | 0.7162 | 126 | 0.0009659 |
| 225 | NCRNA00085 | 0.6889 | 194.7 | 0.000006047 |
| 226 | NDRG2 | 0.9789 | 83.94 | 1.082E−07 |
| 227 | NEAT1__A | 0.6898 | 188.9 | 0.006251 |
| 228 | NEAT1__B | 0.6891 | 59.78 | 0.001232 |
| 229 | NEK9 | 0.7791 | 33.3 | 0.00255 |
| 230 | NFIC | 0.8041 | 74.17 | 3.33E−06 |
| 231 | NR1I2 | 0.777 | 46.68 | 0.0001105 |
| 232 | NTRK3__A | 0.6654 | 54.09 | 0.001975 |
| 233 | NTRK3__B | 0.7374 | 83.81 | 0.00007934 |
| 234 | OBSCN__A | 0.9324 | 436.3 | 5.79E−08 |
| 235 | OLFM1 | 0.6928 | 53.72 | 0.0005697 |
| 236 | PALLD__A | 0.6628 | 70.25 | 0.0001169 |
| 237 | PALLD__B | 0.673 | 43.51 | 0.00002727 |
| 238 | PCOLCE | 0.9136 | 41.3 | 0.0009516 |
| 239 | PDGFRA | 0.6522 | 20.49 | 0.000009416 |
| 240 | PHLDB1 | 0.8075 | 295.8 | 0.002509 |
| 241 | PISD | 0.8139 | 209.3 | 1.30E−06 |
| 242 | PODN | 0.697 | 119.7 | 6.84E−06 |
| 243 | PPP2R5C__A | 0.8799 | 168.5 | 0.00006792 |
| 244 | PPP2R5C__B | 0.7177 | 315.6 | 0.003545 |
| 245 | PTCH2 | 0.8664 | 27.51 | 0.0009989 |
| 246 | PTPRN2 | 0.6926 | 19.93 | 7.26E−05 |
| 247 | PXMP4 | 0.788 | 222.5 | 0.000004164 |
| 248 | PYCARD | 0.9302 | 335.8 | 0.0004632 |
| 249 | RAM | 0.8198 | 17.29 | 6.111E−07 |
| 250 | RBM20 | 0.7132 | 500.5 | 0.0003599 |
| 251 | RFTN1 | 0.7375 | 23.01 | 0.0005169 |
| 252 | RHBDL1__A | 0.8988 | 51.18 | 0.00001338 |
| 253 | RIMS2 | 0.6754 | 5.933 | 0.009377 |
| 254 | RLTPR | 0.7173 | 109.6 | 1.75E−06 |
| 255 | RTN4RL2 | 0.7675 | 20.03 | 0.0001403 |
| 256 | SBNO2 | 0.817 | 116 | 0.0001235 |
| 257 | SEPT11 | 0.6992 | 32.13 | 0.000554 |
| 258 | SEPT9__A | 0.8474 | 318.8 | 0.006383 |
| 259 | SEPT9__B | 0.9704 | 101.2 | 0.000001335 |
| 260 | SERPINB9 | 0.7617 | 83.53 | 0.007034 |
| 261 | SFMBT2__A | 0.803 | 7.161 | 0.003198 |
| 262 | SFMBT2__B | 0.8359 | 21.85 | 1.30E−06 |
| 263 | SFMBT2__C | 0.8994 | 23.85 | 3.37E−07 |
| 264 | SFMBT2__D | 0.6765 | 32.88 | 0.0006383 |
| 265 | SIGIRR | 0.6811 | 47.57 | 0.004517 |
| 266 | SIX4 | 0.8312 | 19.08 | 2.91E−05 |
| 267 | SLC12A8 | 0.7944 | 19.75 | 0.0003137 |
| 268 | SLC13A5__A | 0.6719 | 353 | 0.0006269 |
| 269 | SLC43A3 | 0.7455 | 27.29 | 5.534E−08 |
| 270 | SLC6A3__A | 0.9318 | 24.27 | 1.074E−07 |
| 271 | SLC8A3__B | 0.9239 | 55.38 | 1.944E−09 |
| 272 | SLCO4C1 | 0.6786 | 112.2 | 0.00007596 |
| 273 | SMTN | 0.8052 | 42.68 | 5.47E−05 |
| 274 | SNTG2 | 0.7862 | 14.28 | 0.0004986 |
| 275 | SPOCK2__A | 0.8486 | 68.87 | 2.41E−09 |
| 276 | SPOCK2__B | 0.6956 | 45.22 | 1.64E−05 |
| 277 | SPON1 | 0.7247 | 25.58 | 0.000003926 |
| 278 | SQSTM1 | 0.9228 | 145.7 | 4.725E−10 |
| 279 | ST3GAL2__A | 0.838 | 40.37 | 0.0007039 |
| 280 | SV2A | 0.8137 | 15.68 | 7.13E−05 |
| 281 | TBX1 | 0.6667 | 127.2 | 0.0005607 |
| 282 | TCF3 | 0.7783 | 22.84 | 7.97E−06 |
| 283 | TECR | 0.6767 | 203.8 | 0.001696 |
| 284 | TEPP | 0.8578 | 33.96 | 0.00000822 |
| 285 | TFR2 | 0.6812 | 169.5 | 0.006637 |
| 286 | THAP4 | 0.6528 | 62.88 | 0.0005633 |
| 287 | TICAM2 | 0.6943 | 35.39 | 0.001777 |
| 288 | TMCO1__A | 0.7368 | 27.29 | 0.00008104 |
| 289 | TMCO1__B | 0.6972 | 141.8 | 0.002057 |
| 290 | TMEM130 | 0.6622 | 11.02 | 0.0001735 |
| 291 | TMEM163 | 0.6844 | 12.78 | 0.0000597 |
| 292 | TMEM63B | 0.8026 | 20.36 | 6.39E−06 |

TABLE 2-continued

Area-under-the-curve, fold-change, and p-value for EC tissue in
comparison to EC controls for the markers recited in Table 1.

| DMR No. | Gene Annotation | AUC EC vs. EC control | Fold Change EC vs. EC control | p value EC vs. EC control |
|---|---|---|---|---|
| 293 | TNFRSF10D | 0.6775 | 15.68 | 0.002517 |
| 294 | TRIM71__A | 0.74 | 18.84 | 1.78E−05 |
| 295 | TSHZ3__A | 0.8161 | 13.38 | 3.93E−05 |
| 296 | TSHZ3__B | 0.8312 | 30.94 | 0.001939 |
| 297 | TSHZ3__C | 0.661 | 71.41 | 0.007574 |
| 298 | TSPAN2 | 0.6647 | 72.46 | 0.000005262 |
| 299 | TTBK1 | 0.79 | 29.97 | 3.99E−05 |
| 300 | TTC14 | 0.779 | 481.4 | 0.006875 |
| 301 | UST | 0.7114 | 157.8 | 0.0004509 |
| 302 | VILL | 0.9293 | 66.67 | 5.346E−11 |
| 303 | WNT1 | 0.8359 | 33.69 | 5.21E−06 |
| 304 | WNT7B | 0.8895 | 26.27 | 1.23E−06 |
| 305 | ZMIZ1__A | 0.7273 | 38.92 | 0.001658 |
| 306 | ZMIZ1__B | 0.7707 | 111.2 | 1.06E−09 |
| 307 | ZMIZ1__C | 0.7664 | 60.43 | 0.003325 |
| 308 | ZNF167 | 0.722 | 132.9 | 0.0002713 |
| 309 | ZNF292 | 0.815 | 531.8 | 0.008253 |
| 310 | ZNF302 | 0.9 | 46.65 | 1.08E−05 |
| 311 | ZNF304 | 0.8604 | 142.2 | 0.0006362 |
| 312 | ZNF323__A | 0.9232 | 364.4 | 0.00005473 |
| 313 | ZNF354C | 0.7944 | 56.82 | 4.34E−05 |
| 314 | ZNF506 | 0.9142 | 71.02 | 9.384E−10 |
| 315 | ZNF568__A | 0.7041 | 73.74 | 0.0002323 |
| 316 | ZNF586__B | 0.7045 | 19.73 | 4.81E−08 |
| 317 | ZNF880 | 0.6615 | 33.53 | 1.739E−07 |
| 318 | ZNF90 | 0.9149 | 103.9 | 0.00003791 |

Such EC DMRs included EC specific regions, EC subtype specific regions, as well as those regions which targeted a more universal cancer spectrum.

The top overall DMRs distinguishing EC and normal endometrial tissue are shown in Table 3. The top overall DMRs distinguishing clear cell EC and normal endometrial tissue are shown in Table 4. The top overall DMRs distinguishing carcinosarcoma EC and normal endometrial tissue are shown in Table 5. The top overall DMRs distinguishing endometrioid EC and normal endometrial tissue are shown in Table 6. The top overall DMRs distinguishing serous EC and normal endometrial tissue are shown in Table 7. The grey-scaled red shading over certain genes in Tables 4, 5, 6, and 7 indicates DMRs which overlap with multiple subtypes.

TABLE 3

Top methylated regions distinguishing endometrial
cancer tissue from normal endometrial tissue.

| Gene Name | DMR No. | AUC | FC |
|---|---|---|---|
| EMX2OS | 81 | 0.9309 | 264 |
| CYTH2 | 59 | 0.8856 | 20.37 |
| C17orf107__A | 28 | 0.8328 | 64.08 |
| DIDO1__A | 63 | 0.8777 | 126.3 |
| GDF6 | 102 | 0.8772 | 22.97 |
| NBPF8 | 162 | 0.8718 | 42.83 |
| MAX.chr14.103021656-103021718 | 174 | 0.8679 | 100.9 |
| JSRP1__A | 124 | 0.8642 | 38.78 |
| GATA2__B | 100 | 0.8639 | 19.23 |
| SFMBT2__B | 262 | 0.8431 | 18.31 |

TABLE 4

Top overall DMRs distinguishing clear
cell EC and normal endometrial tissue.

| Gene Name | DMR No. | AUC | FC | p-value |
|---|---|---|---|---|
| DIDO1__A | 63 | 0.98 | 238 | 5.6E−12 |
| NDRG2 | 226 | 0.98 | 84 | 1.08E−07 |
| MAX.chr14.103021656-103021718 | 174 | 0.98 | 127 | 5.89E−07 |
| MMP23B | 218 | 0.97 | 88 | 4.16E−10 |
| EMX2OS | 81 | 0.97 | 235 | 1.49E−07 |
| SEPT9__B | 259 | 0.97 | 101 | 1.34E−06 |
| NBPF8 | 162 | 0.97 | 53 | 1.61E−08 |
| EEF1A2 | 75 | 0.95 | 68 | 3.22E−06 |
| AIM1__A | 11 | 0.94 | 369 | 5.34E−06 |
| BMP4__B | 26 | 0.94 | 33 | 1.18E−08 |
| MAX.chr8.145103829-145103992 | 207 | 0.94 | 26 | 6.52E−08 |
| OBSCN__A | 234 | 0.93 | 436 | 5.79E−08 |
| PYCARD | 248 | 0.93 | 336 | 0.000463 |
| GDF6 | 102 | 0.93 | 38 | 7.98E−07 |
| MDFI__B | 212 | 0.93 | 80 | 3.45E−07 |
| MIAT__A | 214 | 0.93 | 68 | 4.28E−07 |
| SLC8A3 | 271 | 0.92 | 55 | 1.94E−09 |
| ZNF323__A | 312 | 0.92 | 364 | 5.47E−05 |
| SQSTM1 | 278 | 0.92 | 146 | 4.73E−10 |
| AFF3 | 7 | 0.92 | 32 | 2.95E−09 |
| C1orf70 | 34 | 0.91 | 252 | 1.56E−07 |
| GDF7__A | 103 | 0.91 | 54 | 2.74E−08 |
| JSRP1__A | 124 | 0.91 | 72 | 5.16E−10 |
| LRRC8D__A | 152 | 0.90 | 27 | 9.12E−05 |
| FEV | 87 | 0.90 | 14 | 1.08E−09 |
| MAX.chr8.145104263-145104422 | 208 | 0.90 | 52 | 0.000146 |

TABLE 5

Top overall DMRs distinguishing carcinosarcoma
EC and normal endometrial tissue.

| Gene Name | DMR No. | AUC | FC | p-value |
|---|---|---|---|---|
| EMX2OS | 81 | 0.94 | 323 | 4.11E−05 |
| DIDO1_A | 63 | 0.94 | 143 | 1.84E−06 |
| SBNO2 | 256 | 0.94 | 129 | 0.003217 |
| AMIGO3_A | 13 | 0.93 | 40 | 8.39E−05 |
| PCOLCE | 238 | 0.91 | 41 | 0.000952 |
| CLDN7 | 55 | 0.91 | 62 | 0.005037 |
| CYTH2 | 59 | 0.91 | 19 | 4.92E−06 |
| OBSCN_A | 234 | 0.90 | 159 | 0.007225 |
| AHSA2 | 10 | 0.90 | 59 | 0.001032 |
| DLL4 | 67 | 0.90 | 17 | 0.000177 |
| EMX2 | 80 | 0.89 | 308 | 0.007177 |
| MAX.chr14.74100620-74100870 | 177 | 0.88 | 49 | 0.000555 |
| LRRC34 | 146 | 0.88 | 150 | 0.002837 |
| PPP2R5C_A | 243 | 0.88 | 169 | 6.79E−05 |
| SQSTM1 | 278 | 0.88 | 102 | 0.005911 |
| MAX.chr17.73073716-73073814 | 180 | 0.87 | 586 | 0.008309 |
| CYP11A1 | 57 | 0.86 | 61 | 0.001696 |
| ACOXL_A | 2 | 0.86 | 51 | 0.007356 |
| AIM1_B | 12 | 0.86 | 95 | 0.001099 |

TABLE 6

Top overall DMRs distinguishing endometrioid
EC and normal endometrial tissue.

| Gene Name | DMR No. | AUC | FC | p-value |
|---|---|---|---|---|
| MAX.chr10.130339363-130339534 | 165 | 0.97 | 29 | 1.53E−06 |
| SFMBT2_C | 263 | 0.95 | 33 | 6.01E−08 |
| CYTH2 | 59 | 0.94 | 25 | 2.18E−08 |
| SLC6A3 | 270 | 0.93 | 24 | 1.07E−07 |
| VILL | 302 | 0.93 | 67 | 5.35E−11 |
| EMX2OS | 81 | 0.92 | 299 | 9.02E−06 |
| MAX.chr10.22624479-22624553 | 167 | 0.92 | 63 | 1.42E−10 |
| GDF6 | 102 | 0.92 | 28 | 7.96E−07 |
| ZNF90 | 318 | 0.91 | 104 | 3.79E−05 |
| ZNF506 | 314 | 0.91 | 71 | 9.38E−10 |
| JSRP1_A | 124 | 0.91 | 70 | 1.24E−10 |
| C5orf52 | 40 | 0.90 | 166 | 1.66E−07 |
| SFMBT2_B | 262 | 0.90 | 36 | 2.01E−09 |
| NBPF8 | 162 | 0.90 | 66 | 2.95E−07 |
| RHBDL1_A | 252 | 0.90 | 51 | 1.34E−05 |
| DIDO1_A | 63 | 0.90 | 90 | 1.81E−08 |
| KANK1 | 126 | 0.89 | 135 | 1.05E−06 |
| GATA2_B | 100 | 0.89 | 24 | 9.71E−09 |

TABLE 7

Top overall DMRs distinguishing serous
EC and normal endometrial tissue.

| Gene Name | DMR No. | AUC | FC | p-value |
|---|---|---|---|---|
| EMX2OS | 81 | 1.00 | 277 | 3.71E−10 |
| KANK1 | 126 | 0.94 | 65 | 3.2E−07 |
| C1orf70_B | 35 | 0.94 | 49 | 5.25E−06 |
| AMIGO3_A | 13 | 0.92 | 23 | 2.81E−05 |
| DIDO1_A | 63 | 0.92 | 127 | 3.83E−07 |
| LRRC41_C | 149 | 0.91 | 50 | 7.06E−08 |
| NFIC | 230 | 0.91 | 46 | 7.52E−05 |
| FKBP11_A | 88 | 0.91 | 722 | 0.001236 |
| C17orf107_A | 28 | 0.91 | 93 | 6.96E−12 |
| SMTN | 273 | 0.90 | 87 | 2.18E−06 |
| LRRC41_B | 148 | 0.90 | 93 | 9.19E−06 |
| LRRC8D_A | 152 | 0.89 | 59 | 3.13E−06 |
| OBSCN_A | 234 | 0.87 | 128 | 2.48E−05 |

TABLE 7-continued

Top overall DMRs distinguishing serous
EC and normal endometrial tissue.

| Gene Name | DMR No. | AUC | FC | p-value |
|---|---|---|---|---|
| MAX.chr7.104624356-104624730 | 204 | 0.86 | 403 | 0.000153 |
| MIAT_B | 215 | 0.86 | 47 | 3.77E−05 |

A tissue to leukocyte (buffy coat) analysis yielded 129 hypermethylated endometrial tissue DMRs with less than 100 noise in WBCs (Table 8). Table 9 shows the area-under-the-curve, fold-change, and p-value in comparison to EC buffy controls for the markers recited in Table 8.

TABLE 8

Hypermethylated endometrial tissue DMRs
with less than 1% noise in WBCs

| DMR No. | Gene Annotation | Chromosome No. | Region on Chromosome (starting base-ending base) |
|---|---|---|---|
| 319 | ACOXL_B | 2 | 111875309-111875359 |
| 320 | ACTG1 | 17 | 79478295-79478468 |
| 321 | ANKRD35 | 1 | 145562791-145562906 |
| 499 | ARL5C | 17 | 37321564-37321723 |
| 322 | ARRB1 | 11 | 75063559-75063646 |
| 323 | BCL2L11_A | 2 | 111876440-111876609 |
| 324 | BCL2L11_B | 2 | 111876958-111877258 |
| 325 | BCL2L11_C | 2 | 111876624-111876822 |
| 326 | BEST4 | 1 | 45250035-45250159 |
| 327 | BZRAP1 | 17 | 56409702-56409821 |
| 328 | C14orf169_B | 14 | 73958204-73958363 |
| 329 | C14orf169 C | 14 | 73958382-73958475 |
| 330 | C14orf80 | 14 | 105954029-105954198 |
| 331 | C16orf54 | 16 | 29757319-29757405 |
| 332 | C17orf101 | 17 | 80358847-80358919 |
| 333 | C18orf1 | 18 | 13641597-13641678 |
| 334 | C6orf132 | 6 | 42072052-42072186 |
| 335 | C9orf171 | 9 | 135285696-135285783 |
| 336 | CACNA2D4 | 12 | 1906260-1906350 |
| 337 | CCDC61 | 19 | 46519515-46519568 |
| 338 | DEDD2 | 19 | 42703469-42703790 |
| 339 | DGKE | 17 | 54912117-54912243 |
| 340 | EGFL7 | 9 | 139559853-139559951 |
| 341 | EMB | 5 | 49736982-49737041 |
| 342 | EOMES | 3 | 27763388-27763413 |
| 343 | EPS15L1 | 19 | 16482437-16482520 |
| 344 | FAIM2 | 12 | 50297582-50297690 |
| 345 | FAM125B | 9 | 129233651-129233705 |
| 346 | FAM159A | 1 | 53099143-53099216 |
| 347 | FAM189B | 1 | 155220306-155220399 |
| 348 | FAM78A | 9 | 134151289-134151464 |
| 349 | FMNL1 | 17 | 43298726-43298774 |
| 350 | FOXP4 | 6 | 41528837-41528899 |
| 351 | GAL3ST4 | 7 | 99769426-99769470 |
| 352 | GATA2_C | 3 | 128216774-128216891 |
| 353 | GP1BB | 22 | 19706153-19706187 |
| 354 | GYPC_A | 2 | 127413698-127413901 |
| 355 | GYPC_B | 2 | 127414106-127414189 |
| 356 | HAAO | 2 | 43019891-43019972 |
| 357 | HAND2 | 4 | 174450783-174450843 |
| 358 | HDAC7 | 12 | 48206687-48206801 |
| 359 | HOPX_B | 4 | 57522083-57522182 |
| 360 | HOXA7 | 7 | 27196352-27196425 |
| 361 | HOXB4 | 17 | 46659392-46659496 |
| 362 | HRH2 | 5 | 175085144-175085212 |
| 363 | IFFO1_A | 12 | 6664616-6664694 |
| 364 | IFFO1_B | 12 | 6664873-6665023 |
| 119 | IL12RB2 | 1 | 67773620-67773674 |
| 365 | IQSEC3_A | 12 | 187211-187344 |
| 366 | IQSEC3_B | 12 | 187115-187194 |
| 367 | ITGA4_B | 2 | 182321830-182321917 |
| 368 | ITPKA | 15 | 41787637-41787780 |
| 369 | KLF16 | 19 | 1856980-1857037 |

TABLE 8-continued

Hypermethylated endometrial tissue DMRs
with less than 1% noise in WBCs

| DMR No. | Gene Annotation | Chromosome No. | Region on Chromosome (starting base-ending base) |
|---|---|---|---|
| 370 | LIMD2 | 17 | 61778259-61778367 |
| 371 | LOC100129726__A | 2 | 43452130-43452229 |
| 382 | LOC100192379__B | 4 | 122686329-122686394 |
| 373 | LOC339529 | 1 | 244080908-244080979 |
| 374 | LOC389333 | 5 | 138728189-138728287 |
| 375 | LOC440925__A | 2 | 171570158-171570471 |
| 376 | LOC646278 | 15 | 29077327-29077423 |
| 377 | LTBP2 | 14 | 75078651-75078687 |
| 378 | LYL1 | 19 | 13210058-13210180 |
| 379 | LYPLAL1 | 1 | 219347185-219347277 |
| 380 | MAX.chr1.228651512-228651589 | 1 | 228651512-228651589 |
| 381 | MAX.chr1.8014264-8014320 | 1 | 8014264-8014320 |
| 382 | MAX.chr10.22541719-22541758 | 10 | 22541719-22541758 |
| 383 | MAX.chr10.94459281-94459353 | 10 | 94459281-94459353 |
| 384 | MAX.chr11.32355226-32355251 | 11 | 32355226-32355251 |
| 385 | MAX.chr11.8041275-8041318 | 11 | 8041275-8041318 |
| 385 | MAX.chr11.8041275-8041318 | 11 | 8041275-8041318 |
| 386 | MAX.chr14.102172621-102172686 | 14 | 102172621-102172686 |
| 387 | MAX.chr14.105512122-105512239 | 14 | 105512122-105512239 |
| 388 | MAX.chr15.65186405-65186481 | 15 | 65186405-65186481 |
| 389 | MAX.chr15.95128144-95128248 | 15 | 95128144-95128248 |
| 390 | MAX.chr16.11327016-11327312 | 16 | 11327016-11327312 |
| 391 | MAX.chr17.77789297-77789347 | 17 | 77789297-77789347 |
| 392 | MAX.chr19.13266870-13266980 | 19 | 13266870-13266980 |
| 393 | MAX.chr19.42028466-42028519 | 19 | 42028466-42028519 |
| 394 | MAX.chr2.231693015-231693073 | 2 | 231693015-231693073 |
| 395 | MAX.chr2.73511979-73512039 | 2 | 73511979-73512039 |
| 396 | MAX.chr3.187676577-187676668 | 3 | 187676577-187676668 |
| 397 | MAX.chr4.174430676-174430847 | 4 | 174430676-174430847 |
| 398 | MAX.chr5.77147757-77147813 | 5 | 77147757-77147813 |
| 399 | MAX.chr6.130088620-130088690 | 6 | 130088620-130088690 |
| 400 | MAX.chr6.42738968-42739055 | 6 | 42738968-42739055 |
| 401 | MAX.chr8.145900783-145900914 | 8 | 145900783-145900914 |
| 402 | MAX.chr8.80804237-80804301 | 8 | 80804237-80804301 |
| 403 | MAX.chr9.33524209-33524289 | 9 | 33524209-33524289 |
| 404 | MPZ__A | 1 | 161275561-161275996 |
| 405 | N4BP2L1__C | 13 | 33001374-33001575 |
| 406 | N4BP3 | 5 | 177543694-177543863 |
| 407 | NCOR2 | 12 | 124941781-124942044 |
| 408 | NFATC1__A | 18 | 77159542-77159614 |
| 409 | NFATC1__B | 18 | 77159813-77159893 |
| 410 | NKX2-6 | 8 | 23564281-23564374 |
| 411 | NR2F6 | 19 | 17346567-17346673 |
| 412 | NR3C1__A | 5 | 142784971-142785160 |
| 413 | NR3C1__B | 5 | 142784614-142784698 |
| 414 | NTN1 | 17 | 9143174-9143253 |
| 415 | OSM | 22 | 30662648-30662807 |
| 416 | PALLD__C | 4 | 169799226-169799423 |

TABLE 8-continued

Hypermethylated endometrial tissue DMRs
with less than 1% noise in WBCs

| DMR No. | Gene Annotation | Chromosome No. | Region on Chromosome (starting base-ending base) |
|---|---|---|---|
| 417 | PHLDB1__B | 11 | 118481753-118481814 |
| 418 | PIK3CD | 1 | 9777870-9777967 |
| 419 | PLCL2 | 3 | 16925870-16925914 |
| 420 | PNMAL2 | 19 | 46996933-46996985 |
| 421 | PRDM13 | 6 | 100061723-100061766 |
| 422 | PRKAR1B | 7 | 644126-644332 |
| 423 | RAD52 | 12 | 1059296-1059503 |
| 424 | SEPT9__C | 17 | 75447656-75447714 |
| 425 | SNN | 16 | 11763081-11763138 |
| 426 | SPDYA__A | 2 | 29033287-29033484 |
| 427 | SPON2 | 4 | 1161228-1161298 |
| 428 | ST8SIA1 | 12 | 22487403-22487492 |
| 429 | STX16__A | 20 | 57224620-57224975 |
| 430 | SUCLG2 | 3 | 67706348-67706568 |
| 431 | TJP2 | 9 | 71788863-71788954 |
| 432 | TLE4 | 9 | 82188097-82188284 |
| 433 | TNFRSF1B | 1 | 12227425-12227514 |
| 434 | TNFRSF4 | 1 | 1148413-1148487 |
| 435 | TNRC18 | 7 | 5436900-5436991 |
| 436 | TSPAN33 | 7 | 128809205-128809241 |
| 437 | UST__B | 6 | 149068833-149068925 |
| 438 | VENTX | 10 | 135050110-135050178 |
| 439 | WDR86 | 7 | 151078576-151078610 |
| 440 | XKR6 | 8 | 11058545-11058598 |
| 441 | ZDHHC18 | 1 | 27160118-27160221 |
| 442 | ZNF227 | 19 | 44711531-44711781 |
| 315 | ZNF568__A | 19 | 37407197-37407284 |
| 443 | ZNF586__C | 19 | 58281020-58281200 |
| 444 | ZNF671__A | 19 | 58238740-58238799 |

TABLE 9

Area-under-the-curve, fold-change, and p-value for EC in comparison
to EC buffy controls for the markers recited in Table 8.

| DMR No. | Gene Annotation | AUC EC vs. EC buffy control | Fold Change EC vs. EC buffy control | p-value EC vs. EC buffy control |
|---|---|---|---|---|
| 319 | ACOXL__B | 0.6786 | 26080000 | 0.991 |
| 320 | ACTG1 | 0.709 | 34560000 | 0.9928 |
| 321 | ANKRD35 | 1 | 627.5 | 0.005999 |
| 499 | ARL5C | 0.9614 | 137.5 | 0.0001678 |
| 322 | ARRB1 | 0.9044 | 59100000 | 0.9902 |
| 323 | BCL2L11__A | 1 | 237.1 | 0.0004125 |
| 324 | BCL2L11__B | 0.9975 | 370.4 | 0.002033 |
| 325 | BCL2L11__C | 1 | 342.4 | 0.002845 |
| 326 | BEST4 | 0.7845 | 38650000 | 0.9902 |
| 327 | BZRAP1 | 0.9918 | 2116 | 0.0002676 |
| 328 | C14orf169__B | 0.7045 | 71770000 | 0.9904 |
| 329 | C14orf169__C | 0.7045 | 141100000 | 0.9914 |
| 330 | C14orf80 | 0.875 | 162800000 | 0.9914 |
| 331 | C16orf54 | 1 | 542.3 | 7.39E-05 |
| 332 | C17orf101 | 1 | 2.27E+09 | 0.9918 |
| 333 | C18orf1 | 0.7738 | 19.55 | 0.009107 |
| 334 | C6orf132 | 1 | 593.2 | 0.001901 |
| 335 | C9orf171 | 0.7321 | 36790000 | 0.9896 |
| 336 | CACNA2D4 | 0.9338 | 80450000 | 0.9891 |
| 337 | CCDC61 | 0.7109 | 63800000 | 0.9915 |
| 338 | DEDD2 | 1 | 527.9 | 6.12E-08 |
| 339 | DGKE | 0.7426 | 24970000 | 0.9924 |
| 340 | EGFL7 | 0.7344 | 72630000 | 0.9928 |
| 341 | EMB | 0.86 | 189900000 | 0.9916 |
| 342 | EOMES | 0.6633 | 50060000 | 0.9913 |
| 343 | EPS15L1 | 1 | 725500000 | 0.99 |
| 344 | FAIM2 | 0.9828 | 330.1 | 0.00851 |
| 345 | FAM125B | 0.9394 | 7.61E+08 | 0.9899 |
| 346 | FAM159A | 0.6889 | 100800000 | 0.9924 |

TABLE 9-continued

Area-under-the-curve, fold-change, and p-value for EC in comparison
to EC buffy controls for the markers recited in Table 8.

| DMR No. | Gene Annotation | AUC EC vs. EC buffy control | Fold Change EC vs. EC buffy control | p-value EC vs. EC buffy control |
|---|---|---|---|---|
| 347 | FAM189B | 0.995 | 135.3 | 0.003158 |
| 348 | FAM78A | 1 | 1404 | 9.92E−06 |
| 349 | FMNL1 | 0.8333 | 75120000 | 0.9918 |
| 350 | FOXP4 | 0.9776 | 582200000 | 0.9892 |
| 351 | GAL3ST4 | 0.8167 | 90980000 | 0.9908 |
| 352 | GATA2_C | 0.8492 | 109200000 | 0.9901 |
| 353 | GP1BB | 0.7119 | 42170000 | 0.9924 |
| 354 | GYPC_A | 0.9924 | 770700000 | 0.9901 |
| 355 | GYPC_B | 0.9397 | 664100000 | 0.9906 |
| 356 | HAAO | 0.8889 | 1.53E+08 | 0.9906 |
| 357 | HAND2 | 0.7923 | 46610000 | 0.9895 |
| 358 | HDAC7 | 0.7537 | 50550000 | 0.9898 |
| 359 | HOPX_B | 0.6983 | 70210000 | 0.9914 |
| 360 | HOXA7 | 0.7404 | 83950000 | 0.9909 |
| 361 | HOXB4 | 0.697 | 42010000 | 0.9915 |
| 362 | HRH2 | 0.7419 | 78270000 | 0.9913 |
| 363 | IFFO1_A | 0.9692 | 92880000 | 0.9902 |
| 364 | IFFO1_B | 0.9701 | 744200000 | 0.9913 |
| 119 | IL12RB2 | 0.6953 | 16740000 | 0.9928 |
| 365 | IQSEC3_A | 0.7576 | 29400000 | 0.9894 |
| 366 | IQSEC3_B | 0.7302 | 45010000 | 0.9926 |
| 367 | ITGA4_B | 0.7647 | 129900000 | 0.992 |
| 368 | ITPKA | 1 | 499.2 | 0.003773 |
| 369 | KLF16 | 0.9083 | 165100000 | 0.9921 |
| 370 | LIMD2 | 0.9603 | 493100000 | 0.9911 |
| 371 | LOC100129726_A | 0.6692 | 29650000 | 0.9887 |
| 382 | LOC100192379_B | 0.6667 | 3.10E+07 | 0.9939 |
| 373 | LOC339529 | 0.8273 | 115200000 | 0.9902 |
| 374 | LOC389333 | 0.9545 | 393300000 | 0.9917 |
| 375 | LOC440925_A | 0.9959 | 274.8 | 0.007478 |
| 376 | LOC646278 | 0.9016 | 86610000 | 0.9898 |
| 377 | LTBP2 | 0.7636 | 65880000 | 0.9912 |
| 378 | LYL1 | 0.9887 | 545.8 | 0.006049 |
| 379 | LYPLAL1 | 0.9846 | 2.10E+09 | 0.9917 |
| 380 | MAX.chr1.228651512-228651589 | 0.7734 | 51900000 | 0.9889 |
| 381 | MAX.chr1.8014264-8014320 | 0.8929 | 188300000 | 0.9925 |
| 382 | MAX.chr10.22541719-22541758 | 0.8871 | 139100000 | 0.992 |
| 383 | MAX.chr10.94459281-94459353 | 0.8364 | 1.26E+08 | 0.9927 |
| 384 | MAX.chr11.32355226-32355251 | 0.9731 | 471.5 | 0.008476 |
| 385 | MAX.chr11.8041275-8041318 | 0.6562 | 50170000 | 0.9949 |
| 386 | MAX.chr14.102172621-102172686 | 0.9224 | 380600000 | 0.9916 |
| 387 | MAX.chr14.105512122-105512239 | 0.9924 | 512600000 | 0.989 |
| 388 | MAX.chr15.65186405-65186481 | 0.7769 | 134800000 | 0.9917 |
| 389 | MAX.chr15.95128144-95128248 | 0.9678 | 126.9 | 0.003344 |
| 390 | MAX.chr16.11327016-11327312 | 0.9984 | 837.5 | 1.85E−05 |
| 391 | MAX.chr17.77789297-77789347 | 0.8689 | 82590000 | 0.9919 |
| 392 | MAX.chr19.13266870-13266980 | 0.7077 | 104900000 | 0.993 |
| 393 | MAX.chr19.42028466-42028519 | 0.8727 | 246200000 | 0.9902 |
| 394 | MAX.chr2.231693015-231693073 | 0.6932 | 71170000 | 0.9936 |
| 395 | MAX.chr2.73511979-73512039 | 0.6778 | 95180000 | 0.9931 |
| 396 | MAX.chr3.187676577-187676668 | 0.9984 | 677.2 | 1.78E−05 |
| 397 | MAX.chr4.174430676-174430847 | 0.9877 | 105.5 | 0.00112 |

TABLE 9-continued

Area-under-the-curve, fold-change, and p-value for EC in comparison
to EC buffy controls for the markers recited in Table 8.

| DMR No. | Gene Annotation | AUC EC vs. EC buffy control | Fold Change EC vs. EC buffy control | p-value EC vs. EC buffy control |
|---|---|---|---|---|
| 398 | MAX.chr5.77147757-77147813 | 0.6596 | 31920000 | 0.9924 |
| 399 | MAX.chr6.130088620-130088690 | 0.7281 | 75460000 | 0.9915 |
| 400 | MAX.chr6.42738968-42739055 | 0.6923 | 41460000 | 0.9921 |
| 401 | MAX.chr8.145900783-145900914 | 1 | 1127 | 2.26E−05 |
| 402 | MAX.chr8.80804237-80804301 | 0.9519 | 83590000 | 0.9922 |
| 403 | MAX.chr9.33524209-33524289 | 0.7653 | 68470000 | 0.9939 |
| 404 | MPZ_A | 0.8914 | 26.19 | 0.0129 |
| 405 | N4BP2L1_C | 0.675 | 43500000 | 0.9929 |
| 406 | N4BP3 | 1 | 284.9 | 0.003001 |
| 407 | NCOR2 | 0.9992 | 334.7 | 0.002568 |
| 408 | NFATC1_A | 0.9886 | 360.7 | 0.003405 |
| 409 | NFATC1_B | 0.9385 | 73470000 | 0.9885 |
| 410 | NKX2-6 | 0.9889 | 452800000 | 0.9932 |
| 411 | NR2F6 | 0.9403 | 1.10E+09 | 0.9931 |
| 412 | NR3C1_A | 0.7687 | 42200000 | 0.9904 |
| 413 | NR3C1_B | 0.6846 | 41810000 | 0.9926 |
| 414 | NTN1 | 0.8361 | 100500000 | 0.9909 |
| 415 | OSM | 0.9906 | 894.1 | 0.0004214 |
| 416 | PALLD_C | 1 | 369.1 | 0.001153 |
| 417 | PHLDB1_B | 0.6786 | 42240000 | 0.9894 |
| 418 | PIK3CD | 0.9731 | 82.97 | 0.0002239 |
| 419 | PLCL2 | 0.7705 | 67150000 | 0.9898 |
| 420 | PNMAL2 | 0.8433 | 117600000 | 0.9914 |
| 421 | PRDM13 | 0.7347 | 35550000 | 0.9914 |
| 422 | PRKAR1B | 1 | 537 | 0.003643 |
| 423 | RAD52 | 0.9252 | 71.45 | 0.002206 |
| 424 | SEPT9_C | 0.6909 | 30860000 | 0.991 |
| 425 | SNN | 0.71 | 49210000 | 0.994 |
| 426 | SPDYA_A | 0.8696 | 113700000 | 0.9899 |
| 427 | SPON2 | 0.7803 | 64470000 | 0.9911 |
| 428 | ST8SIA1 | 0.6939 | 61890000 | 0.9932 |
| 429 | STX16_A | 1 | 889.9 | 0.0002353 |
| 430 | SUCLG2 | 1 | 4174 | 0.001157 |
| 431 | TJP2 | 0.6923 | 64420000 | 0.9901 |
| 432 | TLE4 | 0.6667 | 65910000 | 0.9928 |
| 433 | TNFRSF1B | 0.9196 | 99080000 | 0.9908 |
| 434 | TNFRSF4 | 0.9615 | 205500000 | 0.9893 |
| 435 | TNRC18 | 0.8906 | 186900000 | 0.9914 |
| 436 | TSPAN33 | 0.8125 | 96600000 | 0.9903 |
| 437 | USTB | 0.6885 | 29650000 | 0.9931 |
| 438 | VENTX | 0.8016 | 32390000 | 0.9904 |
| 439 | WDR86 | 0.8939 | 184500000 | 0.9874 |
| 440 | XKR6 | 0.8021 | 47230000 | 0.9913 |
| 441 | ZDHHC18 | 0.9926 | 5.61E+09 | 0.9902 |
| 442 | ZNF227 | 0.7132 | 51410000 | 0.9916 |
| 315 | ZNF568_A | 0.6967 | 59100000 | 0.9923 |
| 443 | ZNF586_C | 0.7188 | 42520000 | 0.9877 |
| 444 | ZNF671_A | 0.9167 | 200800000 | 0.9923 |

From these marker groups 56 candidates were chosen for an initial pilot. Methylation-specific PCR assays were developed and tested on two rounds of samples; those that were sequenced and larger independent cohorts. Short amplicon primers (<150 bp) were designed to target the most discriminant CpGs within a DMR and tested on controls to ensure that fully methylated fragments amplified robustly and in a linear fashion, that unmethylated and/or unconverted fragments did not amplify. The 112 primer sequences and annealing temperatures for the 56 candidate markers are listed in Table 10.

TABLE 10

| Gene Annotation | DMR No. | Forward Primer 5'-3' | Seq ID | Reverse Primer 5'-3' | Seq ID | Annealing Temperature ° C./Final |
|---|---|---|---|---|---|---|
| SFMBT2_B | 262 | GCG CGC GGT TTT GGG AGA TAA GTA C | 1 | AAA AAA AAC AAC CCC TCG CCT CGA C | 2 | 70 |
| SMTN | 273 | AGG TTT TTA GGA TAT TTA GTT GAG TGG CGG | 3 | ACC TCG ATC CCG AAT TCG AAT TCG AC | 4 | 70 |
| SQSTM1 | 278 | GTT TTC GGT TAT TCG GTG ACG G | 5 | AAA AAA CTA AAA AAC GAA TCG CGC T | 6 | 65 |
| ZNF323_A | 312 | TTT AAT GAT CGA TTA ATC GTA AAG GTC GG | 7 | AAC CAA TAA ACT CAA AAC GAC TAA CGC A | 8 | 65 |
| ZNF506 | 314 | TTA GGT TTT TAG GGG GTT TCG GCG T | 9 | ATC GTC TTC ACT ACT CTA TAC CGT C | 10 | 65 |
| ZNF90 | 318 | AAT TGG GTA AGG AGA AGT CGG TCG T | 11 | ATA ACG AAA CTT AAA CCT CCC CGC A | 12 | 70 |
| ACOXL_A | 2 | AGT TAA GTT TTA ACG GGT GTG GCG G | 13 | AAA CGT CGA TAA AAC GAA CGT CGT A | 14 | 70 |
| CLDN7 | 55 | TAT CGT TGT TTC GAG TCG GGG ACG A | 15 | AAC CGA AAT TCC GAC GAC TAC ACG T | 16 | 65 |
| LRRC41_B | 148 | GGT TCG GAG CGG TTT AAA TAA GCG A | 17 | CTT AAC CCT TCC CGC CTA TCC GTC | 18 | 70 |
| MAX.chr7.1 04624356- 104624730 | 204 | TTG GGG GTT GTC GGT TTT TGG AGA C | 19 | CCG ATC TAA ATA CCC CAA ACG AAA TCG AA | 20 | 70 |
| NDRG2 | 226 | CGT TTT TAG ATT TAG TGG TGG GAA TCG G | 21 | TCG AAC GAA AAA AAT CGA ACT CGT A | 22 | 60 |
| CYP11A1 | 57 | TTT TTC GCG GGT CGT TTA TTT TCG T | 23 | AAA CGA ATA AAC TCG AAC TAT ATC GAA | 24 | 65 |
| FKBP11_A | 88 | TTA CGA TCG GAT TAT AGG GGT TAC GG | 25 | TAC CGA ATC TAA AAA CGA AAA CGA A | 26 | 65 |
| MAX.chr8.1 45103829- 145103992 | 207 | GGG GAG TTA TAG GGG TGA AGG TCG C | 27 | GCC TCC GCC AAA CTC GCT ACG TC | 28 | 70 |
| AHSA2 | 10 | TAT TTG GCG CGT GGG GAG AGG TC | 29 | TCC CTT CCG AAA ATT CTA CGA CGA A | 30 | 65 |
| CYTH2 | 59 | TTT TAG GGT AAA TAG CGG GTT TCG T | 31 | CGA CCG CCC TAC ATA CAA TTC ATC CG | 32 | 65 |
| GATA2_B | 100 | GTG TGA TAG ACG TTA GAG CGG CGG | 33 | CGT TTT AAT CAA AAA AAT CTC CCG TA | 34 | 65 |
| LRRC8D_A | 152 | GGG AGA ATT CGA GTA GTA GTT GTA AAC GG | 35 | AAT AAC CTC GCT ACC AAC CAC CCG C | 36 | 65 |
| MAX.chr8.1 45104263- 145104422 | 208 | GGG CGT TGT TTC GTT TTT TTT ATC GT | 37 | GAA ACG CGC TTA CCC GTC GAA | 38 | 70 |

TABLE 10-continued

| Gene Annotation | DMR No. | Forward Primer 5'-3' | Seq ID | Reverse Primer 5'-3' | Seq ID | Annealing Temperature ° C./Final |
|---|---|---|---|---|---|---|
| OBSCN_A | 234 | GTT CGT TAT CGT TTG GTT TTG TAT AAC GT | 39 | TAT ATC TTA TCA TCC GAC GTC TCG CA | 40 | 65 |
| DIDO1_A | 63 | TAT TTG GGA TTT AGA GAG GTA GCG G | 41 | CCA AAA ACC GAA ACC TAA ACG CT | 42 | 70 |
| GDF6 | 102 | TTT TAT TTC GTA GAC GAT TTT TCG T | 43 | GAA AAA ACC GCA ACT CCG CGC | 44 | 65 |
| MAX.chr10. 130339363- 130339534 | 165 | AAT AAT AGG AAT TAG AGG TTG TCG G | 45 | AAA TAA CAA ACT CCG CGC GCG AA | 46 | 65 |
| MDFI_B | 212 | TAC GGT TCG TAC GAG TGA GTG GAC GT | 47 | ACG CCG AAA ACG AAC AAA AAA CGA T | 48 | 70 |
| DLL4 | 67 | TTT TTC GTA GCG ATC GTA GCG GCG T | 51 | ACC TAC TAA ACA AAC CAA AAA CGA A | 52 | 65 |
| GDF7_A | 103 | TTC GTT TAG AAG GCG GGT GGA AGG TC | 53 | AAA AAA TCT CGC GCG AAA ATA CGC T | 54 | 65 |
| MAX.chr10. 22624479- 22624553 | 167 | GGA AGG TTA GGG GGA AAT TTG TAT TTC GT | 55 | CGT AAC ATC GTC ATT TCT TAA CCG CGA T | 56 | 70 |
| MIAT_A | 214 | TTT CGT ATT AAA ATT TTA TGG GCG T | 57 | TCT AAT CCC GCG AAC GCA ACC G | 58 | 60 |
| PYCARD | 248 | TAG TTT TGT TTA GGG GTA GGA GGA ATA GAA AGC G | 59 | ACA CCA ACG CTT ACC CCG CGA A | 60 | 65 |
| BMP4_B | 26 | TTT TCG ATC GTG GAT GTT CGG AGT C | 61 | GAA AAC CGC GCG ACT CTT ACC GAA | 62 | 70 |
| JSRP1_A | 124 | GGG AGG GGT CGT AGG AGT GTT TTC G | 63 | ATA ACG TTC TAC CGC CTT TCC CCT ACG C | 64 | 70 |
| MAX.chr14. 103021656- 103021718 | 174 | GAA AGC GAA ACG GTT CGG CGG TC | 65 | CAA ACT TCC GAA TCC TAC CCC CGC | 66 | 70 |
| MIAT_B | 215 | TCG AGA GAG GTC GGT TTT TTT TAT CGT | 67 | AAA CTT CCG ATC ACG ACC CCA CGT C | 68 | 70 |
| RHBOL1_A | 252 | TCG TTG GTA AAT GGA GTT ACG G | 69 | GAA AAA ACT ATA AAA AAA CGA ACG AT | 70 | 60 |
| EMX2 | 80 | GTA TTT ATC GCG TTT TCG AGT TCG A | 71 | TAT AAC GCG ACC CCA ACG CT | 72 | 70 |
| KANK1 | 126 | GTA GTC GGA GGG AGA TTT CGT CGG | 73 | ATA AAC TTA ACC GAC CAC GCT CGA A | 74 | 65 |
| MMP23B | 218 | CGG GTT GTA ATT CGA GTC GTC GA | 75 | CAA AAC CTC CGA AAA AAA TCC GAA | 76 | 65 |
| SBNO2 | 256 | GTA TAG GGC GTC GTT TTT AGT TCG A | 77 | AAA AAA TCT ACC GAA AAA TTC CGA A | 78 | 60 |

TABLE 10-continued

| Gene Annotation | DMR No. | Forward Primer 5'-3' | Seq ID | Reverse Primer 5'-3' | Seq ID | Annealing Temperature ° C./Final |
|---|---|---|---|---|---|---|
| C5orf52 | 40 | TTG GTT TAA TTC GTT ATT CGT TTC GT | 79 | AAC AAA CCT TTT CCG CTT CGA CGT A | 80 | 65 |
| EMX2OS | 81 | CGA AGT TCG GGT AGG GTA AGC GTT GC | 81 | CGA CGT AAA AAT ACG AAA CGC ACG AA | 82 | 65 |
| LRRC34 | 146 | GTG AGG CGG TTA TAC GAG TTT CGG C | 83 | CAA AAA ACC TCC ACA AAA TAA ACG AT | 84 | 65 |
| MAX.chr17. 73073716- 73073814 | 180 | TTT TTC GAG TCG TTT TAT TTC GCG G | 85 | GAA CTC CGA ACG CCG CTT AAA CGT A | 86 | 70 |
| NBPF8 | 162 | CGC GTA GGT GTT TAA CGT GAT TAG CGC | 87 | CTT ACA TCC TCA AAA CCC GCC CGA C | 88 | 65 |
| SEPT9_B | 259 | TTA TGG TGG CGG TGT CGG GAG TTA C | 89 | CCC TCT CCT AAA AAC CCC GCT CGA T | 90 | 70 |
| LOC440925_A | 375 | AGT TCG CGT TCG GTT TTT TTG TTC G | 91 | GTC CGT CCC GAT CGC AAT ACG A | 92 | 65 |
| STX16_A | 429 | CGC GTT GCG CGG AAG TTA GAG TC | 93 | CCA CAT AAA ATC GAA AAA ACC GCG AA | 94 | 65 |
| ITPKA | 368 | GGG TTT ATA AGT TCG GAG GTC GA | 95 | CAC CCA ACA CCT AAC GAC GA | 96 | 65 |
| AIM1_A | 11 | AGC GTT TTT AGG GAG TTC GGC GTT C | 97 | AAT CGA AAA AAC GAA AAA AAT CGC A | 98 | 65 |
| EEF1A2 | 75 | TAG GTC GTT TCG TCG TGC GC | 101 | ATA ACC TTA CCG ACG CCG CCG CT | 102 | 70 |
| FEV | 87 | TTT TTG AAG AGA TCG TTT TCG ACG G | 103 | CCC CCT TAA ACC TTA ACC CGA A | 104 | 65 |
| LRRC41_C | 149 | GGC GTT TCG ATT TTT TCG TTC GG | 105 | CCG AAA CTC CAA CAT CTA CCT AAC ACG CC | 106 | 65 |
| NFIC | 230 | CGT AAT TTT TGG CGA GCG ACG TTT GC | 107 | CAA CCT TCG AAA TCC CCC ATC CGC T | 108 | 70 |
| VILL | 302 | GGT TTT GGG GGA TTT AGG GTT CGG | 49 | TCC GCG AAA ACC CCT ACC TAA CGT C | 50 | 70 |
| MPZ_A | 404 | GGG GCG TAT ATA TTA GTT ATC GAG CGA | 99 | AAA AAA AAC CCT AAA AAC CGC CGA A | 100 | 65 |

The results from round one validation were analyzed logistically to determine AUC and fold change. From previous work it was recognized that the epigenetics of cancer subtypes within an organ differ and that the best panels are derived from combinations of subtype markers. Analyses for the tissue and buffy coat controls were run separately. Results are highlighted in Tables 11 (clear cell EC vs. buffy coat), 12 (serous EC vs. buffy coat), 13 (cacinosarcoma EC vs. buffy coat), and 14 (endometrioid EC vs. buffy coat). The gray-scaled red shading over certain genes indicates DMRs which overlap with multiple subtypes. The degree of grey-scaled red shading indicates the discrimination strength of the marker assay. A number of assays were 100% discriminant in EC from buffy coat samples and approaching 100% in the EC vs benign endometrium comparison.

TABLE 11

DMRs distinguishing 1) clear cell EC and buffy coat and 2) clear
cell EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 262 | SFMBT2__B | 0.97 | 1179.65 | 0.72 | 11.52 |
| 273 | SMTN | 0.89 | 199.57 | 0.51 | 7.59 |
| 278 | SQSTM1 | 0.91 | 201.30 | 0.87 | 18.50 |
| 312 | ZNF323__A | 1.00 | 422080.20 | 0.98 | 343.83 |
| 314 | ZNF506 | 0.94 | 451.38 | 0.70 | 8.09 |
| 318 | ZNF90 | 0.93 | 44.22 | 0.50 | 1.77 |
| 2 | ACOXL__A | 0.81 | 122.93 | 0.61 | 1.43 |
| 55 | CLDN7 | 0.97 | 15.54 | 0.73 | 0.65 |
| 148 | LRRC41__B | 0.97 | 142.56 | 0.68 | 6.81 |
| 204 | MAX.chr7.104624356-104624730 | 0.93 | 187.02 | 0.93 | 100.90 |
| 226 | NDRG2 | 0.95 | 285.41 | 0.91 | 111.93 |
| 57 | CYP11A1 | 0.94 | 101.29 | 0.59 | 1.83 |
| 88 | FKBP11__A | 0.83 | 17.00 | 0.65 | 4.46 |
| 207 | MAX.chr8.145103829-145103992 | 0.93 | 1107.83 | 0.74 | 18.09 |
| 10 | AHSA2 | 0.88 | 61.87 | 0.72 | 5.77 |
| 59 | CYTH2 | 0.99 | 152.59 | 0.81 | 3.59 |
| 100 | GATA2__B | 0.89 | 518.49 | 0.67 | 12.96 |
| 152 | LRRC8D__A | 0.92 | 323.21 | 0.74 | 11.32 |
| 208 | MAX.chr8.145104263-145104422 | 0.96 | 258.53 | 0.67 | 12.62 |
| 234 | OBSCN__A | 1.00 | 2614.39 | 0.89 | 30.04 |
| 63 | DIDO1__A | 0.97 | 918.19 | 0.91 | 16.37 |
| 102 | GDF6 | 0.99 | 203.64 | 0.62 | 4.22 |
| 165 | MAX.chr10.130339363-130339534 | 0.92 | 18.64 | 0.75 | 3.52 |
| 212 | MDFI__B | 0.94 | 1749.15 | 0.90 | 42.70 |
| 67 | DLL4 | 0.96 | 12.73 | 0.60 | 0.31 |
| 103 | GDF7__A | 0.92 | 224.96 | 0.84 | 27.86 |
| 167 | MAX.chr10.22624479-22624553 | 0.85 | 2399.57 | 0.75 | 24.84 |
| 214 | MIAT__A | 0.93 | 1055.89 | 0.83 | 98.21 |
| 248 | PYCARD | 0.94 | 106.61 | 0.57 | 6.24 |
| 26 | BMP4__B | 0.95 | 127.50 | 0.56 | 7.73 |
| 124 | JSRP1__A | 0.98 | 81.87 | 0.78 | 4.52 |
| 174 | MAX.chr14.103021656-103021718 | 0.98 | 2953.08 | 0.97 | 184.74 |
| 215 | MIAT__B | 0.87 | 99.67 | 0.38 | 3.32 |
| 252 | RHBDL1__A | 0.71 | 20.30 | 0.76 | 12.49 |
| 80 | EMX2 | 0.92 | 422.01 | 0.85 | 35.48 |
| 126 | KANK1 | 0.73 | 23.85 | 0.64 | 6.84 |
| 218 | MMP23B | 0.97 | 640.18 | 0.92 | 25.53 |
| 256 | SBNO2 | 0.83 | 8.43 | 0.57 | 0.51 |
| 40 | C5orf52 | 0.59 | 59.11 | 0.65 | 0.68 |
| 81 | EMX2OS | 0.98 | 154.84 | 0.89 | 5.95 |
| 146 | LRRC34 | 0.81 | 62.10 | 0.61 | 2.27 |
| 180 | MAX.chr17.73073716-73073814 | 1.00 | 283.78 | 0.87 | 22.84 |
| 162 | NBPF8 | 0.97 | 69.67 | 0.85 | 7.68 |
| 259 | SEPT9__B | 0.99 | 1751.41 | 0.94 | 70.17 |
| 375 | LOC440925__A | 1.00 | 304.06 | 0.49 | 1.04 |
| 429 | STX16__A | 0.90 | 173.42 | 0.94 | 53.85 |
| 368 | ITPKA | 1.00 | 1509.47 | 0.58 | 0.96 |
| 11 | AIM1__A | 0.79 | 15826.65 | 0.78 | 307.38 |
| 75 | EEF1A2 | 0.97 | 289.12 | 0.83 | 41.35 |
| 87 | FEV | 0.94 | 537.52 | 0.84 | 19.39 |
| 149 | LRRC41__C | 0.98 | 392.66 | 0.72 | 18.82 |
| 230 | NFIC | 0.95 | 107.52 | 0.69 | 6.95 |
| 302 | VILL | 0.88 | 49.58 | 0.44 | 3.39 |
| 404 | MPZ__A | 0.85 | 1112.98 | 0.61 | 6.77 |

TABLE 12

DMRs distinguishing 1) serous EC and buffy coat and 2) serous
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 262 | SFMBT2__B | 0.91 | 594.75 | 0.65 | 5.81 |
| 273 | SMTN | 1.00 | 235.25 | 0.70 | 8.95 |

TABLE 12-continued

DMRs distinguishing 1) serous EC and huffy coat and 2) serous
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 278 | SQSTM1 | 1.00 | 155.56 | 0.80 | 14.30 |
| 312 | ZNF323__A | 0.88 | 400850.18 | 0.88 | 326.53 |
| 314 | ZNF506 | 0.81 | 181.26 | 0.62 | 3.25 |
| 318 | ZNF90 | 1.00 | 124.47 | 0.63 | 4.97 |
| 2 | ACOXL__A | 0.87 | 4248.44 | 0.63 | 49.40 |
| 55 | CLDN7 | 1.00 | 15.07 | 0.58 | 0.63 |
| 148 | LRRC41__B | 1.00 | 170.65 | 0.82 | 8.15 |
| 204 | MAX.chr7.104624356-104624730 | 0.94 | 435.76 | 0.94 | 235.10 |
| 226 | NDRG2 | 0.73 | 108.35 | 0.75 | 42.49 |
| 57 | CYP11A1 | 0.91 | 420.04 | 0.73 | 7.61 |
| 88 | FKBP11__A | 0.92 | 153.12 | 0.84 | 40.21 |
| 207 | MAX.chr8.145103829-145103992 | 1.00 | 886.56 | 0.72 | 14.47 |
| 10 | AHSA2 | 0.94 | 33.32 | 0.69 | 3.11 |
| 59 | CYTH2 | 0.97 | 137.39 | 0.70 | 3.23 |
| 100 | GATA2__B | 0.81 | 481.98 | 0.68 | 12.05 |
| 152 | LRRC8D__A | 0.98 | 681.74 | 0.85 | 23.87 |
| 208 | MAX.chr8.145104263-145104422 | 1.00 | 236.41 | 0.70 | 11.54 |
| 234 | OBSCN__A | 0.93 | 2837.86 | 0.76 | 32.61 |
| 63 | DIDO1__A | 0.83 | 1663.93 | 0.80 | 29.67 |
| 102 | GDF6 | 1.00 | 172.69 | 0.67 | 3.58 |
| 165 | MAX.chr10.130339363-130339534 | 0.87 | 5.69 | 0.61 | 1.07 |
| 212 | MDFI__B | 0.74 | 926.85 | 0.75 | 22.63 |
| 67 | DLL4 | 0.94 | 34.95 | 0.62 | 0.85 |
| 103 | GDF7__A | 0.71 | 335.86 | 0.68 | 41.60 |
| 167 | MAX.chr10.22624479-22624553 | 0.77 | 2245.78 | 0.65 | 23.25 |
| 214 | MIAT__A | 0.84 | 378.27 | 0.61 | 35.18 |
| 248 | PYCARD | 1.00 | 29.18 | 0.40 | 1.71 |
| 26 | BMP4__B | 0.97 | 51.17 | 0.46 | 3.10 |
| 124 | JSRP1__A | 0.99 | 78.15 | 0.65 | 4.31 |
| 174 | MAX.chr14.103021656-103021718 | 0.76 | 2225.70 | 0.65 | 139.24 |
| 215 | MIAT__B | 0.90 | 325.27 | 0.69 | 10.85 |
| 252 | RHBDL1__A | 0.78 | 32.70 | 0.76 | 20.12 |
| 80 | EMX2 | 0.68 | 439.81 | 0.71 | 36.98 |
| 126 | KANK1 | 0.91 | 54.42 | 0.88 | 15.60 |
| 218 | MMP23B | 0.77 | 139.13 | 0.80 | 5.55 |
| 256 | SBNO2 | 0.78 | 32.10 | 0.50 | 1.93 |
| 40 | C5orf52 | 0.74 | 54.72 | 0.56 | 0.63 |
| 81 | EMX2OS | 1.00 | 286.88 | 0.91 | 11.02 |
| 146 | LRRC34 | 0.72 | 316.99 | 0.60 | 11.61 |
| 180 | MAX.chr17.73073716-73073814 | 0.80 | 151.03 | 0.74 | 12.16 |
| 162 | NBPF8 | 0.99 | 101.15 | 0.79 | 11.15 |
| 259 | SEPT9__B | 0.72 | 508.74 | 0.64 | 20.38 |
| 375 | LOC440925__A | 1.00 | 347.38 | 0.51 | 1.18 |
| 429 | STX16__A | 0.76 | 159.65 | 0.80 | 49.58 |
| 368 | ITPKA | 1.00 | 1869.01 | 0.50 | 1.18 |
| 11 | AIM1__A | 0.71 | 2731.20 | 0.70 | 53.05 |
| 75 | EEF1A2 | 0.93 | 59.07 | 0.63 | 8.45 |
| 87 | FEV | 0.90 | 648.38 | 0.76 | 23.39 |
| 149 | LRRC41__C | 1.00 | 530.59 | 0.94 | 25.43 |
| 230 | NFIC | 0.92 | 165.59 | 0.73 | 10.71 |
| 302 | VILL | 0.96 | 120.29 | 0.66 | 8.23 |
| 404 | MPZ__A | 0.94 | 3826.67 | 0.89 | 23.28 |

TABLE 13

DMRs distinguishing 1) carcinosarcoma EC and buffy coat and 2) carcinosarcoma
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 262 | SFMBT2__B | 0.99 | 1428.99 | 0.68 | 13.95 |
| 273 | SMTN | 1.00 | 377.39 | 0.76 | 14.36 |
| 278 | SQSTM1 | 0.62 | 284.30 | 0.58 | 26.13 |
| 312 | ZNF323__A | 0.85 | 485857.78 | 0.86 | 395.78 |

TABLE 13-continued

DMRs distinguishing 1) carcinosarcoma EC and buffy coat and 2) carcinosarcoma
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 314 | ZNF506 | 0.97 | 536.08 | 0.79 | 9.60 |
| 318 | ZNF90 | 1.00 | 114.78 | 0.77 | 4.58 |
| 2 | ACOXL__A | 0.73 | 7752.33 | 0.64 | 90.14 |
| 55 | CLDN7 | 0.98 | 115.79 | 0.46 | 4.87 |
| 148 | LRRC41__B | 1.00 | 66.45 | 0.62 | 3.17 |
| 204 | MAX.chr7.104624356-104624730 | 0.84 | 745.78 | 0.85 | 402.36 |
| 226 | NDRG2 | 0.68 | 29.19 | 0.69 | 11.45 |
| 57 | CYP11A1 | 0.93 | 140.16 | 0.66 | 2.54 |
| 88 | FKBP11__A | 0.85 | 25.24 | 0.73 | 6.63 |
| 207 | MAX.chr8.145103829-145103992 | 0.95 | 2543.71 | 0.66 | 41.53 |
| 10 | AHSA2 | 0.96 | 226.81 | 0.77 | 21.16 |
| 59 | CYTH2 | 1.00 | 263.29 | 0.85 | 6.19 |
| 100 | GATA2__B | 0.98 | 576.22 | 0.61 | 14.40 |
| 152 | LRRC8D__A | 0.96 | 776.27 | 0.75 | 27.18 |
| 208 | MAX.chr8.145104263-145104422 | 0.94 | 497.10 | 0.64 | 24.27 |
| 234 | OBSCN__A | 0.99 | 3188.04 | 0.83 | 36.63 |
| 63 | DIDO1__A | 1.00 | 2258.45 | 0.88 | 40.27 |
| 102 | GDF6 | 1.00 | 298.43 | 0.79 | 6.18 |
| 165 | MAX.chr10.130339363-130339534 | 0.87 | 24.92 | 0.60 | 4.71 |
| 212 | MDFI__B | 0.62 | 282.92 | 0.65 | 6.91 |
| 67 | DLL4 | 1.00 | 42.28 | 0.68 | 1.03 |
| 103 | GDF7__A | 0.76 | 455.11 | 0.71 | 56.37 |
| 167 | MAX.chr10.22624479-22624553 | 0.93 | 4917.08 | 0.82 | 50.91 |
| 214 | MIAT__A | 0.80 | 60.34 | 0.59 | 5.61 |
| 248 | PYCARD | 0.98 | 55.62 | 0.51 | 3.25 |
| 26 | BMP4__B | 0.98 | 270.79 | 0.52 | 16.41 |
| 124 | JSRP1__A | 1.00 | 57.52 | 0.61 | 3.18 |
| 174 | MAX.chr14.103021656-103021718 | 0.91 | 4012.26 | 0.88 | 251.00 |
| 215 | MIAT__B | 0.92 | 196.61 | 0.77 | 6.56 |
| 252 | RHBDL1__A | 0.64 | 22.37 | 0.68 | 13.76 |
| 80 | EMX2 | 0.85 | 485.41 | 0.86 | 40.81 |
| 126 | KANK1 | 0.82 | 194.54 | 0.79 | 55.77 |
| 218 | MMP23B | 0.43 | 102.68 | 0.57 | 4.09 |
| 256 | SBNO2 | 0.89 | 297.56 | 0.73 | 17.85 |
| 40 | C5orf52 | 0.76 | 3076.88 | 0.59 | 35.54 |
| 81 | EMX2OS | 1.00 | 383.68 | 0.99 | 14.74 |
| 146 | LRRC34 | 1.00 | 634.47 | 0.90 | 23.23 |
| 180 | MAX.chr17.73073716-73073814 | 0.89 | 618.49 | 0.83 | 49.78 |
| 162 | NBPF8 | 0.98 | 115.64 | 0.86 | 12.75 |
| 259 | SEPT9__B | 0.64 | 233.76 | 0.60 | 9.37 |
| 375 | LOC440925__A | 1.00 | 450.23 | 0.57 | 1.53 |
| 429 | STX16__A | 0.64 | 296.41 | 0.73 | 92.04 |
| 368 | ITPKA | 1.00 | 4030.59 | 0.69 | 2.55 |
| 11 | AIM1__A | 0.81 | 5230.38 | 0.78 | 101.58 |
| 75 | EEF1A2 | 0.85 | 59.43 | 0.54 | 8.50 |
| 87 | FEV | 0.87 | 295.29 | 0.68 | 10.65 |
| 149 | LRRC41__C | 0.84 | 168.11 | 0.58 | 8.06 |
| 230 | NFIC | 1.00 | 141.82 | 0.70 | 9.17 |
| 302 | VILL | 0.99 | 171.70 | 0.88 | 11.74 |
| 404 | MPZ__A | 0.84 | 2691.51 | 0.66 | 16.38 |

TABLE 14

DMRs distinguishing 1) endometrioid EC and buffy coat and 2) endometrioid
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 262 | SFMBT2__B | 0.99 | 4102.95 | 0.87 | 40.06 |
| 273 | SMTN | 1.00 | 177.04 | 0.72 | 6.74 |
| 278 | SQSTM1 | 1.00 | 152.79 | 0.84 | 14.04 |
| 312 | ZNF323__A | 0.89 | 767729.43 | 0.89 | 625.39 |
| 314 | ZNF506 | 0.94 | 1764.70 | 0.87 | 31.61 |
| 318 | ZNF90 | 1.00 | 286.45 | 0.84 | 11.44 |

TABLE 14-continued

DMRs distinguishing 1) endometrioid EC and buffy coat and 2) endometrioid
EC and normal endometrium and normal cervicovaginal tissue

| DMR No. | Gene Name | AUC/Buffy Coat | FC/Buffy Coat | AUC/normal endometrium and normal cervicovaginal tissue | FC/normal endometrium and normal cervicovaginal tissue |
|---|---|---|---|---|---|
| 2 | ACOXL__A | 0.72 | 1420.62 | 0.62 | 16.52 |
| 55 | CLDN7 | 1.00 | 18.78 | 0.55 | 0.79 |
| 148 | LRRC41__B | 1.00 | 137.20 | 0.52 | 6.55 |
| 204 | MAX.chr7.104624356-104624730 | 0.80 | 189.27 | 0.81 | 102.12 |
| 226 | NDRG2 | 0.69 | 189.12 | 0.72 | 74.17 |
| 57 | CYP11A1 | 0.89 | 356.99 | 0.60 | 6.46 |
| 88 | FKBP11__A | 0.96 | 63.66 | 0.83 | 16.72 |
| 207 | MAX.chr8.145103829-145103992 | 1.00 | 4309.89 | 0.93 | 70.36 |
| 10 | AHSA2 | 0.93 | 99.00 | 0.76 | 9.24 |
| 59 | CYTH2 | 1.00 | 443.30 | 0.94 | 10.42 |
| 100 | GATA2__B | 0.91 | 1201.79 | 0.68 | 30.04 |
| 152 | LRRC8D__A | 0.96 | 1104.73 | 0.76 | 38.68 |
| 208 | MAX.chr8.145104263-145104422 | 1.00 | 1291.27 | 0.82 | 63.05 |
| 234 | OBSCN__A | 0.89 | 2144.25 | 0.73 | 24.64 |
| 63 | DIDO1__A | 0.99 | 1143.24 | 0.90 | 20.39 |
| 102 | GDF6 | 1.00 | 182.30 | 0.73 | 3.78 |
| 165 | MAX.chr10.130339363-130339534 | 0.92 | 40.14 | 0.69 | 7.59 |
| 212 | MDFI__B | 0.83 | 545.42 | 0.85 | 13.31 |
| 67 | DLL4 | 0.98 | 17.08 | 0.52 | 0.42 |
| 103 | GDF7__A | 0.59 | 343.11 | 0.57 | 42.50 |
| 167 | MAX.chr10.22624479-22624553 | 0.97 | 12943.30 | 0.92 | 134.01 |
| 214 | MIAT__A | 0.91 | 1058.99 | 0.66 | 98.50 |
| 248 | PYCARD | 1.00 | 47.75 | 0.55 | 2.79 |
| 26 | BMP4__B | 0.99 | 194.14 | 0.68 | 11.76 |
| 124 | JSRP1__A | 1.00 | 136.00 | 0.91 | 7.51 |
| 174 | MAX.chr14.103021656-103021718 | 0.93 | 3958.93 | 0.89 | 247.66 |
| 215 | MIAT__B | 0.94 | 436.40 | 0.73 | 14.56 |
| 252 | RHBDL1__A | 0.89 | 35.39 | 0.86 | 21.78 |
| 80 | EMX2 | 0.75 | 196.50 | 0.75 | 16.52 |
| 126 | KANK1 | 0.93 | 171.50 | 0.88 | 49.17 |
| 218 | MMP23B | 0.44 | 43.50 | 0.59 | 1.73 |
| 256 | SBNO2 | 1.00 | 270.32 | 0.90 | 16.21 |
| 40 | C5orf52 | 0.90 | 10081.84 | 0.88 | 116.45 |
| 81 | EMX2OS | 1.00 | 413.19 | 0.88 | 15.88 |
| 146 | LRRC34 | 0.94 | 1405.18 | 0.81 | 51.45 |
| 180 | MAX.chr17.73073716-73073814 | 0.88 | 297.35 | 0.73 | 23.93 |
| 162 | NBPF8 | 1.00 | 281.71 | 0.99 | 31.05 |
| 259 | SEPT9__B | 0.62 | 839.24 | 0.57 | 33.62 |
| 375 | LOC440925__A | 1.00 | 370.18 | 0.46 | 1.26 |
| 429 | STX16__A | 0.81 | 147.65 | 0.83 | 45.85 |
| 368 | ITPKA | 1.00 | 3924.69 | 0.73 | 2.48 |
| 11 | AIM1__A | 0.67 | 1141.81 | 0.65 | 22.18 |
| 75 | EEF1A2 | 0.87 | 127.52 | 0.60 | 18.24 |
| 87 | FEV | 0.89 | 2127.53 | 0.77 | 76.74 |
| 149 | LRRC41__C | 0.85 | 340.27 | 0.56 | 16.31 |
| 230 | NFIC | 0.99 | 47.68 | 0.68 | 3.08 |
| 302 | VILL | 1.00 | 477.74 | 0.94 | 32.67 |
| 404 | MPZ__A | 0.96 | 9032.17 | 0.86 | 54.96 |

These results provided a rich source of highly performing candidates to take into independent sample testing. Of the original 56 MDMs, 33 were selected. Most fell within the AUC range of 0.90-1.00, but others were included which had extremely high FC numbers (very little background) and/or those which exhibited complementarity with other MDMs. All MDM assays demonstrated high analytical performance—linearity, efficiency, sequence specificity (assessed using melt curve analysis), and strong amplification.

In round 2 validation, as in the previous step, experiments were conducted that ran the entire sample and marker set in one batch. ~10 ng of FFPE-derived sample DNA was run per marker—350 total. EC overall and subtype vs normal tissue (combined) results are listed in Tables 15, 16, 17, 18 and 19. Multiple MDMs showed marked methylation fold changes (10 to >1000) across all EC histologies vs BE (benign endometrium). Cross validated AUCs are listed in Table 20.

TABLE 15

DMRs distinguishing EC and normal endometrial tissue.

| DMR No. | Gene Annotation | AUC (All EC vs normal endometrial tissue) | FC (All EC vs normal endometrial tissue) |
|---|---|---|---|
| 262 | SFMBT2__B | 0.86194 | 22.62 |
| 278 | SQSTM1 | 0.74307 | 50.73 |
| 312 | ZNF323__A | 0.69116 | 481.00 |
| 314 | ZNF506 | 0.81957 | 19.51 |
| 318 | ZNF90 | 0.86506 | 6.43 |
| 204 | MAX.chr7.104624356-104624730 | 0.6905 | 10.48 |
| 207 | MAX.chr8.145103829-145103992 | 0.87773 | 22.51 |
| 59 | CYTH2 | 0.8939 | 16.18 |

TABLE 15-continued

DMRs distinguishing EC and normal endometrial tissue.

| DMR No. | Gene Annotation | AUC (All EC vs normal endometrial tissue) | FC (All EC vs normal endometrial tissue) |
|---|---|---|---|
| 100 | GATA2_B | 0.8156 | 170.63 |
| 152 | LRRC8D_A | 0.84946 | 17.70 |
| 208 | MAX.chr8.145104263-145104422 | 0.82487 | 7.05 |
| 234 | OBSCN_A | 0.85683 | 14.72 |
| 63 | DIDO1_A | 0.84704 | 214.16 |
| 212 | MDFI_B | 0.66076 | 47.95 |
| 103 | GDF7_A | 0.71296 | 32.35 |
| 167 | MAX.chr10.22624479-22624553 | 0.88605 | 77.62 |
| 124 | JSRP1_A | 0.8661 | 3.73 |
| 174 | MAX.chr14.103021656-103021718 | 0.79749 | 94.45 |
| 80 | EMX2 | 0.79196 | 8.63 |
| 126 | KANK1 | 0.76775 | 47.74 |
| 40 | C5orf52 | 0.7391 | 69.44 |
| 81 | EMX2OS | 0.94827 | 29.31 |
| 146 | LRRC34 | 0.77664 | 52.44 |
| 162 | NBPF8 | 0.92492 | 14.57 |
| 259 | SEPT9_B | 0.70265 | 165.86 |
| 375 | LOC440925_A | 0.5348 | 1.29 |
| 429 | STX16_A | 0.694 | 1.50 |
| 368 | ITPKA | 0.77882 | 2.01 |
| 11 | AIM1_A | 0.59943 | 41.13 |
| 75 | EEF1A2 | 0.62411 | 14.11 |
| 149 | LRRC41_C | 0.77683 | 9.42 |
| 302 | VILL | 0.84232 | 7.49 |
| 404 | MPZ_A | 0.85494 | 112.07 |

TABLE 16

DMRs distinguishing clear cell EC and normal endometrial tissue.

| DMR No. | Gene Annotation | AUC (Clear Cell EC vs tissue) |
|---|---|---|
| 262 | SFMBT2_B | 0.93333 |
| 278 | SQSTM1 | 0.90431 |
| 312 | ZNF323_A | 0.9 |
| 314 | ZNF506 | 0.60902 |
| 318 | ZNF90 | 0.90353 |
| 204 | MAX.chr7.104624356-104624730 | 0.76549 |
| 207 | MAX.chr8.145103829-145103992 | 0.9302 |
| 59 | CYTH2 | 1 |
| 100 | GATA2_B | 0.76549 |
| 152 | LRRC8D_A | 0.89725 |
| 208 | MAX.chr8.145104263-145104422 | 0.79373 |
| 234 | OBSCN_A | 0.98745 |
| 63 | DIDO1_A | 0.91922 |
| 212 | MDFI_B | 0.95059 |
| 103 | GDF7_A | 0.93059 |
| 167 | MAX.chr10.22624479-22624553 | 0.87843 |
| 124 | JSRP1_A | 0.92471 |
| 174 | MAX.chr14.103021656-103021718 | 0.96627 |
| 80 | EMX2 | 0.80863 |
| 126 | KANK1 | 0.69098 |
| 40 | C5orf52 | 0.70275 |
| 81 | EMX2OS | 0.96863 |
| 146 | LRRC34 | 0.90588 |
| 162 | NBPF8 | 0.85647 |
| 259 | SEPT9_B | 0.96784 |
| 375 | LOC440925_A | 0.72784 |
| 429 | STX16_A | 0.79608 |
| 368 | ITPKA | 0.7702 |
| 11 | AIM1_A | 0.71216 |
| 75 | EEF1A2 | 0.95373 |

TABLE 16-continued

DMRs distinguishing clear cell EC and normal endometrial tissue.

| DMR No. | Gene Annotation | AUC (Clear Cell EC vs tissue) |
|---|---|---|
| 149 | LRRC41_C | 0.89647 |
| 302 | VILL | 0.89725 |
| 404 | MPZ_A | 0.9098 |

TABLE 17

DMRs distinguishing serous EC and normal endometrial tissue.

| DMR No. | Gene Annotation | AUC (Serous EC vs tissue) |
|---|---|---|
| 262 | SFMBT2_B | 0.78321 |
| 278 | SQSTM1 | 0.66049 |
| 312 | ZNF323_A | 0.80716 |
| 314 | ZNF506 | 0.75012 |
| 318 | ZNF90 | 0.82074 |
| 204 | MAX.chr7.104624356-104624730 | 0.78667 |
| 207 | MAX.chr8.145103829-145103992 | 0.87654 |
| 59 | CYTH2 | 0.89827 |
| 100 | GATA2_B | 0.74963 |
| 152 | LRRC8D_A | 0.8716 |
| 208 | MAX.chr8.145104263-145104422 | 0.77235 |
| 234 | OBSCN_A | 0.91407 |
| 63 | DIDO1_A | 0.94321 |
| 212 | MDFI_B | 0.58346 |
| 103 | GDF7_A | 0.63259 |
| 167 | MAX.chr10.22624479-22624553 | 0.84049 |
| 124 | JSRP1_A | 0.79407 |
| 174 | MAX.chr14.103021656-103021718 | 0.72444 |
| 80 | EMX2 | 0.78815 |
| 126 | KANK1 | 0.73728 |
| 40 | C5orf52 | 0.45728 |
| 81 | EMX2OS | 0.99802 |
| 146 | LRRC34 | 0.75506 |
| 162 | NBPF8 | 0.85728 |
| 259 | SEPT9_B | 0.57926 |
| 375 | LOC440925_A | 0.56815 |
| 429 | STX16_A | 0.55111 |
| 368 | ITPKA | 0.74617 |
| 11 | AIM1_A | 0.6079 |
| 75 | EEF1A2 | 0.68049 |
| 149 | LRRC41_C | 0.9437 |
| 302 | VILL | 0.86963 |
| 404 | MPZ_A | 0.80296 |

TABLE 18

DMRs distinguishing carcinosarcoma EC and normal endometrial tissue.

| DMR No. | Gene Annotation | AUC (Carcinosarcoma EC vs tissue) |
|---|---|---|
| 262 | SFMBT2_B | 0.73095 |
| 278 | SQSTM1 | 0.80786 |
| 312 | ZNF323_A | 0.61357 |
| 314 | ZNF506 | 0.94381 |
| 318 | ZNF90 | 0.90048 |
| 204 | MAX.chr7.104624356-104624730 | 0.74429 |
| 207 | MAX.chr8.145103829-145103992 | 0.85667 |
| 59 | CYTH2 | 0.83048 |
| 100 | GATA2_B | 0.81048 |
| 152 | LRRC8D_A | 0.86429 |
| 208 | MAX.chr8.145104263-145104422 | 0.83524 |
| 234 | OBSCN_A | 0.8519 |
| 63 | DIDO1_A | 0.83119 |
| 212 | MDFI_B | 0.56571 |

TABLE 18-continued

DMRs distinguishing carcinosarcoma
EC and normal endometrial tissue.

| DMR No. | Gene Annotation | AUC (Carcinosarcoma EC vs tissue) |
|---|---|---|
| 103 | GDF7__A | 0.73905 |
| 167 | MAX.chr10.22624479-22624553 | 0.9381 |
| 124 | JSRP1__A | 0.86714 |
| 174 | MAX.chr14.103021656-103021718 | 0.82905 |
| 80 | EMX2 | 0.75619 |
| 126 | KANK1 | 0.8681 |
| 40 | C5orf52 | 0.79095 |
| 81 | EMX2OS | 0.95762 |
| 146 | LRRC34 | 0.80643 |
| 162 | NBPF8 | 0.93429 |
| 259 | SEPT9__B | 0.74738 |
| 375 | LOC440925__A | 0.60571 |
| 429 | STX16__A | 0.64143 |
| 368 | ITPKA | 0.75238 |
| 11 | AIM1__A | 0.54857 |
| 75 | EEF1A2 | 0.46333 |
| 149 | LRRC41__C | 0.73667 |
| 302 | VILL | 0.87667 |
| 404 | MPZ__A | 0.83143 |

TABLE 19

DMRs distinguishing endometrioid
EC and normal endometrial tissue.

| DMR No. | Gene Annotation | AUC (Endometroid grade 3 vs tissue) |
|---|---|---|
| 262 | SFMBT2__B | 0.9177 |
| 278 | SQSTM1 | 0.66575 |
| 312 | ZNF323__A | 0.7 |
| 314 | ZNF506 | 0.79977 |
| 318 | ZNF90 | 0.8708 |
| 204 | MAX.chr7.104624356-104624730 | 0.64276 |
| 207 | MAX.chr8.145103829-145103992 | 0.94253 |
| 59 | CYTH2 | 0.8731 |
| 100 | GATA2__B | 0.8092 |
| 152 | LRRC8D__A | 0.80598 |
| 208 | MAX.chr8.145104263-145104422 | 0.8777 |
| 234 | OBSCN__A | 0.88736 |
| 63 | DIDO1__A | 0.81655 |
| 212 | MDFI_B | 0.67172 |
| 103 | GDF7__A | 0.71517 |
| 167 | MAX.chr10.22624479-22624553 | 0.88138 |
| 124 | JSRP1__A | 0.91218 |
| 174 | MAX.chr14.103021656-103021718 | 0.80598 |
| 80 | EMX2 | 0.81195 |
| 126 | KANK1 | 0.80276 |
| 40 | C5orf52 | 0.83264 |
| 81 | EMX2OS | 0.9269 |
| 146 | LRRC34 | 0.72552 |
| 162 | NBPF8 | 0.96874 |
| 259 | SEPT9__B | 0.69425 |
| 375 | LOC440925__A | 0.42759 |
| 429 | STX16__A | 0.70851 |
| 368 | ITPKA | 0.84276 |
| 11 | AIM1__A | 0.67218 |
| 75 | EEF1A2 | 0.58713 |
| 149 | LRRC41__C | 0.71908 |
| 302 | VILL | 0.84483 |
| 404 | MPZ A | 0.87034 |

TABLE 20

| DMR No. | Gene Annotation | AUC | AUC.Lower | AUC.Upper |
|---|---|---|---|---|
| | Best fit Panel | 0.9797 | 0.9618 | 0.9976 |
| 81 | EMX2OS | 0.9079 | 0.8693 | 0.9465 |
| 59 | CYTH2 | 0.885 | 0.8398 | 0.9302 |
| 162 | NBPF8 | 0.8791 | 0.835 | 0.9231 |
| 167 | MAX.chr10.22624479-22624553 | 0.8529 | 0.804 | 0.9017 |
| 404 | MPZ__A | 0.8387 | 0.786 | 0.8914 |
| 262 | SFMBT2__B | 0.8366 | 0.7849 | 0.8884 |
| 318 | ZNF90 | 0.8308 | 0.7771 | 0.8845 |
| 100 | GATA2__B | 0.8231 | 0.7693 | 0.8769 |
| 63 | DIDO1__A | 0.8134 | 0.7577 | 0.8691 |
| 124 | JSRP1__A | 0.8041 | 0.7483 | 0.8599 |
| 234 | OBSCN__A | 0.804 | 0.7478 | 0.8602 |
| 207 | MAX.chr8.145103829-145103992 | 0.8028 | 0.7467 | 0.8588 |
| 126 | KANK1 | 0.7859 | 0.7276 | 0.8442 |
| 174 | MAX.chr14.103021656-103021718 | 0.7821 | 0.7233 | 0.841 |
| 314 | ZNF506 | 0.7707 | 0.7103 | 0.8312 |
| 152 | LRRC8D__A | 0.7631 | 0.7016 | 0.8246 |
| 368 | ITPKA | 0.7587 | 0.6952 | 0.8221 |
| 302 | VILL | 0.7471 | 0.6835 | 0.8108 |
| 40 | C5orf52 | 0.741 | 0.6762 | 0.8058 |
| 312 | ZNF323__A | 0.7311 | 0.6662 | 0.796 |
| 103 | GDF7__A | 0.7182 | 0.6523 | 0.7842 |
| 259 | SEPT9__B | 0.7131 | 0.6443 | 0.782 |
| 146 | LRRC34 | 0.7107 | 0.6436 | 0.7779 |
| 208 | MAX.chr8.145104263-145104422 | 0.704 | 0.6365 | 0.7715 |
| 80 | EMX2 | 0.6805 | 0.6115 | 0.7495 |
| 149 | LRRC41__C | 0.6747 | 0.6055 | 0.744 |
| 428 | ST8SIA1 | 0.6465 | 0.5744 | 0.7186 |
| 429 | STX16__A | 0.6282 | 0.5561 | 0.7004 |
| 278 | SQSTM1 | 0.623 | 0.5502 | 0.6959 |
| 75 | EEF1A2 | 0.5977 | 0.5233 | 0.6722 |
| 212 | MDFI_B | 0.5898 | 0.5155 | 0.664 |
| 204 | MAX.chr7.104624356-104624730 | 0.5781 | 0.5033 | 0.6528 |
| 11 | AIM1__A | 0.5764 | 0.5011 | 0.6517 |
| 375 | LOC440925__A | 0.4754 | 0.4 | 0.5507 |

Next, the data was plotted in a heat matrix format which allowed complementarity visualization. A cross-validated 3-MDM panel was derived from rPART modeling (EMX2OS, NBPF8, SFMBT2) which discriminated overall EC from BE with 97% specificity and 97% sensitivity with an AUC of 0.98 (see, FIG. 1).

Some MDMs discriminated clear cell histology from BE and all other EC histologies (MDFI, GDF7_A, SEPTIN9, EEF1A2) and C5orf52 discriminated endometrioid histologies (G1/2E, G3E) from BE and all other EC histologies.

In summary, whole methylome sequencing, stringent filtering criteria, and biological validation yielded outstanding candidate MDMs for EC. Some MDMs discriminate all EC histologies from BE with comparably high sensitivity, while others accurately distinguish among histologies.

Example II

This example describes the materials and methods for Example I.
Samples:

Tissue and blood was obtained from Mayo Clinic biospecimen repositories with institutional IRB oversight. Samples were chosen with strict adherence to subject research authorization and inclusion/exclusion criteria. Cancer sub-types included 1) serous EC, 2) clear cell EC, 3) carcinosarcoma EC, and 4) endometrioid EC. Controls included non-neoplastic tissue and whole blood derived leukocytes. Tissues were macro-dissected and histology reviewed by an expert GI pathologist. Samples were age sex matched, randomized, and blinded. DNA from 113 frozen tissues (16 grade 1/2 endometrioid (G1/2E), 16 grade 3 endometrioid (G3E), 11 serous, 11 clear cell ECs, 15 uterine carcinosarcomas, 44 benign endometrial (BE) tissues (14 proliferative, 12 atrophic, 18 disordered proliferative), 70 formalin fixed paraffin embedded (FFPE) cervical cancers (CC) (36 squamous cell, 34 adenocarcinomas), and 18 buffy coats from cancer-free females was purified using the QIAamp DNA Tissue Mini kit (frozen tissues), QIAamp DNA FFPE Tissue kit (FFPE tissues), and QIAamp DNA Blood Mini kit (buffy coat samples) (Qiagen, Valencia CA). DNA was re-purified with AMPure XP beads (Beckman-Coulter, Brea CA) and quantified by PicoGreen (Thermo-Fisher, Waltham MA). DNA integrity was assessed using qPCR.

Sequencing:

RRBS sequencing libraries were prepared following the Meissner protocol (see, Gu et al. Nature Protocols 2011) with modifications. Samples were combined in a 4-plex format and sequenced by the Mayo Genomics Facility on the Illumina HiSeq 2500 instrument (Illumina, San Diego CA). Reads were processed by Illumina pipeline modules for image analysis and base calling. Secondary analysis was performed using SAAP-RRBS, a Mayo developed bioinformatics suite. Briefly, reads were cleaned-up using Trim-Galore and aligned to the GRCh37/hg19 reference genome build with BSMAP. Methylation ratios were determined by calculating $C/(C+T)$ or conversely, $G/(G+A)$ for reads mapping to reverse strand, for CpGs with coverage $\geq 10 \times$ and base quality score $\geq 20$.

Biomarker Selection:

Individual CpGs were ranked by hypermethylation ratio, namely the number of methylated cytosines at a given locus over the total cytosine count at that site. For cases, the ratios were required to be $\geq 0.20$ (20%); for tissue controls, $\leq 0.05$ (5%); for buffy coat controls, $\leq 0.01$ (1%). CpGs which did not meet these criteria were discarded. Subsequently, candidate CpGs were binned by genomic location into DMRs (differentially methylated regions) ranging from approximately 60-200 bp with a minimum cut-off of 5 CpGs per region. DMRs with excessively high CpG density (>30%) were excluded to avoid GC-related amplification problems in the validation phase. For each candidate region, a 2-D matrix was created which compared individual CpGs in a sample to sample fashion for both cases and controls. We analyzed overall EC vs all benign endometria and/or no-cancer buffy coat, as well as subtype comparisons. These CpG matrices were then compared back to the reference sequence to assess whether genomically contiguous methylation sites had been discarded during the initial filtering. From this subset of regions, final selections required coordinated and contiguous hypermethylation (in cases) of individual CpGs across the DMR sequence on a per sample level. Conversely, control samples had to have at least 10-fold less methylation than cases and the CpG pattern had to be more random and less coordinated. At least 10% of cancer samples within a subtype cohort were required to have at least a 50% hypermethylation ratio for every CpG site within the DMR.

In a separate analysis, we utilized a proprietary DMR identification pipeline and regression package to derive DMRs based on average methylation values of the CpG. The difference in average methylation percentage was compared between EC cases, tissue controls and buffy coat controls; a tiled reading frame within 100 base pairs of each mapped CpG was used to identify DMRs where control methylation was <5%; DMRs were only analyzed if the total depth of coverage was 10 reads per subject on average and the variance across subgroups was >0. Assuming a biologically relevant increase in the odds ratio of >3× and a coverage depth of 10 reads, $\geq 18$ samples per group were required to achieve 80% power with a two-sided test at a significance level of 5% and assuming binomial variance inflation factor of 1.

Following regression, DMRs were ranked by p-value, area under the receiver operating characteristic curve (AUC) and fold-change difference between cases and all controls. No adjustments for false discovery were made during this phase as independent validation was planned a priori.

Biomarker Validation:

A subset of the DMRs was chosen for further development. The criteria were primarily the logistic-derived area under the ROC curve metric which provided a performance assessment of the discriminant potential of the region. An AUC of 0.85 was chosen as the cut-off. In addition, the methylation fold-change ratio (average cancer hypermethylation ratio/average control hypermethylation ratio) was calculated and a lower limit of 10 was employed for tissue vs tissue comparisons and 20 for the tissue vs buffy coat comparisons. P values were required to be less than 0.01. DMRs had to be listed in both the average and individual CpG selection processes. Quantitative methylation specific PCR (qMSP) primers were designed for candidate regions using MethPrimer (Li L C and Dahiya R. MethPrimer: designing primers for methylation PCRs. Bioinformatics 2002 November; 18(11):1427-31 PMID: 12424112) and QC checked on 20 ng (6250 equivalents) of positive and negative genomic methylation controls. Multiple annealing temperatures were tested for optimal discrimination. Validation was performed in two stages of qMSP. The first consisted of re-testing the sequenced DNA samples. This was done to verify that the DMRs were truly discriminant and not the result of over-fitting the extremely large next generation datasets. The second utilized a larger set of independent samples:

| Group | N |
| --- | --- |
| Endometrial Cancer - Carcinosarcoma | 36 |
| Endometrial Cancer - Clear Cell | 22 |
| Endometrial Cancer - Endometrioid Gr 1/2 | 36 |
| Endometrial Cancer - Endometrioid Gr 3 | 36 |
| Endometrial Cancer - Serous | 32 |
| Endometrial Benign - Secretory | 5 |
| Endometrial Benign - Proliferative | 32 |
| Endometrial Benign - Atrophic | 28 |
| Endometrial Benign - Disordered Proliferative | 19 |
| Cervical Cancer - Squamous | 36 |
| Cervical Cancer - Adenocarcinoma | 36 |

These tissues were identified as before, with expert clinical and pathological review. DNA purification was performed as previously described. The EZ-96 DNA Methylation kit (Zymo Research, Irvine CA) was used for the bisulfite conversion step. 10 ng of converted DNA (per marker) was amplified using SYBR Green detection on Roche 480 LightCyclers (Roche, Basel Switzerland). Serially diluted universal methylated genomic DNA (Zymo Research) was used as a quantitation standard. A CpG agnostic ACTB (β-actin) assay was used as an input reference and normalization control. Results were expressed as methylated copies (specific marker)/copies of ACTB.

Statistics:

Results were analyzed logistically for individual MDMs (methylated DNA marker) performance. For combinations of markers, two techniques were used. First, the rPart technique was applied to the entire MDM set and limited to combinations of 3 MDMs, upon which an rPart predicted probability of cancer was calculated. The second approach used random forest regression (rForest) which generated 500 individual rPart models that were fit to boot strap samples of the original data (roughly ⅔ of the data for training) and used to estimate the cross-validation error (⅓ of the data for testing) of the entire MDM panel and was repeated 500 times. to avoid spurious splits that either under- or overestimate the true cross-validation metrics. Results were then averaged across the 500 iterations.

Example III

This example describes identification of endometrial cancer tissue markers and plasma markers for detecting breast cancer.

Candidate methylation markers for the detection of EC, clear cell EC, serous EC, carcinosarcoma EC, and endometrioid EC were identified by RRBS of EC tissue samples and normal endometrial tissue samples. To identify methylated DNA markers, 165 samples per patient group (i.e., 19 benign, 34 adenocarcinoma, 36 squamous cell carcinoma, 15 endometrial cancer carcinoma, 11 endometrial cancer clear cell, 5 endometrial cancer endometrioid grade 1, 11 endometrial cancer endometrioid grade 2, 16 endometrial cancer endometrioid grade 3, and 18 normal buffy coat) underwent an RRBS process followed by an alignment to a bisulfite converted human genome. CpG regions of high ratios of methylation in endometrial cancer relative to normal endometrium and buffy coat were selected and mapped to their gene names After markers were selected by RRBS, a total of 61 methylation markers were identified and target enrichment long-probe quantitative amplified signal assays were designed and ordered (see, e.g., WO2017/075061 and U.S. patent application Ser. No. 15,841,006 for general techniques). Table 21 shows the marker chromosomal regions used for the 61 methylation markers. Tables 22 and 23 shows primer information and probe information for the markers. FIG. 2 further provides marker chromosomal regions used for the 61 methylation markers and related primer and probe information.

TABLE 21

Identified methylated regions distinguishing
EC tissue from normal endometrial tissue.

| DMR No. | Gene Annotation | Region on Chromosome (starting base-ending base) |
|---|---|---|
| 445 | AGRN_B | chr1: 975957-976046 |
| 446 | AIM1_C | chr6. 106960288-106960380 |
| 447 | AKR7A3 | chr1: 19615293-19615389 |
| 448 | C17orf107_B | chr17: 4802690-4802828 |
| 449 | DIDO1_B | chr20: 61560628-61560728 |

TABLE 21-continued

Identified methylated regions distinguishing
EC tissue from normal endometrial tissue.

| DMR No. | Gene Annotation | Region on Chromosome (starting base-ending base) |
|---|---|---|
| 81 | EMX2OS | chr10: 119294950-119295039 |
| 450 | FKBP11_B | chr12: 49319059-49319168 |
| 451 | GDF7_B | chr2: 20866007-20866135 |
| 452 | JSRP1_B | chr19: 2253227-2253345 |
| 453 | LHFPL2_B | chr5: 77806193-77806301 |
| 454 | LOC100129726_B | chr2: 43452148-43452235 |
| 150 | LRRC41_D | chr1: 46768830-46768913 |
| 455 | LRRC8D_B | chr1: 90308856-90308965 |
| 456 | MAX.chr10: 22624470-22624553 | chr10: 22624470-22624553 |
| 457 | MAX.chr14: 103021654-103021725 | chr14: 103021654-103021725 |
| 458 | MAX.chr7: 104624356-104624513 | chr7: 104624356-104624513 |
| 459 | MAX.chr7: 104624386-104624529 | chr7: 104624386-104624529 |
| 212 | MDFI_B | chr6: 41606379-41606439 |
| 460 | OBSCN_B | chr1: 228463593-228463689 |
| 461 | RHBDL1_B | chr16: 725588-725658 |
| 462 | SEPT9_D | chr17: 75447656-75447829 |
| 463 | SFMBT2_E | chr10: 7451008-7451110 |
| 464 | SPDYA_B | chr2: 29033347-29033484 |
| 465 | ST3GAL2_B | chr16: 70415003-70415106 |
| 302 | VILL | chr3: 38035645-38035743 |
| 466 | ZNF323_B | chr6: 28303870-28303974 |
| 467 | SLC13A5_B | chr17: 6616765-6616852 |
| 468 | ZMIZ1_D | chr10: 81002927-81003006 |
| 469 | MAX.chr8: 145103900-145103993 | chr8: 145103900-145103993 |
| 470 | C8orf73_B | chr8: 144650834-144650919 |
| 471 | KBTBD11_B | chr8: 1949507-1949586 |
| 472 | LOC100192379_C | chr4: 122686300-122686377 |
| 473 | TRIM71_B | chr3: 32859592-32859712 |
| 474 | LOC440925_B | chr2: 171570323-171570444 |
| 499 | ARL5C | chr17: 37321564-37321723 |
| 475 | STX16_B | chr20: 57224681-57224845 |
| 368 | ITPKA | chr15: 41787637-41787780 |
| 476 | IRF4 | chr6: 393188-393284 |
| 477 | CNTN4 | chr3: 2140464-2140527 |
| 478 | GRIN2A | chr16: 10277158-10277320 |
| 479 | NOTCH3 | chr19: 15306498-15306625 |
| 480 | PAX1 | chr20: 21683741-21683893 |
| 481 | ZNF521 | chr18: 22929721-22929795 |
| 482 | VSX1 | chr20: 25065266-25065458 |
| 483 | CRHR2 | chr7: 30721989-30722099 |
| 484 | FAM19A5 | chr22: 48885810-48885908 |
| 485 | ASCL1 | chr12: 103352059-103352157 |
| 486 | GLT1D1 | chr12: 129338254-129338322 |
| 487 | T | chr6: 166581961-166582112 |
| 488 | CAPN2 | chr1: 223936903-223937040 |
| 489 | RYR2_F | chr1: 237205546-237205717 |
| 490 | SIM2 | chr21: 38119993-38120059 |
| 491 | TRH | chr3: 129693484-129693575 |
| 492 | JAM3 | chr11: 133938908-133939011 |
| 493 | BARX1 | chr9: 96721498-96721597 |
| 494 | ZNF671_B | chr1: 161275554-161276006 |
| 495 | TSPYL5 | chr8: 98290016-98290134 |
| 496 | MPZ_B | chr1: 161275554-161276006 |
| 497 | CXCL12 | chr10: 44881200-44881315 |
| 498 | PTGDR | chr14: 52735270-52735400 |

TABLE 22

Primer Information For Markers Shown in Table 21.

| DMR No. | Gene Annotation | Forward Primer 5'-3' | Seq ID | Reverse Primer 5'-3' | Seq ID |
|---|---|---|---|---|---|
| 445 | AGRN_B | GGTTGCGAGTACGGTA AGGTTT | 109 | AAAACTCAAAATACCGAA ACGCC | 110 |

TABLE 22-continued

Primer Information For Markers Shown in Table 21.

| DMR No. | Gene Annotation | Forward Primer 5'-3' | Seq ID | Reverse Primer 5'-3' | Seq ID |
|---|---|---|---|---|---|
| 446 | AIM1_C | TTGAGAGCGTTGTTAGG GACGAC | 111 | CGCGTTTAACGCCACCT C | 113 |
| 447 | AKR7A3 | CGGGTTTCGTTTATCGG CGG | 113 | AACGTAAAATCGAACTC GTAAACGAC | 114 |
| 448 | C17orf107_B | CGAAGTTTTATTTCGAT TCGGGTTGTATCG | 115 | CCACGCCATATCCCCGC | 116 |
| 449 | DIDO1_B | AGGTTATCGGGTAGCG TTTAGG | 117 | CGTACCCCTCCCCCGCT AC | 118 |
| 81 | EMX2OS | GTCGTTTACGCGAGCG ACG | 119 | CTCGAACAAAACAAACG CTACGTAAC | 120 |
| 450 | FKBP11_B | GGTTTTTATTTGGAGGG TTCGGAC | 121 | ACTACTCAATACGACGAT ATACCGAAC | 122 |
| 451 | GDF7_B | TCGTTCGTTTTTTCGGT TTTTGGTC | 123 | CCTTCTAAACGAAAACAA CGACTAACGAAA | 124 |
| 452 | JSRP1_B | TAGCGTTTTGTCGTTTT TTTTTTGCGT | 125 | CGCAAAAATACCCCCGA AAAAC | 126 |
| 453 | LHFPL2_B | GGAGGGCGGTTAGTAG CGT | 127 | ACGATATCGCTACGCGA CGAAA | 128 |
| 454 | LOC100129726_B | GTTGTGGTGTAATTTGG GTCGC | 129 | ACACGCGCGATACGTTA CAC | 130 |
| 150 | LRRC41_D | CGTTCGTATAGTTCGAA TAGGGCG | 131 | CGACGCCAACGAAAAC TC | 132 |
| 455 | LRRC8D_B | GGAGAATTCGAGTAGTA GTTGTAAACGGA | 133 | CAACCACCCGCCCGCC | 134 |
| 456 | MAX.chr10:226244 70-22624553 | TGTTTACGTGGTATCGT TATTTTTTAATCGC | 135 | CGACGACCGCGAAAAAA AAAAACC | 136 |
| 457 | MAX.chr14:103021 654-103021725 | TCGTGGGGAATAGTAG GACGGC | 137 | CCTCCCGACAAATAAAC GCGA | 138 |
| 458 | MAX.chr7:1046243 56-104624513 | GGAGGTAGGTTCGCGC GG | 139 | CCAACTCAATTCCTCCTC CGC | 140 |
| 459 | MAX.chr7:1046243 86-104624529 | GAGGAGGAATTGAGTT GGCGC | 141 | CAACCCATAATCCGATC CTATCTTCGA | 142 |
| 212 | MDFI_B | TTCGTACGAGTGAGTG GACG | 143 | CAAAAAACGATTCCCCC GCAAA | 144 |
| 460 | OBSCN_B | TGGAGATTTACGTCGAG GGC | 145 | CCACGATCGACAAAACC TACGT | 146 |
| 461 | RHBDL1_B | GCGCGTGTTTTGGTCG C | 147 | TCGTCCGCCTACCCGCC C | 148 |
| 462 | SEPT9_D | GGAGTTACGTTGTTTTT GGGTTTCG | 149 | CTCTCCTAAAAACCCCG CTC | 150 |
| 463 | SFMBT2_E | GGATCGGGATCGAAGT TTGGAGAA | 151 | CTTATCTCCCAAAACCG CGC | 152 |
| 464 | SPDYA_B | TTGGTTGTTTAATCGAA GGGAAGTAAAC | 153 | CTACCTCCCTTAAACAC GTCTCG | 154 |
| 465 | ST3GAL2_B | GGGCGTAGTTATTTTAT AGCGC | 155 | CACCAAAAAAAAACGAT CGCTACGAAA | 156 |
| 302 | VILL | CGGGGAAGACGGAGGT G | 157 | AAACCCCTACCTAACGT CTCCC | 158 |
| 466 | ZNF323_B | CGGGGTTGTAGTATTTT AATGATCGA | 159 | CTTCAACCAATAAACTCA AAACGACTAACG | 160 |

TABLE 22-continued

Primer Information For Markers Shown in Table 21.

| DMR No. | Gene Annotation | Forward Primer 5'-3' | Seq ID | Reverse Primer 5'-3' | Seq ID |
|---|---|---|---|---|---|
| 467 | SLC13A5_B | GGCGTTTTTTCGCGGTT TTG | 161 | GCGTCCCACAAACCCCG | 162 |
| 468 | ZMIZ1_D | CGTAGGGTGGGTGGTT ACGTTC | 163 | AACTTCCCACGACCCG | 164 |
| 469 | MAX.chr8:1451039 00-145103993 | GTTACGCGGTTTTTATT TTTGTGATTTTTCG | 165 | CTCATTAACTTCCAAAAA ACAAACTAACTCGTC | 166 |
| 470 | C8orf73_B | GAGTTCGACGGTCGAG GCG | 167 | ACTACGCCCTCCCACGC | 168 |
| 471 | KBTBD11_B | TCGTTTTAGCGGCGGA AGG | 169 | CCGCGAACCACCGC | 170 |
| 472 | LOC100192379_C | GGTTGTAGTTGGAGGG CGAG | 171 | CGAAACGCCCTCGCGA | 172 |
| 473 | TRIM71_B | GTTGTGTAAGGAGATGT GCGGTTC | 173 | AAACGACGACGCGAACG AA | 174 |
| 474 | LOC440925_B | CGTAGTGCGTTTTCGC GAGTC | 175 | CGCCCTAAAACATTAAAA ATACGAAACCG | 176 |
| 499 | ARL5C | GTTTCGGGGTTTGTTAA GAGACG | 177 | ACTACTACGAATTCCTA CGATTATAACTTCG | 178 |
| 475 | STX16_B | AGTTTTTAGTTCGGTTC GCGC | 179 | CCCGAAAACGCTTCGCA ACG | 180 |
| 368 | ITPKA | GATAAGGTAGGGAAGT TGTGGCG | 181 | CCTCTAATATCACTAACA AACCCCATCG | 182 |
| 476 | IRF4 | CGCGGTGAGTTGCGGT AAC | 183 | CGAAATACTTACCGCTAT CGATCTAATCGA | 184 |
| 477 | CNTN4 | GGTAGTTCGAATTTCGG CGC | 185 | CTCCCTCCCGACGCTCG | 186 |
| 478 | GRIN2A | GTAGTTTTTCGGCGGC GACG | 187 | CCTTATTTACCGCCGTAC GCT | 188 |
| 479 | NOTCH3 | GGTCGCGTTTTGTTTGG CG | 189 | CGCGCGTCGAAAAAAAA CGCG | 190 |
| 480 | PAX1 | CGATCGTGTAGAAGGTT GTAGCG | 191 | TTTCCCGCAACCAACTAT ACGCG | 192 |
| 481 | ZNF521 | CGGGATTTAGCGGGTT CGG | 193 | CCCGAAAACGAAAAACA AAAACGAC | 194 |
| 482 | VSX1 | TCGGGGTGTTTTCGTAG TTGTTAAATTTAC | 195 | CATTCTTTTAACCGCCAA AACGCG | 196 |
| 483 | CRHR2 | GGGTTTTGGTTTTCGTT AGTTTAGTTTC | 197 | ACAACTCTAAACGACCG AAAATAACG | 198 |
| 484 | FAM19A5 | GCGGTCGGAGTTTAGT TAGCG | 199 | ACCTACGACTACCTCCT AAACGCG | 200 |
| 485 | ASCL1 | GTCGTAGTTTTAGTAGT TTTTTTTGTCGTTCG | 201 | CGACCGCCGCGACTAC | 202 |
| 486 | GLT1D1 | GACGCGGGGCGTTTAG T | 203 | CGACTCGAAACGACCCC GA | 204 |
| 487 | T | GGAGTTTTAGGCGGCG TTACG | 205 | ACCGCGAAAACACCCGA C | 206 |
| 488 | CAPN2 | GTTCGCGCGGTTTTAC GGT | 207 | CGCCCTTCTCCTCCCGC | 208 |
| 489 | RYR2_F | GGAGGTTTCGCGTTTC GATTA | 209 | CGAACGATCCCCGCCTA C | 210 |

TABLE 22-continued

Primer Information For Markers Shown in Table 21.

| DMR No. | Gene Annotation | Forward Primer 5'-3' | Seq ID | Reverse Primer 5'-3' | Seq ID |
|---|---|---|---|---|---|
| 490 | SIM2 | GGTTTAGCGCGGGTTTT TCG | 211 | CCCCGAACTTCCCGAAC T | 212 |
| 491 | TRH | TTTTCGTTGATTTTATTC GAGTCGTC | 213 | GAACCCTCTTCAAATAAA CCGC | 214 |
| 492 | JAM3 | TGGTCGTTTTAGCGTTA TGTCG | 215 | CGAAAACTACAAACCGC GC | 216 |
| 493 | BARX1 | CGTTAATTTGTTAGATA GAGGGCG | 217 | TCCGAACAACCGCCTAC | 218 |
| 494 | ZNF671_B | GTTGTCGGGAGCGGTA GG | 219 | CCAATATCCCGAAACGC GTCT | 220 |
| 495 | TSPYL5 | TTTGTTTCGGTTTTTGG CG | 221 | CGCCACCATAAACGACC | 222 |
| 496 | MPZ_B | GGTTAGGGGTGGAGTT CGTTA | 223 | ACTCCGAACTCTACTCAT CCTTTC | 224 |
| 497 | CXCL12 | TCGGCGGTTTTTAGTAA AAGCG | 225 | AAATCTCCCGTCCCACT CC | 226 |
| 498 | PTGDR | GGGTTCGGGGATTTATA ATTACGG | 227 | CTAAATCACCTCCTACTA CTAACGCTAATAAC | 228 |

TABLE 23

Probe Information For Markers Shown in Table 21.

| DMR No. | Gene Annotation | Probe Sequence | Seq ID |
|---|---|---|---|
| 445 | AGRN_B | CGCGCCGAGG CCGTACCCACGTCCA/3C6/ | 229 |
| 446 | AIM1_C | AGGCCACGGACG CGTCGTCGAACACCG/3C6/ | 230 |
| 447 | AKR7A3 | CGCGCCGAGG CGTCGAACACCTTCGAC/3C6/ | 231 |
| 448 | C17orf107_B | AGGCCACGGACG CGACTACGCCACGTAAA/3C6/ | 232 |
| 449 | DIDO1_B | CGCGCCGAGG GTTTCGGTTTTTGGGAGG/3C6/ | 233 |
| 81 | EMX2OS | AGGCCACGGACG CGACAACTAAAACTCCGTACG/3C6/ | 234 |
| 450 | FKBP11_6 | CGCGCCGAGG CGGGATTTTCGGTTTCGA/3C6/ | 235 |
| 451 | GDF7_B | AGGCCACGGACG CGTTTACGTATATAGTCGGTAGT/3C6/ | 236 |
| 452 | JSRP1_B | CGCGCCGAGG CGCTCACGAACTAAACGATCC/3C6/ | 237 |
| 453 | LHFPL2_B | AGGCCACGGACG TCGTTAGGTTTCGTTTCGT/3C6/ | 238 |
| 454 | LOC100129726_6 | CGCGCCGAGG CGGTTTTCGCGGGA/3C6/ | 239 |
| 150 | LRRC41_D | AGGCCACGGACG CGACCTCGAACCCCAA/3C6/ | 240 |
| 455 | LRRC8D_B | CGCGCCGAGG CCGCTCGCTCACAA/3C6/ | 241 |
| 456 | MAX.chr10:22624470-22624553 | AGGCCACGGACG CGGTTTTACGAAATGTAAATTT/3C6/ | 242 |

TABLE 23-continued

| DMR No. | Gene Annotation | Probe Sequence | Seq ID |
|---|---|---|---|
| 457 | MAX.chr14:103021654-103021725 | CGCGCCGAGG CGTCGAGGTCGTTTCG/3C6/ | 243 |
| 458 | MAX.chr7:104624356-104624513 | AGGCCACGGACG GCGGAAGTGCGTT/3C6/ | 244 |
| 459 | MAX.chr7:104624386-104624529 | CGCGCCGAGG CGCGGGTTAGTTGTT/3C6/ | 245 |
| 212 | MDF1_B | AGGCCACGGACG ATACGCGCCTCCCA/3C6/ | 246 |
| 460 | OBSCN_B | CGCGCCGAGG CGTTCGTTATCGTTTGGTTT/3C6/ | 247 |
| 461 | RHBDL1_B | AGGCCACGGACG CCTACCGCACACGC/3C6/ | 248 |
| 462 | SEPT9_D | CGCGCCGAGG CGATCCTACCGACCTCGA/3C6/ | 249 |
| 463 | SFMBT2_E | AGGCCACGGACG CGCTCCCGCCCTTCT/3C6/ | 250 |
| 464 | SPDYA_B | CGCGCCGAGG CGGTTTTAACGTAAGTTTGATTG/3C6/ | 251 |
| 465 | ST3GAL2_B | AGGCCACGGACG CGGTCGAGGTGGGA/3C6/ | 252 |
| 302 | VILL | CGCGCCGAGG GCGGGTGGAGAAGG/3C6/ | 253 |
| 466 | ZNF323_B | AGGCCACGGACG GCGGGTGGAGAAGG/3C6/ | 254 |
| 467 | SLC13A5_B | AGGCCACGGACG GCATTTCCGACCTTTACGA/3C6/ | 255 |
| 468 | ZMIZ1_D | CGCGCCGAGG GAAAAATAACCCCGCCC/3C6/ | 256 |
| 469 | MAX.chr8:145103900-145103993 | AGGCCACGGACG CGTAGGGTTCGCGAG/3C6/ | 257 |
| 470 | C8orf73_B | CGCGCCGAGG CGATACATCCGCGCG/3C6/ | 258 |
| 471 | KBTBD11_B | AGGCCACGGACG GCGGATTGAGTTTCGTG/3C6/ | 259 |
| 472 | LOC100192379_C | AGGCCACGGACG GCGCGGTTATTTTTTCGT/3C6/ | 260 |
| 473 | TRIM71_B | CGCGCCGAGG GCGCGTCGTTCGTATATTT/3C6/ | 261 |
| 474 | LOC440925_B | AGGCCACGGACG CGTCGGCGTCGTTTT/3C6/ | 262 |
| 499 | ARL5C | CGCGCCGAGG GCGTTAAAAACCTCGCG/3C6/ | 263 |
| 475 | STX16_B | CGCGCCGAGG GCGTTATACTCTTTCTCTAAACAC/3C6/ | 264 |
| 368 | ITPKA | AGGCCACGGACG CGGCGATTTAGTTTTTTGTCG/3C6/ | 265 |
| 476 | IRF4 | CGCGCCGAGG GACCTCCGAACTTATAAACCC/3C6/ | 266 |
| 477 | CNTN4 | AGGCCACGGACG CGGGAAGTTTCGTTAGTGG/3C6/ | 267 |
| 478 | GRIN2A | CGCGCCGAGG CGTTAGGTTTTTTTAGTCGTCG/3C6/ | 268 |
| 479 | NOTCH3 | AGGCCACGGACG TCTCGAAACGAATAACCGC/3C6/ | 269 |
| 480 | PAX1 | CGCGCCGAGG GCTACGCTAAACGCCG/3C6/ | 270 |
| 481 | ZNF521 | AGGCCACGGACG GATCGAAAACACACAACCC/3C6/ | 271 |

TABLE 23-continued

Probe Information For Markers Shown in Table 21.

| DMR No. | Gene Annotation | Probe Sequence | Seq ID |
|---|---|---|---|
| 482 | VSX1 | CGCGCCGAGG GGCGGGCGTATTAGT/3C6/ | 272 |
| 483 | CRHR2 | AGGCCACGGACG CGGGTCGCGTTTAGG/3C6/ | 273 |
| 484 | FAM19A5 | AGGCCACGGACG CGATTTTTCGGGTAGTTTTTGG/3C6/ | 274 |
| 485 | ASCL1 | CGCGCCGAGG GGTTTTTCGGTCGAGATG/3C6/ | 275 |
| 486 | GLT1D1 | AGGCCACGGACG CGACCGTAACAAAAAAACAAAC/3C6/ | 276 |
| 487 | T | CGCGCCGAGG ACGCGACTAAAAAAAACCTAAC/3C6/ | 277 |
| 488 | CAPN2 | AGGCCACGGACG CGCCGAAACAAACTAATCC/3C6/ | 278 |
| 489 | RYR2_F | CGCGCCGAGG CGCGAAACTTCAAAAATACGA/3C6/ | 279 |
| 490 | SIM2 | AGGCCACGGACG ATTCGCGTTCGAGCG/3C6/ | 280 |
| 491 | TRH | AGGCCACGGACG GCGGTAGTGGTCGTAG/3C6/ | 281 |
| 492 | JAM3 | AGGCCACGGACG CGTTTGGCGTAGATATAAGC/3C6/ | 282 |
| 493 | BARX1 | AGGCCACGGACG CCGCGCTACCGCTA/3C6/ | 283 |
| 494 | ZNF671_B | CGCGCCGAGG CCGCGCTACCGCTA/3C6/ | 284 |
| 495 | TSPYL5 | AGGCCACGGACG CGAAAAATCCCACGC/3C6/ | 285 |
| 496 | MPZ_B | CGCGCCGAGG GCGTTTCGATCGGGG/3C6/ | 286 |
| 497 | CXCL12 | AGGCCACGGACG GCGGGAGGATTTTCGATTTC/3C6 | 287 |
| 498 | PTGDR | CGCGCCGAGG CGTAACTCCATCTCGATAACC/3C6/ | 288 |

All developed assays were triplexed with the reference assay B3GALT6 which reports to Quasar670 (see, Table 26). The assays were tested on 156 benign and cancer samples with the following distribution and subtypes: 21 cervical cancer adenocarcinoma, 20 cervical cancer squamous, 13 endometrial cancer carcinosarcoma, 11 endometrial cancer clear cell, 10 endometrial cancer serous, 4 endometrial cancer endometrioid grade 1, 9 endometrial cancer endometrioid grade 2, 16 endometrial cancer endometrioid grade 3, 16 benign cervicovaginal, 6 endometrial benign atrophic, 3 endometrial benign disordered proliferative, 6 endometrial benign proliferative, endometrial benign secretory, 4 endometrial hyperplasia complex no atypia, 10 endometrial hyperplasia complex with atypia, and 2 endometrial hyperplasia simple no atypia.

Sensitivities for each methylation marker were calculated at a 95% cutoff per subtype and listed in Tables 24 and 25. Table 24 shows the endometrial tissue sensitivity at 95% for the markers shown in Table 21 for carcinosarcoma EC, clear cell EC, and serous EC. Table 25 shows the shows the endometrial tissue sensitivity at 95% for the markers shown in Table 21 for endometrioid EC Grade 1, endometrioid EC Grade 2, and endometrioid EC Grade 3.

TABLE 24

Endometrial tissue sensitivity at 95% for the markers shown in Table 21 for carcinosarcoma EC, clear cell EC, and serous EC.

| DMR No. | Marker | Carcino-sarcoma EC | Clear Cell EC | Serous EC |
|---|---|---|---|---|
| 495 | TSPYL5 | 77% | 55% | 70% |
| 496 | MPZ_B | 46% | 27% | 70% |
| 491 | TRH | 85% | 55% | 50% |
| 497 | CXCL12 | 8% | 27% | 10% |
| 476 | IRF4 | 38% | 45% | 40% |
| 477 | CNTN4 | 8% | 45% | 30% |
| 478 | GRIN2A | 15% | 45% | 20% |
| 479 | NOTCH3 | 62% | 9% | 20% |
| 480 | PAX1 | 23% | 45% | 20% |
| 481 | ZNF521 | 8% | 55% | 30% |
| 482 | VSX1 | 23% | 55% | 30% |
| 492 | JAM3 | 15% | 27% | 20% |
| 483 | CRHR2 | 23% | 45% | 10% |
| 484 | FAM19A5 | 15% | 36% | 10% |
| 485 | ASCL1 | 23% | 45% | 10% |
| 486 | GLT1D1 | 15% | 36% | 10% |
| 487 | T | 23% | 45% | 10% |
| 488 | CAPN2 | 31% | 55% | 40% |
| 489 | RYR2_F | 8% | 45% | 10% |

TABLE 24-continued

Endometrial tissue sensitivity at 95% for the markers shown in
Table 21 for carcinosarcoma EC, clear cell EC, and serous EC.

| DMR No. | Marker | Carcino-sarcoma EC | Clear Cell EC | Serous EC |
|---|---|---|---|---|
| 498 | PTGDR | 54% | 73% | 60% |
| 493 | BARX1 | 31% | 18% | 10% |
| 494 | ZNF671_B | 54% | 55% | 80% |
| 490 | SIM2 | 46% | 18% | 0% |
| 472 | LOC100192379_C | 0% | 0% | 30% |
| 446 | AIM1_C | 31% | 55% | 40% |
| 445 | AGRN_B | 38% | 82% | 60% |
| 459 | MAX.chr7: 104624386-104624529 | 92% | 91% | 80% |
| 81 | EMX2OS | 100% | 91% | 90% |
| 449 | DIDO1_B | 85% | 91% | 80% |
| 451 | GDF7_B | 46% | 64% | 60% |
| 450 | FKBP11_B | 85% | 64% | 80% |
| 453 | LHFPL2_B | 62% | 55% | 10% |
| 447 | AKR7A3 | 38% | 64% | 20% |
| 150 | LRRC41_D | 31% | 64% | 90% |
| 454 | LOC100129726_B | 62% | 9% | 30% |
| 448 | C17orf107_B | 69% | 55% | 80% |
| 456 | MAX.chr10: 22624470-22624553 | 46% | 64% | 30% |
| 455 | LRRC8D_B | 62% | 64% | 60% |
| 458 | MAX.chr7: 104624356-104624513 | 69% | 64% | 70% |

TABLE 24-continued

Endometrial tissue sensitivity at 95% for the markers shown in
Table 21 for carcinosarcoma EC, clear cell EC, and serous EC.

| DMR No. | Marker | Carcino-sarcoma EC | Clear Cell EC | Serous EC |
|---|---|---|---|---|
| 457 | MAX.chr14: 103021654-103021725 | 46% | 82% | 40% |
| 212 | MDFI_B | 15% | 55% | 20% |
| 464 | SPDYA_B | 54% | 73% | 50% |
| 461 | RHBDL1_B | 46% | 36% | 60% |
| 460 | OBSCN_B | 69% | 91% | 60% |
| 463 | SFMBT2_E | 23% | 45% | 10% |
| 462 | SEPT9_D | 38% | 82% | 10% |
| 465 | ST3GAL2_B | 92% | 27% | 20% |
| 452 | JSRP1_B | 46% | 82% | 70% |
| 368 | ITPKA | 8% | 0% | 0% |
| 466 | ZNF323_B | 62% | 55% | 40% |
| 302 | VILL | 54% | 18% | 40% |
| 468 | ZMIZ1_D | 23% | 64% | 20% |
| 467 | SLC13A5_B | 23% | 45% | 0% |
| 470 | C8orf73_B | 38% | 82% | 40% |
| 469 | MAX.chr8: 145103900-145103993 | 38% | 64% | 30% |
| 471 | KBTBD11_B | 8% | 9% | 20% |
| 499 | ARL5C | 69% | 73% | 80% |
| 472 | LOC100192379_C | 15% | 0% | 40% |
| 475 | STX16_B | 15% | 27% | 40% |
| 474 | LOC440925_B | 54% | 36% | 30% |
| 473 | TRIM71_B | 23% | 36% | 40% |

TABLE 25

Endometrial tissue sensitivity at 95% for the markers shown in Table 21 for endometrioid
EC Grade 1, endometrioid EC Grade 2, and endometrioid EC Grade 3.

| DMR No. | Marker | Endometrioid EC Grade 1 | Endometrioid EC Grade 2 | Endometrioid EC Grade 3 |
|---|---|---|---|---|
| 495 | TSPYL5 | 100% | 89% | 94% |
| 496 | MPZ_B | 75% | 89% | 88% |
| 491 | TRH | 100% | 89% | 88% |
| 497 | CXCL12 | 0% | 22% | 25% |
| 476 | IRF4 | 50% | 67% | 63% |
| 477 | CNTN4 | 75% | 89% | 63% |
| 478 | GRIN2A | 50% | 78% | 50% |
| 479 | NOTCH3 | 0% | 0% | 0% |
| 480 | PAX1 | 75% | 78% | 38% |
| 481 | ZNF521 | 50% | 22% | 31% |
| 482 | VSX1 | 75% | 67% | 63% |
| 492 | JAM3 | 100% | 67% | 38% |
| 483 | CRHR2 | 50% | 78% | 50% |
| 484 | FAM19A5 | 100% | 89% | 56% |
| 485 | ASCL1 | 50% | 67% | 38% |
| 486 | GLT1D1 | 75% | 89% | 56% |
| 487 | T | 50% | 67% | 44% |
| 488 | CAPN2 | 50% | 67% | 31% |
| 489 | RYR2_F | 75% | 89% | 63% |
| 498 | PTGDR | 100% | 89% | 94% |
| 493 | BARX1 | 75% | 56% | 56% |
| 494 | ZNF671_B | 50% | 56% | 69% |
| 490 | SIM2 | 0% | 44% | 38% |
| 472 | LOC100192379_C | 25% | 33% | 31% |
| 446 | AIM1_C | 0% | 0% | 19% |
| 445 | AGRN_B | 0% | 22% | 38% |
| 459 | MAX.chr7: 104624386-104624529 | 0% | 44% | 69% |
| 81 | EMX2OS | 75% | 89% | 81% |
| 449 | DIDO1_B | 0% | 44% | 81% |
| 451 | GDF7_B | 25% | 44% | 44% |
| 450 | FKBP11_B | 25% | 56% | 69% |
| 453 | LHFPL2_B | 0% | 11% | 25% |
| 447 | AKR7A3 | 0% | 33% | 44% |
| 150 | LRRC41_D | 0% | 11% | 25% |
| 454 | LOC100129726_B | 25% | 11% | 44% |
| 448 | C17orf107_B | 0% | 56% | 44% |

TABLE 25-continued

Endometrial tissue sensitivity at 95% for the markers shown in Table 21 for endometrioid
EC Grade 1, endometrioid EC Grade 2, and endometrioid EC Grade 3.

| DMR No. | Marker | Endometrioid EC Grade 1 | Endometrioid EC Grade 2 | Endometrioid EC Grade 3 |
|---|---|---|---|---|
| 456 | MAX.chr10: 22624470-22624553 | 75% | 89% | 75% |
| 455 | LRRC8D_B | 25% | 56% | 50% |
| 458 | MAX.chr7: 104624356-104624513 | 0% | 11% | 38% |
| 457 | MAX.chr14: 103021654-103021725 | 50% | 67% | 56% |
| 212 | MDFI_B | 25% | 33% | 25% |
| 464 | SPDYA_B | 75% | 89% | 81% |
| 461 | RHBDL1_B | 0% | 56% | 63% |
| 460 | OBSCN_B | 0% | 22% | 56% |
| 463 | SFMBT2_E | 100% | 89% | 63% |
| 462 | SEPT9_D | 0% | 22% | 19% |
| 465 | ST3GAL2_B | 0% | 33% | 38% |
| 452 | JSRP1_B | 100% | 100% | 75% |
| 368 | ITPKA | 0% | 0% | 0% |
| 466 | ZNF323_B | 0% | 11% | 50% |
| 302 | VILL | 50% | 67% | 81% |
| 468 | ZMIZ1_D | 0% | 67% | 31% |
| 467 | SLC13A5_B | 50% | 78% | 31% |
| 470 | C8orf73_B | 0% | 56% | 56% |
| 469 | MAX.chr8: 145103900-145103993 | 50% | 78% | 69% |
| 471 | KBTBD11_B | 25% | 33% | 31% |
| 499 | ARL5C | 100% | 78% | 75% |
| 472 | LOC100192379_C | 25% | 56% | 38% |
| 475 | STX16_B | 0% | 11% | 6% |
| 474 | LOC440925_B | 25% | 11% | 19% |
| 473 | TRIM71_B | 25% | 22% | 31% |

For such tests, multiplex PCR reactions were setup and completed. Each multiplex PCR reaction was setup with an intermediate primer mix containing 2 µM forward primer and 2 µM reverse primer of each marker. Multiplex PCR reaction 1 consisted of each of the following markers: AIM1_C, AGRN_B, C17orf107_B, MAX.chr7:104624386-104624529, EMX2OS, DIDO1_B, GDF7_B, FKBP11_B, LHFPL2_B, AKR7A3, LRRC41_D, LOC100129726_B, and B3GALT6. Multiplex PCR reaction 2 consisted of each of the following markers: MAX.chr10:22624470-22624553, LRRC8D_B, MAX.chr7:104624356-104624513, MAX.chr14:103021654-103021725, MDFI_B, SPDYA_B, RHBDL1_B, OBSCN_B, SFMBT2_E, SEPT9_D, ST3GAL2_B, JSRP1_B, ITPKA, and B3GALT6. Multiplex PCR reaction 3 consisted of each of the following markers: ZNF323_B, VILL, ZMIZ1_D, SLC13A5_B, C8orf73_B, MAX.chr8:145103900-145103993, KBTBD11_B, ARL5C, TRIM71_B, LOC100192379_C, STX16_B, LOC440925_B, and B3GALT6. Multiplex PCR reaction 4 consisted of each of the following markers: TSPYL5, MPZ_B, TRH, CXCL12, IRF4, CNTN4, GRIN2A, NOTCH3, PAX1, ZNF521, VSX1, JAM3, and B3GALT6. Multiplex PCR reaction 5 consisted of each of the following markers: CRHR2, FAM19A5, ASCL1, GLT1D1, T, CAPN2, RYR2_F, PTGDR, BARX1, ZNF671_B, SIM2, and B3GALT6.

Each multiplex PCR reaction was setup to a final concentration of 0.2 µM reaction buffer, 0.075 µM primer mix, 0.025 µM Hotstart Go Taq (5 U/L) resulting in 25 µL of master mix that was combined with 50 µL of DNA template for a final reaction volume of 75 µL. The thermal profile for the multiplex PCR entailed 12 cycles of a pre-incubation stage of 95° for 5 minutes, a 2-step amplification stage of 95° for 30 seconds, 64° for 60 seconds, and a cooling stage of 4° that was held infinitely. Once the multiplex PCR was complete, the PCR product was diluted 1:10 using Te and subsequently 10 µL were used for each LQAS reaction. Each LQAS assay was developed in triplex form consisting of 2 methylation markers and B3GALT6 as the reference gene. Each LQAS assay was built using 2 µM of each primer for each methylation marker and B3GALT6, 5 µM of each methylation marker probe, 5 µM of each FRET cassette with 2500 µM dNTPs.

From multiplex PCR product 1, the following 6 LQAS assays were run (see, Table 26): (1.) AIM1_C, AGRN_B, B3GALT6; (2.) C17orf107_B, MAX.chr7:104624386-104624529, B3GALT6; (3.) EMX2OS, DIDO1_B, B3GALT6; (4.) GDF7_B, FKBP11_B, B3GALT6; (5.) LHFPL2_B, AKR7A3, B3GALT6; (6.) LRRC41_D, LOC100129726_B, B3GALT6. From multiplex PCR product 2, the following 7 LQAS assays were run (see, Table 26): (1.) MAX.chr10:22624470-22624553, LRRC8D_B, B3GALT6; (2.) MAX.chr7:104624356-104624513, MAX.chr14:103021654-103021725, B3GALT6; (3.) MDFI, SPDYA_B, B3GALT6; (4.) RHBDL1_B, OBSCN_B, B3GALT6; (5.) SFMBT2_E, SEPT9_D, B3GALT6; (6.) ST3GAL2_B, JSRP1_B, B3GALT6; (7.) ITPKA, B3GALT6. From multiplex PCR product 3, the following 6 LQAS assays were run (see, Table 26): (1.) ZNF323_B, VILL, B3GALT6; (2.) ZMIZ1_D, SLC13A5_B, B3GALT6; (3.) C8orf73_B, MAX.chr8: 145103900-145103993, B3GALT6; (4.) KBTBD11_B, ARL5C, B3GALT6; (5.) TRIM71_B, LOC100192379_C, B3GALT6; (6.) STX16_B, LOC440925_B, and B3GALT6. From multiplex PCR product 4, the following 6 LQAS assays were run (see, Table 26): (1.) TSPYL5, MPZ_B, B3GALT6; (2.) TRH, CXCL12, B3GALT6; (3.) IRF4, CNTN4, B3GALT6; (4.) GRIN2A, NOTCH3, B3GALT6; (5.) PAX1, ZNF521, B3GALT6; (6.) VSX1, JAM3, and B3GALT6. From multiplex PCR product 5, the following 5 LQAS assays were run (see, Table 26): (1.) EMX1, ARHGEF4, BTACT; (2.) OPLAH, CYP26C1, BTACT; (3.) ZNF781, DLX4, BTACT; (4.) PTGDR, KLHDC7B, BTACT; (5.) GRIN2D, chr17_737, and BTACT. From multiplex PCR product 6, the following 6 LQAS assays were run (see, Table 27): (1.) CRHR2, FAM19A5, B3GALT6; (2.) ASCL1, GLT1D1, B3GALT6; (3.) T, CAPN2, B3GALT6; (4.) RYR2_F, PTGDR, B3GALT6; (5.) BARX1, ZNF671_B, B3GALT6; (6.) SIM2 and B3GALT6.

TABLE 26

| | LQAS Triplex Assays | |
|---|---|---|
| DMR NO. | Marker | LQAS Assay Triplex |
| 445 | AGRN__B | AIM1__C-AGRN__B-B3GALT6 |
| 446 | AIM1__C | |
| 448 | C17orf107__B | C17orf107__B-MAX.chr7: 104624386-104624529-B3GALT6 |
| 459 | MAX.chr7: 104624386-104624529 | |
| 81 | EMX2OS | EMX2OS-DIDO1__B-B3GALT6 |
| 449 | DIDO1__B | |
| 451 | GDF7__B | GDF7__B-FKBP11__B-B3GALT6 |
| 450 | FKBP11__B | |
| 453 | LHFPL2__B | LHFPL2__B-AKR7A3-B3GALT6 |
| 447 | AKR7A3 | |
| 150 | LRRC41__D | LRRC41__D-LOC100129726__E-B3GALT6 |
| 454 | LOC100129726__B | |
| 456 | MAX.chr10: 22624470-22624553 | MAX.chr10: 22624470-22624553-LRRC8D B-B3GALT6 |
| 455 | LRRC8D__B | |
| 458 | MAX.chr7: 104624356-104624513 | MAX.chr7: 104624356-104624513-MAX.chr14: 103021654- |
| 457 | MAX.chr14: 103021654-103021725 | 103021725-B3GALT6 |
| 212 | MDFI__B | MDFI__B-SPDYA__B-B3GALT6 |
| 464 | SPDYA__B | |
| 461 | RHBDL1__B | RHBDL1__B-OBSCN__B-B3GALT6 |
| 460 | OBSCN__B | |
| 463 | SFMBT2__E | SFMBT2__E-SEPT9__D-B3GALT6 |
| 462 | SEPT9__D | |
| 465 | ST3GAL2__B | ST3GAL2__B-JSRP1__B-B3GALT6 |
| 452 | JSRP1__B | |
| 368 | ITPKA | ITPKA-B3GALT6 |
| 466 | ZNF323__B | ZNF323__B-VILL-B3GALT6 |
| | VILL | |
| 468 | ZMIZ1__D | ZMIZ1__D-SLC13A5__B-B3GALT6 |
| 467 | SLC13A5__B | |
| 470 | C8orf73__B | C8orf73__B-MAX.chr8: 145103900-145103993-B3GALT6 |
| 469 | MAX.chr8: 145103900-145103993 | |
| 471 | KBTBD11__B | KBTBD11__B-ARL5C-B3GALT6 |
| 35 | ARL5C | |
| 473 | TRIM71__B | TRIM71__B-LOC100192379__C-B3GALT6 |
| 472 | LOC100192379__C | |
| 475 | STX16__B | |
| 474 | LOC440925__B | STX16__B-LOC440925__B-B3GALT6 |
| 495 | TSPYL5 | TSPYL5-MPZ__B-B3GALT6 |
| 496 | MPZ__B | |
| 491 | TRH | TRH-CXCL12-B3GALT6 |
| 497 | CXCL12 | |
| 476 | IRF4 | IRF4-CNTN4-B3GALT6 |
| 477 | CNTN4 | |
| 478 | GRIN2A | GRIN2A-NOTCH3-B3GALT6 |
| 479 | NOTCH3 | |
| 480 | PAX1 | PAX1-ZNF521-B3GALT6 |
| 481 | ZNF521 | |
| 482 | VSX1 | VSX1-JAM3-B3GALT6 |
| 492 | JAM3 | |
| 483 | CRHR2 | CRHR2-FAM19A5-B3GALT6 |
| 484 | FAM19A5 | |
| 485 | ASCL1 | ASCL1-GLT1D1-B3GALT6 |
| 486 | GLT1D1 | |
| 487 | T | T-CAPN2-B3GALT6 |
| 488 | CAPN2 | |
| 489 | RYR2__F | RYR2__F-PTGDR-B3GALT6 |
| 498 | PTGDR | |
| 493 | BARX1 | BARX1-ZNF671__B-B3GALT6 |
| 494 | ZNF671__B | |
| 490 | SIM2 | SIM2-B3GALT6 |

All LQAS assays were setup and run with standard, previously published conditions.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

---

We claim:

1. A method, comprising:
    treating DNA in a sample from a subject having or
        suspected of having endometrial cancer or a subtype of
        endometrial cancer with a reagent that modifies DNA in
        a methylation-specific manner;
    amplifying the treated DNA using a set of primers for one
        or more genes; and
    determining the methylation level of the one or more
        genes using polymerase chain reaction, nucleic acid
        sequencing, mass spectrometry, a methylation-specific
        nuclease, mass-based separation, and/or target capture;
    wherein the one or more genes is selected from GYPC,
        MAX.chr10.22624479-22624553,
        MAX.chr19.37288607-37288752, JSRP1, SPDYA,
        ZNF506 and SFMBT2.

2. The method of claim 1, wherein the reagent comprises
one or more of a methylation-sensitive restriction enzyme, a
methylation-dependent restriction enzyme, and/or a bisulfite
reagent.

3. The method of claim 2, wherein the DNA is treated
with a bisulfite reagent to produce bisulfite-treated DNA.

4. The method of claim 1, wherein determining the
methylation level of the one or more genes comprises using
methylation-specific PCR, quantitative methylation-specific
PCR, methylation-specific DNA restriction enzyme analy-
sis, quantitative bisulfite pyrosequencing, a flap endonu-
clease assay, a PCR-flap assay, and/or bisulfite genomic
sequencing PCR.

5. The method of claim 1, wherein the sample comprises
one or more of a plasma sample, a blood sample, and/or a
tissue sample.

6. The method of claim 5, wherein the tissue sample is an
endometrial tissue sample.

7. The method of claim 1, further comprising measuring
at least one reference marker selected from B3GALT6
and/or β-actin.

8. The method of claim 1, wherein the endometrial cancer
or the subtype of endometrial cancer comprises one or more
of clear cell endometrial cancer, carcinosarcoma endome-
trial cancer, endometrioid endometrial cancer, and/or serous
endometrial cancer.

9. The method of claim 1, wherein determining the
methylation level of the one or more genes further comprises
multiplex amplification.

10. The method of claim 1, wherein determining the
methylation level of the one or more genes comprises
measuring a methylation level of at least one CpG site for
the one or more genes.

11. The method of claim 10, wherein the at least one CpG
site for the one or more genes is present in a coding region
or a regulatory region.

12. The method of claim 10, wherein measuring the
methylation level of the at least one CpG site for the one or
more genes comprises determining a methylation score
and/or determining a methylation frequency.

13. The method of claim 1, wherein determining the
methylation level of the one or more genes further comprises
comparing the methylation level to a methylation level of a
corresponding gene or genes in a control sample.

14. The method of claim 13, wherein the control sample
is from a subject that does not have cancer.

15. The method of claim 13, wherein the control sample
is from a subject that does not have endometrial cancer or a
subtype of endometrial cancer.

16. The method of claim 1, wherein the one or more genes
comprises GYPC.

17. The method of claim 1, wherein the one or more genes
comprises MAX.chr10.22624479-22624553.

18. The method of claim 1, wherein the one or more genes
comprises MAX.chr19.37288607-37288752.

19. The method of claim 1, wherein the one or more genes
comprises JSRP1.

20. The method of claim 1, wherein the one or more genes
comprises SPDYA.

21. The method of claim 1, wherein the one or more genes
comprises ZNF506.

22. The method of claim 1, wherein the one or more genes
comprises SFMBT2.

23. The method of claim 1, wherein the one or more genes
comprises GYPC and MAX.chr10.22624479-22624553.

24. The method of claim 1, wherein the one or more genes
comprises GYPC and MAX.chr19.37288607-37288752.

25. The method of claim 1, wherein the one or more genes
comprises GYPC and JSRP1.

26. The method of claim 1, wherein the one or more genes
comprises GYPC and SPDYA.

27. The method of claim 1, wherein the one or more genes
comprises GYPC and ZNF506.

28. The method of claim 1, wherein the one or more genes
comprises GYPC and SFMBT2.

29. The method of claim 1, wherein the one or more genes
comprises two genes selected from GYPC,
MAX.chr10.22624479-22624553, MAX.chr19.37288607-
37288752, JSRP1, SPDYA, ZNF506 and SFMBT2.

* * * * *